(12) United States Patent
Lupold et al.

(10) Patent No.: US 9,018,138 B2
(45) Date of Patent: Apr. 28, 2015

(54) COMPOSITIONS AND METHODS FOR GENERATING AND SCREENING ADENOVIRAL LIBRARIES

(75) Inventors: Shawn E. Lupold, Ellicott City, MD (US); Ronald Rodriguez, Glenwood, MD (US); Wasim H. Chowdhury, Laurel, MD (US); Tarana A. Kudrolli, Frederick, MD (US)

(73) Assignee: The Johns Hopkins University, Baltimore, MD (US)

(*) Notice: Subject to any disclaimer, the term of this patent is extended or adjusted under 35 U.S.C. 154(b) by 1270 days.

(21) Appl. No.: 12/193,624

(22) Filed: Aug. 18, 2008

(65) Prior Publication Data

US 2009/0074658 A1 Mar. 19, 2009

Related U.S. Application Data

(60) Provisional application No. 60/993,115, filed on Sep. 10, 2007, provisional application No. 60/964,971, filed on Aug. 16, 2007.

(51) Int. Cl.
| | |
|---|---|
| *C40B 50/06* | (2006.01) |
| *C07K 14/005* | (2006.01) |
| *C12N 7/00* | (2006.01) |
| *C12N 15/10* | (2006.01) |
| *C12N 15/86* | (2006.01) |

(52) U.S. Cl.
CPC .............. *C07K 14/005* (2013.01); *C12N 7/00* (2013.01); *C12N 15/1037* (2013.01); *C12N 15/1086* (2013.01); *C12N 15/86* (2013.01); *C12N 2710/10322* (2013.01); *C12N 2710/10343* (2013.01); *C12N 2710/10345* (2013.01); *C12N 2810/405* (2013.01)

(58) Field of Classification Search
None
See application file for complete search history.

(56) References Cited

FOREIGN PATENT DOCUMENTS

WO WO 2006/099615 * 3/2006

OTHER PUBLICATIONS

Nakano et al. (Production of viral vectors using recombinase-mediated cassette exchange, 2005, Nucleic Acids Research, vol. 33, e76, pp. 1-8).*
Danthinne et al. (Production of first generation adenovirus vectors: a review, 2000, Gene Therapy, vol. 7, pp. 1707-1714).*
Dmitriev et al. (An adenovirus vector with genetically modified fibers demonstrates expanded tropism via utilization of a coxsackievirus and adenovirus receptor-independent cell entry mechanism, 1998, Journal of Virology, vol. 72, pp. 9706-9713).*
Langer et al. (A genetic screen identifies novel non-compatible loxP sites, 2002, Nucleic Acids Research, vol. 30, pp. 3067-3077).*
Lupoid et al. (pFex: a novel fiber exchange system for the creation of modified-fiber gene therapy vectors, 2004, Molecular Therapy, vol. 9, Supp 1, p. S53, Abstract 137).*
Belousova et al., "Modulation of Adenovirus Vector Tropism via Incorporation of Polypeptide Ligands into the Fiber Protein," Jrl. of Virology, pp. 8621-8631 (Sep. 2002).
Bergelson et al., "Isolation of a Common Receptor for Coxsackie B Viruses and Adenoviruses 2 and 5," Science, 275, 1320 (1997).

(Continued)

*Primary Examiner* — Christian Boesen
(74) *Attorney, Agent, or Firm* — Mintz Levin Cohn Ferris Glovsky and Popeo, P.C.; Peter F. Corless, Esq.

(57) ABSTRACT

The present invention provides DNA libraries, libraries of viral clones and libraries of infectious viral particles and methods of generating and screening these libraries.

13 Claims, 70 Drawing Sheets

Schematic of E1 Recombination followed by pFex Fiber Exchange. The pShuttle-Fib is the completed adenoviral vector. Virus is created by digestion with Pac I followed by transfection into desired cell line.

(56) References Cited

OTHER PUBLICATIONS

Berget et al., "Spliced segments at the 5' terminus of adenovirus 2 late mRNA," Proc. Natl. Acad. Sci. USA, vol. 74, No. 8, pp. 3171-3175 (Aug. 1977).

Chow et al., "An Amazing Sequence Arrangement at the 5' Ends of Adenovirus 2 Messenger RNA," Cell, vol. 12, 1-8 (Sep. 1977).

He et al., "A simplified system for generating recombinant adenoviruses," Proc. Natl. Acad. Sci. USA, vol. 95, pp. 2509-2514 (Mar. 1998).

Krasnykh et al., "Characterization of an Adenovirus Vector Containing a Heterologous Peptide Epitope in the HI Loop of the Fiber Knob," Jrl. of Virology, pp. 1844-1852 (Mar. 1998).

Langer et al., "A genetic screen identifies novel non-compatible loxP sites," Nucleic Acids Research, vol. 30(14), pp. 3067-3077 (2002).

Mizuguchi et al., "CAR- or av integrin-binding ablated adenovirus vectors, but not fiber-modified vectors containing RGD peptide, do not change the systemic gene transfer properties in mice," Gene Therapy, 9, p. 769-776 (2002).

Nevins et al., "Groups of Adenovirus Type 2 mRNA's Derived from a Large Primary Transcript: Probable Nuclear Origin and Possible Common 3' Ends," Jrl. of Virology, pp. 811-823 (Mar. 1978).

Okegawa et al., "The Dual Impact of Coxsackie and Adenovirus Receptor Expression on Human Prostate Cancer Gene Therapy," Cancer Research, 60, pp. 5031-5036 (Sep. 15, 2000).

Pierce et al., "A positive selection vector for cloning high molecular weight DNA by the bacteriophage P1 system: Improved cloning efficacy," Proc. Natl. Acad. Sci. USA, vol. 89, pp. 2056-2060 (Mar. 1992).

Roelvink et al., "Identification of a Conserved Receptor-Binding Site on the Fiber Proteins of CAR-Recognizing Adenoviridae," Science 286, 1568 (1999).

Tomko et al., "HCAR and MCAR: The human and mouse cellular receptors for subgroup C adenoviruses and group B coxsackieviruses," Proc. Natl. Acad. Sci. USA, vol. 94, pp. 3352-3356 (Apr. 1997).

van Beusechem et al., "Efficient and Selective Gene Transfer into Primary Human Brain Tumors by Using Single-Chain Antibody-Targeted Adenoviral Vectors with Native Tropism Abolished," Jrl. of Virology, pp. 2753-2762 (Mar. 2002).

Wickham et al., "Increased In Vitro and In Vivo Gene Transfer by Adenovirus Vectors Containing Chimeric Fiber Proteins," Jrl. of Virology, pp. 8221-8229 (Nov. 1997).

Wickham et al., "Integrins avb3 and avb5 Promote Adenovirus Internalization but Not Virus Attachment," Cell, vol. 73, 309-319 (Apr. 23, 1993).

Zeng et al., "AdEasy System Made Easier by Selecting the Viral Backbone Plasmid Preceding Homologous Recombination," BioTechniques, vol. 31, pp. 260-262 (Aug. 2001).

Ziff et al., "Coincidence of the Promoter and Capped 5' Terminus of RNA from the Adenovirus 2 Major Late Transcription Unit," Cell, vol. 15, 1463-1475 (Dec. 1978).

\* cited by examiner

Schematic of lox site. The *Lox*P sequence is given as an example.

5' ATA ACT TCG TAT AGC ATA CAT TAT ACG AAG TTA T 3'

3' TAT TGA AGC ATA TCG TAT GTA ATA TGC TTC AAT A 5'

Lox sequences with half-site mutations (*italics*) provide unidirectional recombination.

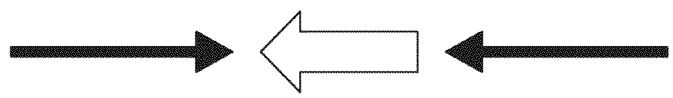

| Lox P | ATTACTTCGTATA | GCATACAT | TATACGAAGTTAT |
| Lox 511 | ATAACTTCGTATA | G*T*ATACAT | TATACGAAGTTAT |
| Lox 66 | ATAACTTCGTATA | GCATACAT | TATACGAA*CGGTA* |
| Lox 71 | *TACCG*TTCGTATA | GCATACAT | TATACGAAGTTAT |

FIG. 2A

Various spacer sequences produce non-compatible *lox* sites to prevent excision. Changes are in *italics*.

Spacer Sequences:

| P | GCATACAT |
| 511 | G*T*ATACAT |
| m2 | *TGGTTTCT* |
| m3 | *TGGTATTA* |
| M7 | *TTCTATCT* |
| M11 | *TGGTATCG* |

FIG. 2B

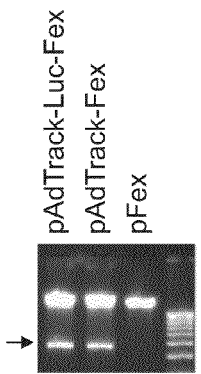
FIG. 15A
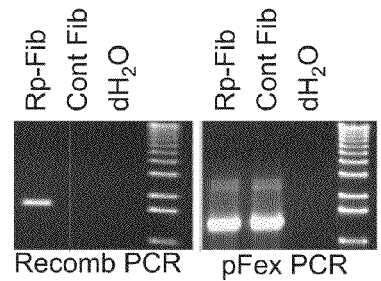
FIG. 15B
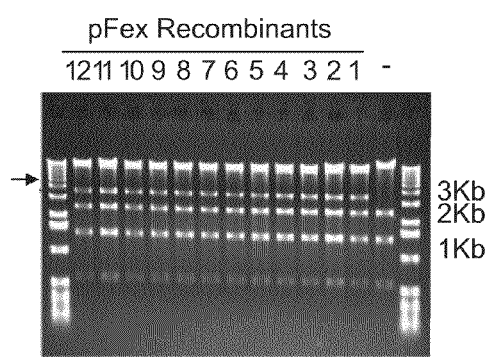
FIG. 15C
Efficiency of Fiber Plasmid Exchange
|  | pFex Colonies | Fiber Shuttle Colonies | Recombinant Colonies |
|---|---|---|---|
| Lox Negative Control | 29,000 | >3 X $10^7$ | 0 |
| WT Fiber Shuttle | 17,000 | >3 X $10^7$ | 1,170 |
| ΔTAYT | 17,100 | >3 X $10^7$ | 780 |
| RGD4C | 40,200 | >3 X $10^7$ | 2,620 |
| ΔTAYT, RGD4C | 40,000 | >3 X $10^7$ | 2,629 |
| MEAN | 28,575 | >3 X $10^7$ | 1,800 |
FIG. 15D Quantification of CAR Dependent and Independent Infection.

Primers for constructing and sequencing pFex.

| Primer | Sequence | Primer | Sequence |
|---|---|---|---|
| 5' Lox71 | [Phosp]CGTACCGTTCGTATAGCATACAT TATACGAAGTTATA | pFEXfor08 | CCGCAGAATAAGCCACACCC |
| 3' Lox71 | [Phosp]CCGGTATAACTTCGTATAATGTA TGCTATACGAACGGTACGAT | pFEXfor09 | TAACAAAAATACCGCGATCC |
| 5' Lox m2/66 | [Phosp]CCGGTATAACTTCGTATATGGTT TCTTATACGAACGGTA | pFEXfor10 | ACAGCTCCTCGGTCATGTCC |
| 3' Lox m2/66 | [Phosp]GATCTACCGTTCGTATAAGAAAC CATATACGAAGTTATA | pFEXfor11 | CGTTTTCCCACGTTACGTAA |
| AdE-Dist 5' | AACCGGTATACATTGCCCAAGAATAAAG | pFEXrev01 | CACTATAGGGCGAATTGGGC |
| AdE-Dist 3' | TCATAAGTGCGGCGACGATA | pFEXrev02 | GCCCTTTTTTACACTGTGAC |
| loxmve1 | GTTGTGTGGAATTGTGAGCGG | pFEXrev03 | TTTATGCAGAAACCCGCAGA |
| loxmve2 | CATGTACCGGTGGGTGCGGATGGACA GGAAC | pFEXrev04 | ATATTGAGAAGGTGGCGAGA |
| pFEXfor01 | CTAACAATTCGTTCAAGCCG | pFEXrev05 | TGTTTGTCACGCCCGCACCT |
| pFEXfor02 | TCAGCGGTTTCATCACTTTT | pFEXrev06 | AGAGGTTTATATGGTACCGG |
| pFEXfor03 | CTGACCATTCTTGTGTTTGG | pFEXrev07 | ACTTAAGTGAGCTGCCCGGG |
| pFEXfor04 | GTCTCCTTTTTTATGTACTGTG | pFEXrev08 | TTATGCCCATGCAACAGAAA |
| pFEXfor05 | TTATACGAAGTTATACCGGT | pFEXrev09 | TATTACACGCCATGATATGC |
| pFEXfor06 | AATAAACTGCTGCCGCCGCC | pFEXrev10 | CGGTGTAGAGGATTATAAATCAATC |
| pFEXfor07 | ATCAATGTTGGCACAACACA | pFEXrev11 | CATGCTTGGTTATGTTTCTA |

FIG. 23

Primers for constructing and sequencing Fiber Shuttles

| Primer | Sequence |
| --- | --- |
| S-lox m2/71-X5 | [Phos]CTAGTACCGTTCGTATATGGTTTCTTATACGAAGTTATC |
| S-lox m2/71-X3 | [Phos]TCGAGATAACTTCGTATAAGAAACCATATACGAACGGTA |
| N-Lox 66-A-5 | [Phos]GGCCGCATAACTTCGTATAGCATACATTATACGAACGGTAG |
| N-Lox 66-A-3 | [Phos]GTACCTACCGTTCGTATAATGTATGCTATACGAAGTTATGC |
| Splce1 | [Phos]TCGAGAACTATCTTCATGTTGTTGCAGATGAAGCGCGCAAGACCGTCTGAAGATACCTTCAACCCCGTGTATCCATATGACACGGAAA |
| Splce2 | [Phos]CCGGTTTCCGTGTCATATGGATACACGGGGTTGAAGGTATCTTCAGACGGTCTTGCGCGCTTCATCTGCAACAACATGAAGATAGTTC |
| 5FBR-537REP | GTTGTGTCTCCGGATTCCTGTGTACCGTTTAGTGTAATGG |
| 3FBR-537REP | GGACCCAGAATATTGGAACT |
| Fiber-S2 | CTCACCCCCTCTAACTACTG |
| Fiber-S3 | CAGGAGATGGGCTTGAATTT |
| 5N-Dir | [Phos] CCGGCGAATTCGCAGGTGGTGGTGGTGGTT |
| 3N-Dir | [Phos] CCGGAACCACCACCACCACCTGCGAATTCG |
| 5'RGD | [Phos]AATTGGGAAGAGGTGACACCCCCT |
| 5'RGD | [Phos]AATTGGGAAGAGGTGACACCCCCT |
| WTFibFix-1 | CCAAACACAAATCCCCTCAAA |
| WTFibFix-2 | ATAAGAATGCGGCCGCTTTATTCTTGGGCAATGTAT |

FIG. 24

SEQ ID NO:7

TCGAGATAACTTCGTATAAGAAACCATATACGAACGGTACTAGTGTCGACCTGCAG
GCATGCAAGCTTGGCGTAATCATGGTCATAGCTGTTTCCTGTGTGAAATTGTTATCC
GCTCACAATTCCACACAACATACGAGCCGGAAGCATAAAGTGTAAAGCCTGGGGTG
CCTAATGAGTGAGCTAACTCACATTAATTGCGTTGCGCTCACTGCCCGCTTTCCAGTC
GGGAAACCTGTCGTGCCAGCTGCATTAATGAATCGGCCAACGCGCGGGGAGAGGCG
GTTTGCGTATTGGGCGCTCTTCCGCTTCCTCGCTCACTGACTCGCTGCGCTCGGTCGT
TCGGCTGCGGCGAGCGGTATCAGCTCACTCAAAGGCGGTAATACGGTTATCCACAG
AATCAGGGGATAACGCAGGAAAGAACATGTGAGCAAAAGGCCAGCAAAAGGCCAG
GAACCGTAAAAAGGCCGCGTTGCTGGCGTTTTTCCATAGGCTCCGCCCCCTGACGA
GCATCACAAAAATCGACGCTCAAGTCAGAGGTGGCGAAACCCGACAGGACTATAAA
GATACCAGGCGTTTCCCCCTGGAAGCTCCCTCGTGCGCTCTCCTGTTCCGACCCTGCC
GCTTACCGGATACCTGTCCGCCTTTCTCCCTTCGGGAAGCGTGGCGCTTTCTCATAGC
TCACGCTGTAGGTATCTCAGTTCGGTGTAGGTCGTTCGCTCCAAGCTGGGCTGTGTG
CACGAACCCCCCGTTCAGCCCGACCGCTGCGCCTTATCCGGTAACTATCGTCTTGAG
TCCAACCCGGTAAGACACGACTTATCGCCACTGGCAGCAGCCACTGGTAACAGGAT
TAGCAGAGCGAGGTATGTAGGCGGTGCTACAGAGTTCTTGAAGTGGTGGCCTAACT
ACGGCTACACTAGAAGGACAGTATTTGGTATCTGCGCTCTGCTGAAGCCAGTTACCT
TCGGAAAAAGAGTTGGTAGCTCTTGATCCGGCAAACAAACCACCGCTGGTAGCGGT
GGTTTTTTTGTTTGCAAGCAGCAGATTACGCGCAGAAAAAAAGGATCTCAAGAAGA
TCCTTTGATCTTTTCTACGGGGTCTGACGCTCAGTGGAACGAAAACTCACGTTAAGG
GATTTTGGTCATGAGATTATCAAAAAGGATCTTCACCTAGATCCTTTTAAATTAAAA
ATGAAGTTTTAAATCAATCTAAAGTATATATGAGTAAACTTGGTCTGACAGTTACCA
ATGCTTAATCAGTGAGGCACCTATCTCAGCGATCTGTCTATTTCGTTCATCCATAGTT
GCCTGACTCCCCGTCGTGTAGATAACTACGATACGGGAGGGCTTACCATCTGGCCCC
AGTGCTGCAATGATACCGCGAGACCCACGCTCACCGGCTCCAGATTTATCAGCAATA
AACCAGCCAGCCGGAAGGGCCGAGCGCAGAAGTGGTCCTGCAACTTTATCCGCCTC
CATCCAGTCTATTAATTGTTGCCGGGAAGCTAGAGTAAGTAGTTCGCCAGTTAATAG
TTTGCGCAACGTTGTTGCCATTGCTACAGGCATCGTGGTGTCACGCTCGTCGTTTGGT
ATGGCTTCATTCAGCTCCGGTTCCCAACGATCAAGGCGAGTTACATGATCCCCCATG
TTGTGCAAAAAAGCGGTTAGCTCCTTCGGTCCTCCGATCGTTGTCAGAAGTAAGTTG
GCCGCAGTGTTATCACTCATGGTTATGGCAGCACTGCATAATTCTCTTACTGTCATGC
CATCCGTAAGATGCTTTTCTGTGACTGGTGAGTACTCAACCAAGTCATTCTGAGAAT
AGTGTATGCGGCGACCGAGTTGCTCTTGCCCGGCGTCAATACGGGATAATACCGCGC
CACATAGCAGAACTTTAAAAGTGCTCATCATTGGAAAACGTTCTTCGGGGCGAAAA
CTCTCAAGGATCTTACCGCTGTTGAGATCCAGTTCGATGTAACCCACTCGTGCACCC
AACTGATCTTCAGCATCTTTTACTTTCACCAGCGTTTCTGGGTGAGCAAAAACAGGA
AGGCAAAATGCCGCAAAAAAGGGAATAAGGGCGACACGGAAATGTTGAATACTCA
TACTCTTCCTTTTTCAATATTATTGAAGCATTTATCAGGGTTATTGTCTCATGAGCGG
ATACATATTTGAATGTATTTAGAAAAATAAACAAATAGGGGTTCCGCGCACATTTCC
CCGAAAAGTGCCACCTGACGTCTAAGAAACCATTATTATCATGACATTAACCTATAA
AAATAGGCGTATCACGAGGCCCTTTCGTCTCGCGCGTTTCGGTGATGACGGTGAAAA
CCTCTGACACATGCAGCTCCCGGAGACGGTCACAGCTTGTCTGTAAGCGGATGCCGG
GAGCAGACAAGCCCGTCAGGGCGCGTCAGCGGGTGTTGGCGGGTGTCGGGGCTGGC

FIG. 29A

Sequence of RPuc-Rescue1

```
TTAACTATGCGGCATCAGAGCAGATTGTACTGAGAGTGCACCATATGCGGTGTGAA
ATACCGCACAGATGCGTAAGGAGAAAATACCGCATCAGGCGCCATTCGCCATTCAG
GCTGCGCAACTGTTGGGAAGGGCGATCGGTGCGGGCCTCTTCGCTATTACGCCAGCT
GGCGAAAGGGGGATGTGCTGCAAGGCGATTAAGTTGGGTAACGCCAGGGTTTTCCC
AGTCACGACGTTGTAAAACGACGGCCAGTGAATTCGAGCTCGGTACCTACCGTTCGT
ATAATGTATGCTATACGAAGTTATGCGGCCGCCACTATTATTTAGTGAAATGAGATA
TTATGATATTTTCTGAATTGTGATTAAAAAGGCAACTTTATGCCCATGCAACAGAAA
CTATAAAAAATACAGAGAATGAAAAGAAACAGATAGATTTTTTAGTTCTTTAGGCCC
GTAGTCTGCAAATCCTTTTATGATTTTCTATCAAACAAAAGAGGAAAATAGACCAGT
TGCAATCCAAACGAGAGTCTAATAGAATGAGGTCGAAAAGTAAATCGCGCGGGTTT
GTTACTGATAAAGCAGGCAAGACCTAAAATGTGTAAAGGGCAAAGTGTATACTTTG
GCGTCACCCCTTACATATTTTAGGTCTTTTTTTATTGTGCGTAACTAACTTGCCATCTT
CAAACAGGAGGGCTGGAAGAAGCAGACCGCTAACACAGTACATAAAAAAGGAGAC
ATGAACGATGAACATCAAAAAGTTTGCAAAACAAGCAACAGTATTAACCTTTACTA
CCGCACTGCTGGCAGGAGGCGCAACTCAAGCGTTTGCGAAAGAAACGAACCAAAAG
CCATATAAGGAAACATACGGCATTTCCCATATTACACGCCATGATATGCTGCAAATC
CCTGAACAGCAAAAAAATGAAAAATATCAAGTTCCTGAATTCGATTCGTCCACAATT
AAAAATATCTCTTCTGCAAAAGGCCTGGACGTTTGGGACAGCTGGCCATTACAAAAC
GCTGACGGCACTGTCGCAAACTATCGCGGCTACCACATCGTCTTTGCATTAGCCGGA
GATCCTAAAAATGCGGATGACACATCGATTTACATGTTCTATCAAAAAGTCGGCGAA
ACTTCTATTGACAGCTGGAAAAACGCTGGCCGCGTCTTTAAAGACAGCGACAAATTC
GATGCAAATGATTCTATCCTAAAAGACCAAACACAAGAATGGTCAGGTTCAGCCAC
ATTTACATCTGACGGAAAAATCCGTTTATTCTACACTGATTTCTCCGGTAAACATTAC
GGCAAACAAACACTGACAACTGCACAAGTTAACGTATCAGCATCAGACAGCTCTTT
GAACATCAACGGTGTAGAGGATTATAAATCAATCTTTGACGGTGACGGAAAAACGT
ATCAAAATGTACAGCAGTTCATCGATGAAGGCAACTACAGCTCAGGCGACAACCAT
ACGCTGAGAGATCCTCACTACGTAGAAGATAAAGGCCACAAATACTTAGTATTTGA
AGCAAACACTGGAACTGAAGATGGCTACCAAGGCGAAGAATCTTTATTTAACAAAG
CATACTATGGCAAAAGCACATCATTCTTCCGTCAAGAAAGTCAAAAACTTCTGCAAA
GCGATAAAAAACGCACGGCTGAGTTAGCAAACGGCGCTCTCGGTATGATTGAGCTA
AACGATGATTACACACTGAAAAAAGTGATGAAACCGCTGATTGCATCTAACACAGT
AACAGATGAAATTGAACGCGCGAACGTCTTTAAAATGAACGGCAAATGGTACCTGT
TCACTGACTCCCGCGGATCAAAAATGACGATTGACGGCATTTCGTCTAACGATATTT
ACATGCTTGGTTATGTTTCTAATTCTTTAACTGGCCCATACAAGCCGCTGAACAAAA
CTGGCCTTGTGTTAAAAATGGATCTTGATCCTAACGATGTAACCTTTACTTACTCACA
CTTCGCTGTACCTCAAGCGAAAGGAAACAATGTCGTGGTGATTACAAGCTATATGAC
AAACAGAGGATTCTACGCAGACAAACAATCAACGTTTGCGCCAAGCTTCCTGCTGA
ACATCAAAGGCAAGAAACATCTGTTGTCAAAGACAGCATCCTTGAACAAGGACAA
TTAACAGTTAACAAATAAAAACGCAAAAGAAAATGCCGATGGCCGCGGCGTTGTGA
CAATTTACCGAACAACTCCGCGGCC GGGAAGCCGATCTCGGCTTGAACGAATTGTTA
GGTGGCGGTACTTGGGTCGATATCAAAGTGCATCACTTCTC
```

FIG. 29B pShuttle-Fib (SEQ ID NO:1)

GCGCTCTTCCGCTTCCTCGCTCACTGACTCGCTGCGCTCGGTCGTTCGGCTGCGGCGA
GCGGTATCAGCTCACTCAAAGGCGGTAATACGGTTATCCACAGAATCAGGGGATAA
CGCAGGAAAGAACATGTGAGCAAAAGGCCAGCAAAAGGCCAGGAACCGTAAAAAG
GCCGCGTTGCTGGCGTTTTTCCATAGGCTCCGCCCCCTGACGAGCATCACAAAAAT
CGACGCTCAAGTCAGAGGTGGCGAAACCCGACAGGACTATAAAGATACCAGGCGTT
TCCCCCTGGAAGCTCCCTCGTGCGCTCTCCTGTTCCGACCCTGCCGCTTACCGGATAC
CTGTCCGCCTTTCTCCCTTCGGGAAGCGTGGCGCTTTCTCATAGCTCACGCTGTAGGT
ATCTCAGTTCGGTGTAGGTCGTTCGCTCCAAGCTGGGCTGTGTGCACGAACCCCCCG
TTCAGCCCGACCGCTGCGCCTTATCCGGTAACTATCGTCTTGAGTCCAACCCGGTAA
GACACGACTTATCGCCACTGGCAGCAGCCACTGGTAACAGGATTAGCAGAGCGAGG
TATGTAGGCGGTGCTACAGAGTTCTTGAAGTGGTGGCCTAACTACGGCTACACTAGA
AGGACAGTATTTGGTATCTGCGCTCTGCTGAAGCCAGTTACCTTCGGAAAAAGAGTT
GGTAGCTCTTGATCCGGCAAACAAACCACCGCTGGTAGCGGTGGTTTTTTTGTTTGC
AAGCAGCAGATTACGCGCAGAAAAAAAGGATCTCAAGAAGATCCTTTGATCTTTTCT
ACGGGGTCTGACGCTCAGTGGAACGAAAACTCACGTTAAGGGATTTTGGTCATGAG
ATTATCAAAAAGGATCTTCACCTAGATCCTTTTAAATTAAAAATGAAGTTTTAAATC
AATCTAAAGTATATATGAGTAAACTTGGTCTGACAGTTACCAATGCTTAATCAGTGA
GGCACCTATCTCAGCGATCTGTCTATTTCGTTCATCCATAGTTGCCTGACTCCCCGTC
GTGTAGATAACTACGATACGGGAGGGCTTACCATCTGGCCCCAGTGCTGCAATGATA
CCGCGAGACCCACGCTCACCGGCTCCAGATTTATCAGCAATAAACCAGCCAGCCGG
AAGGGCCGAGCGCAGAAGTGGTCCTGCAACTTATCCGCCTCCATCCAGTCTATTAA
TTGTTGCCGGGAAGCTAGAGTAAGTAGTTCGCCAGTTAATAGTTTGCGCAACGTTGT
TGNNNNNNAAAAAGGATCTTCACCTAGATCCTTTTCACGTAGAAAGCCAGTCCGCA
GAAACGGTGCTGACCCCGGATGAATGTCAGCTACTGGGCTATCTGGACAAGGGAAA
ACGCAAGCGCAAAGAGAAAGCAGGTAGCTTGCAGTGGGCTTACATGGCGATAGCTA
GACTGGGCGGTTTTATGGACAGCAAGCGAACCGGAATTGCCAGCTGGGGCGCCCTC
TGGTAAGGTTGGGAAGCCCTGCAAAGTAAACTGGATGGCTTTCTCGCCGCCAAGGA
TCTGATGGCGCAGGGGATCAAGCTCTGATCAAGAGACAGGATGAGGATCGTTTCGC
ATGATTGAACAAGATGGATTGCACGCAGGTTCTCCGGCCGCTTGGGTGGAGAGGCT
ATTCGGCTATGACTGGGCACAACAGACAATCGGCTGCTCTGATGCCGCCGTGTTCCG
GCTGTCAGCGCAGGGGCGCCCGGTTCTTTTTGTCAAGACCGACCTGTCCGGTGCCCT
GAATGAACTGCAAGACGAGGCAGCGCGGCTATCGTGGCTGGCCACGACGGGCGTTC
CTTGCGCAGCTGTGCTCGACGTTGTCACTGAAGCGGGAAGGGACTGGCTGCTATTGG
GCGAAGTGCCGGGGCAGGATCTCCTGTCATCTCACCTTGCTCCTGCCGAGAAAGTAT
CCATCATGGCTGATGCAATGCGGCGGCTGCATACGCTTGATCCGGCTACCTGCCCAT
TCGACCACCAAGCGAAACATCGCATCGAGCGAGCACGTACTCGGATGGAAGCCGGT
CTTGTCGATCAGGATGATCTGGACGAAGAGCATCAGGGGCTCGCGCCAGCCGAACT
GTTCGCCAGGCTCAAGGCGAGCATGCCCGACGGCGAGGATCTCGTCGTGACCCATG
GCGATGCCTGCTTGCCGAATATCATGGTGGAAAATGGCCGCTTTTCTGGATTCATCG
ACTGTGGCCGGCTGGGTGTGGCGGACCGCTATCAGGACATAGCGTTGGCTACCCGTG

FIG. 30A

```
ATATTGCTGAAGAGCTTGGCGGCGAATGGGCTGACCGCTTCCTCGTGCTTTACGGTA
TCGCCGCTCCCGATTCGCAGCGCATCGCCTTCTATCGCCTTCTTGACGAGTTCTTCTG
AATTTTGTTAAAATTTTTGTTAAATCAGCTCATTTTTTAACCAATAGGCCGAAATCGG
CAACATCCCTTATAAATCAAAAGAATAGACCGCGATAGGGTTGAGTGTTGTTCCAGT
TTGGAACAAGAGTCCACTATTAAAGAACGTGGACTCCAACGTCAAAGGGCGAAAAA
CCGTCTATCAGGGCGATGGCCCACTACGT GAACCATCACCCAAATCAAGTTTTTTGC
GGTCGAGGTGCCGTAAAGCTCTAAATCGGAACCCTAAAGGGAGCCCCCGATTTAGA
GCTTGACGGGGAAAGCCGGCGAACGTGGCGAGAAAGGAAGGGAAGAAAGCGAAAG
GAGCGGGCGCTAGGGCGCTGGCAAGTGTAGCGGTCACGCTGCGCGTAACCACCACA
CCCGCGCGCTTAATGCGCCGNNNNNNNNNNNNNNNNNNNNNNNNNNNNNNNNNNN
NNNNNNNNNNNNNNNNNNNNNNNNNNNNNNNNNTTAATTAANNNTCCCTTCCAGCT
CTCTGCCCCTTTTGGATTGAAGCCAATATGATAATGAGGGGGTGGAGTTTGTGACGT
GGCGCGGGGCGTGGGAACGGGGCGGGTGACGTAGTAGTGTGGCGGAAGTGTGATGT
TGCAAGTGTGGCGGAACACATGTAAGCGACGGATGTGGCAAAAGTGACGTTTTTGG
TGTGCGCCGGTGTACACAGGAAGTGACAATTTTCGCGCGGTTTTAGGCGGATGTTGT
AGTAAATTTGGGCGTAACCGAGTAAGATTTGGCCATTTTCGCGGGAAAACTGAATA
AGAGGAAGTGAAATCTGAATAATTTTGTGTTACTCATAGCGCGTAANNNCGCGTTAA
GATACATTGATGAGTTTGGACAAACCACAACTAGAATGCAGTGAAAAAAATGCTTT
ATTTGTGAAATTTGTGATGCTATTGCTTTATTTGTAACCATTATAAGCTGCAATAAAC
AAGTTAACAACAACAATTGCATTCATTTTATGTTTCAGGTTCAGGGGGAGGTGTGGG
AGGTTTTTTAAAGCAAGTAAAACCTCTACAAATGTGGTATGGCTGATTATGATCAGT
TATCTAGATCCGGTGGATCTGAGTCCGGACTTGTACAGCTCGTCCATGCCGAGAGTG
ATCCCGGCGGCGGTCACGAACTCCAGCAGGACCATGTGATCGCGCTTCTCGTTGGGG
TCTTTGCTCAGGGCGGACTGGGTGCTCAGGTAGTGGTTGTCGGGCAGCAGCACGGG
GCCGTCGCCGATGGGGGTGTTCTGCTGGTAGTGGTCGGCGAGCTGCACGCTGCCGTC
CTCGATGTTGTGGCGGATCTTGAAGTTCACCTTGATGCCGTTCTTCTGCTTGTCGGCC
ATGATATAGACGTTGTGGCTGTTGTAGTTGTACTCCAGCTTGTGCCCCAGGATGTTG
CCGTCCTCCTTGAAGTCGATGCCCTTCAGCTCGATGCGGTTCACCAGGGTGTCGCCC
TCGAACTTCACCTCGGCGCGGGTCTTGTAGTTGCCGTCGTCCTTGAAGAAGATGGTG
CGCTCCTGGACGTAGCCTTCGGGCATGGCGGACTTGAAGAAGTCGTGCTGCTTCATG
TGGTCGGGGTAGCGGCTGAAGCACTGCACGCCGTAGGTCAGGGTGGTCACGAGGGT
GGGCCAGGGCACGGGCAGCTTGCCGGTGGTGCAGATGAACTTCAGGGTCAGCTTGC
CGTAGGTGGCATCGCCCTCGCCCTCGCCGGACACGCTGAACTTGTGGCCGTTTACGT
CGCCGTCCAGCTCGACCAGGATGGGCACCACCCCGGTGAACAGCTCCTCGCCCTTGC
TCACCATGGTGGCGACCGGTAGCGCTAGCGGATCTGACGGTTCACTAAACCAGCTCT
GCTTATATAGACCTCCCACCGTACACGCCTACCGCCCATTTGCGTCAATGGGGCGGA
GTTGTTACGACATTTTGGAAAGTCCCGTTGATTTTGGTGCCAAAACAAACTCCCATT
GACGTCAATGGGGTGGAGACTTGGAAATCCCCGTGAGTCAAACCGCTATCCACGCC
CATTGATGTACTGCCAAAACCGCATCACCATGGTAATAGCGATGACTAATACGTAGA
TGTACTGCCAAGTAGGAAAGTCCCATAAGGTCATGTACTGGGCATAATGCCAGGCG
GGCCATTTACCGTCATTGACGTCAATAGGGGGCGTACTTGGCATATGATACACTTGA
TGTACTGCCAAGTGGGCAGTTTACCGTAAATACTCCACCCATTGACGTCAATGGAAA
GTCCCTATTGGCGTTACTATGGGAACATACGTCATTATTGACGTCAATGGGCGGGGG
```

FIG. 30B

```
TCGTTGGGCGGTCAGCCAGGCGGGCCATTTACCGTAAGTTATGTAACGCGGAACTCC
ATATATGGGCTATGAACTAATGACCCCGTAATTGATTACTATTANNNCTAGCAGATC
TGGTACCGTCGACGCGGCCGCGATATCCTCGAGAAGCTTTCTAGAGNNNTAAGGGT
GGGAAAGAATATATAAGGTGGGGGTCTTATGTAGTTTTGTATCTGTTTTGCAGCAGC
CGCCGCCGCCATGAGCACCAACTCGTTTGATGGAAGCATTGTGAGCTCATATTTGAC
AACGCGCATGCCCCCATGGGCCGGGGTGCGTCAGAATGTGATGGGCTCCAGCATTG
ATGGTCGCCCCGTCCTGCCCGCAAACTCTACTACCTTGACCTACGAGACCGTGTCTG
GAACGCCGTTGGAGACTGCAGCCTCCGCCGCCGCTTCAGCCGCTGCAGCCACCGCCC
GCGGGATTGTGACTGACTTTGCTTTCCTGAGCCCGCTTGCAAGCAGTGCAGCTTCCC
GTTCATCCGCCCGCGATGACAAGTTGACGGCTCTTTTGGCACAATTGGATTCTTTGA
CCCGGGAACTTAATGTCGTTTCTCAGCAGCTGTTGGATCTGCGCCAGCAGGTTTCTG
CCCTGAAGGCTTCCTCCCCTCCCAATGCGGTTTAAAACATAAATAAAAAACCAGACT
CTGTTTGGATTTGGATCAAGCAAGTGTCTTGCTGTCTTTATTTAGGGGTTTTGCGCGC
GCGGTAGGCCCGGGACCAGCGGTCTCGGTCGTTGAGGGTCCTGTGTATTTTTTCCAG
GACGTGGTAAAGGTGACTCTGGATGTTCAGATACATGGGCATAAGCCCGTCTCTGGG
GTGGAGGTAGCACCACTGCAGAGCTTCATGCTGCGGGGTGGTGTTGTAGATGATCCA
GTCGTAGCAGGAGCGCTGGGCGTGGTGCCTAAAAATGTCTTTCAGTAGCAAGCTGAT
TGCCAGGGGCAGGCCCTTGGTGTAAGTGTTTACAAAGCGGTTAAGCTGGGATGGGT
GCATACGTGGGGATATGAGATGCATCTTGGACTGTATTTTTAGGTTGGCTATGTTCC
CAGCCATATCCCTCCGGGGATTCATGTTGTGCAGAACCACCAGCACAGTGTATCCGG
TGCACTTGGGAAATTTGTCATGTAGCTTAGAAGGAAATGCGTGGAAGAACTTGGAG
ACGCCCTTGTGACCTCCAAGATTTTCCATGCATTCGTCCATAATGATGGCAATGGGC
CCACGGGCGGCGGCCTGGGCGAAGATATTTCTGGGATCACTAACGTCATAGTTGTGT
TCCAGGATGAGATCGTCATAGGCCATTTTTACAAAGCGCGGGCGGAGGGTGCCAGA
CTGCGGTATAATGGTTCCATCCGGCCCAGGGGCGTAGTTACCCTCACAGATTTGCAT
TTCCCACGCTTTGAGTTCAGATGGGGGGATCATGTCTACCTGCGGGGCGATGAAGAA
AACGGTTTCCGGGGTAGGGGAGATCAGCTGGGAAGAAAGCAGGTTCCTGAGCAGCT
GCGACTTACCGCAGCCGGTGGGCCCGTAAATCACACCTATTACCGGGTGCAACTGGT
AGTTAAGAGAGCTGCAGCTGCCGTCATCCCTGAGCAGGGGGCCACTTCGTTAAGC
ATGTCCCTGACTCGCATGTTTTCCCTGACCAAATCCGCCAGAAGGCGCTCGCCGCCC
AGCGATAGCAGTTCTTGCAAGGAAGCAAAGTTTTTCAACGGTTTGAGACCGTCCGCC
GTAGGCATGCTTTTGAGCGTTTGACCAAGCAGTTCCAGGCGGTCCCACAGCTCGGTC
ACCTGCTCTACGGCATCTCGATCCAGCATATCTCCTCGTTTCGCGGGTTGGGGCGGC
TTTCGCTGTACGGCAGTAGTCGGTGCTCGTCCAGACGGGCCAGGGTCATGTCTTTCC
ACGGGCGCAGGGTCCTCGTCAGCGTAGTCTGGGTCACGGTGAAGGGGTGCGCTCCG
GGCTGCGCGCTGGCCAGGGTGCGCTTGAGGCTGGTCCTGCTGGTGCTGAAGCGCTGC
CGGTCTTCGCCCTGCGCGTCGGCCAGGTAGCATTTGACCATGGTGTCATAGTCCAGC
CCCTCCGCGGCGTGGCCCTTGGCGCGC AGCTTGCCCTTGGAGGAGGCGCCGCACGA
GGGGCAGTGCAGACTTTTGAGGGCGTAGAGCTTGGGCGCGAGAAATACCGATTCCG
GGGAGTAGGCATCCGCGCCGCAGGCCCCGCAGACGGTCTCGCATTCCACGAGCCAG
GTGAGCTCTGGCCGTTCGGGGTCAAAAACCAGGTTTCCCCCATGCTTTTTGATGCGT
TTCTTACCTCTGGTTTCCATGAGCCGGTGTCCACGCTCGGTGACGAAAAGGCTGTCC
GTGTCCCCGTATACAGACTACTTGAGAGGCCTGTCCTCGAGCGGTGTTCCGCGGTCC
```

FIG. 30C

```
TCCTCGTATAGAAACTCGGACCACTCTGAGACAAAGGCTCGCGTCCAGGCCAGCAC
GAAGGAGGCTAAGTGGGAGGGGTAGCGGTCGTTGTCCACTAGGGGTCCACTCGCT
CCAGGGTGTGAAGACACATGTCGCCCTCTTCGGCATCAAGGAAGGTGATTGGTTTGT
AGGTGTAGGCCACGTGACCGGGTGTTCCTGAAGGGGGGCTATAAAAGGGGGTGGGG
GCGCGTTCGTCCTCACTCTCTTCCGCATCGCTGTCTGCGAGGGCCAGCTGTTGGGGT
GAGTACTCCCTCTGAAAAGCGGGCATGACTTCTGCGCTAAGATTGTCAGTTTCCAAA
AACGAGGAGGATTTGATATTCACCTGGCCCGCGGTGATGCCTTTGAGGGTGGCCGCA
TCCATCTGGTCAGAAAAGACAATCTTTTTGTTGTCAAGCTTGGTGGCAAACGACCCG
TAGAGGGCGTTGGACAGCAACTTGGCGATGGAGCGCAGGGTTTGGTTTTTGTCGCGA
TCGGCGCGCTCCTTGGCCGCGATGTTTAGCTGCACGTATTCGCGCGCAACGCACCGC
CATTCGGGAAAGACGGTGGTGCGCTCGTCGGGCACCAGGTGCACGCGCCAACCGCG
GTTGTGCAGGGTGACAAGGTCAACGCTGGTGGCTACCTCTCCGCGTAGGCGCTCGTT
GGTCCAGCAGAGGCGGCCGCCCTTGCGCGAGCAGAATGGCGGTAGGGGGTCTAGCT
GCGTCTCGTCCGGGGGTCTGCGTCCACGGTAAAGACCCCGGGCAGCAGGCGCGCG
TCGAAGTAGTCTATCTTGCATCCTTGCAAGTCTAGCGCCTGCTGCCATGCGCGGGCG
GCAAGCGCGCGCTCGTATGGGTTGAGTGGGGGACCCCATGGCATGGGGTGGGTGAG
CGCGGAGGCGTACATGCCGCAAATGTCGTAAACGTAGAGGGGCTCTCTGAGTATTC
CAAGATATGTAGGGTAGCATCTTCCACCGCGGATGCTGGCGCGCACGTAATCGTATA
GTTCGTGCGAGGGAGCGAGGAGGTCGGGACCGAGGTTGCTACGGGCGGGCTGCTCT
GCTCGGAAGACTATCTGCCTGAAGATGGCATGTGAGTTGGATGATATGGTTGGACGC
TGGAAGACGTTGAAGCTGGCGTCTGTGAGACCTACCGCGTCACGCACGAAGGAGGC
GTAGGAGTCGCGCAGCTTGTTGACCAGCTCGGCGGTGACCTGCACGTCTAGGGCGC
AGTAGTCCAGGGTTTCCTTGATGATGTCATACTTATCCTGTCCCTTTTTTTTCCACAG
CTCGCGGTTGAGGACAAACTCTTCGCGGTCTTTCCAGTACTCTTGGATCGGAAACCC
GTCGGCCTCCGAACGGTAAGAGCCTAGCATGTAGAACTGGTTGACGGCCTGGTAGG
CGCAGCATCCCTTTTCTACGGGTAGCGCGTATGCCTGCGCGGCCTTCCGGAGCGAGG
TGTGGGTGAGCGCAAAGGTGTCCCTGACCATGACTTTGAGGTACTGGTATTTGAAGT
CAGTGTCGTCGCATCCGCCCTGCTCCCAGAGCAAAAAGTCCGTGCGCTTTTGGAAC
GCGGATTTGGCAGGGCGAAGGTGACATCGTTGAAGAGTATCTTTCCCGCGCGAGGC
ATAAAGTTGCGTGTGATGCGGAAGGGTCCCGGCACCTCGGAACGGTTGTTAATTACC
TGGGCGGCGAGCACGATCTCGTCAAAGCCGTTGATGTTGTGGCCCACAATGTAAAGT
TCCAAGAAGCGCGGGATGCCCTTGATGGAAGGCAATTTTTTAAGTTCCTCGTAGGTG
AGCTCTTCAGGGGAGCTGAGCCCGTGCTCTGAAAGGGCCCAGTCTGCAAGATGAGG
GTTGGAAGCGACGAATGAGCTCCACAGGTCACGGGCCATTAGCATTTGCAGGTGGT
CGCGAAAGGTCCTAAACTGGCGACCTATGGCCATTTTTTCTGGGGTGATGCAGTAGA
AGGTAAGCGGGTCTTGTTCCCAGCGGTCCCATCCAAGGTTCGCGGCTAGGTCTCGCG
CGGCAGTCACTAGAGGCTCATCTCCGCCGAACTTCATGACCAGCATGAAGGGCACG
AGCTGCTTCCCAAAGGCCCCCATCCAAGTATAGGTCTCTACATCGTAGGTGACAAAG
AGACGCTCGGTGCGAGGATGCGAGCCGATCGGGAAGAACTGGATCTCCCGCCACCA
ATTGGAGGAGTGGCTATTGATGTGGTGAAAGTAGAAGTCCCTGCGACGGGCCGAAC
ACTCGTGCTGGCTTTTGTAAAAACGTGCGCAGTACTGGCAGCGGTGCACGGGCTGTA
CATCCTGCACGAGGTTGACCTGACGACCGCGCACAAGGAAGCAGAGTGGGAATTTG
AGCCCCTCGCCTGGCGGGTTTGGCTGGTGGTCTTCTACTTCGGCTGCTTGTCCTTGAC
```

FIG. 30D

```
CGTCTGGCTGCTCGAGGGGAGTTACGGTGGATCGGACCACCACGCCGCGCGAGCCC
AAAGTCCAGATGTCCGCGCGGCGGTCGGAGCTTGATGACAACATCGCGCAGATG
GGAGCTGTCCATGGTCTGGAGCTCCCGCGGCGTCAGGTCAGGCGGGAGCTCCTGCA
GGTTTACCTCGCATAGACGGGTCAGGGCGCGGGCTAGATCCAGGTGATACCTAATTT
CCAGGGGCTGGTTGGTGGCGGCGTCGATGGCTTGCAAGAGGCCGCATCCCCGCGGC
GCGACTACGGTACCGCGCGGCGGGCGGTGGGCCGCGGGGGTGTCCTTGGATGATGC
ATCTAAAAGCGGTGACGCGGGCGAGCCCCGGAGGTAGGGGGGCTCCGGACCCGC
CGGGAGAGGGGGCAGGGGCACGTCGGCGCCGCGCGGGCAGGAGCTGGTGCTGC
GCGCGTAGGTTGCTGGCGAACGCGACGACGCGGCGGTTGATCTCCTGAATCTGGCG
CCTCTGCGTGAAGACGACGGGCCCGGTGAGCTTGAGCCTGAAAGAGAGTTCGACAG
AATCAATTTCGGTGTCGTTGACGGCGGCCTGGCGCAAAATCTCCTGCACGTCTCCTG
AGTTGTCTTGATAGGCGATCTCGGCCATGAACTGCTCGATCTCTTCCTCCTGGAGATC
TCCGCGTCCGGCTCGCTCCACGGTGGCGGCGAGGTCGTTGGAAATGCGGGCCATGA
GCTGCGAGAAGGCGTTGAGGCCTCCCTCGTTCCAGACGCGGCTGTAGACCACGCCC
CCTTCGGCATCGCGGGCGCGCATGACCACCTGCGCGAGATTGAGCTCCACGTGCCG
GGCGAAGACGGCGTAGTTTCGCAGGCGCTGAAAGAGGTAGTTGAGGGTGGTGGCGG
TGTGTTCTGCCACGAAGAAGTACATAACCCAGCGTCGCAACGTGGATTCGTTGATAT
CCCCCAAGGCCTCAAGGCGCTCCATGGCCTCGTAGAAGTCCACGGCGAAGTTGAAA
AACTGGGAGTTGCGCGCCGACACGGTTAACTCCTCCTCCAGAAGACGGATGAGCTC
GGCGACAGTGTCGCGCACCTCGCGCTCAAAGGCTACAGGGGCCTCTTCTTCTTCTTC
AATCTCCTCTTCCATAAGGGCCTCCCCTTCTTCTTCTTCTGGCGGCGGTGGGGGAGGG
GGGACACGGCGGCGACGACGGCGCACCGGGAGGCGGTCGACAAAGCGCTCGATCA
TCTCCCCGCGGCGACGGCGCATGGTCTCGGTGACGGCGCGGCCGTTCTCGCGGGGG
CGCAGTTGGAAGACGCCGCCCGTCATGTCCCGGTTATGGGTTGGCGGGGGGCTGCC
ATGCGGCAGGGATACGGCGCTAACGATGCATCTCAACAATTGTTGTGTAGGTACTCC
GCCGCCGAGGGACCTGAGCGAGTCCGCATCGACCGGATCGGAAAACCTCTCGAGAA
AGGCGTCTAACCAGTCACAGTCGCAAGGTAGGCTGAGCACCGTGGCGGGCGGCAGC
GGGCGGCGGTCGGGGTTGTTTCTGGCGGAGGTGCTGCTGATGATGTAATTAAAGTAG
GCGGTCTTGAGACGGCGGATGGTCGACAGAAGCACCATGTCCTTGGGTCCGGCCTG
CTGAATGCGCAGGCGGTCGGCCATGCCCCAGGCTTCGTTTTGACATCGGCGCAGGTC
TTTGTAGTAGTCTTGCATGAGCCTTTCTACCGGCACTTCTTCTTCTCCTTCCTCTTGTC
CTGCATCTCTTGCATCTATCGCTGCGGCGGCGGCGGAGTTTGGCCGTAGGTGGCGCC
CTCTTCCTCCCATGCGTGTGACCCCGAAGCCCCTCATCGGCTGAAGCAGGGCTAGGT
CGGCGACAACGCGCTCGGCTAATATGGCCTGCTGCACCTGCGTGAGGGTAGACTGG
AAGTCATCCATGTCCACAAAGCGGTGGTATGCGCCCGTGTTGATGGTGTAAGTGCAG
TTGGCCATAACGGACCAGTTAACGGTCTGGTGACCCGGCTGCGAGAGCTCGGTGTAC
CTGAGACGCGAGTAAGCCCTCGAGTCAAATACGTAGTCGTTGCAAGTCCGCACCAG
GTACTGGTATCCCACCAAAAAGTGCGGCGGCGGCTGGCGGTAGAGGGGCCAGCGTA
GGGTGGCCGGGGCTCCGGGGCGAGATCTTCCAACATAAGGCGATGATATCCGTAG
ATGTACCTGGACATCCAGGTGATGCCGGCGGCGGTGGTGGAGGCGCGCGGAAAGTC
GCGGACGCGGTTCCAGATGTTGCGCAGCGGCAAAAAGTGCTCCATGGTCGGGACGC
TCTGGCCGGTCAGGCGCGCGCAATCGTTGACGCTCTACCGTGCAAAAGGAGAGCCT
GTAAGCGGGCACTCTTCCGTGGTCTGGTGGATAAATTCGCAAGGGTATCATGGCGGA
```

FIG. 30E

```
CGACCGGGGTTCGAGCCCCGTATCCGGCCGTCCGCCGTGATCCATGCGGTTACCGCC
CGCGTGTCGAACCCAGGTGTGCGACGTCAGACAACGGGGGAGTGCTCCTTTTGGCTT
CCTTCCAGGCGCGGCGGCTGCTGCGCTAGCTTTTTTGGCCACTGGCCGCGCGCAGCG
TAAGCGGTTAGGCTGGAAAGCGAAAGCATTAAGTGGCTCGCTCCCTGTAGCCGGAG
GGTTATTTTCCAAGGGGTTGAGTCGCGGGACCCCCGGTTCGAGTCTCGGACCGGCCGG
ACTGCGGCGAACGGGGGTTTGCCTCCCCGTCATGCAAGACCCCGCTTGCAAATTCCT
CCGGAAACAGGGACGAGCCCCTTTTTTGCTTTTCCCAGATGCATCCGGTGCTGCGGC
AGATGCGCCCCCCTCCTCAGCAGCGGCAAGAGCAAGAGCAGCGGCAGACATGCAGG
GCACCCTCCCCTCCTCCTACCGCGTCAGGAGGGGCGACATCCGCGGTTGACGCGGCA
GCAGATGGTGATTACGAACCCCGCGGCGCCGGGCCCGGCACTACCTGGACTTGGA
GGAGGGCGAGGGCCTGGCGCGGCTAGGAGCGCCCTCTCCTGAGCGGTACCCAAGGG
TGCAGCTGAAGCGTGATACGCGTGAGGCGTACGTGCCGCGGCAGAACCTGTTTCGC
GACCGCGAGGGAGAGGAGCCCGAGGAGATGCGGGATCGAAAGTTCCACGCAGGGC
GCGAGCTGCGGCATGGCCTGAATCGCGAGCGGTTGCTGCGCGAGGAGGACTTTGAG
CCCGACGCGCGAACCGGGATTAGTCCCGCGCGCGCACACGTGGCGGCCGCCGACCT
GGTAACCGCATACGAGCAGACGGTGAACCAGGAGATTAACTTTCAAAAAAGCTTTA
ACAACCACGTGCGTACGCTTGTGGCGCGCGAGGAGGTGGCTATAGGACTGATGCAT
CTGTGGGACTTTGTAAGCGCGCTGGAGCAAAACCCAAATAGCAAGCCGCTCATGGC
GCAGCTGTTCCTTATAGTGCAGCACAGCAGGGACAACGAGGCATTCAGGGATGCGC
TGCTAAACATAGTAGAGCCCGAGGGCCGCTGGCTGCTCGATTTGATAAACATCCTGC
AGAGCATAGTGGTGCAGGAGCGCAGCTTGAGCCTGGCTGACAAGGTGGCCGCCATC
AACTATTCCATGCTTAGCCTGGGCAAGTTTTACGCCCGCAAGATATACCATACCCCT
TACGTTCCCATAGACAAGGAGGTAAAGATCGAGGGGTTCTACATGCGCATGGCGCT
GAAGGTGCTTACCTTGAGCGACGACCTGGGCGTTTATCGCAACGAGCGCATCCACA
AGGCCGTGAGCGTGAGCCGGCGGCGCGAGCTCAGCGACCGCGAGCTGATGCACAGC
CTGCAAAGGGCCCTGGCTGGCACGGGCAGCGGCGATAGAGAGGCCGAGTCCTACTT
TGACGCGGGCGCTGACCTGCGCTGGGCCCCAAGCCGACGCGCCCTGGAGGCAGCTG
GGGCCGGACCTGGGCTGGCGGTGGCACCCGCGCGCGCTGGCAACGTCGGCGGCGTG
GAGGAATATGACGAGGACGATGAGTACGAGCCAGAGGACGGCGAGTACTAAGCGG
TGATGTTTCTGATCAGATGATGCAAGACGCAACGGACCCGGCGGTGCGGGCGGCGC
TGCAGAGCCAGCCGTCCGGCCTTAACTCCACGGACGACTGGCGCCAGGTCATGGAC
CGCATCATGTCGCTGACTGCGCGCAATCCTGACGCGTTCCGGCAGCAGCCGCAGGCC
AACCGGCTCTCCGCAATTCTGGAAGCGGTGGTCCCGGCGCGCGCAAACCCCACGCA
CGAGAAGGTGCTGGCGATCGTAAACGCGCTGGCCGAAAACAGGGCCATCCGGCCCG
ACGAGGCCGGCCTGGTCTACGACGCGCTGCTTCAGCGCGTGGCTCGTTACAACAGC
GGCAACGTGCAGACCAACCTGGACCGGCTGGTGGGGGATGTGCGCGAGGCCGTGGC
GCAGCGTGAGCGCGCGCAGCAGCAGGGCAACCTGGGCTCCATGGTTGCACTAAACG
CCTTCCTGAGTACACAGCCCGCCAACGTGCCGCGGGGACAGGAGGACTACACCAAC
TTTGTGAGCGCACTGCGGCTAATGGTGACTGAGACACCGCAAAGTGAGGTGTACCA
GTCTGGGCCAGACTATTTTTTCCAGACCAGTAGACAAGGCCTGCAGACCGTAAACCT
GAGCCAGGCTTTCAAAAACTTGCAGGGGCTGTGGGGGGTGCGGGCTCCCACAGGCG
ACCGCGCGACCGTGTCTAGCTTGCTGACGCCCAACTCGCGCCTGTTGCTGCTGCTAA
TAGCGCCCTTCACGGACAGTGGCAGCGTGTCCCGGGACACATACCTAGGTCACTTGC
```

FIG. 30F

```
TGACACTGTACCGCGAGGCCATAGGTCAGGCGCATGTGGACGAGCATACTTTCCAG
GAGATTACAAGTGTCAGCCGCGCGCTGGGGCAGGAGGACACGGGCAGCCTGGAGG
CAACCCTAAACTACCTGCTGACCAACCGGCGGCAGAAGATCCCCTCGTTGCACAGTT
TAAACAGCGAGGAGGAGCGCATTTTGCGCTACGTGCAGCAGAGCGTGAGCCTTAAC
CTGATGCGCGACGGGGTAACGCCCAGCGTGGCGCTGGACATGACCGCGCGCAACAT
GGAACCGGGCATGTATGCCTCAAACCGGCCGTTTATCAACCGCCTAATGGACTACTT
GCATCGCGCGGCCGCCGTGAACCCCGAGTATTTCACCAATGCCATCTTGAACCCGCA
CTGGCTACCGCCCCTGGTTTCTACACCGGGGGATTCGAGGTGCCCGAGGGTAACGA
TGGATTCCTCTGGGACGACATAGACGACAGCGTGTTTTCCCCGCAACCGCAGACCCT
GCTAGAGTTGCAACAGCGCGAGCAGGCAGAGGCGGCGCTGCGAAAGGAAAGCTTC
CGCAGGCCAAGCAGCTTGTCCGATCTAGGCGCTGCGGCCCCGCGGTCAGATGCTAG
TAGCCCATTTCCAAGCTTGATAGGGTCTCTTACCAGCACTCGCACCACCCGCCCGCG
CCTGCTGGGCGAGGAGGAGTACCTAAACAACTCGCTGCTGCAGCCGCAGCGCGAAA
AAAACCTGCCTCCGGCATTTCCCAACAACGGGATAGAGAGCCTAGTGGACAAGATG
AGTAGATGGAAGACGTACGCGCAGGAGCACAGGGACGTGCCAGGCCCGCGCCCGC
CCACCCGTCGTCAAAGGCACGACCGTCAGCGGGGTCTGGTGTGGGAGGACGATGAC
TCGGCAGACGACAGCAGCGTCCTGGATTTGGGAGGGAGTGGCAACCCGTTTGCGCA
CCTTCGCCCCAGGCTGGGGAGAATGTTTTAAAAAAAAAAAAGCATGATGCAAAATA
AAAAACTCACCAAGGCCATGGCACCGAGCGTTGGTTTTCTTGTATTCCCCTTAGTAT
GCGGCGCGCGGCGATGTATGAGGAAGGTCCTCCTCCCTCCTACGAGAGTGTGGTGA
GCGCGGCGCCAGTGGCGGCGGCGCTGGGTTCTCCCTTCGATGCTCCCCTGGACCCGC
CGTTTGTGCCTCCGCGGTACCTGCGGCCTACCGGGGGGAGAAACAGCATCCGTTACT
CTGAGTTGGCACCCCTATTCGACACCACCCGTGTGTACCTGGTGGACAACAAGTCAA
CGGATGTGGCATCCCTGAACTACCAGAACGACCACAGCAACTTTCTGACCACGGTC
ATTCAAAACAATGACTACAGCCCGGGGGAGGCAAGCACACAGACCATCAATCTTGA
CGACCGGTCGCACTGGGGCGGCGACCTGAAAACCATCCTGCATACCAACATGCCAA
ATGTGAACGAGTTCATGTTTACCAATAAGTTTAAGGCGCGGGTGATGGTGTCGCGCT
TGCCTACTAAGGACAATCAGGTGGAGCTGAAATACGAGTGGGTGGAGTTCACGCTG
CCCGAGGGCAACTACTCCGAGACCATGACCATAGACCTTATGAACAACGCGATCGT
GGAGCACTACTTGAAAGTGGGCAGACAGAACGGGGTTCTGGAAAGCGACATCGGGG
TAAAGTTTGACACCCGCAACTTCAGACTGGGGTTTGACCCCGTCACTGGTCTTGTCA
TGCCTGGGGTATATACAAACGAAGCCTTCCATCCAGACATCATTTTGCTGCCAGGAT
GCGGGGTGGACTTCACCCACAGCCGCCTGAGCAACTTGTTGGGCATCCGCAAGCGG
CAACCCTTCCAGGAGGGCTTTAGGATCACCTACGATGATCTGGAGGGTGGTAACATT
CCCGCACTGTTGGATGTGGACGCCTACCAGGCGAGCTTGAAAGATGACACCGAACA
GGGCGGGGGTGGCGCAGGCGGCAGCAACAGCAGTGGCAGCGGCGCGGAAGAGAAC
TCCAACGCGGCAGCCGCGGCAATGCAGCCGGTGGAGGACATGAACGATCATGCCAT
TCGCGGCGACACCTTTGCCACACGGGCTGAGGAGAAGCGCGCTGAGGCCGAAGCAG
CGGCCGAAGCTGCCGCCCCGCTGCGCAACCCGAGGTCGAGAAGCCTCAGAAGAAA
CCGGTGATCAAACCCCTGACAGAGGACAGCAAGAAACGCAGTTACAACCTAATAAG
CAATGACAGCACCTTCACCCAGTACCGCAGCTGGTACCTTGCATACAACTACGGCGA
CCCTCAGACCGGAATCCGCTCATGGACCCTGCTTTGCACTCCTGACGTAACCTGCGG
CTCGGAGCAGGTCTACTGGTCGTTGCCAGACATGATGCAAGACCCCGTGACCTTCCG
CTCCACGCGCCAGATCAGCAACTTTCCGGTGGTGGGCGCCGAGCTGTTGCCCGTGCA
```

FIG. 30G

```
CTCCAAGAGCTTCTACAACGACCAGGCCGTCTACTCCCAACTCATCCGCCAGTTTAC
CTCTCTGACCCACGTGTTCAATCGCTTTCCCGAGAACCAGATTTTGGCGCGCCCGCC
AGCCCCCACCATCACCACCGTCAGTGAAAACGTTCCTGCTCTCACAGATCACGGGAC
GCTACCGCTGCGCAACAGCATCGGAGGAGTCCAGCGAGTGACCATTACTGACGCCA
GACGCCGCACCTGCCCCTACGTTTACAAGGCCCTGGGCATAGTCTCGCCGCGCGTCC
TATCGAGCCGCACTTTTTGAGCAAGCATGTCCATCCTTATATCGCCCAGCAATAACA
CAGGCTGGGGCCTGCGCTTCCCAAGCAAGATGTTTGGCGGGGCCAAGAAGCGCTCC
GACCAACACCCAGTGCGCGTGCGCGGGCACTACCGCGCGCCCTGGGGCGCGCACAA
ACGCGGCCGCACTGGGCGCACCACCGTCGATGACGCCATCGACGCGGTGGTGGAGG
AGGCGCGCAACTACACGCCCACGCCGCCACCAGTGTCCACAGTGGACGCGGCCATT
CAGACCGTGGTGCGCGGAGCCCGGCGCTATGCTAAAATGAAGAGACGGCGGAGGC
GCGTAGCACGTCGCCACCGCCGCCGACCCGGCACTGCCGCCCAACGCGCGGCGGCG
GCCCTGCTTAACCGCGCACGTCGCACCGGCCGACGGGCGGCCATGCGGGCCGCTCG
AAGGCTGGCCGCGGGTATTGTCACTGTGCCCCCAGGTCCAGGCGACGAGCGGCCG
CCGCAGCAGCCGCGGCCATTAGTGCTATGACTCAGGGTCGCAGGGGCAACGTGTAT
TGGGTGCGCGACTCGGTTAGCGGCCTGCGCGTGCCCGTGCGCACCCGCCCCCCGCGC
AACTAGATTGCAAGAAAAAACTACTTAGACTCGTACTGTTGTATGTATCCAGCGGCG
GCGGCGCGCAACGAAGCTATGTCCAAGCGCAAAATCAAAGAAGAGATGCTCCAGGT
CATCGCGCCGGAGATCTATGGCCCCCCGAAGAAGGAAGAGCAGGATTACAAGCCCC
GAAAGCTAAAGCGGGTCAAAAAGAAAAAGAAAGATGATGATGATGAACTTGACGA
CGAGGTGGAACTGCTGCACGCTACCGCGCCCAGGCGACGGGTACAGTGGAAAGGTC
GACGCGTAAAACGTGTTTTGCGACCCGGCACCACCGTAGTCTTTACGCCCGGTGAGC
GCTCCACCCGCACCTACAAGCGCGTGTATGATGAGGTGTACGGCGACGAGGACCTG
CTTGAGCAGGCCAACGAGCGCCTCGGGGAGTTTGCCTACGGAAAGCGGCATAAGGA
CATGCTGGCGTTGCCGCTGGACGAGGGCAACCCAACACCTAGCCTAAAGCCCGTAA
CACTGCAGCAGGTGCTGCCCGCGCTTGCACCGTCCGAAGAAAAGCGCGGCCTAAAG
CGCGAGTCTGGTGACTTGGCACCCACCGTGCAGCTGATGGTACCCAAGCGCCAGCG
ACTGGAAGATGTCTTGGAAAAAATGACCGTGGAACCTGGGCTGGAGCCCGAGGTCC
GCGTGCGGCCAATCAAGCAGGTGGCGCCGGGACTGGGCGTGCAGACCGTGGACGTT
CAGATACCCACTACCAGTAGCACCAGTATTGCCACCGCCACAGAGGGCATGGAGAC
ACAAACGTCCCCGGTTGCCTCAGCGGTGGCGGATGCCGCGGTGCAGGCGGTCGCTG
CGGCCGCGTCCAAGACCTCTACGGAGGTGCAAACGGACCCGTGGATGTTTCGCGTTT
CAGCCCCCCGGCGCCCGCGCGGTTCGAGGAAGTACGGCGCCGCCAGCGCGCTACTG
CCCGAATATGCCCTACATCCTTCCATTGCGCCTACCCCGGCTATCGTGGCTACACCT
ACCGCCCCAGAAGACGAGCAACTACCCGACGCCGAACCACCACTGGAACCCGCCGC
CGCCGTCGCCGTCGCCAGCCCGTGCTGGCCCCGATTTCCGTGCGCAGGGTGGCTCGC
GAAGGAGGCAGGACCCTGGTGCTGCCAACAGCGCGCTACCACCCCAGCATCGTTTA
AAAGCCGGTCTTTGTGGTTCTTGCAGATATGGCCCTCACCTGCCGCCTCCGTTTCCCG
GTGCCGGGATTCCGAGGAAGAATGCACCGTAGGAGGGGCATGGCCGGCCACGGCCT
GACGGGCGGCATGCGTCGTGCGCACCACCGGCGGCGGCGCGCGTCGCACCGTCGCA
TGCGCGGCGGTATCCTGCCCCTCCTTATTCCACTGATCGCCGCGGCGATTGGCGCCG
TGCCCGGAATTGCATCCGTGGCCTTGCAGGCGCAGAGACACTGATTAAAAACAAGT
TGCATGTGGAAAAATCAAAATAAAAAGTCTGGACTCTCACGCTCGCTTGGTCCTGTA
```

FIG. 30H

```
ACTATTTTGTAGAATGGAAGACATCAACTTTGCGTCTCTGGCCCCGCGACACGGCTC
GCGCCCGTTCATGGGAAACTGGCAAGATATCGGCACCAGCAATATGAGCGGTGGCG
CCTTCAGCTGGGGCTCGCTGTGGAGCGGCATTAAAAATTTCGGTTCCACCGTTAAGA
ACTATGGCAGCAAGGCCTGGAACAGCAGCACAGGCCAGATGCTGAGGGATAAGTTG
AAAGAGCAAAATTTCCAACAAAAGGTGGTAGATGGCCTGGCCTCTGGCATTAGCGG
GGTGGTGGACCTGGCCAACCAGGCAGTGCAAAATAAGATTAACAGTAAGCTTGATC
CCCGCCCTCCCGTAGAGGAGCCTCCACCGGCCGTGGAGACAGTGTCTCCAGAGGGG
CGTGGCGAAAAGCGTCCGCGCCCCGACAGGGAAGAAACTCTGGTGACGCAAATAGA
CGAGCCTCCCTCGTACGAGGAGGCACTAAAGCAAGGCCTGCCCACCACCCGTCCCA
TCGCGCCCATGGCTACCGGAGTGCTGGGCCAGCACACACCCGTAACGCTGGACCTG
CCTCCCCCCGCCGACACCCAGCAGAAACCTGTGCTGCCAGGCCCGACCGCCGTTGTT
GTAACCCGTCCTAGCCGCGCGTCCCTGCGCCGCGCCGCCAGCGGTCCGCGATCGTTG
CGGCCCGTAGCCAGTGGCAACTGGCAAAGCACACTGAACAGCATCGTGGGTCTGGG
GGTGCAATCCCTGAAGCGCCGACGATGCTTCTGAATAGCTAACGTGTCGTATGTGTG
TCATGTATGCGTCCATGTCGCCGCCAGAGGAGCTGCTGAGCCGCCGCGCGCCCGCTT
TCCAAGATGGCTACCCCTTCGATGATGCCGCAGTGGTCTTACATGCACATCTCGGGC
CAGGACGCCTCGGAGTACCTGAGCCCCGGGCTGGTGCAGTTTGCCCGCGCCACCGA
GACGTACTTCAGCCTGAATAACAAGTTTAGAAACCCCACGGTGGCGCCTACGCACG
ACGTGACCACAGACCGGTCCCAGCGTTTGACGCTGCGGTTCATCCCTGTGGACCGTG
AGGATACTGCGTACTCGTACAAGGCGCGGTTCACCCTAGCTGTGGGTGATAACCGTG
TGCTGGACATGGCTTCCACGTACTTTGACATCCGCGGCGTGCTGGACAGGGGCCCTA
CTTTTAAGCCCTACTCTGGCACTGCCTACAACGCCCTGGCTCCCAAGGGTGCCCCAA
ATCCTTGCGAATGGGATGAAGCTGCTACTGCTCTTGAAATAAACCTAGAAGAAGAG
GACGATGACAACGAAGACGAAGTAGACGAGCAAGCTGAGCAGCAAAAAACTCACG
TATTTGGGCAGGCGCCTTATTCTGGTATAAATATTACAAAGGAGGGTATTCAAATAG
GTGTCGAAGGTCAAACACCTAAATATGCCGATAAAACATTTCAACCTGAACCTCAA
ATAGGAGAATCTCAGTGGTACGAAACTGAAATTAATCATGCAGCTGGGAGAGTCCT
TAAAAAGACTACCCCAATGAAACCATGTTACGGTTCATATGCAAAACCCACAAATG
AAAATGGAGGGCAAGGCATTCTTGTAAAGCAACAAAATGGAAAGCTAGAAAGTCA
AGTGGAAATGCAATTTTTCTCAACTACTGAGGCGACCGCAGGCAATGGTGATAACTT
GACTCCTAAAGTGGTATTGTACAGTGAAGATGTAGATATAGAAACCCCAGACACTC
ATATTTCTTACATGCCCACTATTAAGGAAGGTAACTCACGAGAACTAATGGGCCAAC
AATCTATGCCCAACAGGCCTAATTACATTGCTTTTAGGGACAATTTTATTGGTCTAAT
GTATTACAACAGCACGGGTAATATGGGTGTTCTGGCGGGCCAAGCATCGCAGTTGA
ATGCTGTTGTAGATTTGCAAGACAGAAACACAGAGCTTTCATACCAGCTTTTGCTTG
ATTCCATTGGTGATAGAACCAGGTACTTTTCTATGTGGAATCAGGCTGTTGACAGCT
ATGATCCAGATGTTAGAATTATTGAAAATCATGGAACTGAAGATGAACTTCCAAATT
ACTGCTTTCCACTGGGAGGTGTGATTAATACAGAGACTCTTACCAAGGTAAAACCTA
AAACAGGTCAGGAAAATGGATGGGAAAAGATGCTACAGAATTTTCAGATAAAAAT
GAAATAAGAGTTGGAAATAATTTTGCCATGGAAATCAATCTAAATGCCAACCTGTG
GAGAAATTTCCTGTACTCCAACATAGCGCTGTATTTGCCCGACAAGCTAAAGTACAG
TCCTTCCAACGTAAAAATTTCTGATAACCCAAACACCTACGACTACATGAACAAGCG
AGTGGTGGCTCCCGGGTTAGTGGACTGCTACATTAACCTTGGAGCACGCTGGTCCCT
TGACTATATGGACAACGTCAACCCATTTAACCACCACCGCAATGCTGGCCTGCGCTA
```

FIG. 301

```
CCGCTCAATGTTGCTGGGCAATGGTCGCTATGTGCCCTTCCACATCCAGGTGCCTCA
GAAGTTCTTTGCCATTAAAAACCTCCTTCTCCTGCCGGGCTCATACACCTACGAGTG
GAACTTCAGGAAGGATGTTAACATGGTTCTGCAGAGCTCCCTAGGAAATGACCTAA
GGGTTGACGGAGCCAGCATTAAGTTTGATAGCATTTGCCTTTACGCCACCTTCTTCCC
CATGGCCCACAACACCGCCTCCACGCTTGAGGCCATGCTTAGAAACGACACCAACG
ACCAGTCCTTTAACGACTATCTCTCCGCCGCCAACATGCTCTACCCTATACCCGCCA
ACGCTACCAACGTGCCCATATCCATCCCCTCCCGCAACTGGGCGGCTTTCCGCGGCT
GGGCCTTCACGCGCCTTAAGACTAAGGAAACCCCATCACTGGGCTCGGGCTACGAC
CCTTATTACACCTACTCTGGCTCTATACCCTACCTAGATGGAACCTTTTACCTCAACC
ACACCTTTAAGAAGGTGGCCATTACCTTTGACTCTTCTGTCAGCTGGCCTGGCAATG
ACCGCCTGCTTACCCCCAACGAGTTTGAAATTAAGCGCTCAGTTGACGGGGAGGGTT
ACAACGTTGCCCAGTGTAACATGACCAAAGACTGGTTCCTGGTACAAATGCTAGCTA
ACTACAACATTGGCTACCAGGGCTTCTATATCCCAGAGAGCTACAAGGACCGCATGT
ACTCCTTCTTTAGAAACTTCCAGCCCATGAGCCGTCAGGTGGTGGATGATACTAAAT
ACAAGGACTACCAACAGGTGGGCATCCTACACCAACACAACAACTCTGGATTTGTT
GGCTACCTTGCCCCCACCATGCGCGAAGGACAGGCCTACCCTGCTAACTTCCCCTAT
CCGCTTATAGGCAAGACCGCAGTTGACAGCATTACCCAGAAAAAGTTTCTTTGCGAT
CGCACCCTTTGGCGCATCCCATTCTCCAGTAACTTTATGTCCATGGGCGCACTCACA
GACCTGGGCCAAAACCTTCTCTACGCCAACTCCGCCCACGCGCTAGACATGACTTTT
GAGGTGGATCCCATGGACGAGCCCACCCTTCTTTATGTTTTGTTTGAAGTCTTTGACG
TGGTCCGTGTGCACCGGCCGCACCGCGGCGTCATCGAAACCGTGTACCTGCGCACGC
CCTTCTCGGCCGGCAACGCCACAACATAAAGAAGCAAGCAACATCAACAACAGCTG
CCGCCATGGGCTCCAGTGAGCAGGAACTGAAAGCCATTGTCAAAGATCTTGGTTGTG
GGCCATATTTTTTGGGCACCTATGACAAGCGCTTTCCAGGCTTTGTTTCTCCACACAA
GCTCGCCTGCGCCATAGTCAATACGGCCGGTCGCGAGACTGGGGGCGTACACTGGA
TGGCCTTTGCCTGGAACCCGCACTCAAAAACATGCTACCTCTTTGAGCCCTTTGGCTT
TTCTGACCAGCGACTCAAGCAGGTTTACCAGTTTGAGTACGAGTCACTCCTGCGCCG
TAGCGCCATTGCTTCTTCCCCCGACCGCTGTATAACGCTGGAAAAGTCCACCCAAAG
CGTACAGGGGCCCAACTCGGCCGCCTGTGGACTATTCTGCTGCATGTTTCTCCACGC
CTTTGCCAACTGGCCCCAAACTCCCATGGATCACAACCCCACCATGAACCTTATTAC
CGGGGTACCCAACTCCATGCTCAACAGTCCCCAGGTACAGCCCACCCTGCGTCGCAA
CCAGGAACAGCTCTACAGCTTCCTGGAGCGCCACTCGCCCTACTTCCGCAGCCACAG
TGCGCAGATTAGGAGCGCCACTTCTTTTTGTCACTTGAAAAACATGTAAAAATAATG
TACTAGAGACACTTTCAATAAAGGCAAATGCTTTTATTTGTACACTCTCGGGTGATT
ATTTACCCCCACCCTTGCCGTCTGCGCCGTTTAAAAATCAAAGGGGTTCTGCCGCGC
ATCGCTATGCGCCACTGGCAGGGACACGTTGCGATACTGGTGTTTAGTGCTCCACTT
AAACTCAGGCACAACCATCCGCGGCAGCTCGGTGAAGTTTTCACTCCACAGGCTGC
GCACCATCACCAACGCGTTTAGCAGGTCGGGCGCCGATATCTTGAAGTCGCAGTTGG
GGCCTCCGCCCTGCGCGCGCGAGTTGCGATACACAGGGTTGCAGCACTGGAACACT
ATCAGCGCCGGGTGGTGCACGCTGGCCAGCACGCTCTTGTCGGAGATCAGATCCGC
GTCCAGGTCCTCCGCGTTGCTCAGGGCGAACGGAGTCAACTTTGGTAGCTGCCTTCC
CAAAAAGGGCGCGTGCCCAGGCTTTGAGTTGCACTCGCACCGTAGTGGCATCAAAA
GGTGACCGTGCCCGGTCTGGGCGTTAGGATACAGCGCCTGCATAAAAGCCTTGATCT
GCTTAAAAGCCACCTGAGCCTTTGCGCCTTCAGAGAAGAACATGCCGCAAGACTTG
```

FIG. 30J

```
CCGGAAAACTGATTGGCCGGACAGGCCGCGTCGTGCACGCAGCACCTTGCGTCGGT
GTTGGAGATCTGCACCACATTTCGGCCCCACCGGTTCTTCACGATCTTGGCCTTGCTA
GACTGCTCCTTCAGCGCGCGCTGCCCGTTTTCGCTCGTCACATCCATTTCAATCACGT
GCTCCTTATTTATCATAATGCTTCCGTGTAGACACTTAAGCTCGCCTTCGATCTCAGC
GCAGCGGTGCAGCCACAACGCGCAGCCCGTGGGCTCGTGATGCTTGTAGGTCACCT
CTGCAAACGACTGCAGGTACGCCTGCAGGAATCGCCCCATCATCGTCACAAAGGTC
TTGTTGCTGGTGAAGGTCAGCTGCAACCCGCGGTGCTCCTCGTTCAGCCAGGTCTTG
CATACGGCCGCCAGAGCTTCCACTTGGTCAGGCAGTAGTTTGAAGTTCGCCTTTAGA
TCGTTATCCACGTGGTACTTGTCCATCAGCGCGCGCGCAGCCTCCATGCCCTTCTCCC
ACGCAGACACGATCGGCACACTCAGCGGGTTCATCACCGTAATTTCACTTTCCGCTT
CGCTGGGCTCTTCCTCTTCCTCTTGCGTCCGCATACCACGCGCCACTGGGTCGTCTTC
ATTCAGCCGCCGCACTGTGCGCTTACCTCCTTTGCCATGCTTGATTAGCACCGGTGG
GTTGCTGAAACCCACCATTTGTAGCGCCACATCTTCTCTTTCTTCCTCGCTGTCCACG
ATTACCTCTGGTGATGGCGGGCGCTCGGGCTTGGGAGAAGGGCGCTTCTTTTTCTTC
TTGGGCGCAATGGCCAAATCCGCCGCCGAGGTCGATGGCCGCGGGCTGGGTGTGCG
CGGCACCAGCGCGTCTTGTGATGAGTCTTCCTCGTCCTCGGACTCGATACGCCGCCT
CATCCGCTTTTTTGGGGGCGCCCGGGGAGGCGGCGGCGACGGGGACGGGGACGACA
CGTCCTCCATGGTTGGGGACGTCGCGCCGCACCGCGTCCGCGCTCGGGGGTGGTTT
CGCGCTGCTCCTCTTCCCGACTGGCCATTTCCTTCTCCTATAGGCAGAAAAAGATCA
TGGAGTCAGTCGAGAAGAAGGACAGCCTAACCGCCCCCTCTGAGTTCGCCACCACC
GCCTCCACCGATGCCGCCAACGCGCCTACCACCTTCCCCGTCGAGGCACCCCGCTT
GAGGAGGAGGAAGTGATTATCGAGCAGGACCCAGGTTTTGTAAGCGAAGACGACGA
GGACCGCTCAGTACCAACAGAGGATAAAAAGCAAGACCAGGACAACGCAGAGGCA
AACGAGGAACAAGTCGGGCGGGGGGACGAAAGGCATGGCGACTACCTAGATGTGG
GAGACGACGTGCTGTTGAAGCATCTGCAGCGCCAGTGCGCCATTATCTGCGACGCGT
TGCAAGAGCGCAGCGATGTGCCCCTCGCCATAGCGGATGTCAGCCTTGCCTACGAA
CGCCACCTATTCTCACCGCGCGTACCCCCAAACGCCAAGAAAACGGCACATGCGA
GCCCAACCCGCGCCTCAACTTCTACCCCGTATTTGCCGTGCCAGAGGTGCTTGCCAC
CTATCACATCTTTTTCCAAAACTGCAAGATACCCCTATCCTGCCGTGCCAACCGCAG
CCGAGCGGACAAGCAGCTGGCCTTGCGGCAGGGCGCTGTCATACCTGATATCGCCT
CGCTCAACGAAGTGCCAAAAATCTTTGAGGGTCTTGGACGCGACGAGAAGCGCGCG
GCAAACGCTCTGCAACAGGAAAACAGCGAAAATGAAAGTCACTCTGGAGTGTTGGT
GGAACTCGAGGGTGACAACGCGCGCCTAGCCGTACTAAAACGCAGCATCGAGGTCA
CCCACTTTGCCTACCCGGCACTTAACCTACCCCCAAGGTCATGAGCACAGTCATGA
GTGAGCTGATCGTGCGCCGTGCGCAGCCCCTGGAGAGGGATGCAAATTTGCAAGAA
CAAACAGAGGAGGGCCTACCCGCAGTTGGCGACGAGCAGCTAGCGCGCTGGCTTCA
AACGCGCGAGCCTGCCGACTTGGAGGAGCGACGCAAACTAATGATGGCCGCAGTGC
TCGTTACCGTGGAGCTTGAGTGCATGCAGCGGTTCTTTGCTGACCCGGAGATGCAGC
GCAAGCTAGAGGAAACATTGCACTACACCTTTCGACAGGGCTACGTACGCCAGGCC
TGCAAGATCTCCAACGTGGAGCTCTGCAACCTGGTCTCCTACCTTGGAATTTTGCAC
GAAAACCGCCTTGGGCAAAACGTGCTTCATTCCACGCTCAAGGGCGAGGCGCGCCG
CGACTACGTCCGCGACTGCGTTTACTTATTTCTATGCTACACCTGGCAGACGGCCAT
GGGCGTTTGGCAGCAGTGCTTGGAGGAGTGCAACCTCAAGGAGCTGCAGAAACTGC
TAAAGCAAAACTTGAAGGACCTATGGACGGCCTTCAACGAGCGCTCCGTGGCCGCG
```

FIG. 30K

```
CACCTGGCGGACATCATTTTCCCCGAACGCCTGCTTAAAACCCTGCAACAGGGTCTG
CCAGACTTCACCAGTCAAAGCATGTTGCAGAACTTTAGGAACTTTATCCTAGAGCGC
TCAGGAATCTTGCCCGCCACCTGCTGTGCACTTCCTAGCGACTTTGTGCCCATTAAGT
ACCGCGAATGCCCTCCGCCGCTTTGGGGCCACTGCTACCTTCTGCAGCTAGCCAACT
ACCTTGCCTACCACTCTGACATAATGGAAGACGTGAGCGGTGACGGTCTACTGGAGT
GTCACTGTCGCTGCAACCTATGCACCCCGCACCGCTCCCTGGTTTGCAATTCGCAGC
TGCTTAACGAAAGTCAAATTATCGGTACCTTTGAGCTGCAGGGTCCCTCGCCTGACG
AAAAGTCCGCGGCTCCGGGGTTGAAACTCACTCCGGGGCTGTGGACGTCGGCTTAC
CTTCGCAAATTTGTACCTGAGGACTACCACGCCCACGAGATTAGGTTCTACGAAGAC
CAATCCCGCCCGCCAAATGCGGAGCTTACCGCCTGCGTCATTACCCAGGGCCACATT
CTTGGCCAATTGCAAGCCATCAACAAAGCCCGCCAAGAGTTTCTGCTACGAAAGGG
ACGGGGGGTTTACTTGGACCCCCAGTCCGGCGAGGAGCTCAACCCAATCCCCCCGC
CGCCGCAGCCCTATCAGCAGCAGCCGCGGGCCCTTGCTTCCCAGGATGGCACCCAA
AAAGAAGCTGCAGCTGCCGCCGCCACCCACGGACGAGGAGGAATACTGGGACAGTC
AGGCAGAGGAGGTTTTGGACGAGGAGGAGGAGGACATGATGGAAGACTGGGAGAG
CCTAGACGAGGAAGCTTCCGAGGTCGAAGAGGTGTCAGACGAAACACCGTCACCCT
CGGTCGCATTCCCCTCGCCGGCGCCCCAGAAATCGGCAACCGGTTCCAGCATGGCTA
CAACCTCCGCTCCTCAGGCGCCGCCGGCACTGCCCGTTCGCCGACCCAACCGTAGAT
GGGACACCACTGGAACCAGGGCCGGTAAGTCCAAGCAGCCGCCGCCGTTAGCCCAA
GAGCAACAACAGCGCCAAGGCTACCGCTCATGGCGCGGGCACAAGAACGCCATAGT
TGCTTGCTTGCAAGACTGTGGGGGCAACATCTCCTTCGCCCGCCGCTTTCTTCTCTAC
CATCACGGCGTGGCCTTCCCCCGTAACATCCTGCATTACTACCGTCATCTCTACAGC
CCATACTGCACCGGCGGCAGCGGCAGCGGCAGCAACAGCAGCGGCCACACAGAAG
CAAAGGCGACCGGATAGCAAGACTCTGACAAAGCCCAAGAAATCCACAGCGGCGG
CAGCAGCAGGAGGAGGAGCGCTGCGTCTGGCGCCCAACGAACCCGTATCGACCCGC
GAGCTTAGAAACAGGATTTTTCCCACTCTGTATGCTATATTTCAACAGAGCAGGGGC
CAAGAACAAGAGCTGAAAATAAAAAACAGGTCTCTGCGATCCCTCACCCGCAGCTG
CCTGTATCACAAAAGCGAAGATCAGCTTCGGCGCACGCTGGAAGACGCGGAGGCTC
TCTTCAGTAAATACTGCGCGCTGACTCTTAAGGACTAGTTTCGCGCCCTTTCTCAAAT
TTAAGCGCGAAAACTACGTCATCTCCAGCGGCCACACCCGGCGCCAGCACCTGTCGT
CAGCGCCATTATGAGCAAGGAAATTCCCACGCCCTACATGTGGAGTTACCAGCCAC
AAATGGGACTTGCGGCTGGAGCTGCCCAAGACTACTCAACCCGAATAAACTACATG
AGCGCGGGACCCCACATGATATCCCGGGTCAACGGAATCCGCGCCCACCGAAACCG
AATTCTCTTGGAACAGGCGGCTATTACCACCACACCTCGTAATAACCTTAATCCCCG
TAGTTGGCCCGCTGCCCTGGTGTACCAGGAAAGTCCCGCTCCCACCACTGTGGTACT
TCCCAGAGACGCCCAGGCCGAAGTTCAGATGACTAACTCAGGGGCGCAGCTTGCGG
GCGGCTTTCGTCACAGGGTGCGGTCGCCCGGGCAGGGTATAACTCACCTGACAATC
AGAGGGCGAGGTATTCAGCTCAACGACGAGTCGGTGAGCTCCTCGCTTGGTCTCCGT
CCGGACGGGACATTTCAGATCGGCGGCGCCGGCCGTCCTTCATTCACGCCTCGTCAG
GCAATCCTAACTCTGCAGACCTCGTCCTCTGAGCCGCGCTCTGGAGGCATTGGAACT
CTGCAATTTATTGAGGAGTTTGTGCCATCGGTCTACTTTAACCCCTTCTCGGGACCTC
CCGGCCACTATCCGGATCAATTTATTCCTAACTTTGACGCGGTAAAGGACTCGGCGG
ACGGCTACGACTGAATGTTAAGTGGAGAGGCAGAGCAACTGCGCCTGAAACACCTG
GTCCACTGTCGCCGCCACAAGTGCTTTGCCCGCGACTCCGGTGAGTTTTGCTACTTTG
```

FIG. 30L

```
AATTGCCCGAGGATCATATCGAGGGCCCGGCGCACGGCGTCCGGCTTACCGCCCAG
GGAGAGCTTGCCCGTAGCCTGATTCGGGAGTTTACCCAGCGCCCCTGCTAGTTGAG
CGGGACAGGGGACCCTGTGTTCTCACTGTGATTTGCAACTGTCCTAACCTTGGATTA
CATCAAGATCCTCTAGTTATAACTAGAGTACCCGGGGATCTTATTCCCTTTAACTAAT
AAAAAAAAATAATAAAGCATCACTTACTTAAAATCAGTTAGCAAATTTCTGTCCAGT
TTATTCAGCAGCACCTCCTTGCCCTCCTCCCAGCTCTGGTATTGCAGCTTCCTCCTGG
CTGCAAACTTTCTCCACAATCTAAATGGAATGTCAGTTTCCTCCTGTTCCTGTCCATC
CGCACCCACCGGTATAACTTCGTATATGGTTTCTTATACGAACGGTACAAGAACAAG
AGCTGAAAATAAAAAACAGGTCTCTGCGATCCCTCACCCGCAGCTGCCTGTATCACA
AAAGCGAAGATCAGCTTCGGCGCACGCTGGAAGACGCGGAGGCTCTCTTCAGTAAA
TACTGCGCGCTGACTCTTAAGGACTAGTTTCGCGCCCTTTCTCAAATTTAAGCGCGA
AAACTACGTCATCTCCAGCGGCCACACCCGGCGCCAGCACCTGTCGTCAGCGCCATT
ATGAGCAAGGAAATTCCCACGCCCTACATGTGGAGTTACCAGCCACAAATGGGACT
TGCGGCTGGAGCTGCCCAAGACTACTCAACCCGAATAAACTACATGAGCGCGGGAC
CCCACATGATATCCCGGGTCAACGGAATCCGCGCCCACCGAAACCGAATTCTCTTGG
AACAGGCGGCTATTACCACCACACCTCGTAATAACCTTAATCCCCGTAGTTGGCCCG
CTGCCCTGGTGTACCAGGAAAGTCCCGCTCCCACCACTGTGGTACTTCCCAGAGACG
CCCAGGCCGAAGTTCAGATGACTAACTCAGGGGCGCAGCTTGCGGGCGGCTTTCGT
CACAGGGTGCGGTCGCCCGGGCAGGGTATAACTCACCTGACAATCAGAGGGCGAGG
TATTCAGCTCAACGACGAGTCGGTGAGCTCCTCGCTTGGTCTCCGTCCGGACGGGAC
ATTTCAGATCGGCGGCGCCGGCCGTCCTTCATTCACGCCTCGTCAGGCAATCCTAAC
TCTGCAGACCTCGTCCTCTGAGCCGCGCTCTGGAGGCATTGGAACTCTGCAATTTAT
TGAGGAGTTTGTGCCATCGGTCTACTTTAACCCCTTCTCGGGACCTCCCGGCCACTAT
CCGGATCAATTTATTCCTAACTTTGACGCGGTAAAGGACTCGGCGGACGGCTACGAC
TGAATGTTAAGTGGAGAGGCAGAGCAACTGCGCCTGAAACACCTGGTCCACTGTCG
CCGCCACAAGTGCTTTGCCCGCGACTCCGGTGAGTTTTGCTACTTTGAATTGCCCGA
GGATCATATCGAGGGCCCGGCGCACGGCGTCCGGCTTACCGCCCAGGGAGAGCTTG
CCCGTAGCCTGATTCGGGAGTTTACCCAGCGCCCCTGCTAGTTGAGCGGGACAGGG
GACCCTGTGTTCTCACTGTGATTTGCAACTGTCCTAACCTTGGATTACATCAAGATCC
TCTAGTTATAACTAGAGTACCCGGGGATCTTATTCCCTTTAACTAATAAAAAAAAAT
AATAAAGCATCACTTACTTAAAATCAGTTAGCAAATTTCTGTCCAGTTTATTCAGCA
GCACCTCCTTGCCCTCCTCCCAGCTCTGGTATTGCAGCTTCCTCCTGGCTGCAAACTT
TCTCCACAATCTAAATGGAATGTCAGTTTCCTCCTGTTCCTGTCCATCCGCACCCACT
ATCTTCATGTTGTTGCAGATACCGGTATAACTTCGTATATGGTTTCTTATACGAAGTT
ATCTCGAGAACTATCTTCATGTTGTTGCAGATGAAGCGCGCAAGACCGTCTGAAGAT
ACCTTCAACCCCGTGTATCCATATGACACGGAAACCGGTCCTCCAACTGTGCCTTTT
CTTACTCCTCCCTTTGTATCCCCCAATGGGTTTCAAGAGAGTCCCCCTGGGGTACTCT
CTTTGCGCCTATCCGAACCTCTAGTTACCTCCAATGGCATGCTTGCGCTCAAAATGG
GCAACGGCCTCTCTCTGGACGAGGCCGGCAACCTTACCTCCCAAAATGTAACCACTG
TGAGCCCACCTCTCAAAAAAACCAAGTCAAACATAAACCTGGAAATATCTGCACCC
CTCACAGTTACCTCAGAAGCCCTAACTGTGGCTGCCGCCGCACCTCTAATGGTCGCG
GGCAACACACTCACCATGCAATCACAGGCCCCGCTAACCGTGCACGACTCCAAACT
TAGCATTGCCACCCAAGGACCCCTCACAGTGTCAGAAGGAAAGCTAGCCCTGCAAA
CATCAGGCCCCCTCACCACCACCGATAGCAGTACCCTTACTATCACTGCCTCACCCC
```

FIG. 30M

```
CTCTAACTACTGCCACTGGTAGCTTGGGCATTGACTTGAAAGAGCCCATTTATACAC
AAAATGGAAAACTAGGACTAAAGTACGGGGCTCCTTTGCATGTAACAGACGACCTA
AACACTTTGACCGTAGCAACTGGTCCAGGTGTGACTATTAATAATACTTCCTTGCAA
ACTAAAGTTACTGGAGCCTTGGGTTTTGATTCACAAGGCAATATGCAACTTAATGTA
GCAGGAGGACTAAGGATTGATTCTCAAAACAGACGCCTTATACTTGATGTTAGTTAT
CCGTTTGATGCTCAAAACCAACTAAATCTAAGACTAGGACAGGGCCCTCTTTTTATA
AACTCAGCCCACAACTTGGATATTAACTACAACAAAGGCCTTTACTTGTTTACAGCT
TCAAACAATTCCAAAAAGCTTGAGGTTAACCTAAGCACTGCCAAGGGGTTGATGTTT
GACGCTACAGCCATAGCCATTAATGCAGGAGATGGGCTTGAATTTGGTTCACCTAAT
GCACCAAACACAAATCCCCTCAAAACAAAAATTGGCCATGGCCTAGAATTTGATTC
AAACAAGGCTATGGTTCCTAAACTAGGAACTGGCCTTAGTTTTGACAGCACAGGTGC
CATTACAGTAGGAAACAAAAATAATGATAAGCTAACTTTGTGGACCACACCAGCTC
CATCTCCTAACTGTAGACTAAATGCAGAGAAAGATGCTAAACTCACTTTGGTCTTAA
CAAAATGTGGCAGTCAAATACTTGCTACAGTTTCAGTTTTGGCTGTTAAAGGCAGTT
TGGCTCCAATATCTGGAACAGTTCAAAGTGCTCATCTTATTATAAGATTTGACGAAA
ATGGAGTGCTACTAAACAATTCCTTCCTGGACCCAGAATATTGGAACTTTAGAAATG
GAGATCTTACTGAAGGCACAGCCTATACAAACGCTGTTGGATTTATGCCTAACCTAT
CAGCTTATCCAAAATCTCACGGTAAAACTGCCAAAAGTAACATTGTCAGTCAAGTTT
ACTTAAACGGAGACAAAACTAAACCTGTAACACTAACCATTACACTAAGCGGTACA
CAGGAATCCGGAGACACAACTCCAAGTGCATACTCTATGTCATTTTCATGGGACTGG
TCTGGCCACAACTACATTAATGAAATATTTGCCACATCCTCTTACACTTTTTCATACA
TTGCCCAAGAATAAAGAAGCGGCCGCATAACTTCGTATAGCATACATTATACGAAG
TTATACCGGTATACATTGCCCAAGAATAAAGAATCGTTTGTGTTATGTTTCAACGTG
TTTATTTTTCAATTGCAGAAAATTTCAAGTCATTTTTCATTCAGTAGTATAGCCCCAC
CACCACATAGCTTATACAGATCACCGTACCTTAATCAAACTCACAGAACCCTAGTAT
TCAACCTGCCACCTCCCTCCCAACACACAGAGTACACAGTCCTTTCTCCCCGGCTGG
CCTTAAAAAGCATCATATCATGGGTAACAGACATATTCTTAGGTGTTATATTCCACA
CGGTTTCCTGTCGAGCCAAACGCTCATCAGTGATATTAATAAACTCCCCGGGCAGCT
CACTTAAGTTCATGTCGCTGTCCAGCTGCTGAGCCACAGGCTGCTGTCCAACTTGCG
GTTGCTTAACGGGCGGCGAAGGAGAAGTCCACGCCTACATGGGGGTAGAGTCATAA
TCGTGCATCAGGATAGGGCGGTGGTGCTGCAGCAGCGCGCGAATAAACTGCTGCCG
CCGCCGCTCCGTCCTGCAGGAATACAACATGGCAGTGGTCTCCTCAGCGATGATTCG
CACCGCCCGCAGCATAAGGCGCCTTGTCCTCCGGGCACAGCAGCGCACCCTGATCTC
ACTTAAATCAGCACAGTAACTGCAGCACAGCACCACAATATTGTTCAAAATCCCAC
AGTGCAAGGCGCTGTATCCAAAGCTCATGGCGGGGACCACAGAACCCACGTGGCCA
TCATACCACAAGCGCAGGTAGATTAAGTGGCGACCCCTCATAAACACGCTGGACAT
AAACATTACCTCTTTTGGCATGTTGTAATTCACCACCTCCCGGTACCATATAAACCTC
TGATTAAACATGGCGCCATCCACCACCATCCTAAACCAGCTGGCCAAAACCTGCCCG
CCGGCTATACACTGCAGGGAACCGGGACTGGAACAATGACAGTGGAGAGCCCAGG
ACTCGTAACCATGGATCATCATGCTCGTCATGATATCAATGTTGGCACAACACAGGC
ACACGTGCATACACTTCCTCAGGATTACAAGCTCCTCCCGCGTTAGAACCATATCCC
AGGGAACAACCCATTCCTGAATCAGCGTAAATCCCACACTGCAGGGAAGACCTCGC
ACGTAACTCACGTTGTGCATTGTCAAAGTGTTACATTCGGGCAGCAGCGGATGATCC
TCCAGTATGGTAGCGCGGGTTTCTGTCTCAAAAGGAGGTAGACGATCCCTACTGTAC
```

FIG. 30N

```
GGAGTGCGCCGAGACAACCGAGATCGTGTTGGTCGTAGTGTCATGCCAAATGGAAC
GCCGGACGTAGTCATATTTCCTGAAGCAAAACCAGGTGCGGGCGTGACAAACAGAT
CTGCGTCTCCGGTCTCGCCGCTTAGATCGCTCTGTGTAGTAGTTGTAGTATATCCACT
CTCTCAAAGCATCCAGGCGCCCCCTGGCTTCGGGTTCTATGTAAACTCCTTCATGCG
CCGCTGCCCTGATAACATCCACCACCGCAGAATAAGCCACACCCAGCCAACCTACA
CATTCGTTCTGCGAGTCACACACGGGAGGAGCGGGAAGAGCTGGAAGAACCATGTT
TTTTTTTTTATTCCAAAAGATTATCCAAAACCTCAAAATGAAGATCTATTAAGTGAA
CGCGCTCCCCTCCGGTGGCGTGGTCAAACTCTACAGCCAAAGAACAGATAATGGCA
TTTGTAAGATGTTGCACAATGGCTTCCAAAAGGCAAACGGCCCTCACGTCCAAGTGG
ACGTAAAGGCTAAACCCTTCAGGGTGAATCTCCTCTATAAACATTCCAGCACCTTCA
ACCATGCCCAAATAATTCTCATCTCGCCACCTTCTCAATATATCTCTAAGCAAATCCC
GAATATTAAGTCCGGCCATTGTAAAAATCTGCTCCAGAGCGCCCTCCACCTTCAGCC
TCAAGCAGCGAATCATGATTGCAAAAATTCAGGTTCCTCACAGACCTGTATAAGATT
CAAAAGCGGAACATTAACAAAAATACCGCGATCCCGTAGGTCCCTTCGCAGGGCCA
GCTGAACATAATCGTGCAGGTCTGCACGGACCAGCGCGGCCACTTCCCCGCCAGGA
ACCTTGACAAAAGAACCCACACTGATTATGACACGCATACTCGGAGCTATGCTAAC
CAGCGTAGCCCCGATGTAAGCTTTGTTGCATGGGCGGCGATATAAAATGCAAGGTG
CTGCTCAAAAAATCAGGCAAAGCCTCGCGCAAAAAAGAAAGCACATCGTAGTCATG
CTCATGCAGATAAAGGCAGGTAAGCTCCGGAACCACCACAGAAAAAGACACCATTT
TTCTCTCAAACATGTCTGCGGGTTTCTGCATAAACACAAAATAAAATAACAAAAAAA
CATTTAAACATTAGAAGCCTGTCTTACAACAGGAAAAACAACCCTTATAAGCATAA
GACGGACTACGGCCATGCCGGCGTGACCGTAAAAAAACTGGTCACCGTGATTAAAA
AGCACCACCGACAGCTCCTCGGTCATGTCCGGAGTCATAATGTAAGACTCGGTAAA
CACATCAGGTTGATTCATCGGTCAGTGCTAAAAAGCGACCGAAATAGCCCGGGGGA
ATACATACCCGCAGGCGTAGAGACAACATTACAGCCCCCATAGGAGGTATAACAAA
ATTAATAGGAGAGAAAAACACATAAACACCTGAAAAACCCTCCTGCCTAGGCAAAA
TAGCACCCTCCCGCTCCAGAACAACATACAGCGCTTCACAGCGGCAGCCTAACAGT
CAGCCTTACCAGTAAAAAAGAAAACCTATTAAAAAAACACCACTCGACACGGCACC
AGCTCAATCAGTCACAGTGTAAAAAAGGGCCAAGTGCAGAGCGAGTATATATAGGA
CTAAAAAATGACGTAACGGTTAAAGTCCACAAAAAACACCCAGAAAACCGCACGCG
AACCTACGCCCAGAAACGAAAGCCAAAAAACCCACAACTTCCTCAAATCGTCACTT
CCGTTTTCCCACGTTACGTAACTTCCCATTTTAAGAAAACTACAATTCCCAACACATA
CAAGTTACTCCGCCCTAAAACCTACGTCACCCGCCCCGTTCCCACGCCCCGCGCCAC
GTCACAAACTCCACCCCCTCATTATCATATTGGCTTCAATCCAAAATAAGGTATATT
ATTGATGATTTAATTAAGGATCCNNNCCTGTCCTCGACCGATGCCCTTGAGAGCCTT
CAACCCAGTCAGCTCCTTCCGGTGGGCGCGGGGCATGACTATCGTCGCCGCACTTAT
GACTGTCTTCTTTATCATGCAACTCGTAGGACAGGTGCCGGCAGCGCTCTGGGTCAT
TTTCGGCGAGGACCGCTTTCGCTGGAGCGCGACGATGATCGGCCTGTCGCTTGCGGT
ATTCGGAATCTTGCACGCCCTCGCTCAAGCCTTCGTCACTGGTCCCGCCACCAAACG
TTTCGGCGAGAAGCAGGCCATTATCGCCGGCATGGCGGCCGACGCGCTGGGCTACG
TCTTGCTGGCGTTCGCGACGCGAGGCTGGATGGCCTTCCCCATTATGATTCTTCTCGC
TTCCGGCGGCATCGGGATGCCCGCGTTGCAGGCCATGCTGTCCAGGCAGGTAGATG
ACGACCATCAGGGACAGCTTCAAGGATCGCTCGCGGCTCTTACCAGCCTAACTTCGA
TCACTGGACCGCTGATCGTCACGGCGATTTATGCCGCCTCGGCGAGCACATGGAACG
```

FIG. 30O

```
GGTTGGCATGGATTGTAGGCGCCGCCCTATACCTTGTCTGCCTCCCCGCGTTGCGTC
GCGGTGCATGGAGCCGGGCCACCTCGACCTGAATGGAAGCCGGCGGCACCTCGCTA
ACGGATTCACCACTCCAAGAATTGGAGCCAATCAATTCTTGCGGAGAACTGTGAATG
CGCAAACCAACCCTTGGCAGAACATATCCATCGCGTCCGCCATCTCCAGCAGCCGCA
CGCGGCGCATCTCGGGCAGCGTTGGGTCCTGGCCACGGGTGCGCATGATCGTGCTCC
TGTCGTTGAGGACCCGGCTAGGCTGGCGGGGTTGCCTTACTGGTTAGCAGAATGAAT
CACCGATACGCGAGCGAACGTGAAGCGACTGCTGCTGCAAAACGTCTGCGACCTGA
GCAACAACATGAATGGTCTTCGGTTTCCGTGTTTCGTAAAGTCTGGAAACGCGGAAG
TCAGCGCCCTGCACCATTATGTTCCGGATCTGCATCGCAGGATGCTGCTGGCTACCC
TGTGGAACACCTACATCTGTATTAACGAAGCGCTGGCATTGACCCTGAGTGATTTTT
CTCTGGTCCCGCCGCATCCATACCGCCAGTTGTTTACCCTCACAACGTTCCAGTAAC
CGGGCATGTTCATCATCAGTAACCCGTATCGTGAGCATCCTCTCTCGTTTCATCGGTA
TCATTACCCCCATGAACAGAAATTCCCCCTTACACGGAGGCATCAAGTGACCAAAC
AGGAAAAAACCGCCCTTAACATGGCCCGCTTTATCAGAAGCCAGACATTAACGCTT
CTGGAGAAACTCAACGAGCTGGACGCGGATGAACAGGCAGACATCTGTGAATCGCT
TCACGACCACGCTGATGAGCTTTACCGCAGCTGCCTCGCGCGTTTCGGTGATGACGG
TGAAAACCTCTGACACATGCAGCTCCCGGAGACGGTCACAGCTTGTCTGTAAGCGG
ATGCCGGGAGCAGACAAGCCCGTCAGGGCGCGTCAGCGGGTGTTGGCGGGTGTCGG
GGCGCAGCCATGACCCAGTCACGTAGCGATAGCGGAGTGTATACTGGCTTAACTAT
GCGGCATCAGAGCAGATTGTACTGAGAGTGCACCATATGCGGTGTGAAATACCGCA
CAGATGCGTAAGGAGAAAATACCGCAT
```

FIG. 30P pShuttle (SEQ ID NO:2).

```
TTAATTAANNNNTCCCTTCCAGCTCTCTGCCCCTTTTGGATTGAAGCCAATATGATAAT
GAGGGGGTGGAGTTTGTGACGTGGCGCGGGGCGTGGGAACGGGGCGGGTGACGTA
GTAGTGTGGCGGAAGTGTGATGTTGCAAGTGTGGCGGAACACATGTAAGCGACGGA
TGTGGCAAAAGTGACGTTTTTGGTGTGCGCCGGTGTACACAGGAAGTGACAATTTTC
GCGCGGTTTTAGGCGGATGTTGTAGTAAATTTGGGCGTAACCGAGTAAGATTTGGCC
ATTTTCGCGGGAAAACTGAATAAGAGGAAGTGAAATCTGAATAATTTTGTGTTACTC
ATAGCGCGTAANNNCGCGTTAAGATACATTGATGAGTTTGGACAAACCACAACTAG
AATGCAGTGAAAAAAATGCTTTATTTGTGAAATTTGTGATGCTATTGCTTTATTTGTA
ACCATTATAAGCTGCAATAAACAAGTTAACAACAACAATTGCATTCATTTTATGTTT
CAGGTTCAGGGGGAGGTGTGGGAGGTTTTTTAAAGCAAGTAAAACCTCTACAAATG
TGGTATGGCTGATTATGATCAGTTATCTAGATCCGGTGGATCTGAGTCCGGACTTGT
ACAGCTCGTCCATGCCGAGAGTGATCCCGGCGGCGGTCACGAACTCCAGCAGGACC
ATGTGATCGCGCTTCTCGTTGGGGTCTTTGCTCAGGGCGGACTGGGTGCTCAGGTAG
TGGTTGTCGGGCAGCAGCACGGGGCCGTCGCCGATGGGGGTGTTCTGCTGGTAGTG
GTCGGCGAGCTGCACGCTGCCGTCCTCGATGTTGTGGCGGATCTTGAAGTTCACCTT
GATGCCGTTCTTCTGCTTGTCGGCCATGATATAGACGTTGTGGCTGTTGTAGTTGTAC
TCCAGCTTGTGCCCCAGGATGTTGCCGTCCTCCTTGAAGTCGATGCCCTTCAGCTCG
ATGCGGTTCACCAGGGTGTCGCCCTCGAACTTCACCTCGGCGCGGGTCTTGTAGTTG
CCGTCGTCCTTGAAGAAGATGGTGCGCTCCTGGACGTAGCCTTCGGGCATGGCGGAC
TTGAAGAAGTCGTGCTGCTTCATGTGGTCGGGGTAGCGGCTGAAGCACTGCACGCCG
TAGGTCAGGGTGGTCACGAGGGTGGGCCAGGGCACGGGCAGCTTGCCGGTGGTGCA
GATGAACTTCAGGGTCAGCTTGCCGTAGGTGGCATCGCCCTCGCCCTCGCCGGACAC
GCTGAACTTGTGGCCGTTTACGTCGCCGTCCAGCTCGACCAGGATGGGCACCACCCC
GGTGAACAGCTCCTCGCCCTTGCTCACCATGGTGGCGACCGGTAGCGCTAGCGGATC
TGACGGTTCACTAAACCAGCTCTGCTTATATAGACCTCCCACCGTACACGCCTACCG
CCCATTTGCGTCAATGGGGCGGAGTTGTTACGACATTTTGGAAAGTCCCGTTGATTT
TGGTGCCAAAACAAACTCCCATTGACGTCAATGGGGTGGAGACTTGGAAATCCCCG
TGAGTCAAACCGCTATCCACGCCCATTGATGTACTGCCAAAACCGCATCACCATGGT
AATAGCGATGACTAATACGTAGATGTACTGCCAAGTAGGAAAGTCCCATAAGGTCA
TGTACTGGGCATAATGCCAGGCGGGCCATTTACCGTCATTGACGTCAATAGGGGGCG
TACTTGGCATATGATACACTTGATGTACTGCCAAGTGGGCAGTTTACCGTAAATACT
CCACCCATTGACGTCAATGGAAAGTCCCTATTGGCGTTACTATGGGAACATACGTCA
TTATTGACGTCAATGGGCGGGGGTCGTTGGGCGGTCAGCCAGGCGGGCCATTTACCG
TAAGTTATGTAACGCGGAACTCCATATATGGGCTATGAACTAATGACCCCGTAATTG
ATTACTATTANNNCTAGCAGATCTGGTACCGTCGACGCGGCCGCGATATCCTCGAGA
AGCTTTCTAGAGNNNTAAGGGTGGGAAAGAATATATAAGGTGGGGGTCTTATGTAG
TTTTGTATCTGTTTTGCAGCAGCCGCCGCCGCCATGAGCACCAACTCGTTTGATGGA
AGCATTGTGAGCTCATATTTGACAACGCGCATGCCCCATGGGCCGGGGTGCGTCAG
AATGTGATGGGCTCCAGCATTGATGGTCGCCCCGTCCTGCCCGCAAACTCTACTACC
TTGACCTACGAGACCGTGTCTGGAACGCCGTTGGAGACTGCAGCCTCCGCCGCCGCT
TCAGCCGCTGCAGCCACCGCCCGCGGGATTGTGACTGACTTTGCTTTCCTGAGCCCG
CTTGCAAGCAGTGCAGCTTCCCCGTTCATCCGCCCGCGATGACAAGTTGACGGCTCTT
```

FIG. 31A

```
TTGGCACAATTGGATTCTTTGACCCGGGAACTTAATGTCGTTTCTCAGCAGCTGTTGG
ATCTGCGCCAGCAGGTTTCTGCCCTGAAGGCTTCCTCCCCTCCCAATGCGGTTTAAA
ACATAAATAAAAAACCAGACTCTGTTTGGATTTGGATCAAGCAAGTGTCTTGCTGTC
TTTATTTAGGGGTTTTGCGCGCGCGGTAGGCCCGGGACCAGCGGTCTCGGTCGTTGA
GGGTCCTGTGTATTTTTTCCAGGACGTGGTAAAGGTGACTCTGGATGTTCAGATACA
TGGGCATAAGCCCGTCTCTGGGGTGGAGGTAGCACCACTGCAGAGCTTCATGCTGCG
GGGTGGTGTTGTAGATGATCCAGTCGTAGCAGGAGCGCTGGGCGTGGTGCCTAAAA
ATGTCTTTCAGTAGCAAGCTGATTGCCAGGGGCAGGCCCTTGGTGTAAGTGTTTACA
AAGCGGTTAAGCTGGGATGGGTGCATACGTGGGGATATGAGATGCATCTTGGACTG
TATTTTTAGGTTGGCTATGTTCCAGCCATATCCCTCCGGGGATTCATGTTGTGCAGA
ACCACCAGCACAGTGTATCCGGTGCACTTGGGAAATTTGTCATGTAGCTTAGAAGGA
AATGCGTGGAAGAACTTGGAGACGCCCTTGTGACCTCCAAGATTTTCCATGCATTCG
TCCATAATGATGGCAATGGGCCCACGGGCGGCGGCCTGGGCGAAGATATTTCTGGG
ATCACTAACGTCATAGTTGTGTTCCAGGATGAGATCGTCATAGGCCATTTTTACAAA
GCGCGGGCGGAGGGTGCCAGACTGCGGTATAATGGTTCCATCCGGCCCAGGGGCGT
AGTTACCCTCACAGATTTGCATTTCCCACGCTTTGAGTTCAGATGGGGGGATCATGT
CTACCTGCGGGGCGATGAAGAAAACGGTTTCCGGGGTAGGGGAGATCAGCTGGGAA
GAAAGCAGGTTCCTGAGCAGCTGCGACTTACCGCAGCCGGTGGGCCCGTAAATCAC
ACCTATTACCGGGTGCAACTGGTAGTTAAGAGAGCTGCAGCTGCCGTCATCCCTGAG
CAGGGGGGCCACTTCGTTAAGCATGTCCCTGACTCGCATGTTTTCCCTGACCAAATC
CGCCAGAAGGCGCTCGCCGCCCAGCGATAGCAGTTCTTGCAAGGAAGCAAAGTTTT
TCAACGGTTTGAGACCGTCCGCCGTAGGCATGCTTTTGAGCGTTTGACCAAGCAGTT
CCAGGCGGTCCCACAGCTCGGTCACCTGCTCTACGGCATCTCGATCCAGCATATCTC
CTCGTTTCGCGGGTTGGGGCGGCTTTCGCTGTACGGCAGTAGTCGGTGCTCGTCCAG
ACGGGCCAGGGTCATGTCTTTCCACGGGCGCAGGGTCCTCGTCAGCGTAGTCTGGGT
CACGGTGAAGGGGTGCGCTCCGGGCTGCGCGCTGGCCAGGGTGCGCTTGAGGCTGG
TCCTGCTGGTGCTGAAGCGCTGCCGGTCTTCGCCCTGCGCGTCGGCCAGGTAGCATT
TGACCATGGTGTCATAGTCCAGCCCCTCCGCGGCGTGGCCCTTGGCGCGCAGCTTGC
CCTTGGAGGAGGCGCCGCACGAGGGGCAGTGCAGACTTTTGAGGGCGTAGAGCTTG
GGCGCGAGAAATACCGATTCCGGGGAGTAGGCATCCGCGCCGCAGGCCCCGCAGAC
GGTCTCGCATTCCACGAGCCAGGTGAGCTCTGGCCGTTCGGGGTCAAAAACCAGGTT
TCCCCCATGCTTTTTGATGCGTTTCTTACCTCTGGTTTCCATGAGCCGGTGTCCACGC
TCGGTGACGAAAAGGCTGTCCGTGTCCCCGTATACAGACTNNNGTTTAAACGAATTC
NNNTATAAAATGCAAGGTGCTGCTCAAAAAATCAGGCAAAGCCTCGCGCAAAAAAG
AAAGCACATCGTAGTCATGCTCATGCAGATAAAGGCAGGTAAGCTCCGGAACCACC
ACAGAAAAAGACACCATTTTTCTCTCAAACATGTCTGCGGGTTTCTGCATAAACACA
AAATAAAATAACAAAAAAACATTTAAACATTAGAAGCCTGTCTTACAACAGGAAAA
ACAACCCTTATAAGCATAAGACGGACTACGGCCATGCCGGCGTGACCGTAAAAAAA
CTGGTCACCGTGATTAAAAAGCACCACCGACAGCTCCTCGGTCATGTCCGGAGTCAT
AATGTAAGACTCGGTAAACACATCAGGTTGATTCATCGGTCAGTGCTAAAAAGCGA
CCGAAATAGCCCGGGGGAATACATACCCGCAGGCGTAGAGACAACATTACAGCCCC
CATAGGAGGTATAACAAAATTAATAGGAGAGAAAAACACATAAACACCTGAAAAA
CCCTCCTGCCTAGGCAAAATAGCACCCTCCCGCTCCAGAACAACATACAGCGCTTCA
CAGCGGCAGCCTAACAGTCAGCCTTACCAGTAAAAAAGAAAACCTATTAAAAAAAC
```

FIG. 31B

```
ACCACTCGACACGGCACCAGCTCAATCAGTCACAGTGTAAAAAAGGGCCAAGTGCA
GAGCGAGTATATATAGGACTAAAAAATGACGTAACGGTTAAAGTCCACAAAAAACA
CCCAGAAAACCGCACGCGAACCTACGCCCAGAAACGAAAGCCAAAAAACCCACAA
CTTCCTCAAATCGTCACTTCCGTTTTCCCACGTTACGTAACTTCCCATTTTAAGAAAA
CTACAATTCCCAACACATACAAGTTACTCCGCCCTAAAACCTACGTCACCCGCCCCG
TTCCCACGCCCCGCGCCACGTCACAAACTCCACCCCCTCATTATCATATTGGCTTCA
ATCCAAAATAAGGTATATTATTGATGATNNNTTAATTAAGGATCCNNNCGGTGTGAA
ATACCGCACAGATGCGTAAGGAGAAAATACCGCATCAGGCGCTCTTCCGCTTCCTCG
CTCACTGACTCGCTGCGCTCGGTCGTTCGGCTGCGGCGAGCGGTATCAGCTCACTCA
AAGGCGGTAATACGGTTATCCACAGAATCAGGGGATAACGCAGGAAAGAACATGTG
AGCAAAAGGCCAGCAAAAGGCCAGGAACCGTAAAAAGGCCGCGTTGCTGGCGTTTT
TCCATAGGCTCCGCCCCCCTGACGAGCATCACAAAAATCGACGCTCAAGTCAGAGG
TGGCGAAACCCGACAGGACTATAAAGATACCAGGCGTTTCCCCCTGGAAGCTCCCT
CGTGCGCTCTCCTGTTCCGACCCTGCCGCTTACCGGATACCTGTCCGCCTTTCTCCCT
TCGGGAAGCGTGGCGCTTTCTCATAGCTCACGCTGTAGGTATCTCAGTTCGGTGTAG
GTCGTTCGCTCCAAGCTGGGCTGTGTGCACGAACCCCCCGTTCAGCCCGACCGCTGC
GCCTTATCCGGTAACTATCGTCTTGAGTCCAACCCGGTAAGACACGACTTATCGCCA
CTGGCAGCAGCCACTGGTAACAGGATTAGCAGAGCGAGGTATGTAGGCGGTGCTAC
AGAGTTCTTGAAGTGGTGGCCTAACTACGGCTACACTAGAAGGACAGTATTTGGTAT
CTGCGCTCTGCTGAAGCCAGTTACCTTCGGAAAAAGAGTTGGTAGCTCTTGATCCGG
CAAACAAACCACCGCTGGTAGCGGTGGTTTTTTTGTTTGCAAGCAGCAGATTACGCG
CAGAAAAAAAGGATCTCAAGAAGATCCTTTGATCTTTTCTACGGGGTCTGACGCTCA
GTGGAACGAAAACTCACGTTAAGGGATTTTGGTCATGAGATTATCAAAAAGGATCTT
CACCTAGATCCTTTTAAATTAAAAATGAAGTTTTAAATCAATCTAAAGTATATATGA
GTAAACTTGGTCTGACAGTTACCAATGCTTAATCAGTGAGGCACCTATCTCAGCGAT
CTGTCTATTTCGTTCATCCATAGTTGCCTGACTCCCCGTCGTGTAGATAACTACGATA
CGGGAGGGCTTACCATCTGGCCCCAGTGCTGCAATGATACCGCGAGACCCACGCTC
ACCGGCTCCAGATTTATCAGCAATAAACCAGCCAGCCGGAAGGGCCGAGCGCAGAA
GTGGTCCTGCAACTTTATCCGCCTCCATCCAGTCTATTAATTGTTGCCGGGAAGCTAG
AGTAAGTAGTTCGCCAGTTAATAGTTTGCGCAACGTTGTTGNNNNNNAAAAAGGAT
CTTCACCTAGATCCTTTTCACGTAGAAAGCCAGTCCGCAGAAACGGTGCTGACCCCG
GATGAATGTCAGCTACTGGGCTATCTGGACAAGGGAAAACGCAAGCGCAAAGAGAA
AGCAGGTAGCTTGCAGTGGGCTTACATGGCGATAGCTAGACTGGGCGGTTTTATGGA
CAGCAAGCGAACCGGAATTGCCAGCTGGGGCGCCCTCTGGTAAGGTTGGGAAGCCC
TGCAAAGTAAACTGGATGGCTTTCTCGCCGCCAAGGATCTGATGGCGCAGGGGATC
AAGCTCTGATCAAGAGACAGGATGAGGATCGTTTCGCATGATTGAACAAGATGGAT
TGCACGCAGGTTCTCCGGCCGCTTGGGTGGAGAGGCTATTCGGCTATGACTGGGCAC
AACAGACAATCGGCTGCTCTGATGCCGCCGTGTTCCGGCTGTCAGCGCAGGGGCGC
CCGGTTCTTTTTGTCAAGACCGACCTGTCCGGTGCCCTGAATGAACTGCAAGACGAG
GCAGCGCGGCTATCGTGGCTGGCCACGACGGGCGTTCCTTGCGCAGCTGTGCTCGAC
GTTGTCACTGAAGCGGGAAGGGACTGGCTGCTATTGGGCGAAGTGCCGGGGCAGGA
TCTCCTGTCATCTCACCTTGCTCCTGCCGAGAAAGTATCCATCATGGCTGATGCAATG
CGGCGGCTGCATACGCTTGATCCGGCTACCTGCCCATTCGACCACCAAGCGAAACAT
CGCATCGAGCGAGCACGTACTCGGATGGAAGCCGGTCTTGTCGATCAGGATGATCT
```

FIG. 31C

```
GGACGAAGAGCATCAGGGGCTCGCGCCAGCCGAACTGTTCGCCAGGCTCAAGGCGA
GCATGCCCGACGGCGAGGATCTCGTCGTGACCCATGGCGATGCCTGCTTGCCGAATA
TCATGGTGGAAAATGGCCGCTTTTCTGGATTCATCGACTGTGGCCGGCTGGGTGTGG
CGGACCGCTATCAGGACATAGCGTTGGCTACCCGTGATATTGCTGAAGAGCTTGGCG
GCGAATGGGCTGACCGCTTCCTCGTGCTTTACGGTATCGCCGCTCCCGATTCGCAGC
GCATCGCCTTCTATCGCCTTCTTGACGAGTTCTTCTGAATTTTGTTAAAATTTTTGTTA
AATCAGCTCATTTTTTAACCAATAGGCCGAAATCGGCAACATCCCTTATAAATCAAA
AGAATAGACCGCGATAGGGTTGAGTGTTGTTCCAGTTTGGAACAAGAGTCCACTATT
AAAGAACGTGGACTCCAACGTCAAAGGGCGAAAAACCGTCTATCAGGGCGATGGCC
CACTACGTGAACCATCACCCAAATCAAGTTTTTTGCGGTCGAGGTGCCGTAAAGCTC
TAAATCGGAACCCTAAAGGGAGCCCCCGATTTAGAGCTTGACGGGGAAAGCCGGCG
AACGTGGCGAGAAAGGAAGGGAAGAAAGCGAAAGGAGCGGGCGCTAGGGCGCTGG
CAAGTGTAGCGGTCACGCTGCGCGTAACCACCACACCCGCGCGCTTAATGCGCCGN
NNNNNNNNNNNNNNNNNNNNNNNNNNNNNNNNNNNNNNNNNNNNNNNNNNNNNNN
NNNNNNNNN
```

FIG. 31D

RP-Fib (SEQ ID NO:3)

```
TCGAGAACTATCTTCATGTTGTTGCAGATGAAGCGCGCAAGACCGTCTGAAGATACC
TTCAACCCCGTGTATCCATATGACACGGAAACCGGTCCTCCAACTGTGCCTTTTCTTA
CTCCTCCCTTTGTATCCCCCAATGGGTTTCAAGAGAGTCCCCCTGGGGTACTCTCTTT
GCGCCTATCCGAACCTCTAGTTACCTCCAATGGCATGCTTGCGCTCAAAATGGGCAA
CGGCCTCTCTCTGGACGAGGCCGGCAACCTTACCTCCCAAAATGTAACCACTGTGAG
CCCACCTCTCAAAAAAACCAAGTCAAACATAAACCTGGAAATATCTGCACCCCTCA
CAGTTACCTCAGAAGCCCTAACTGTGGCTGCCGCCGCACCTCTAATGGTCGCGGGCA
ACACACTCACCATGCAATCACAGGCCCCGCTAACCGTGCACGACTCCAAACTTAGC
ATTGCCACCCAAGGACCCCTCACAGTGTCAGAAGGAAAGCTAGCCCTGCAAACATC
AGGCCCCCTCACCACCACCGATAGCAGTACCCTTACTATCACTGCCTCACCCCCTCT
AACTACTGCCACTGGTAGCTTGGGCATTGACTTGAAAGAGCCCATTTATACACAAAA
TGGAAAACTAGGACTAAAGTACGGGGCTCCTTTGCATGTAACAGACGACCTAAACA
CTTTGACCGTAGCAACTGGTCCAGGTGTGACTATTAATAATACTTCCTTGCAAACTA
AAGTTACTGGAGCCTTGGGTTTTGATTCACAAGGCAATATGCAACTTAATGTAGCAG
GAGGACTAAGGATTGATTCTCAAAACAGACGCCTTATACTTGATGTTAGTTATCCGT
TTGATGCTCAAAACCAACTAAATCTAAGACTAGGACAGGGCCCTCTTTTTATAAACT
CAGCCCACAACTTGGATATTAACTACAACAAAGGCCTTTACTTGTTTACAGCTTCAA
ACAATTCCAAAAAGCTTGAGGTTAACCTAAGCACTGCCAAGGGGTTGATGTTTGACG
CTACAGCCATAGCCATTAATGCAGGAGATGGGCTTGAATTTGGTTCACCTAATGCAC
CAAACACAAATCCCCTCAAAACAAAAATTGGCCATGGCCTAGAATTTGATTCAAAC
AAGGCTATGGTTCCTAAACTAGGAACTGGCCTTAGTTTTGACAGCACAGGTGCCATT
ACAGTAGGAAACAAAAATAATGATAAGCTAACTTTGTGGACCACACCAGCTCCATC
TCCTAACTGTAGACTAAATGCAGAGAAAGATGCTAAACTCACTTTGGTCTTAACAAA
ATGTGGCAGTCAAATACTTGCTACAGTTTCAGTTTTGGCTGTTAAAGGCAGTTTGGC
TCCAATATCTGGAACAGTTCAAAGTGCTCATCTTATTATAAGATTTGACGAAAATGG
AGTGCTACTAAACAATTCCTTCCTGGACCCAGAATATTGGAACTTTAGAAATGGAGA
TCTTACTGAAGGCACAGCCTATACAAACGCTGTTGGATTTATGCCTAACCTATCAGC
TTATCCAAAATCTCACGGTAAAACTGCCAAAAGTAACATTGTCAGTCAAGTTTACTT
AAACGGAGACAAAACTAAACCTGTAACACTAACCATTACACTAAGCGGTACACAGG
AATCCGGAGACACAACTCCAAGTGCATACTCTATGTCATTTTCATGGGACTGGTCTG
GCCACAACTACATTAATGAAATATTTGCCACATCCTCTTACACTTTTTCATACATTGC
CCAAGAATAAAGAAGCGGCCGCATAACTTCGTATAGCATACATTATACGAACGGTA
GGTACCGAGCTCGAATTCACTGGCCGTCGTTTTACAACGTCGTGACTGGGAAAACCC
TGGCGTTACCCAACTTAATCGCCTTGCAGCACATCCCCCTTTCGCCAGCTGGCGTAA
TAGCGAAGAGGCCCGCACCGATCGCCCTTCCCAACAGTTGCGCAGCCTGAATGGCG
AATGGCGCCTGATGCGGTATTTTCTCCTTACGCATCTGTGCGGTATTTCACACCGCAT
ATGGTGCACTCTCAGTACAATCTGCTCTGATGCCGCATAGTTAAGCCAGCCCCGACA
CCCGCCAACACCCGCTGACGCGCCCTGACGGGCTTGTCTGCTCCCGGCATCCGCTTA
CAGACAAGCTGTGACCGTCTCCGGGAGCTGCATGTGTCAGAGGTTTTCACCGTCATC
ACCGAAACGCGCGAGACGAAAGGGCCTCGTGATACGCCTATTTTTATAGGTTAATGT
CATGATAATAATGGTTTCTTAGACGTCAGGTGGCACTTTTCGGGGAAATGTGCGCGG
```

FIG. 32A

```
AACCCCTATTTGTTTATTTTTCTAAATACATTCAAATATGTATCCGCTCATGAGACAA
TAACCCTGATAAATGCTTCAATAATATTGAAAAAGGAAGAGTATGAGTATTCAACAT
TTCCGTGTCGCCCTTATTCCCTTTTTTGCGGCATTTTGCCTTCCTGTTTTTGCTCACCC
AGAAACGCTGGTGAAAGTAAAAGATGCTGAAGATCAGTTGGGTGCACGAGTGGGTT
ACATCGAACTGGATCTCAACAGCGGTAAGATCCTTGAGAGTTTTCGCCCCGAAGAAC
GTTTTCCAATGATGAGCACTTTTAAAGTTCTGCTATGTGGCGCGGTATTATCCCGTAT
TGACGCCGGGCAAGAGCAACTCGGTCGCCGCATACACTATTCTCAGAATGACTTGGT
TGAGTACTCACCAGTCACAGAAAAGCATCTTACGGATGGCATGACAGTAAGAGAAT
TATGCAGTGCTGCCATAACCATGAGTGATAACACTGCGGCCAACTTACTTCTGACAA
CGATCGGAGGACCGAAGGAGCTAACCGCTTTTTTGCACAACATGGGGGATCATGTA
ACTCGCCTTGATCGTTGGGAACCGGAGCTGAATGAAGCCATACCAAACGACGAGCG
TGACACCACGATGCCTGTAGCAATGGCAACAACGTTGCGCAAACTATTAACTGGCG
AACTACTTACTCTAGCTTCCCGGCAACAATTAATAGACTGGATGGAGGCGGATAAA
GTTGCAGGACCACTTCTGCGCTCGGCCCTTCCGGCTGGCTGGTTTATTGCTGATAAAT
CTGGAGCCGGTGAGCGTGGGTCTCGCGGTATCATTGCAGCACTGGGGCCAGATGGT
AAGCCCTCCCGTATCGTAGTTATCTACACGACGGGGAGTCAGGCAACTATGGATGA
ACGAAATAGACAGATCGCTGAGATAGGTGCCTCACTGATTAAGCATTGGTAACTGTC
AGACCAAGTTTACTCATATATACTTTAGATTGATTTAAAACTTCATTTTTAATTTAAA
AGGATCTAGGTGAAGATCCTTTTTGATAATCTCATGACCAAAATCCCTTAACGTGAG
TTTTCGTTCCACTGAGCGTCAGACCCCGTAGAAAAGATCAAAGGATCTTCTTGAGAT
CCTTTTTTTCTGCGCGTAATCTGCTGCTTGCAAACAAAAAAACCACCGCTACCAGCG
GTGGTTTGTTTGCCGGATCAAGAGCTACCAACTCTTTTTCCGAAGGTAACTGGCTTC
AGCAGAGCGCAGATACCAAATACTGTCCTTCTAGTGTAGCCGTAGTTAGGCCACCAC
TTCAAGAACTCTGTAGCACCGCCTACATACCTCGCTCTGCTAATCCTGTTACCAGTG
GCTGCTGCCAGTGGCGATAAGTCGTGTCTTACCGGGTTGGACTCAAGACGATAGTTA
CCGGATAAGGCGCAGCGGTCGGGCTGAACGGGGGGTTCGTGCACACAGCCCAGCTT
GGAGCGAACGACCTACACCGAACTGAGATACCTACAGCGTGAGCTATGAGAAAGCG
CCACGCTTCCCGAAGGGAGAAAGGCGGACAGGTATCCGGTAAGCGGCAGGGTCGG
AACAGGAGAGCGCACGAGGGAGCTTCCAGGGGGAAACGCCTGGTATCTTTATAGTC
CTGTCGGGTTTCGCCACCTCTGACTTGAGCGTCGATTTTTGTGATGCTCGTCAGGGG
GCGGAGCCTATGGAAAAACGCCAGCAACGCGGCCTTTTTACGGTTCCTGGCCTTTTG
CTGGCCTTTTGCTCACATGTTCTTTCCTGCGTTATCCCCTGATTCTGTGGATAACCGT
ATTACCGCCTTTGAGTGAGCTGATACCGCTCGCCGCAGCCGAACGACCGAGCGCAG
CGAGTCAGTGAGCGAGGAAGCGGAAGAGCGCCCAATACGCAAACCGCCTCTCCCCG
CGCGTTGGCCGATTCATTAATGCAGCTGGCACGACAGGTTTCCCGACTGGAAAGCGG
GCAGTGAGCGCAACGCAATTAATGTGAGTTAGCTCACTCATTAGGCACCCCAGGCTT
TACACTTTATGCTTCCGGCTCGTATGTTGTGTGGAATTGTGAGCGGATAACAATTTCA
CACAGGAAACAGCTATGACCATGATTACGCCAAGCTTGCATGCCTGCAGGTCGACA
CTAGTACCGTTCGTATATGGTTTCTTATACGAAGTTATC
```

FIG. 32B

RPuc-Fib (SEQ ID NO:4)

CCGGTTTCCGTGTCATATGGATACACGGGGTTGAAGGTATCTTCAGACGGTCTTGCG
CGCTTCATCTGCAACAACATGAAGATAGTTCTCGAGATAACTTCGTATAAGAAACCA
TATACGAACGGTACTAGTGTCGACCTGCAGGCATGCAAGCTTGGCGTAATCATGGTC
ATAGCTGTTTCCTGTGTGAAATTGTTATCCGCTCACAATTCCACACAACATACGAGC
CGGAAGCATAAAGTGTAAAGCCTGGGGTGCCTAATGAGTGAGCTAACTCACATTAA
TTGCGTTGCGCTCACTGCCCGCTTTCCAGTCGGGAAACCTGTCGTGCCAGCTGCATT
AATGAATCGGCCAACGCGCGGGGAGAGGCGGTTTGCGTATTGGGCGCTCTTCCGCTT
CCTCGCTCACTGACTCGCTGCGCTCGGTCGTTCGGCTGCGGCGAGCGGTATCAGCTC
ACTCAAAGGCGGTAATACGGTTATCCACAGAATCAGGGGATAACGCAGGAAAGAAC
ATGTGAGCAAAAGGCCAGCAAAAGGCCAGGAACCGTAAAAAGGCCGCGTTGCTGG
CGTTTTTCCATAGGCTCCGCCCCCCTGACGAGCATCACAAAAATCGACGCTCAAGTC
AGAGGTGGCGAAACCCGACAGGACTATAAAGATACCAGGCGTTTCCCCCTGGAAGC
TCCCTCGTGCGCTCTCCTGTTCCGACCCTGCCGCTTACCGGATACCTGTCCGCCTTTC
TCCCTTCGGGAAGCGTGGCGCTTTCTCATAGCTCACGCTGTAGGTATCTCAGTTCGGT
GTAGGTCGTTCGCTCCAAGCTGGGCTGTGTGCACGAACCCCCCGTTCAGCCCGACCG
CTGCGCCTTATCCGGTAACTATCGTCTTGAGTCCAACCCGGTAAGACACGACTTATC
GCCACTGGCAGCAGCCACTGGTAACAGGATTAGCAGAGCGAGGTATGTAGGCGGTG
CTACAGAGTTCTTGAAGTGGTGGCCTAACTACGGCTACACTAGAAGGACAGTATTTG
GTATCTGCGCTCTGCTGAAGCCAGTTACCTTCGGAAAAAGAGTTGGTAGCTCTTGAT
CCGGCAAACAAACCACCGCTGGTAGCGGTGGTTTTTTTGTTTGCAAGCAGCAGATTA
CGCGCAGAAAAAAAGGATCTCAAGAAGATCCTTTGATCTTTTCTACGGGGTCTGACG
CTCAGTGGAACGAAAACTCACGTTAAGGGATTTTGGTCATGAGATTATCAAAAAGG
ATCTTCACCTAGATCCTTTTAAATTAAAAATGAAGTTTTAAATCAATCTAAAGTATAT
ATGAGTAAACTTGGTCTGACAGTTACCAATGCTTAATCAGTGAGGCACCTATCTCAG
CGATCTGTCTATTTCGTTCATCCATAGTTGCCTGACTCCCCGTCGTGTAGATAACTAC
GATACGGGAGGGCTTACCATCTGGCCCCAGTGCTGCAATGATACCGCGAGACCCAC
GCTCACCGGCTCCAGATTTATCAGCAATAAACCAGCCAGCCGGAAGGGCCGAGCGC
AGAAGTGGTCCTGCAACTTTATCCGCCTCCATCCAGTCTATTAATTGTTGCCGGGAA
GCTAGAGTAAGTAGTTCGCCAGTTAATAGTTTGCGCAACGTTGTTGCCATTGCTACA
GGCATCGTGGTGTCACGCTCGTCGTTTGGTATGGCTTCATTCAGCTCCGGTTCCCAAC
GATCAAGGCGAGTTACATGATCCCCCATGTTGTGCAAAAAAGCGGTTAGCTCCTTCG
GTCCTCCGATCGTTGTCAGAAGTAAGTTGGCCGCAGTGTTATCACTCATGGTTATGG
CAGCACTGCATAATTCTCTTACTGTCATGCCATCCGTAAGATGCTTTTCTGTGACTGG
TGAGTACTCAACCAAGTCATTCTGAGAATAGTGTATGCGGCGACCGAGTTGCTCTTG
CCCGGCGTCAATACGGGATAATACCGCGCCACATAGCAGAACTTTAAAAGTGCTCA
TCATTGGAAAACGTTCTTCGGGGCGAAAACTCTCAAGGATCTTACCGCTGTTGAGAT
CCAGTTCGATGTAACCCACTCGTGCACCCAACTGATCTTCAGCATCTTTTACTTTCAC
CAGCGTTTCTGGGTGAGCAAAAACAGGAAGGCAAAATGCCGCAAAAAAGGGAATA
AGGGCGACACGGAAATGTTGAATACTCATACTCTTCCTTTTTCAATATTATTGAAGC
ATTTATCAGGGTTATTGTCTCATGAGCGGATACATATTTGAATGTATTTAGAAAAAT
AAACAAATAGGGGTTCCGCGCACATTTCCCCGAAAAGTGCCACCTGACGTCTAAGA

FIG. 33A

```
AACCATTATTATCATGACATTAACCTATAAAAATAGGCGTATCACGAGGCCCTTTCG
TCTCGCGCGTTTCGGTGATGACGGTGAAAACCTCTGACACATGCAGCTCCCGGAGAC
GGTCACAGCTTGTCTGTAAGCGGATGCCGGGAGCAGACAAGCCCGTCAGGGCGCGT
CAGCGGGTGTTGGCGGGTGTCGGGGCTGGCTTAACTATGCGGCATCAGAGCAGATT
GTACTGAGAGTGCACCATATGCGGTGTGAAATACCGCACAGATGCGTAAGGAGAAA
ATACCGCATCAGGCGCCATTCGCCATTCAGGCTGCGCAACTGTTGGGAAGGGCGAT
CGGTGCGGGCCTCTTCGCTATTACGCCAGCTGGCGAAAGGGGGATGTGCTGCAAGG
CGATTAAGTTGGGTAACGCCAGGGTTTTCCCAGTCACGACGTTGTAAAACGACGGCC
AGTGAATTCGAGCTCGGTACCTACCGTTCGTATAATGTATGCTATACGAAGTTATGC
GGCCGCTTCTTTATTCTTGGGCAATGTATGAAAAAGTGTAAGAGGATGTGGCAAATA
TTTCATTAATGTAGTTGTGGCCAGACCAGTCCCATGAAAATGACATAGAGTATGCAC
TTGGAGTTGTGTCTCCGGATTCCTGTGTACCGTTTAGTGTAATGGTTAGTGTTACAGG
TTTAGTTTTGTCTCCGTTTAAGTAAACTTGACTGACAATGTTACTTTTGGCAGTTTTA
CCGTGAGATTTTGGATAAGCTGATAGGTTAGGCATAAATCCAACAGCGTTTGTATAG
GCTGTGCCTTCAGTAAGATCTCCATTTCTAAAGTTCCAATATTCTGGGTCCAGGAAG
GAATTGTTTAGTAGCACTCCATTTTCGTCAAATCTTATAATAAGATGAGCACTTTGA
ACTGTTCCAGATATTGGAGCCAAACTGCCTTTAACAGCCAAAACTGAAACTGTAGCA
AGTATTTGACTGCCACATTTTGTTAAGACCAAAGTGAGTTTAGCATCTTTCTCTGCAT
TTAGTCTACAGTTAGGAGATGGAGCTGGTGTGGTCCACAAAGTTAGCTTATCATTAT
TTTTGTTTCCTACTGTAATGGCACCTGTGCTGTCAAAACTAAGGCCAGTTCCTAGTTT
AGGAACCATAGCCTTGTTTGAATCAAATTCTAGGCCATGGCCAATTTTTGTTTTGAG
GGGATTTGTGTTTGGTGCATTAGGTGAACCAAATTCAAGCCCATCTCCTGCATTAAT
GGCTATGGCTGTAGCGTCAAACATCAACCCCTTGGCAGTGCTTAGGTTAACCTCAAG
CTTTTTGGAATTGTTTGAAGCTGTAAACAAGTAAAGGCCTTTGTTGTAGTTAATATCC
AAGTTGTGGGCTGAGTTTATAAAAAGAGGGCCCTGTCCTAGTCTTAGATTTAGTTGG
TTTTGAGCATCAAACGGATAACTAACATCAAGTATAAGGCGTCTGTTTTGAGAATCA
ATCCTTAGTCCTCCTGCTACATTAAGTTGCATATTGCCTTGTGAATCAAAACCCAAG
GCTCCAGTAACTTTAGTTTGCAAGGAAGTATTATTAATAGTCACACCTGGACCAGTT
GCTACGGTCAAAGTGTTTAGGTCGTCTGTTACATGCAAAGGAGCCCCGTACTTTAGT
CCTAGTTTTCCATTTTGTGTATAAATGGGCTCTTTCAAGTCAATGCCCAAGCTACCAG
TGGCAGTAGTTAGAGGGGGTGAGGCAGTGATAGTAAGGGTACTGCTATCGGTGGTG
GTGAGGGGGCCTGATGTTTGCAGGGCTAGCTTTCCTTCTGACACTGTGAGGGTCCT
TGGGTGGCAATGCTAAGTTTGGAGTCGTGCACGGTTAGCGGGGCCTGTGATTGCATG
GTGAGTGTGTTGCCCGCGACCATTAGAGGTGCGGCGGCAGCCACAGTTAGGGCTTCT
GAGGTAACTGTGAGGGGTGCAGATATTTCCAGGTTTATGTTTGACTTGGTTTTTTTGA
GAGGTGGGCTCACAGTGGTTACATTTTGGGAGGTAAGGTTGCCGGCCTCGTCCAGAG
AGAGGCCGTTGCCCATTTTGAGCGCAAGCATGCCATTGGAGGTAACTAGAGGTTCG
GATAGGCGCAAAGAGAGTACCCCAGGGGGACTCTCTTGAAACCCATTGGGGGATAC
AAAGGGAGGAGTAAGAAAAGGCACAGTTGGAGGA
```

FIG. 33B

RP-Blast-Fib (SEQ ID NO:5)

```
TCGAGAACTATCTTCATGTTGTTGCAGATGAAGCGCGCAAGACCGTCTGAAGATACC
TTCAACCCCGTGTATCCATATGACACGGAAACCGGTCCTCCAACTGTGCCTTTTCTTA
CTCCTCCCTTTGTATCCCCCAATGGGTTTCAAGAGAGTCCCCCTGGGGTACTCTCTTT
GCGCCTATCCGAACCTCTAGTTACCTCCAATGGCATGCTTGCGCTCAAAATGGGCAA
CGGCCTCTCTCTGGACGAGGCCGGCAACCTTACCTCCCAAAATGTAACCACTGTGAG
CCCACCTCTCAAAAAAACCAAGTCAAACATAAACCTGGAAATATCTGCACCCCTCA
CAGTTACCTCAGAAGCCCTAACTGTGGCTGCCGCCGCACCTCTAATGGTCGCGGGCA
ACACACTCACCATGCAATCACAGGCCCCGCTAACCGTGCACGACTCCAAACTTAGC
ATTGCCACCCAAGGACCCCTCACAGTGTCAGAAGGAAAGCTAGCCCTGCAAACATC
AGGCCCCCTCACCACCACCGATAGCAGTACCCTTACTATCACTGCCTCACCCCCTCT
AACTACTGCCACTGGTAGCTTGGGCATTGACTTGAAAGAGCCCATTTATACACAAAA
TGGAAAACTAGGACTAAAGTACGGGGCTCCTTTGCATGTAACAGACGACCTAAACA
CTTTGACCGTAGCAACTGGTCCAGGTGTGACTATTAATAATACTTCCTTGCAAACTA
AAGTTACTGGAGCCTTGGGTTTTGATTCACAAGGCAATATGCAACTTAATGTAGCAG
GAGGACTAAGGATTGATTCTCAAAACAGACGCCTTATACTTGATGTTAGTTATCCGT
TTGATGCTCAAAACCAACTAAATCTAAGACTAGGACAGGGCCCTCTTTTTATAAACT
CAGCCCACAACTTGGATATTAACTACAACAAAGGCCTTTACTTGTTTACAGCTTCAA
ACAATTCCAAAAAGCTTGAGGTTAACCTAAGCACTGCCAAGGGGTTGATGTTTGACG
CTACAGCCATAGCCATTAATGCAGGAGATGGGCTTGAATTTGGTTCACCTAATGCAC
CAAACACAAATCCCCTCAAAACAAAAATTGGCCATGGCCTAGAATTTGATTCAAAC
AAGGCTATGGTTCCTAAACTAGGAACTGGCCTTAGTTTTGACAGCACAGGTGCCATT
ACAGTAGGAAACAAAAATAATGATAAGCTAACTTTGTGGACCACACCAGCTCCATC
TCCTAACTGTAGACTAAATGCAGAGAAAGATGCTAAACTCACTTTGGTCTTAACAAA
ATGTGGCAGTCAAATACTTGCTACAGTTTCAGTTTTGGCTGTTAAAGGCAGTTTGGC
TCCAATATCTGGAACAGTTCAAAGTGCTCATCTTATTATAAGATTTGACGAAAATGG
AGTGCTACTAAACAATTCCTTCCTGGACCCAGAATATTGGAACTTTAGAAATGGAGA
TCTTACTGAAGGCACAGCCTATACAAACGCTGTTGGATTTATGCCTAACCTATCAGC
TTATCCAAAATCTCACGGTAAAACTGCCAAAAGTAACATTGTCAGTCAAGTTTACTT
AAACGGAGACAAAACTAAACCTGTAACACTAACCATTACACTAAGCGGTACACAGG
AATCCGGAGACACAACTCCAAGTGCATACTCTATGTCATTTTCATGGGACTGGTCTG
GCCACAACTACATTAATGAAATATTTGCCACATCCTCTTACACTTTTTCATACATTGC
CCAAGAATAAAGAAGCGGCCGCATAACTTCGTATAGCATACATTATACGAACGGTA
GGTACCAGGTAAGTGTACCCAATTCGCCCTATAGTGAGTCGTATTACAATTCACTGG
CCGTCGTTTTACAACGCCTGATGCGGTATTTTCTCCTTACGCATCTGTGCGGTATTTC
ACACCGCATATATGGTGCACTCTCAGTACAATCTGCTCTGATGCCGCATAGTTAAGC
CAGCCCCGACACCCGCCAACACCCGCTGACGCGCCCTGACGGGCTTGTCTGCTCCCG
GCATCCGCTTACAGACAAGCTGTGACCGTCTCCGGGAGCTGCATGTGTCAGAGGTTT
TCACCGTCATCACCGAAACGCGCGAGACGAAAGGGCCTCGTGATACGCCTATTTTTA
TAGGTTAATGTCATGATAATAATGGTTTCTTAGACGTCAGGTGGCACTTTTCGGGGA
AATGTGCGCGGAACCCCTATTTGTTTATTTTTCTAAATACATTCAAATATGTATCCGC
TCATGAGACAATAACCCTGATAAATGCTTCAATAATATTGAAAAAGGAAGAGTATG
```

FIG. 34A

```
AGTATTCAACATTTCCGTGTCGCCCTTATTCCCTTTTTTGCGGCATTTTGCCTTCCTGT
TTTTGCTCACCCAGAAACGCTGGTGAAAGTAAAAGATGCTGAAGATCAGTTGGGTG
CACGAGTGGGTTACATCGAACTGGATCTCAACAGCGGTAAGATCCTTGAGAGTTTTC
GCCCCGAAGAACGTTTTCCAATGATGAGCACTTTTAAAGTTCTGCTATGTGGCGCGG
TATTATCCCGTATTGACGCCGGGCAAGAGCAACTCGGTCGCCGCATACACTATTCTC
AGAATGACTTGGTTGAGTACTCACCAGTCACAGAAAAGCATCTTACGGATGGCATG
ACAGTAAGAGAATTATGCAGTGCTGCCATAACCATGAGTGATAACACTGCGGCCAA
CTTACTTCTGACAACGATCGGAGGACCGAAGGAGCTAACCGCTTTTTTGCACAACAT
GGGGGATCATGTAACTCGCCTTGATCGTTGGGAACCGGAGCTGAATGAAGCCATAC
CAAACGACGAGCGTGACACCACGATGCCTGTAGCAATGGCAACAACGTTGCGCAAA
CTATTAACTGGCGAACTACTTACTCTAGCTTCCCGGCAACAATTAATAGACTGGATG
GAGGCGGATAAAGTTGCAGGACCACTTCTGCGCTCGGCCCTTCCGGCTGGCTGGTTT
ATTGCTGATAAATCTGGAGCCGGTGAGCGTGGGTCTCGCGGTATCATTGCAGCACTG
GGGCCAGATGGTAAGCCCTCCCGTATCGTAGTTATCTACACGACGGGGAGTCAGGC
AACTATGGATGAACGAAATAGACAGATCGCTGAGATAGGTGCCTCACTGATTAAGC
ATTGGTAACTGTCAGACCAAGTTTACTCATATATACTTTAGATTGATTTAAAACTTCA
TTTTTAATTTAAAAGGATCTAGGTGAAGATCCTTTTTGATAATCTCATGACCAAAATC
CCTTAACGTGAGTTTTCGTTCCACTGAGCGTCAGACCCCGTAGAAAAGATCAAAGGA
TCTTCTTGAGATCCTTTTTTTCTGCGCGTAATCTGCTGCTTGCAAACAAAAAAACCAC
CGCTACCAGCGGTGGTTTGTTTGCCGGATCAAGAGCTACCAACTCTTTTTCCGAAGG
TAACTGGCTTCAGCAGAGCGCAGATACCAAATACTGTCCTTCTAGTGTAGCCGTAGT
TAGGCCACCACTTCAAGAACTCTGTAGCACCGCCTACATACCTCGCTCTGCTAATCC
TGTTACCAGTGGCTGCTGCCAGTGGCGATAAGTCGTGTCTTACCGGGTTGGACTCAA
GACGATAGTTACCGGATAAGGCGCAGCGGTCGGGCTGAACGGGGGGTTCGTGCACA
CAGCCCAGCTTGGAGCGAACGACCTACACCGAACTGAGATACCTACAGCGTGAGCA
TTGAGAAAGCGCCACGCTTCCCGAAGGGAGAAAGGCGGACAGGTATCCGGTAAGCG
GCAGGGTCGGAACAGGAGAGCGCACGAGGGAGCTTCCAGGGGGAAACGCCTGGTA
TCTTTATAGTCCTGTCGGGTTTCGCCACCTCTGACTTGAGCGTCGATTTTTGTGATGC
TCGTCAGGGGGCGGAGCCTATGGAAAAACGCCAGCAACGCGGCCTTTTTACGGTT
CCTGGCCTTTTGCTGGCCTTTTGCTCACATGCTGGGCCCAGCCGGCCAGATCTGAGC
TCGCGGCCGCGATATCGCTAGCTCGAGGTCCGTTACATAACTTACGGTAAATGGCCC
GCCTGGCTGACCGCCCAACGACCCCCGCCCATTGACGTCAATAATGACGTATGTTCC
CATAGTAACGCCAATAGGGACTTTCCATTGACGTCAATGGGTGGAGTATTTACGGTA
AACTGCCCACTTGGCAGTACATCAAGTGTATCATATGCCAAGTACGCCCCCTATTGA
CGTCAATGACGGTAAATGGCCCGCCTGGCATTATGCCCAGTACATGACCTTATGGGA
CTTTCCTACTTGGCAGTACATCTACGTATTAGTCATCGCTATTACCATGGTGATGCGG
TTTTGGCAGTACATCAATGGGCGTGGATAGCGGTTTGACTCACGGGGATTTCCAAGT
CTCCACCCCATTGACGTCAATGGGAGTTTGTTTTGGCACCAAAATCAACGGGACTTT
CCAAAATGTCGTAACAACTCCGCCCCATTGACGCAAATGGGCGGTAGGCGTGTACG
GTGGGAGGTCTATATAAGCAGAGCTCGTTTAGTGAACCGTCAGATCGCCTGGAGAC
GCCATCCACGCTGTTTTGACCTCCATAGAAGACACCGGGACCGATCCAGCCTCCGCG
GCCGGGAACGGTGCATTGGAACGGACCGTGTTGACAATTAATCATCGGCATAGTAT
ATCGGCATAGTATAATACGACAAGGTGAGGAACTAAACCATGGCCAAGCCTTTGTC
```

FIG. 34B

```
TCAAGAAGAATCCACCCTCATTGAAAGAGCAACGGCTACAATCAACAGCATCCCCA
TCTCTGAAGACTACAGCGTCGCCAGCGCAGCTCTCTCTAGCGACGGCCGCATCTTCA
CTGGTGTCAATGTATATCATTTTACTGGGGGACCTTGTGCAGAACTCGTGGTGCTGG
GCACTGCTGCTGCTGCGGCAGCTGGCAACCTGACTTGTATCGTCGCGATCGGAAATG
AGAACAGGGGCATCTTGAGCCCCTGCGGACGGTGCCGACAGGTGCTTCTCGATCTG
CATCCTGGGATCAAAGCCATAGTGAAGGACAGTGATGGACAGCCGACGGCAGTTGG
GATTCGTGAATTGCTGCCCTCTGGTTATGTGTGGGAGGGCTAAGCACTTCGTGGCCG
AGGAGCAGGACTGACACTCGACCTCGAAACTTGTTTATTGCAGCTTATAATGGTTAC
AAATAAAGCAATAGCATCACAAATTTCACAAATAAAGCATTTTTTTCACTGCATTCT
AGTTGTGGTTTGTCCAAACTCATCAATGTATCTTATCATGTCTGAATTCCCGGGGATC
CTCTAGTACCGTTCGTATATGGTTTCTTATACGAAGTTATC
```

FIG. 34C pFEX (SEQ ID NO:6)

```
TAAGGATCCNNNCCTGTCCTCGACCGATGCCCTTGAGAGCCTTCAACCCAGTCAGCT
CCTTCCGGTGGGCGCGGGGCATGACTATCGTCGCCGCACTTATGACTGTCTTCTTTAT
CATGCAACTCGTAGGACAGGTGCCGGCAGCGCTCTGGGTCATTTTCGGCGAGGACC
GCTTTCGCTGGAGCGCGACGATGATCGGCCTGTCGCTTGCGGTATTCGGAATCTTGC
ACGCCCTCGCTCAAGCCTTCGTCACTGGTCCCGCCACCAAACGTTTCGGCGAGAAGC
AGGCCATTATCGCCGGCATGGCGGCCGACGCGCTGGGCTACGTCTTGCTGGCGTTCG
CGACGCGAGGCTGGATGGCCTTCCCCATTATGATTCTTCTCGCTTCCGGCGGCATCG
GGATGCCCGCGTTGCAGGCCATGCTGTCCAGGCAGGTAGATGACGACCATCAGGGA
CAGCTTCAAGGATCGCTCGCGGCTCTTACCAGCCTAACTTCGATCACTGGACCGCTG
ATCGTCACGGCGATTTATGCCGCCTCGGCGAGCACATGGAACGGGTTGGCATGGATT
GTAGGCGCCGCCCTATACCTTGTCTGCCTCCCCGCGTTGCGTCGCGGTGCATGGAGC
CGGGCCACCTCGACCTGAATGGAAGCCGGCGGCACCTCGCTAACGGATTCACCACT
CCAAGAATTGGAGCCAATCAATTCTTGCGGAGAACTGTGAATGCGCAAACCAACCC
TTGGCAGAACATATCCATCGCGTCCGCCATCTCCAGCAGCCGCACGCGGCGCATCTC
GGGCAGCGTTGGGTCCTGGCCACGGGTGCGCATGATCGTGCTCCTGTCGTTGAGGAC
CCGGCTAGGCTGGCGGGGTTGCCTTACTGGTTAGCAGAATGAATCACCGATACGCG
AGCGAACGTGAAGCGACTGCTGCTGCAAAACGTCTGCGACCTGAGCAACAACATGA
ATGGTCTTCGGTTTCCGTGTTTCGTAAAGTCTGGAAACGCGGAAGTCAGCGCCCTGC
ACCATTATGTTCCGGATCTGCATCGCAGGATGCTGCTGGCTACCCTGTGGAACACCT
ACATCTGTATTAACGAAGCGCTGGCATTGACCCTGAGTGATTTTTCTCTGGTCCCGCC
GCATCCATACCGCCAGTTGTTTACCCTCACAACGTTCCAGTAACCGGGCATGTTCAT
CATCAGTAACCCGTATCGTGAGCATCCTCTCTCGTTTCATCGGTATCATTACCCCCAT
GAACAGAAATTCCCCCTTACACGGAGGCATCAAGTGACCAAACAGGAAAAAACCGC
CCTTAACATGGCCCGCTTTATCAGAAGCCAGACATTAACGCTTCTGGAGAAACTCAA
CGAGCTGGACGCGGATGAACAGGCAGACATCTGTGAATCGCTTCACGACCACGCTG
ATGAGCTTTACCGCAGCTGCCTCGCGCGTTTCGGTGATGACGGTGAAAACCTCTGAC
ACATGCAGCTCCCGGAGACGGTCACAGCTTGTCTGTAAGCGGATGCCGGGAGCAGA
CAAGCCCGTCAGGGCGCGTCAGCGGGTGTTGGCGGGTGTCGGGGCGCAGCCATGAC
CCAGTCACGTAGCGATAGCGGAGTGTATACTGGCTTAACTATGCGGCATCAGAGCA
GATTGTACTGAGAGTGCACCATATGCGGTGTGAAATACCGCACAGATGCGTAAGGA
GAAAATACCGCATCAGGCGCTCTTCCGCTTCCTCGCTCACTGACTCGCTGCGCTCGG
TCGTTCGGCTGCGGCGAGCGGTATCAGCTCACTCAAAGGCGGTAATACGGTTATCCA
CAGAATCAGGGGATAACGCAGGAAAGAACATGTGAGCAAAAGGCCAGCAAAAGGC
CAGGAACCGTAAAAAGGCCGCGTTGCTGGCGTTTTTCCATAGGCTCCGCCCCCCTGA
CGAGCATCACAAAAATCGACGCTCAAGTCAGAGGTGGCGAAACCCGACAGGACTAT
AAAGATACCAGGCGTTTCCCCCTGGAAGCTCCCTCGTGCGCTCTCCTGTTCCGACCC
TGCCGCTTACCGGATACCTGTCCGCCTTTCTCCCTTCGGGAAGCGTGGCGCTTTCTCA
ATGCTCACGCTGTAGGTATCTCAGTTCGGTGTAGGTCGTTCGCTCCAAGCTGGGCTG
TGTGCACGAACCCCCCGTTCAGCCCGACCGCTGCGCCTTATCCGGTAACTATCGTCT
TGAGTCCAACCCGGTAAGACACGACTTATCGCCACTGGCAGCAGCCACTGGTAACA
GGATTAGCAGAGCGAGGTATGTAGGCGGTGCTACAGAGTTCTTGAAGTGGTGGCCT
```

FIG. 35A

```
AACTACGGCTACACTAGAAGGACAGTATTTGGTATCTGCGCTCTGCTGAAGCCAGTT
ACCTTCGGAAAAAGAGTTGGTAGCTCTTGATCCGGCAAACAAACCACCGCTGGTAG
CGGTGGTTTTTTTGTTTGCAAGCAGCAGATTACGCGCAGAAAAAAAGGATCTCAAGA
AGATCCTTTGATCTTTTCTACGGGGTCTGACGCTCAGTGGAACGAAAACTCACGTTA
AGGGATTTTGGTCATGAGATTATCAAAAAGGATCTTCACCTAGATCCTTTTAAATTA
AAAATGAAGTTTTAAATCAATCTAAAGTATATATGAGTAAACTTGGTCTGACAGTTA
CCAATGCTTAATCAGTGAGGCACCTATCTCAGCGATCTGTCTATTTCGTTCATCCATA
GTTGCCTGACTCCCCGTCGTGTAGATAACTACGATACGGGAGGGCTTACCATCTGGC
CCCAGTGCTGCAATGATACCGCGAGACCCACGCTCACCGGCTCCAGATTTATCAGCA
ATAAACCAGCCAGCCGGAAGGGCCGAGCGCAGAAGTGGTCCTGCAACTTTATCCGC
CTCCATCCAGTCTATTAATTGTTGCCGGGAAGCTAGAGTAAGTAGTTCGCCAGTTAA
TAGTTTGCGCAACGTTGTTGCCATTGCTGCAGGCATCGTGGTGTCACGCTCGTCGTTT
GGTATGGCTTCATTCAGCTCCGGTTCCCAACGATCAAGGCGAGTTACATGATCCCCC
ATGTTGTGCAAAAAAGCGGTTAGCTCCTTCGGTCCTCCGATCGTTGTCAGAAGTAAG
TTGGCCGCAGTGTTATCACTCATGGTTATGGCAGCACTGCATAATTCTCTTACTGTCA
TGCCATCCGTAAGATGCTTTTCTGTGACTGGTGAGTACTCAACCAAGTCATTCTGAG
AATAGTGTATGCGGCGACCGAGTTGCTCTTGCCCGGCGTCAACACGGGATAATACCG
CGCCACATAGCAGAACTTTAAAAGTGCTCATCATTGGAAAACGTTCTTCGGGGCGAA
AACTCTCAAGGATCTTACCGCTGTTGAGATCCAGTTCGATGTAACCCACTCGTGCAC
CCAACTGATCTTCAGCATCTTTTACTTTCACCAGCGTTTCTGGGTGAGCAAAAACAG
GAAGGCAAAATGCCGCAAAAAAGGGAATAAGGGCGACACGGAAATGTTGAATACT
CATACTCTTCCTTTTTCAATATTATTGAAGCATTTATCAGGGTTATTGTCTCATGAGC
GGATACATATTTGAATGTATTTAGAAAAATAAACAAATAGGGGTTCCGCGCACATTT
CCCCGAAAAGTGCCACCTGNNNGAATTCGAATCTAGTATCGATTCGAANNNCTTAA
GGGTGGGAAAGAATATATAAGGTGGGGGTCTTATGTAGTTTTGTATCTGTTTTGCAG
CAGCCGCCGCCGCCATGAGCACCAACTCGTTTGATGGAAGCATTGTGAGCTCATATT
TGACAACGCGCATGCCCCCATGGGCCGGGGTGCGTCAGAATGTGATGGGCTCCAGC
ATTGATGGTCGCCCCGTCCTGCCCGCAAACTCTACTACCTTGACCTACGAGACCGTG
TCTGGAACGCCGTTGGAGACTGCAGCCTCCGCCGCCGCTTCAGCCGCTGCAGCCACC
GCCCGCGGGATTGTGACTGACTTTGCTTTCCTGAGCCCGCTTGCAAGCAGTGCAGCT
TCCCGTTCATCCGCCCGCGATGACAAGTTGACGGCTCTTTTGGCACAATTGGATTCTT
TGACCCGGGAACTTAATGTCGTTTCTCAGCAGCTGTTGGATCTGCGCCAGCAGGTTT
CTGCCCTGAAGGCTTCCTCCCCTCCCAATGCGGTTTAAAACATAAATAAAAAACCAG
ACTCTGTTTGGATTTGGATCAAGCAAGTGTCTTGCTGTCTTTATTTAGGGGTTTTGCG
CGCGCGGTAGGCCCGGGACCAGCGGTCTCGGTCGTTGAGGGTCCTGTGTATTTTTTC
CAGGACGTGGTAAAGGTGACTCTGGATGTTCAGATACATGGGCATAAGCCCGTCTCT
GGGGTGGAGGTAGCACCACTGCAGAGCTTCATGCTGCGGGGTGGTGTTGTAGATGA
TCCAGTCGTAGCAGGAGCGCTGGGCGTGGTGCCTAAAAATGTCTTTCAGTAGCAAGC
TGATTGCCAGGGGCAGGCCCTTGGTGTAAGTGTTTACAAAGCGGTTAAGCTGGGATG
GGTGCATACGTGGGGATATGAGATGCATCTTGGACTGTATTTTTAGGTTGGCTATGT
TCCCAGCCATATCCCTCCGGGGATTCATGTTGTGCAGAACCACCAGCACAGTGTATC
CGGTGCACTTGGGAAATTTGTCATGTAGCTTAGAAGGAAATGCGTGGAAGAACTTG
GAGACGCCCTTGTGACCTCCAAGATTTTCCATGCATTCGTCCATAATGATGGCAATG
GGCCCACGGGCGGCGGCCTGGGCGAAGATATTTCTGGGATCACTAACGTCATAGTT
```

FIG. 35B

```
GTGTTCCAGGATGAGATCGTCATAGGCCATTTTTACAAAGCGCGGGCGGAGGGTGC
CAGACTGCGGTATAATGGTTCCATCCGGCCCAGGGGCGTAGTTACCCTCACAGATTT
GCATTTCCCACGCTTTGAGTTCAGATGGGGGGATCATGTCTACCTGCGGGGCGATGA
AGAAAACGGTTTCCGGGGTAGGGGAGATCAGCTGGGAAGAAAGCAGGTTCCTGAGC
AGCTGCGACTTACCGCAGCCGGTGGGCCCGTAAATCACACCTATTACCGGGTGCAA
CTGGTAGTTAAGAGAGCTGCAGCTGCCGTCATCCCTGAGCAGGGGGGCCACTTCGTT
AAGCATGTCCCTGACTCGCATGTTTTCCCTGACCAAATCCGCCAGAAGGCGCTCGCC
GCCCAGCGATAGCAGTTCTTGCAAGGAAGCAAAGTTTTTCAACGGTTTGAGACCGTC
CGCCGTAGGCATGCTTTTGAGCGTTTGACCAAGCAGTTCCAGGCGGTCCCACAGCTC
GGTCACCTGCTCTACGGCATCTCGATCCAGCATATCTCCTCGTTTCGCGGGTTGGGG
CGGCTTTCGCTGTACGGCAGTAGTCGGTGCTCGTCCAGACGGGCCAGGGTCATGTCT
TTCCACGGGCGCAGGGTCCTCGTCAGCGTAGTCTGGGTCACGGTGAAGGGGTGCGCT
CCGGGCTGCGCGCTGGCCAGGGTGCGCTTGAGGCTGGTCCTGCTGGTGCTGAAGCG
CTGCCGGTCTTCGCCCTGCGCGTCGGCCAGGTAGCATTTGACCATGGTGTCATAGTC
CAGCCCCTCCGCGGCGTGGCCCTTGGCGCGCAGCTTGCCCTTGGAGGAGGCGCCGC
ACGAGGGGCAGTGCAGACTTTTGAGGGCGTAGAGCTTGGGCGCGAGAAATACCGAT
TCCGGGGAGTAGGCATCCGCGCCGCAGGCCCCGCAGACGGTCTCGCATTCCACGAG
CCAGGTGAGCTCTGGCCGTTCGGGGTCAAAAACCAGGTTTCCCCCATGCTTTTTGAT
GCGTTTCTTACCTCTGGTTTCCATGAGCCGGTGTCCACGCTCGGTGACGAAAAGGCT
GTCCGTGTCCCCGTATACAGACTTGAGAGGCCTGTCCTCGAGCGGTGTTCCGCGGTC
CTCCTCGTATAGAAACTCGGACCACTCTGAGACAAAGGCTCGCGTCCAGGCCAGCA
CGAAGGAGGCTAAGTGGGAGGGGTAGCGGTCGTTGTCCACTAGGGGGTCCACTCGC
TCCAGGGTGTGAAGACACATGTCGCCCTCTTCGGCATCAAGGAAGGTGATTGGTTTG
TAGGTGTAGGCCACGTGACCGGGTGTTCCTGAAGGGGGGCTATAAAAGGGGGTGGG
GGCGCGTTCGTCCTCACTCTCTTCCGCATCGCTGTCTGCGAGGGCCAGCTGTTGGGG
TGAGTACTCCCTCTGAAAAGCGGGCATGACTTCTGCGCTAAGATTGTCAGTTTCCAA
AAACGAGGAGGATTTGATATTCACCTGGCCCGCGGTGATGCCTTTGAGGGTGGCCGC
ATCCATCTGGTCAGAAAAGACAATCTTTTTGTTGTCAAGCTTGGTGGCAAACGACCC
GTAGAGGGCGTTGGACAGCAACTTGGCGATGGAGCGCAGGGTTTGGTTTTTGTCGCG
ATCGGCGCGCTCCTTGGCCGCGATGTTTAGCTGCACGTATTCGCGCGCAACGCACCG
CCATTCGGGAAAGACGGTGGTGCGCTCGTCGGGCACCAGGTGCACGCGCCAACCGC
GGTTGTGCAGGGTGACAAGGTCAACGCTGGTGGCTACCTCTCCGCGTAGGCGCTCGT
TGGTCCAGCAGAGGCGGCCGCCCTTGCGCGAGCAGAATGGCGGTAGGGGTCTAGC
TGCGTCTCGTCCGGGGGTCTGCGTCCACGGTAAAGACCCCGGGCAGCAGGCGCGC
GTCGAAGTAGTCTATCTTGCATCCTTGCAAGTCTAGCGCCTGCTGCCATGCGCGGGC
GGCAAGCGCGCGCTCGTATGGGTTGAGTGGGGGACCCCATGGCATGGGGTGGGTGA
GCGCGGAGGCGTACATGCCGCAAATGTCGTAAACGTAGAGGGGCTCTCTGAGTATT
CCAAGATATGTAGGGTAGCATCTTCCACCGCGGATGCTGGCGCGCACGTAATCGTAT
AGTTCGTGCGAGGGAGCGAGGAGGTCGGGACCGAGGTTGCTACGGGCGGGCTGCTC
TGCTCGGAAGACTATCTGCCTGAAGATGGCATGTGAGTTGGATGATATGGTTGGACG
CTGGAAGACGTTGAAGCTGGCGTCTGTGAGACCTACCGCGTCACGCACGAAGGAGG
CGTAGGAGTCGCGCAGCTTGTTGACCAGCTCGGCGGTGACCTGCACGTCTAGGGCG
CAGTAGTCCAGGGTTTCCTTGATGATGTCATACTTATCCTGTCCCTTTTTTTTCCACA
```

FIG. 35C

```
GCTCGCGGTTGAGGACAAACTCTTCGCGGTCTTTCCAGTACTCTTGGATCGGAAACC
CGTCGGCCTCCGAACGGTAAGAGCCTAGCATGTAGAACTGGTTGACGGCCTGGTAG
GCGCAGCATCCCTTTTCTACGGGTAGCGCGTATGCCTGCGCGGCCTTCCGGAGCGAG
GTGTGGGTGAGCGCAAAGGTGTCCCTGACCATGACTTTGAGGTACTGGTATTTGAAG
TCAGTGTCGTCGCATCCGCCCTGCTCCCAGAGCAAAAAGTCCGTGCGCTTTTTGGAA
CGCGGATTTGGCAGGGCGAAGGTGACATCGTTGAAGAGTATCTTTCCCGCGCGAGG
CATAAAGTTGCGTGTGATGCGGAAGGGTCCCGGCACCTCGGAACGGTTGTTAATTAC
CTGGGCGGCGAGCACGATCTCGTCAAAGCCGTTGATGTTGTGGCCCACAATGTAAA
GTTCCAAGAAGCGCGGGATGCCCTTGATGGAAGGCAATTTTTAAGTTCCTCGTAGG
TGAGCTCTTCAGGGGAGCTGAGCCCGTGCTCTGAAAGGGCCCAGTCTGCAAGATGA
GGGTTGGAAGCGACGAATGAGCTCCACAGGTCACGGGCCATTAGCATTTGCAGGTG
GTCGCGAAAGGTCCTAAACTGGCGACCTATGGCCATTTTTTCTGGGGTGATGCAGTA
GAAGGTAAGCGGGTCTTGTTCCCAGCGGTCCCATCCAAGGTTCGCGGCTAGGTCTCG
CGCGGCAGTCACTAGAGGCTCATCTCCGCCGAACTTCATGACCAGCATGAAGGGCA
CGAGCTGCTTCCCAAAGGCCCCCATCCAAGTATAGGTCTCTACATCGTAGGTGACAA
AGAGACGCTCGGTGCGAGGATGCGAGCCGATCGGGAAGAACTGGATCTCCCGCCAC
CAATTGGAGGAGTGGCTATTGATGTGGTGAAAGTAGAAGTCCCTGCGACGGGCCGA
ACACTCGTGCTGGCTTTTGTAAAAACGTGCGCAGTACTGGCAGCGGTGCACGGGCTG
TACATCCTGCACGAGGTTGACCTGACGACCGCGCACAAGGAAGCAGAGTGGGAATT
TGAGCCCCTCGCCTGGCGGGTTTGGCTGGTGGTCTTCTACTTCGGCTGCTTGTCCTTG
ACCGTCTGGCTGCTCGAGGGGAGTTACGGTGGATCGGACCACCACGCCGCGCGAGC
CCAAAGTCCAGATGTCCGCGCGCGGCGGTCGGAGCTTGATGACAACATCGCGCAGA
TGGGAGCTGTCCATGGTCTGGAGCTCCCGCGGCGTCAGGTCAGGCGGGAGCTCCTG
CAGGTTTACCTCGCATAGACGGGTCAGGGCGCGGGCTAGATCCAGGTGATACCTAA
TTTCCAGGGGCTGGTTGGTGGCGGCGTCGATGGCTTGCAAGAGGCCGCATCCCCGCG
GCGCGACTACGGTACCGCGCGGCGGGCGGTGGGCCGCGGGGGTGTCCTTGGATGAT
GCATCTAAAAGCGGTGACGCGGGCGAGCCCCCGGAGGTAGGGGGGGCTCCGGACCC
GCCGGGAGAGGGGGCAGGGGCACGTCGGCGCCGCGCGCGGGCAGGAGCTGGTGCT
GCGCGCGTAGGTTGCTGGCGAACGCGACGACGCGGCGGTTGATCTCCTGAATCTGG
CGCCTCTGCGTGAAGACGACGGGCCCGGTGAGCTTGAGCCTGAAAGAGAGTTCGAC
AGAATCAATTTCGGTGTCGTTGACGGCGGCCTGGCGCAAAATCTCCTGCACGTCTCC
TGAGTTGTCTTGATAGGCGATCTCGGCCATGAACTGCTCGATCTCTTCCTCCTGGAG
ATCTCCGCGTCCGGCTCGCTCCACGGTGGCGGCGAGGTCGTTGGAAATGCGGGCCAT
GAGCTGCGAGAAGGCGTTGAGGCCTCCCTCGTTCCAGACGCGGCTGTAGACCACGC
CCCCTTCGGCATCGCGGGCGCGCATGACCACCTGCGCGAGATTGAGCTCCACGTGCC
GGGCGAAGACGGCGTAGTTTCGCAGGCGCTGAAAGAGGTAGTTGAGGGTGGTGGCG
GTGTGTTCTGCCACGAAGAAGTACATAACCCAGCGTCGCAACGTGGATTCGTTGATA
TCCCCCAAGGCCTCAAGGCGCTCCATGGCCTCGTAGAAGTCCACGGCGAAGTTGAA
AAACTGGGAGTTGCGCGCCGACACGGTTAACTCCTCCTCCAGAAGACGGATGAGCT
CGGCGACAGTGTCGCGCACCTCGCGCTCAAAGGCTACAGGGGCCTCTTCTTCTTCTT
CAATCTCCTCTTCCATAAGGGCCTCCCCTTCTTCTTCTTCTGGCGGCGGTGGGGGAGG
GGGACACGGCGGCGACGACGGCGCACCGGGAGGCGGTCGACAAAGCGCTCGATC
ATCTCCCCGCGGCGACGGCGCATGGTCTCGGTGACGGCGCGGCCGTTCTCGCGGGG
```

FIG. 35D

```
GCGCAGTTGGAAGACGCCGCCCGTCATGTCCCGGTTATGGGTTGGCGGGGGGCTGC
CATGCGGCAGGGATACGGCGCTAACGATGCATCTCAACAATTGTTGTGTAGGTACTC
CGCCGCCGAGGGACCTGAGCGAGTCCGCATCGACCGGATCGGAAAACCTCTCGAGA
AAGGCGTCTAACCAGTCACAGTCGCAAGGTAGGCTGAGCACCGTGGCGGGCGGCAG
CGGGCGGCGGTCGGGGTTGTTTCTGGCGGAGGTGCTGCTGATGATGTAATTAAAGTA
GGCGGTCTTGAGACGGCGGATGGTCGACAGAAGCACCATGTCCTTGGGTCCGGCCT
GCTGAATGCGCAGGCGGTCGGCCATGCCCCAGGCTTCGTTTTGACATCGGCGCAGGT
CTTTGTAGTAGTCTTGCATGAGCCTTTCTACCGGCACTTCTTCTTCTCCTTCCTCTTGT
CCTGCATCTCTTGCATCTATCGCTGCGGCGGCGGCGGAGTTTGGCCGTAGGTGGCGC
CCTCTTCCTCCCATGCGTGTGACCCCGAAGCCCCTCATCGGCTGAAGCAGGGCTAGG
TCGGCGACAACGCGCTCGGCTAATATGGCCTGCTGCACCTGCGTGAGGGTAGACTG
GAAGTCATCCATGTCCACAAAGCGGTGGTATGCGCCCGTGTTGATGGTGTAAGTGCA
GTTGGCCATAACGGACCAGTTAACGGTCTGGTGACCCGGCTGCGAGAGCTCGGTGT
ACCTGAGACGCGAGTAAGCCCTCGAGTCAAATACGTAGTCGTTGCAAGTCCGCACC
AGGTACTGGTATCCCACCAAAAAGTGCGGCGGCGGCTGGCGGTAGAGGGGCCAGCG
TAGGGTGGCCGGGGCTCCGGGGGCGAGATCTTCCAACATAAGGCGATGATATCCGT
AGATGTACCTGGACATCCAGGTGATGCCGGCGGCGGTGGTGGAGGCGCGCGGAAAG
TCGCGGACGCGGTTCCAGATGTTGCGCAGCGGCAAAAAGTGCTCCATGGTCGGGAC
GCTCTGGCCGGTCAGGCGCGCGCAATCGTTGACGCTCTACCGTGCAAAAGGAGAGC
CTGTAAGCGGGCACTCTTCCGTGGTCTGGTGGATAAATTCGCAAGGGTATCATGGCG
GACGACCGGGGTTCGAGCCCCGTATCCGGCCGTCCGCCGTGATCCATGCGGTTACCG
CCCGCGTGTCGAACCCAGGTGTGCGACGTCAGACAACGGGGGAGTGCTCCTTTTGG
CTTCCTTCCAGGCGCGGCGGCTGCTGCGCTAGCTTTTTTGGCCACTGGCCGCGCGCA
GCGTAAGCGGTTAGGCTGGAAAGCGAAAGCATTAAGTGGCTCGCTCCCTGTAGCCG
GAGGGTTATTTTCCAAGGGTTGAGTCGCGGGACCCCCGGTTCGAGTCTCGGACCGGC
CGGACTGCGGCGAACGGGGGTTTGCCTCCCCGTCATGCAAGACCCCGCTTGCAAATT
CCTCCGGAAACAGGGACGAGCCCCTTTTTTGCTTTTCCCAGATGCATCCGGTGCTGC
GGCAGATGCGCCCCCCTCCTCAGCAGCGGCAAGAGCAAGAGCAGCGGCAGACATGC
AGGGCACCCTCCCCTCCTCCTACCGCGTCAGGAGGGGCGACATCCGCGGTTGACGC
GGCAGCAGATGGTGATTACGAACCCCCGCGGCGCCGGGCCCGGCACTACCTGGACT
TGGAGGAGGGCGAGGGCCTGGCGCGGCTAGGAGCGCCCTCTCCTGAGCGGTACCCA
AGGGTGCAGCTGAAGCGTGATACGCGTGAGGCGTACGTGCCGCGGCAGAACCTGTT
TCGCGACCGCGAGGGAGAGGAGCCCGAGGAGATGCGGGATCGAAAGTTCCACGCA
GGGCGCGAGCTGCGGCATGGCCTGAATCGCGAGCGGTTGCTGCGCGAGGAGGACTT
TGAGCCCGACGCGCGAACCGGGATTAGTCCCGCGCGCGCACACGTGGCGGCCGCCG
ACCTGGTAACCGCATACGAGCAGACGGTGAACCAGGAGATTAACTTTCAAAAAAGC
TTTAACAACCACGTGCGTACGCTTGTGGCGCGCGAGGAGGTGGCTATAGGACTGAT
GCATCTGTGGGACTTTGTAAGCGCGCTGGAGCAAAACCCAAATAGCAAGCCGCTCA
TGGCGCAGCTGTTCCTTATAGTGCAGCACAGCAGGGACAACGAGGCATTCAGGGAT
GCGCTGCTAAACATAGTAGAGCCCGAGGGCCGCTGGCTGCTCGATTTGATAAACATC
CTGCAGAGCATAGTGGTGCAGGAGCGCAGCTTGAGCCTGGCTGACAAGGTGGCCGC
CATCAACTATTCCATGCTTAGCCTGGGCAAGTTTTACGCCCGCAAGATATACCATAC
CCCTTACGTTCCCATAGACAAGGAGGTAAAGATCGAGGGGTTCTACATGCGCATGG
```

FIG. 35E

```
CGCTGAAGGTGCTTACCTTGAGCGACGACCTGGGCGTTTATCGCAACGAGCGCATCC
ACAAGGCCGTGAGCGTGAGCCGGCGGCGCGAGCTCAGCGACCGCGAGCTGATGCAC
AGCCTGCAAAGGGCCCTGGCTGGCACGGGCAGCGGCGATAGAGAGGCCGAGTCCTA
CTTTGACGCGGGCGCTGACCTGCGCTGGGCCCCAAGCCGACGCGCCCTGGAGGCAG
CTGGGGCCGGACCTGGGCTGGCGGTGGCACCCGCGCGCGCTGGCAACGTCGGCGGC
GTGGAGGAATATGACGAGGACGATGAGTACGAGCCAGAGGACGGCGAGTACTAAG
CGGTGATGTTTCTGATCAGATGATGCAAGACGCAACGGACCCGGCGGTGCGGGCGG
CGCTGCAGAGCCAGCCGTCCGGCCTTAACTCCACGGACGACTGGCGCCAGGTCATG
GACCGCATCATGTCGCTGACTGCGCGCAATCCTGACGCGTTCCGGCAGCAGCCGCA
GGCCAACCGGCTCTCCGCAATTCTGGAAGCGGTGGTCCCGGCGCGCGCAAACCCCA
CGCACGAGAAGGTGCTGGCGATCGTAAACGCGCTGGCCGAAAACAGGGCCATCCGG
CCCGACGAGGCCGGCCTGGTCTACGACGCGCTGCTTCAGCGCGTGGCTCGTTACAAC
AGCGGCAACGTGCAGACCAACCTGGACCGGCTGGTGGGGATGTGCGCGAGGCCGT
GGCGCAGCGTGAGCGCGCGCAGCAGCAGGGCAACCTGGGCTCCATGGTTGCACTAA
ACGCCTTCCTGAGTACACAGCCCGCCAACGTGCCGCGGGGACAGGAGGACTACACC
AACTTTGTGAGCGCACTGCGGCTAATGGTGACTGAGACACCGCAAAGTGAGGTGTA
CCAGTCTGGGCCAGACTATTTTTTCCAGACCAGTAGACAAGGCCTGCAGACCGTAAA
CCTGAGCCAGGCTTTCAAAAACTTGCAGGGGCTGTGGGGGGTGCGGGCTCCCACAG
GCGACCGCGCGACCGTGTCTAGCTTGCTGACGCCCAACTCGCGCCTGTTGCTGCTGC
TAATAGCGCCCTTCACGGACAGTGGCAGCGTGTCCCGGGACACATACCTAGGTCACT
TGCTGACACTGTACCGCGAGGCCATAGGTCAGGCGCATGTGGACGAGCATACTTTCC
AGGAGATTACAAGTGTCAGCCGCGCGCTGGGGCAGGAGGACACGGGCAGCCTGGA
GGCAACCCTAAACTACCTGCTGACCAACCGGCGGCAGAAGATCCCCTCGTTGCACA
GTTTAAACAGCGAGGAGGAGCGCATTTTGCGCTACGTGCAGCAGAGCGTGAGCCTT
AACCTGATGCGCGACGGGGTAACGCCCAGCGTGGCGCTGGACATGACCGCGCGCAA
CATGGAACCGGGCATGTATGCCTCAAACCGGCCGTTTATCAACCGCCTAATGGACTA
CTTGCATCGCGCGGCCGCCGTGAACCCCGAGTATTTCACCAATGCCATCTTGAACCC
GCACTGGCTACCGCCCCCTGGTTTCTACACCGGGGGATTCGAGGTGCCCGAGGGTAA
CGATGGATTCCTCTGGGACGACATAGACGACAGCGTGTTTTCCCCGCAACCGCAGAC
CCTGCTAGAGTTGCAACAGCGCGAGCAGGCAGAGGCGGCGCTGCGAAAGGAAAGC
TTCCGCAGGCCAAGCAGCTTGTCCGATCTAGGCGCTGCGGCCCCGCGGTCAGATGCT
AGTAGCCCATTTCCAAGCTTGATAGGGTCTCTTACCAGCACTCGCACCACCCGCCCG
CGCCTGCTGGGCGAGGAGGAGTACCTAAACAACTCGCTGCTGCAGCCGCAGCGCGA
AAAAAACCTGCCTCCGGCATTTCCCAACAACGGGATAGAGAGCCTAGTGGACAAGA
TGAGTAGATGGAAGACGTACGCGCAGGAGCACAGGGACGTGCCAGGCCCGCGCCC
GCCCACCCGTCGTCAAAGGCACGACCGTCAGCGGGGTCTGGTGTGGGAGGACGATG
ACTCGGCAGACGACAGCAGCGTCCTGGATTTGGGAGGGAGTGGCAACCCGTTTGCG
CACCTTCGCCCCAGGCTGGGGAGAATGTTTTAAAAAAAAAAAAAGCATGATGCAAAA
TAAAAAACTCACCAAGGCCATGGCACCGAGCGTTGGTTTTCTTGTATTCCCCTTAGT
ATGCGGCGCGCGGCGATGTATGAGGAAGGTCCTCCTCCCTCCTACGAGAGTGTGGTG
AGCGCGGCGCCAGTGGCGGCGGCGCTGGGTTCTCCCTTCGATGCTCCCCTGGACCCG
CCGTTTGTGCCTCCGCGGTACCTGCGGCCTACCGGGGGAGAAACAGCATCCGTTAC
TCTGAGTTGGCACCCCTATTCGACACCACCCGTGTGTACCTGGTGGACAACAAGTCA
```

FIG. 35F

```
ACGGATGTGGCATCCCTGAACTACCAGAACGACCACAGCAACTTTCTGACCACGGT
CATTCAAAACAATGACTACAGCCCGGGGGAGGCAAGCACACAGACCATCAATCTTG
ACGACCGGTCGCACTGGGGCGGCGACCTGAAAACCATCCTGCATACCAACATGCCA
AATGTGAACGAGTTCATGTTTACCAATAAGTTTAAGGCGCGGGTGATGGTGTCGCGC
TTGCCTACTAAGGACAATCAGGTGGAGCTGAAATACGAGTGGGTGGAGTTCACGCT
GCCCGAGGGCAACTACTCCGAGACCATGACCATAGACCTTATGAACAACGCGATCG
TGGAGCACTACTTGAAAGTGGGCAGACAGAACGGGGTTCTGGAAAGCGACATCGGG
GTAAAGTTTGACACCCGCAACTTCAGACTGGGGTTTGACCCCGTCACTGGTCTTGTC
ATGCCTGGGGTATATACAAACGAAGCCTTCCATCCAGACATCATTTTGCTGCCAGGA
TGCGGGGTGGACTTCACCCACAGCCGCCTGAGCAACTTGTTGGGCATCCGCAAGCG
GCAACCCTTCCAGGAGGGCTTTAGGATCACCTACGATGATCTGGAGGGTGGTAACAT
TCCCGCACTGTTGGATGTGGACGCCTACCAGGCGAGCTTGAAAGATGACACCGAAC
AGGGCGGGGGTGGCGCAGGCGGCAGCAACAGCAGTGGCAGCGGCGCGGAAGAGAA
CTCCAACGCGGCAGCCGCGGCAATGCAGCCGGTGGAGGACATGAACGATCATGCCA
TTCGCGGCGACACCTTTGCCACACGGGCTGAGGAGAAGCGCGCTGAGGCCGAAGCA
GCGGCCGAAGCTGCCGCCCCCGCTGCGCAACCCGAGGTCGAGAAGCCTCAGAAGAA
ACCGGTGATCAAACCCCTGACAGAGGACAGCAAGAAACGCAGTTACAACCTAATAA
GCAATGACAGCACCTTCACCCAGTACCGCAGCTGGTACCTTGCATACAACTACGGCG
ACCCTCAGACCGGAATCCGCTCATGGACCCTGCTTTGCACTCCTGACGTAACCTGCG
GCTCGGAGCAGGTCTACTGGTCGTTGCCAGACATGATGCAAGACCCCGTGACCTTCC
GCTCCACGCGCCAGATCAGCAACTTTCCGGTGGTGGGCGCCGAGCTGTTGCCCGTGC
ACTCCAAGAGCTTCTACAACGACCAGGCCGTCTACTCCCAACTCATCCGCCAGTTTA
CCTCTCTGACCCACGTGTTCAATCGCTTTCCCGAGAACCAGATTTTGGCGCGCCCGC
CAGCCCCCACCATCACCACCGTCAGTGAAAACGTTCCTGCTCTCACAGATCACGGGA
CGCTACCGCTGCGCAACAGCATCGGAGGAGTCCAGCGAGTGACCATTACTGACGCC
AGACGCCGCACCTGCCCCTACGTTTACAAGGCCCTGGGCATAGTCTCGCCGCGCGTC
CTATCGAGCCGCACTTTTTGAGCAAGCATGTCCATCCTTATATCGCCCAGCAATAAC
ACAGGCTGGGGCCTGCGCTTCCCAAGCAAGATGTTTGGCGGGGCCAAGAAGCGCTC
CGACCAACACCCAGTGCGCGTGCGCGGGCACTACCGCGCGCCCTGGGGCGCGCACA
AACGCGGCCGCACTGGGCGCACCACCGTCGATGACGCCATCGACGCGGTGGTGGAG
GAGGCGCGCAACTACACGCCCACGCCGCCACCAGTGTCCACAGTGGACGCGGCCAT
TCAGACCGTGGTGCGCGGAGCCCGGCGCTATGCTAAAATGAAGAGACGGCGGAGGC
GCGTAGCACGTCGCCACCGCCGCCGACCCGGCACTGCCGCCCAACGCGCGGCGGCG
GCCCTGCTTAACCGCGCACGTCGCACCGGCCGACGGGCGGCCATGCGGGCCGCTCG
AAGGCTGGCCGCGGGTATTGTCACTGTGCCCCCAGGTCCAGGCGACGAGCGGCCG
CCGCAGCAGCCGCGGCCATTAGTGCTATGACTCAGGGTCGCAGGGGCAACGTGTAT
TGGGTGCGCGACTCGGTTAGCGGCCTGCGCGTGCCCGTGCGCACCCGCCCCCGCGC
AACTAGATTGCAAGAAAAAACTACTTAGACTCGTACTGTTGTATGTATCCAGCGGCG
GCGGCGCGCAACGAAGCTATGTCCAAGCGCAAAATCAAAGAAGAGATGCTCCAGGT
CATCGCGCCGGAGATCTATGGCCCCCCGAAGAAGGAAGAGCAGGATTACAAGCCCC
GAAAGCTAAAGCGGGTCAAAAAGAAAAAGAAAGATGATGATGATGAACTTGACGA
CGAGGTGGAACTGCTGCACGCTACCGCGCCCAGGCGACGGGTACAGTGGAAAGGTC
GACGCGTAAAACGTGTTTTGCGACCCGGCACCACCGTAGTCTTTACGCCCGGTGAGC
```

FIG. 35G

```
GCTCCACCCGCACCTACAAGCGCGTGTATGATGAGGTGTACGGCGACGAGGACCTG
CTTGAGCAGGCCAACGAGCGCCTCGGGGAGTTTGCCTACGGAAAGCGGCATAAGGA
CATGCTGGCGTTGCCGCTGGACGAGGGCAACCCAACACCTAGCCTAAAGCCCGTAA
CACTGCAGCAGGTGCTGCCCGCGCTTGCACCGTCCGAAGAAAAGCGCGGCCTAAAG
CGCGAGTCTGGTGACTTGGCACCCACCGTGCAGCTGATGGTACCCAAGCGCCAGCG
ACTGGAAGATGTCTTGGAAAAAATGACCGTGGAACCTGGGCTGGAGCCCGAGGTCC
GCGTGCGGCCAATCAAGCAGGTGGCGCCGGGACTGGGCGTGCAGACCGTGGACGTT
CAGATACCCACTACCAGTAGCACCAGTATTGCCACCGCCACAGAGGGCATGGAGAC
ACAAACGTCCCCGGTTGCCTCAGCGGTGGCGGATGCCGCGGTGCAGGCGGTCGCTG
CGGCCGCGTCCAAGACCTCTACGGAGGTGCAAACGGACCCGTGGATGTTTCGCGTTT
CAGCCCCCGGCGCCCGCGCGGTTCGAGGAAGTACGGCGCCGCCAGCGCGCTACTG
CCCGAATATGCCCTACATCCTTCCATTGCGCCTACCCCGGCTATCGTGGCTACACCT
ACCGCCCCAGAAGACGAGCAACTACCCGACGCCGAACCACCACTGGAACCCGCCGC
CGCCGTCGCCGTCGCCAGCCCGTGCTGGCCCCGATTTCCGTGCGCAGGGTGGCTCGC
GAAGGAGGCAGGACCCTGGTGCTGCCAACAGCGCGCTACCACCCCAGCATCGTTTA
AAAGCCGGTCTTTGTGGTTCTTGCAGATATGGCCCTCACCTGCCGCCTCCGTTTCCCG
GTGCCGGGATTCCGAGGAAGAATGCACCGTAGGAGGGGCATGGCCGGCCACGGCCT
GACGGGCGGCATGCGTCGTGCGCACCACCGGCGGCGGCGCGCGTCGCACCGTCGCA
TGCGCGGCGGTATCCTGCCCCTCCTTATTCCACTGATCGCCGCGGCGATTGGCGCCG
TGCCCGGAATTGCATCCGTGGCCTTGCAGGCGCAGAGACACTGATTAAAAACAAGT
TGCATGTGGAAAAATCAAAATAAAAAGTCTGGACTCTCACGCTCGCTTGGTCCTGTA
ACTATTTTGTAGAATGGAAGACATCAACTTTGCGTCTCTGGCCCCGCGACACGGCTC
GCGCCCGTTCATGGGAAACTGGCAAGATATCGGCACCAGCAATATGAGCGGTGGCG
CCTTCAGCTGGGGCTCGCTGTGGAGCGGCATTAAAAATTTCGGTTCCACCGTTAAGA
ACTATGGCAGCAAGGCCTGGAACAGCAGCACAGGCCAGATGCTGAGGGATAAGTTG
AAAGAGCAAAATTTCCAACAAAAGGTGGTAGATGGCCTGGCCTCTGGCATTAGCGG
GGTGGTGGACCTGGCCAACCAGGCAGTGCAAAATAAGATTAACAGTAAGCTTGATC
CCCGCCCTCCCGTAGAGGAGCCTCCACCGGCCGTGGAGACAGTGTCTCCAGAGGGG
CGTGGCGAAAAGCGTCCGCGCCCCGACAGGGAAGAAACTCTGGTGACGCAAATAGA
CGAGCCTCCCTCGTACGAGGAGGCACTAAAGCAAGGCCTGCCCACCACCCGTCCCA
TCGCGCCCATGGCTACCGGAGTGCTGGGCCAGCACACACCCGTAACGCTGGACCTG
CCTCCCCCCGCCGACACCCAGCAGAAACCTGTGCTGCCAGGCCCGACCGCCGTTGTT
GTAACCCGTCCTAGCCGCGCGTCCCTGCGCCGCGCCGCCAGCGGTCCGCGATCGTTG
CGGCCCGTAGCCAGTGGCAACTGGCAAAGCACACTGAACAGCATCGTGGGTCTGGG
GGTGCAATCCCTGAAGCGCCGACGATGCTTCTGAATAGCTAACGTGTCGTATGTGTG
TCATGTATGCGTCCATGTCGCCGCCAGAGGAGCTGCTGAGCCGCCGCGCGCCCGCTT
TCCAAGATGGCTACCCCTTCGATGATGCCGCAGTGGTCTTACATGCACATCTCGGGC
CAGGACGCCTCGGAGTACCTGAGCCCCGGGCTGGTGCAGTTTGCCCGCGCCACCGA
GACGTACTTCAGCCTGAATAACAAGTTTAGAAACCCCACGGTGGCGCCTACGCACG
ACGTGACCACAGACCGGTCCCAGCGTTTGACGCTGCGGTTCATCCCTGTGGACCGTG
AGGATACTGCGTACTCGTACAAGGCGCGGTTCACCCTAGCTGTGGGTGATAACCGTG
TGCTGGACATGGCTTCCACGTACTTTGACATCCGCGGCGTGCTGGACAGGGGCCCTA
CTTTTAAGCCCTACTCTGGCACTGCCTACAACGCCCTGGCTCCCAAGGGTGCCCCAA
```

FIG. 35H

```
ATCCTTGCGAATGGGATGAAGCTGCTACTGCTCTTGAAATAAACCTAGAAGAAGAG
GACGATGACAACGAAGACGAAGTAGACGAGCAAGCTGAGCAGCAAAAAACTCACG
TATTTGGGCAGGCGCCTTATTCTGGTATAAATATTACAAAGGAGGGTATTCAAATAG
GTGTCGAAGGTCAAACACCTAAATATGCCGATAAAACATTTCAACCTGAACCTCAA
ATAGGAGAATCTCAGTGGTACGAAACTGAAATTAATCATGCAGCTGGGAGAGTCCT
TAAAAAGACTACCCCAATGAAACCATGTTACGGTTCATATGCAAAACCCACAAATG
AAAATGGAGGGCAAGGCATTCTTGTAAAGCAACAAAATGGAAAGCTAGAAAGTCA
AGTGGAAATGCAATTTTTCTCAACTACTGAGGCGACCGCAGGCAATGGTGATAACTT
GACTCCTAAAGTGGTATTGTACAGTGAAGATGTAGATATAGAAACCCCAGACACTC
ATATTTCTTACATGCCCACTATTAAGGAAGGTAACTCACGAGAACTAATGGGCCAAC
AATCTATGCCCAACAGGCCTAATTACATTGCTTTTAGGGACAATTTTATTGGTCTAAT
GTATTACAACAGCACGGGTAATATGGGTGTTCTGGCGGGCCAAGCATCGCAGTTGA
ATGCTGTTGTAGATTTGCAAGACAGAAACACAGAGCTTTCATACCAGCTTTTGCTTG
ATTCCATTGGTGATAGAACCAGGTACTTTTCTATGTGGAATCAGGCTGTTGACAGCT
ATGATCCAGATGTTAGAATTATTGAAAATCATGGAACTGAAGATGAACTTCCAAATT
ACTGCTTTCCACTGGGAGGTGTGATTAATACAGAGACTCTTACCAAGGTAAAACCTA
AAACAGGTCAGGAAAATGGATGGGAAAAAGATGCTACAGAATTTTCAGATAAAAAT
GAAATAAGAGTTGGAAATAATTTTGCCATGGAAATCAATCTAAATGCCAACCTGTG
GAGAAATTTCCTGTACTCCAACATAGCGCTGTATTTGCCCGACAAGCTAAAGTACAG
TCCTTCCAACGTAAAAATTTCTGATAACCCAAACACCTACGACTACATGAACAAGCG
AGTGGTGGCTCCCGGGTTAGTGGACTGCTACATTAACCTTGGAGCACGCTGGTCCCT
TGACTATATGGACAACGTCAACCCATTTAACCACCACCGCAATGCTGGCCTGCGCTA
CCGCTCAATGTTGCTGGGCAATGGTCGCTATGTGCCCTTCCACATCCAGGTGCCTCA
GAAGTTCTTTGCCATTAAAAACCTCCTTCTCCTGCCGGGCTCATACACCTACGAGTG
GAACTTCAGGAAGGATGTTAACATGGTTCTGCAGAGCTCCCTAGGAAATGACCTAA
GGGTTGACGGAGCCAGCATTAAGTTTGATAGCATTTGCCTTTACGCCACCTTCTTCCC
CATGGCCCACAACACCGCCTCCACGCTTGAGGCCATGCTTAGAAACGACACCAACG
ACCAGTCCTTTAACGACTATCTCTCCGCCGCCAACATGCTCTACCCTATACCCGCCA
ACGCTACCAACGTGCCCATATCCATCCCCTCCCGCAACTGGGCGGCTTTCCGCGGCT
GGGCCTTCACGCGCCTTAAGACTAAGGAAACCCCATCACTGGGCTCGGGCTACGAC
CCTTATTACACCTACTCTGGCTCTATACCCTACCTAGATGGAACCTTTTACCTCAACC
ACACCTTTAAGAAGGTGGCCATTACCTTTGACTCTTCTGTCAGCTGGCCTGGCAATG
ACCGCCTGCTTACCCCCAACGAGTTTGAAATTAAGCGCTCAGTTGACGGGGAGGGTT
ACAACGTTGCCCAGTGTAACATGACCAAAGACTGGTTCCTGGTACAAATGCTAGCTA
ACTACAACATTGGCTACCAGGGCTTCTATATCCCAGAGAGCTACAAGGACCGCATGT
ACTCCTTCTTTAGAAACTTCCAGCCCATGAGCCGTCAGGTGGTGGATGATACTAAAT
ACAAGGACTACCAACAGGTGGGCATCCTACACCAACACAACAACTCTGGATTTGTT
GGCTACCTTGCCCCCACCATGCGCGAAGGACAGGCCTACCCTGCTAACTTCCCCTAT
CCGCTTATAGGCAAGACCGCAGTTGACAGCATTACCCAGAAAAAGTTTCTTTGCGAT
CGCACCCTTTGGCGCATCCCATTCTCCAGTAACTTTATGTCCATGGGCGCACTCACA
GACCTGGGCCAAAACCTTCTCTACGCCAACTCCGCCCACGCGCTAGACATGACTTTT
GAGGTGGATCCCATGGACGAGCCCACCCTTCTTTATGTTTTGTTTGAAGTCTTTGACG
```

FIG. 35I

```
TGGTCCGTGTGCACCGGCCGCACCGCGGCGTCATCGAAACCGTGTACCTGCGCACGC
CCTTCTCGGCCGGCAACGCCACAACATAAAGAAGCAAGCAACATCAACAACAGCTG
CCGCCATGGGCTCCAGTGAGCAGGAACTGAAAGCCATTGTCAAAGATCTTGGTTGTG
GGCCATATTTTTTGGGCACCTATGACAAGCGCTTTCCAGGCTTTGTTTCTCCACACAA
GCTCGCCTGCGCCATAGTCAATACGGCCGGTCGCGAGACTGGGGGCGTACACTGGA
TGGCCTTTGCCTGGAACCCGCACTCAAAAACATGCTACCTCTTTGAGCCCTTTGGCTT
TTCTGACCAGCGACTCAAGCAGGTTTACCAGTTTGAGTACGAGTCACTCCTGCGCCG
TAGCGCCATTGCTTCTTCCCCCGACCGCTGTATAACGCTGGAAAAGTCCACCCAAAG
CGTACAGGGGCCCAACTCGGCCGCCTGTGGACTATTCTGCTGCATGTTTCTCCACGC
CTTTGCCAACTGGCCCCAAACTCCCATGGATCACAACCCCACCATGAACCTTATTAC
CGGGGTACCCAACTCCATGCTCAACAGTCCCCAGGTACAGCCCACCCTGCGTCGCAA
CCAGGAACAGCTCTACAGCTTCCTGGAGCGCCACTCGCCCTACTTCCGCAGCCACAG
TGCGCAGATTAGGAGCGCCACTTCTTTTTGTCACTTGAAAAACATGTAAAAATAATG
TACTAGAGACACTTTCAATAAAGGCAAATGCTTTTATTTGTACACTCTCGGGTGATT
ATTTACCCCCACCCTTGCCGTCTGCGCCGTTTAAAAATCAAAGGGGTTCTGCCGCGC
ATCGCTATGCGCCACTGGCAGGGACACGTTGCGATACTGGTGTTTAGTGCTCCACTT
AAACTCAGGCACAACCATCCGCGGCAGCTCGGTGAAGTTTTCACTCCACAGGCTGC
GCACCATCACCAACGCGTTTAGCAGGTCGGGCGCCGATATCTTGAAGTCGCAGTTGG
GGCCTCCGCCCTGCGCGCGCGAGTTGCGATACACAGGGTTGCAGCACTGGAACACT
ATCAGCGCCGGGTGGTGCACGCTGGCCAGCACGCTCTTGTCGGAGATCAGATCCGC
GTCCAGGTCCTCCGCGTTGCTCAGGGCGAACGGAGTCAACTTTGGTAGCTGCCTTCC
CAAAAAGGGCGCGTGCCCAGGCTTTGAGTTGCACTCGCACCGTAGTGGCATCAAAA
GGTGACCGTGCCCGGTCTGGGCGTTAGGATACAGCGCCTGCATAAAAGCCTTGATCT
GCTTAAAAGCCACCTGAGCCTTTGCGCCTTCAGAGAAGAACATGCCGCAAGACTTG
CCGGAAAACTGATTGGCCGGACAGGCCGCGTCGTGCACGCAGCACCTTGCGTCGGT
GTTGGAGATCTGCACCACATTTCGGCCCCACCGGTTCTTCACGATCTTGGCCTTGCTA
GACTGCTCCTTCAGCGCGCGCTGCCCGTTTTCGCTCGTCACATCCATTTCAATCACGT
GCTCCTTATTTATCATAATGCTTCCGTGTAGACACTTAAGCTCGCCTTCGATCTCAGC
GCAGCGGTGCAGCCACAACGCGCAGCCCGTGGGCTCGTGATGCTTGTAGGTCACCT
CTGCAAACGACTGCAGGTACGCCTGCAGGAATCGCCCCATCATCGTCACAAAGGTC
TTGTTGCTGGTGAAGGTCAGCTGCAACCCGCGGTGCTCCTCGTTCAGCCAGGTCTTG
CATACGGCCGCCAGAGCTTCCACTTGGTCAGGCAGTAGTTTGAAGTTCGCCTTTAGA
TCGTTATCCACGTGGTACTTGTCCATCAGCGCGCGCGCAGCCTCCATGCCCTTCTCCC
ACGCAGACACGATCGGCACACTCAGCGGGTTCATCACCGTAATTTCACTTTCCGCTT
CGCTGGGCTCTTCCTCTTCCTCTTGCGTCCGCATACCACGCGCCACTGGGTCGTCTTC
ATTCAGCCGCCGCACTGTGCGCTTACCTCCTTTGCCATGCTTGATTAGCACCGGTGG
GTTGCTGAAACCCACCATTTGTAGCGCCACATCTTCTCTTTCTTCCTCGCTGTCCACG
ATTACCTCTGGTGATGGCGGGCGCTCGGGCTTGGGAGAAGGGCGCTTCTTTTTCTTC
TTGGGCGCAATGGCCAAATCCGCCGCCGAGGTCGATGGCCGCGGGCTGGGTGTGCG
CGGCACCAGCGCGTCTTGTGATGAGTCTTCCTCGTCCTCGGACTCGATACGCCGCCT
CATCCGCTTTTTTGGGGGCGCCCGGGGAGGCGGCGGCGACGGGGACGGGGACGACA
CGTCCTCCATGGTTGGGGACGTCGCGCCGCACCGCGTCCGCGCTCGGGGGTGGTTT
CGCGCTGCTCCTCTTCCCGACTGGCCATTTCCTTCTCCTATAGGCAGAAAAAGATCA
TGGAGTCAGTCGAGAAGAAGGACAGCCTAACCGCCCCCTCTGAGTTCGCCACCACC
```

FIG. 35J

```
GCCTCCACCGATGCCGCCAACGCGCCTACCACCTTCCCCGTCGAGGCACCCCCGCTT
GAGGAGGAGGAAGTGATTATCGAGCAGGACCCAGGTTTTGTAAGCGAAGACGACGA
GGACCGCTCAGTACCAACAGAGGATAAAAAGCAAGACCAGGACAACGCAGAGGCA
AACGAGGAACAAGTCGGGCGGGGGGACGAAAGGCATGGCGACTACCTAGATGTGG
GAGACGACGTGCTGTTGAAGCATCTGCAGCGCCAGTGCGCCATTATCTGCGACGCGT
TGCAAGAGCGCAGCGATGTGCCCCTCGCCATAGCGGATGTCAGCCTTGCCTACGAA
CGCCACCTATTCTCACCGCGCGTACCCCCAAACGCCAAGAAAACGGCACATGCGA
GCCCAACCCGCGCCTCAACTTCTACCCCGTATTTGCCGTGCCAGAGGTGCTTGCCAC
CTATCACATCTTTTTCCAAAACTGCAAGATACCCCTATCCTGCCGTGCCAACCGCAG
CCGAGCGGACAAGCAGCTGGCCTTGCGGCAGGGCGCTGTCATACCTGATATCGCCT
CGCTCAACGAAGTGCCAAAAATCTTTGAGGGTCTTGGACGCGACGAGAAGCGCGCG
GCAAACGCTCTGCAACAGGAAAACAGCGAAAATGAAAGTCACTCTGGAGTGTTGGT
GGAACTCGAGGGTGACAACGCGCGCCTAGCCGTACTAAAACGCAGCATCGAGGTCA
CCCACTTTGCCTACCCGGCACTTAACCTACCCCCCAAGGTCATGAGCACAGTCATGA
GTGAGCTGATCGTGCGCCGTGCGCAGCCCCTGGAGAGGGATGCAAATTTGCAAGAA
CAAACAGAGGAGGGCCTACCCGCAGTTGGCGACGAGCAGCTAGCGCGCTGGCTTCA
AACGCGCGAGCCTGCCGACTTGGAGGAGCGACGCAAACTAATGATGGCCGCAGTGC
TCGTTACCGTGGAGCTTGAGTGCATGCAGCGGTTCTTTGCTGACCCGGAGATGCAGC
GCAAGCTAGAGGAAACATTGCACTACACCTTTCGACAGGGCTACGTACGCCAGGCC
TGCAAGATCTCCAACGTGGAGCTCTGCAACCTGGTCTCCTACCTTGGAATTTTGCAC
GAAAACCGCCTTGGGCAAAACGTGCTTCATTCCACGCTCAAGGGCGAGGCGCGCCG
CGACTACGTCCGCGACTGCGTTTACTTATTTCTATGCTACACCTGGCAGACGGCCAT
GGGCGTTTGGCAGCAGTGCTTGGAGGAGTGCAACCTCAAGGAGCTGCAGAAACTGC
TAAAGCAAAACTTGAAGGACCTATGGACGGCCTTCAACGAGCGCTCCGTGGCCGCG
CACCTGGCGGACATCATTTTCCCCGAACGCCTGCTTAAAACCCTGCAACAGGGTCTG
CCAGACTTCACCAGTCAAAGCATGTTGCAGAACTTTAGGAACTTTATCCTAGAGCGC
TCAGGAATCTTGCCCGCCACCTGCTGTGCACTTCCTAGCGACTTTGTGCCCATTAAGT
ACCGCGAATGCCCTCCGCCGCTTTGGGGCCACTGCTACCTTCTGCAGCTAGCCAACT
ACCTTGCCTACCACTCTGACATAATGGAAGACGTGAGCGGTGACGGTCTACTGGAGT
GTCACTGTCGCTGCAACCTATGCACCCCGCACCGCTCCCTGGTTTGCAATTCGCAGC
TGCTTAACGAAAGTCAAATTATCGGTACCTTTGAGCTGCAGGGTCCCTCGCCTGACG
AAAAGTCCGCGGCTCCGGGGTTGAAACTCACTCCGGGGCTGTGGACGTCGGCTTAC
CTTCGCAAATTTGTACCTGAGGACTACCACGCCCACGAGATTAGGTTCTACGAAGAC
CAATCCCGCCCGCCAAATGCGGAGCTTACCGCCTGCGTCATTACCCAGGGCCACATT
CTTGGCCAATTGCAAGCCATCAACAAAGCCCGCCAAGAGTTTCTGCTACGAAAGGG
ACGGGGGGTTTACTTGGACCCCCAGTCCGGCGAGGAGCTCAACCCAATCCCCCCGC
CGCCGCAGCCCTATCAGCAGCAGCCGCGGGCCCTTGCTTCCCAGGATGGCACCCAA
AAAGAAGCTGCAGCTGCCGCCGCCACCCACGGACGAGGAGGAATACTGGGACAGTC
AGGCAGAGGAGGTTTTGGACGAGGAGGAGGAGGACATGATGGAAGACTGGGAGAG
CCTAGACGAGGAAGCTTCCGAGGTCGAAGAGGTGTCAGACGAAACACCGTCACCCT
CGGTCGCATTCCCCTCGCCGGCGCCCCAGAAATCGGCAACCGGTTCCAGCATGGCTA
CAACCTCCGCTCCTCAGGCGCCGCCGGCACTGCCCGTTCGCCGACCCAACCGTAGAT
GGGACACCACTGGAACCAGGGCCGGTAAGTCCAAGCAGCCGCCGCCGTTAGCCCAA
```

FIG. 35K

```
GAGCAACAACAGCGCCAAGGCTACCGCTCATGGCGCGGGCACAAGAACGCCATAGT
TGCTTGCTTGCAAGACTGTGGGGGCAACATCTCCTTCGCCCGCCGCTTTCTTCTCTAC
CATCACGGCGTGGCCTTCCCCCGTAACATCCTGCATTACTACCGTCATCTCTACAGC
CCATACTGCACCGGCGGCAGCGGCAGCGGCAGCAACAGCAGCGGCCACACAGAAG
CAAAGGCGACCGGATAGCAAGACTCTGACAAAGCCCAAGAAATCCACAGCGGCGG
CAGCAGCAGGAGGAGGAGCGCTGCGTCTGGCGCCCAACGAACCCGTATCGACCCGC
GAGCTTAGAAACAGGATTTTTCCCACTCTGTATGCTATATTTCAACAGAGCAGGGGC
CAAGAACAAGAGCTGAAAATAAAAAACAGGTCTCTGCGATCCCTCACCCGCAGCTG
CCTGTATCACAAAAGCGAAGATCAGCTTCGGCGCACGCTGGAAGACGCGGAGGCTC
TCTTCAGTAAATACTGCGCGCTGACTCTTAAGGACTAGTTTCGCGCCCTTTCTCAAAT
TTAAGCGCGAAAACTACGTCATCTCCAGCGGCCACACCCGGCGCCAGCACCTGTCGT
CAGCGCCATTATGAGCAAGGAAATTCCCACGCCCTACATGTGGAGTTACCAGCCAC
AAATGGGACTTGCGGCTGGAGCTGCCCAAGACTACTCAACCCGAATAAACTACATG
AGCGCGGGACCCCACATGATATCCCGGGTCAACGGAATCCGCGCCCACCGAAACCG
AATTCTCTTGGAACAGGCGGCTATTACCACCACACCTCGTAATAACCTTAATCCCCG
TAGTTGGCCCGCTGCCCTGGTGTACCAGGAAAGTCCCGCTCCCACCACTGTGGTACT
TCCCAGAGACGCCCAGGCCGAAGTTCAGATGACTAACTCAGGGGCGCAGCTTGCGG
GCGGCTTTCGTCACAGGGTGCGGTCGCCCGGGCAGGGTATAACTCACCTGACAATC
AGAGGGCGAGGTATTCAGCTCAACGACGAGTCGGTGAGCTCCTCGCTTGGTCTCCGT
CCGGACGGGACATTTCAGATCGGCGGCGCCGGCCGTCCTTCATTCACGCCTCGTCAG
GCAATCCTAACTCTGCAGACCTCGTCCTCTGAGCCGCGCTCTGGAGGCATTGGAACT
CTGCAATTTATTGAGGAGTTTGTGCCATCGGTCTACTTTAACCCCTTCTCGGGACCTC
CCGGCCACTATCCGGATCAATTTATTCCTAACTTTGACGCGGTAAAGGACTCGGCGG
ACGGCTACGACTGAATGTTAAGTGGAGAGGCAGAGCAACTGCGCCTGAAACACCTG
GTCCACTGTCGCCGCCACAAGTGCTTTGCCCGCGACTCCGGTGAGTTTTGCTACTTTG
AATTGCCCGAGGATCATATCGAGGGCCCGGCGCACGGCGTCCGGCTTACCGCCCAG
GGAGAGCTTGCCCGTAGCCTGATTCGGGAGTTTACCCAGCGCCCCCTGCTAGTTGAG
CGGGACAGGGGACCCTGTGTTCTCACTGTGATTTGCAACTGTCCTAACCTTGGATTA
CATCAAGATCCTCTAGTTATAACTAGAGTACCCGGGGATCTTATTCCCTTTAACTAAT
AAAAAAAAATAATAAAGCATCACTTACTTAAAATCAGTTAGCAAATTTCTGTCCAGT
TTATTCAGCAGCACCTCCTTGCCCTCCTCCCAGCTCTGGTATTGCAGCTTCCTCCTGG
CTGCAAACTTTCTCCACAATCTAAATGGAATGTCAGTTTCCTCCTGTTCCTGTCCATC
CGCACCCACCGGTATAACTTCGTATATGGTTTCTTATACGAACGGTAGATCTATATCT
ATGATCTCGCAGTCTCCGGCGAGCACCGGAGGCAGGGCATTGCCACCGCGCTCATC
AATCTCCTCAAGCATGAGGCCAACGCGCTTGGTGCTTATGTGATCTACGTGCAAGCA
GATTACGGTGACGATCCCGCAGTGGCTCTCTATACAAAGTTGGGCATACGGGAAGA
AGTGATGCACTTTGATATCGACCCAAGTACCGCCACCTAACAATTCGTTCAAGCCGA
GATCGGCTTCCCGGCCGCGGAGTTGTTCGGTAAATTGTCACAACGCCGCGGCCATCG
GCATTTTCTTTTGCGTTTTTATTTGTTAACTGTTAATTGTCCTTGTTCAAGGATGCTGT
CTTTGACAACAGATGTTTTCTTGCCTTTGATGTTCAGCAGGAAGCTTGGCGCAAACG
TTGATTGTTTGTCTGCGTAGAATCCTCTGTTTGTCATATAGCTTGTAATCACCACGAC
ATTGTTTCCTTTCGCTTGAGGTACAGCGAAGTGTGAGTAAGTAAAGGTTACATCGTT
AGGATCAAGATCCATTTTTAACACAAGGCCAGTTTTGTTCAGCGGCTTGTATGGGCC
```

FIG. 35L

```
AGTTAAAGAATTAGAAACATAACCAAGCATGTAAATATCGTTAGACGAAATGCCGT
CAATCGTCATTTTTGATCCGCGGGAGTCAGTGAACAGGTACCATTTGCCGTTCATTTT
AAAGACGTTCGCGCGTTCAATTTCATCTGTTACTGTGTTAGATGCAATCAGCGGTTTC
ATCACTTTTTTCAGTGTGTAATCATCGTTTAGCTCAATCATACCGAGAGCGCCGTTTG
CTAACTCAGCCGTGCGTTTTTTATCGCTTTGCAGAAGTTTTTGACTTTCTTGACGGAA
GAATGATGTGCTTTTGCCATAGTATGCTTTGTTAAATAAAGATTCTTCGCCTTGGTAG
CCATCTTCAGTTCCAGTGTTTGCTTCAAATACTAAGTATTTGTGGCCTTTATCTTCTA
CGTAGTGAGGATCTCTCAGCGTATGGTTGTCGCCTGAGCTGTAGTTGCCTTCATCGA
TGAACTGCTGTACATTTTGATACGTTTTTCCGTCACCGTCAAAGATTGATTTATAATC
CTCTACACCGTTGATGTTCAAAGAGCTGTCTGATGCTGATACGTTAACTTGTGCAGTT
GTCAGTGTTTGTTTGCCGTAATGTTTACCGGAGAAATCAGTGTAGAATAAACGGATT
TTTCCGTCAGATGTAAATGTGGCTGAACCTGACCATTCTTGTGTTTGGTCTTTTAGGA
TAGAATCATTTGCATCGAATTTGTCGCTGTCTTTAAAGACGCGGCCAGCGTTTTTCCA
GCTGTCAATAGAAGTTTCGCCGACTTTTTGATAGAACATGTAAATCGATGTGTCATC
CGCATTTTTAGGATCTCCGGCTAATGCAAAGACGATGTGGTAGCCGCGATAGTTTGC
GACAGTGCCGTCAGCGTTTTGTAATGGCCAGCTGTCCCAAACGTCCAGGCCTTTTGC
AGAAGAGATATTTTTAATTGTGGACGAATCGAATTCAGGAACTTGATATTTTTCATT
TTTTTGCTGTTCAGGGATTTGCAGCATATCATGGCGTGTAATATGGGAAATGCCGTA
TGTTTCCTTATATGGCTTTTGGTTCGTTTCTTTCGCAAACGCTTGAGTTGCGCCTCCTG
CCAGCAGTGCGGTAGTAAAGGTTAATACTGTTGCTTGTTTTGCAAACTTTTTGATGTT
CATCGTTCATGTCTCCTTTTTATGTACTGTGTTAGCGGTCTGCTTCTTCCAGCCCTCC
TGTTTGAAGATGGCAAGTTAGTTACGCACAATAAAAAAAGACCTAAAATATGTAAG
GGGTGACGCCAAAGTATACACTTTGCCCTTTACACATTTTAGGTCTTGCCTGCTTTAT
CAGTAACAAACCCGCGCGATTTACTTTTCGACCTCATTCTATTAGACTCTCGTTTGGA
TTGCAACTGGTCTATTTTCCTCTTTTGTTTGATAGAAAATCATAAAAGGATTTGCAGA
CTACGGGCCTAAAGAACTAAAAAATCTATCTGTTTCTTTTCATTCTCTGTATTTTTA
TAGTTTCTGTTGCATGGGCATAAAGTTGCCTTTTTAATCACAATTCAGAAAATATCAT
AATATCTCATTTCACTAAATAATAGTGAACGGCAGGTATATGTGATGGGTTAAAAAG
GATCGATCCTCTAGCTAGAGTCGATCGTACCGTTCGTATAGCATACATTATACGAAG
TTATACCGGTATACATTGCCCAAGAATAAAGAATCGTTTGTGTTATGTTTCAACGTG
TTTATTTTTCAATTGCAGAAAATTTCAAGTCATTTTTCATTCAGTAGTATAGCCCCAC
CACCACATAGCTTATACAGATCACCGTACCTTAATCAAACTCACAGAACCCTAGTAT
TCAACCTGCCACCTCCCTCCCAACACACAGAGTACACAGTCCTTTCTCCCCGGCTGG
CCTTAAAAAGCATCATATCATGGGTAACAGACATATTCTTAGGTGTTATATTCCACA
CGGTTTCCTGTCGAGCCAAACGCTCATCAGTGATATTAATAAACTCCCCGGGCAGCT
CACTTAAGTTCATGTCGCTGTCCAGCTGCTGAGCCACAGGCTGCTGTCCAACTTGCG
GTTGCTTAACGGGCGGCGAAGGAGAAGTCCACGCCTACATGGGGGTAGAGTCATAA
TCGTGCATCAGGATAGGGCGGTGGTGCTGCAGCAGCGCGCGAATAAACTGCTGCCG
CCGCCGCTCCGTCCTGCAGGAATACAACATGGCAGTGGTCTCCTCAGCGATGATTCG
CACCGCCCGCAGCATAAGGCGCCTTGTCCTCCGGGCACAGCAGCGCACCCTGATCTC
ACTTAAATCAGCACAGTAACTGCAGCACAGCACCACAATATTGTTCAAAATCCCAC
AGTGCAAGGCGCTGTATCCAAAGCTCATGGCGGGGACCACAGAACCCACGTGGCCA
TCATACCACAAGCGCAGGTAGATTAAGTGGCGACCCCTCATAAACACGCTGGACAT
```

FIG. 35M

```
AAACATTACCTCTTTTGGCATGTTGTAATTCACCACCTCCCGGTACCATATAAACCTC
TGATTAAACATGGCGCCATCCACCACCATCCTAAACCAGCTGGCCAAAACCTGCCCG
CCGGCTATACACTGCAGGGAACCGGGACTGGAACAATGACAGTGGAGAGCCCAGG
ACTCGTAACCATGGATCATCATGCTCGTCATGATATCAATGTTGGCACAACACAGGC
ACACGTGCATACACTTCCTCAGGATTACAAGCTCCTCCCGCGTTAGAACCATATCCC
AGGGAACAACCCATTCCTGAATCAGCGTAAATCCCACACTGCAGGGAAGACCTCGC
ACGTAACTCACGTTGTGCATTGTCAAAGTGTTACATTCGGGCAGCAGCGGATGATCC
TCCAGTATGGTAGCGCGGGTTTCTGTCTCAAAAGGAGGTAGACGATCCCTACTGTAC
GGAGTGCGCCGAGACAACCGAGATCGTGTTGGTCGTAGTGTCATGCCAAATGGAAC
GCCGGACGTAGTCATATTTCCTGAAGCAAAACCAGGTGCGGGCGTGACAAACAGAT
CTGCGTCTCCGGTCTCGCCGCTTAGATCGCTCTGTGTAGTAGTTGTAGTATATCCACT
CTCTCAAAGCATCCAGGCGCCCCCTGGCTTCGGGTTCTATGTAAACTCCTTCATGCG
CCGCTGCCCTGATAACATCCACCACCGCAGAATAAGCCACACCCAGCCAACCTACA
CATTCGTTCTGCGAGTCACACACGGGAGGAGCGGGAAGAGCTGGAAGAACCATGTT
TTTTTTTTTATTCCAAAAGATTATCCAAAACCTCAAAATGAAGATCTATTAAGTGAA
CGCGCTCCCCTCCGGTGGCGTGGTCAAACTCTACAGCCAAAGAACAGATAATGGCA
TTTGTAAGATGTTGCACAATGGCTTCCAAAAGGCAAACGGCCCTCACGTCCAAGTGG
ACGTAAAGGCTAAACCCTTCAGGGTGAATCTCCTCTATAAACATTCCAGCACCTTCA
ACCATGCCCAAATAATTCTCATCTCGCCACCTTCTCAATATATCTCTAAGCAAATCCC
GAATATTAAGTCCGGCCATTGTAAAAATCTGCTCCAGAGCGCCCTCCACCTTCAGCC
TCAAGCAGCGAATCATGATTGCAAAAATTCAGGTTCCTCACAGACCTGTATAAGATT
CAAAAGCGGAACATTAACAAAAATACCGCGATCCCGTAGGTCCCTTCGCAGGGCCA
GCTGAACATAATCGTGCAGGTCTGCACGGACCAGCGCGGCCACTTCCCCGCCAGGA
ACCTTGACAAAAGAACCCACACTGATTATGACACGCATACTCGGAGCTATGCTAAC
CAGCGTAGCCCCGATGTAAGCTTTGTTGCATGGGCGGCGATATAAAATGCAAGGTG
CTGCTCAAAAAATCAGGCAAAGCCTCGCGCAAAAAAGAAAGCACATCGTAGTCATG
CTCATGCAGATAAAGGCAGGTAAGCTCCGGAACCACCACAGAAAAAGACACCATTT
TTCTCTCAAACATGTCTGCGGGTTTCTGCATAAACACAAAATAAAATAACAAAAAAA
CATTTAAACATTAGAAGCCTGTCTTACAACAGGAAAAACAACCCTTATAAGCATAA
GACGGACTACGGCCATGCCGGCGTGACCGTAAAAAAACTGGTCACCGTGATTAAAA
AGCACCACCGACAGCTCCTCGGTCATGTCCGGAGTCATAATGTAAGACTCGGTAAA
CACATCAGGTTGATTCATCGGTCAGTGCTAAAAAGCGACCGAAATAGCCCGGGGGA
ATACATACCCGCAGGCGTAGAGACAACATTACAGCCCCCATAGGAGGTATAACAAA
ATTAATAGGAGAGAAAAACACATAAACACCTGAAAAACCCTCCTGCCTAGGCAAAA
TAGCACCCTCCCGCTCCAGAACAACATACAGCGCTTCACAGCGGCAGCCTAACAGT
CAGCCTTACCAGTAAAAAGAAAACCTATTAAAAAAACACCACTCGACACGGCACC
AGCTCAATCAGTCACAGTGTAAAAAAGGGCCAAGTGCAGAGCGAGTATATATAGGA
CTAAAAAATGACGTAACGGTTAAAGTCCACAAAAAACACCCAGAAAACCGCACGCG
AACCTACGCCCAGAAACGAAAGCCAAAAAACCCACAACTTCCTCAAATCGTCACTT
CCGTTTTCCCACGTTACGTAACTTCCCATTTTAAGAAAACTACAATTCCCAACACATA
CAAGTTACTCCGCCCTAAAACCTACGTCACCCGCCCCGTTCCCACGCCCCGCGCCAC
GTCACAAACTCCACCCCCTCATTATCATATTGGCTTCAATCCAAAATAAGGTATATT
ATTGATGATTTAAT
```

FIG. 35N

Modified Fiber sequence: SEQ ID NO: 8

ATGAAGCGCGCAAGACCGTCTGAAGATACCTTCAACCCCGTGTATCCATA
TGACACGGAAACCGGTCCTCCAACTGTGCCTTTTCTTACTCCTCCCTTTG
TATCCCCCAATGGGTTTCAAGAGAGTCCCCCTGGGGTACTCTCTTTGCGC
CTATCCGAACCTCTAGTTACCTCCAATGGCATGCTTGCGCTCAAAATGGG
CAACGGCCTCTCTCTGGACGAGGCCGGCAACCTTACCTCCCAAAATGTAA
CCACTGTGAGCCCACCTCTCAAAAAAACCAAGTCAAACATAAACCTGGAA
ATATCTGCACCCCTCACAGTTACCTCAGAAGCCCTAACTGTGGCTGCCGC
CGCACCTCTAATGGTCGCGGGCAACACACTCACCATGCAATCACAGGCCC
CGCTAACCGTGCACGACTCCAAACTTAGCATTGCCACCCAAGGACCCCTC
ACAGTGTCAGAAGGAAAGCTAGCCCTGCAAACATCAGGCCCCCTCACCAC
CACCGATAGCAGTACCCTTACTATCACTGCCTCACCCCCTCTAACTACTG
CCACTGGTAGCTTGGGCATTGACTTGAAAGAGCCCATTTATACACAAAAT
GGAAAACTAGGACTAAAGTACGGGGCTCCTTTGCATGTAACAGACGACCT
AAACACTTTGACCGTAGCAACTGGTCCAGGTGTGACTATTAATAATACTT
CCTTGCAAACTAAAGTTACTGGAGCCTTGGGTTTTGATTCACAAGGCAAT
ATGCAACTTAATGTAGCAGGAGGACTAAGGATTGATTCTCAAAACAGACG
CCTTATACTTGATGTTAGTTATCCGTTTGATGCTCAAAACCAACTAAATC
TAAGACTAGGACAGGGCCCTCTTTTTATAAACTCAGCCCACAACTTGGAT
ATTAACTACAACAAAGGCCTTTACTTGTTTACAGCTTCAAACAATTCCAA
AAAGCTTGAGGTTAACCTAAGCACTGCCAAGGGGTTGATGTTTGACGCTA
CAGCCATAGCCATTAATGCAGGAGATGGGCTTGAATTTGGTTCACCTAAT
GCACCAAACACAAATCCCCTCAAAACAAAAATTGGCCATGGCCTAGAATT
TGATTCAAACAAGGCTATGGTTCCTAAACTAGGAACTGGCCTTAGTTTTG
ACAGCACAGGTGCCATTACAGTAGGAAACAAAAATAATGATAAGCTAACT
TTGTGGACCACACCAGCTCCATCTCCTAACTGTAGACTAAATGCAGAGAA
AGATGCTAAACTCACTTTGGTCTTAACAAAATGTGGCAGTCAAATACTTG
CTACAGTTTCAGTTTTGGCTGTTAAAGGCAGTTTGGCTCCAATATCTGGA
ACAGTTCAAAGTGCTCATCTTATTATAAGATTTGACGAAAATGGAGTGCT
ACTAAACAATTCCTTCCTGGACCCAGAATATTGGAACTTTAGAAATGGAG
ATCTTACTGAAGGCAACGCTGTTGGATTTATGCCTAACCTATCAGCTTAT
CCAAAATCTCACGGTAAAACTGCCAAAAGTAACATTGTCAGTCAAGTTTA
CTTAAACGGAGACAAAACTAAACCTGTAACACTAACCATTACACTAAACG
GTACACAGGAATCCGGCGAATTATGCGACTGCAGGGGCGACTGCTTCTGT
GCCGGAGACACAACTCCAAGTGCATACTCTATGTCATTTTCATGGGACTG
GTCTGGCCACAACTACATTAATGAAATATTTGCCACATCCTCTTACACTT
TTTCATACATTGCCCAAGAATA

FIG. 36

COMPOSITIONS AND METHODS FOR GENERATING AND SCREENING ADENOVIRAL LIBRARIES

CROSS-REFERENCE TO RELATED APPLICATION

This application claims the benefit of the following U.S. Provisional Application No. 60/964,971, filed Aug. 16, 2007, and U.S. Provisional Application No. 60/993,115, filed Sep. 10, 2007, the entire contents of which are incorporated herein by reference.

STATEMENT OF RIGHTS TO INVENTIONS MADE UNDER FEDERALLY SPONSORED RESEARCH

This work was supported by the following grants from the National Institutes of Health, Grant Nos: 2P50CA58236-09A1 and 1R01CA121153-01A2; and the Department of Defense Prostate Cancer Research Program under Award Number DAMD17-03-2-0033. The government has certain rights in the invention.

BACKGROUND OF THE INVENTION

Adenoviruses are widely used vectors for gene delivery because of their ability to transduce a wide range of dividing and nondividing cell types. Adenoviruses typically bind and enter cells through a process involving the interactions of the adenovirus fiber protein, which is thought to mediate cell binding via a Fiber receptor, the coxsackievirus-adenovirus receptor (CAR) that is expressed on mammalian cells. The use of adenoviral vectors as therapeutic agents has been hampered, in part, by broad viral tropism and diminished expression of CAR in many cancers. Genetic strategies to re-target viral infection to alternate receptors through modifications of capsid genes has also been impeded by the large viral genome and complex adenoviral gene organization, and the fact that capsid gene alterations often interfere with protein structure, viral packaging, and infection. Improved compositions and methods are required to screen genetic alterations in viral capsid proteins.

SUMMARY OF THE INVENTION

As described below, the present invention provides DNA libraries, libraries of viral clones and libraries of infectious viral particles and methods of generating and screening these libraries. More specifically, the invention provides a capsid-displayed fiber library that is particularly useful for the identification of modified fiber polypeptides, including mutant fiber polypeptides, chimeric fiber polypeptides comprising fiber sequences derived from one or more adenovirus serotypes, chimeric fiber polypeptides comprising fiber sequences and other non-fiber polypeptides, fiber polypeptides containing a random or rationally designed peptide insert, and methods of screening such modified fiber polypeptide libraries to identify those capable of mediating re-targeted viral infection or improved biodistribution, and an adenoviral vector system that facilitates generation of a capsid-displayed library.

The invention generally features a method of identifying a modified capsid-displayed adenoviral polypeptide, the method involves contacting a population (e.g., two or more cells, such as 10, 25, 50, 100, 250, 500, 1000, 2000, 3000, or more) of mammalian cells with an adenoviral library generated by co-transforming a population of cells expressing Cre-recombinase with linearized shuttle plasmids, each containing a selectable marker, and transfer plasmids, each containing a variant capsid-displayed adenoviral gene flanked by lox sites, where the variant capsid-displayed adenoviral gene contains a mutation relative to the native adenoviral gene sequence and recombining the variant capsid-displayed adenoviral gene and the negatively selectable marker to generate an adenovirus expressing a modified capsid-displayed adenoviral polypeptide; identifying an adenovirus expressing a modified capsid-displayed adenoviral polypeptide that increases adenovirus binding to a mammalian cell relative to a wild-type adenovirus; and isolating the variant capsid-displayed adenoviral gene, thereby identifying a modified capsid-displayed adenoviral polypeptide that re-targets an adenovirus.

In one aspect, the invention features a method of identifying a nucleic acid sequence encoding a modified fiber polypeptide that re-targets an adenovirus, the method involves contacting a population of mammalian cells with an adenoviral library generated by co-transforming a population of cells expressing Cre-recombinase with linearized shuttle plasmids, each containing a selectable marker, and transfer plasmids, each containing a variant fiber gene flanked by lox sites, and a mutation that disrupts binding to a coxsackievirus-adenovirus receptor (CAR), and recombining the variant fiber gene and the negatively selectable marker to generate an adenovirus expressing a modified fiber polypeptide; identifying a viral unit (e.g., plaque or replicating virus) resulting from a CAR-independent adenovirus infection; amplifying the variant fiber gene from the viral unit; isolating the variant fiber gene in a rescue vector by co-transforming a CRE expressing bacterial cell with a rescue plasmid containing a nucleic acid sequence encoding a negatively selectable marker flanked by lox sites and a transfer plasmid, containing a variant fiber gene flanked by lox sites, and recombining the variant fiber gene and the negatively selectable marker to generate a rescue plasmid containing the variant fiber gene; and characterizing the variant fiber gene, thereby identifying a modified fiber polypeptide that re-targets an adenovirus.

In various embodiments of the above aspects, the modified adenoviral or fiber polypeptide contains a mutation (e.g., a point mutation, an insertion, or a deletion). In another embodiment, the method is carried out in vitro or in vivo. In one embodiment, the insertion is of an amino acid sequence containing 5, 10, 25, 50, 75, 100, or 200 amino acids. In another embodiment, the modified adenoviral or fiber polypeptide is a chimeric polypeptide (e.g., a chimeric polypeptide that contains amino acid sequences derived from one or more adenovirus serotypes, from one or more non-adenoviral polypeptides, from a random amino acid sequence, or from a rationally designed peptide insert). In still other embodiments, the characterizing step involves sequencing, assaying biodistribution or clearance of the modified adenoviral polypeptide or fiber polypeptide.

In another aspect, the invention provides a method of isolating a nucleic acid molecule of interest from an adenovirus, the method involves co-transforming a CRE expressing bacterial cell with a rescue plasmid containing a nucleic acid sequence encoding a negatively selectable marker flanked by lox sites and a transfer plasmid, containing a nucleic acid molecule of interest flanked by lox sites, and recombining the nucleic acid molecule of interest and the negatively selectable marker to generate a rescue plasmid containing the nucleic acid molecule of interest. In one embodiment, the nucleic acid molecule of interest is a variant fiber nucleic acid molecule.

In yet another aspect, the invention provides a rescue vector containing the sequence of SEQ ID NO:7. In one embodiment, the vector further contains a variant fiber gene flanked by lox sites and a mutation that disrupts binding to a coxsackievirus-adenovirus receptor (CAR). In one embodiment, the variant fiber gene further contains a mutation (e.g., a point mutation, insertion, deletion). In another embodiment, the mutation is the insertion of a heterologous nucleic acid segment.

In yet another aspect, the invention provides a host cell (e.g., bacterial or mammalian) containing the rescue vector of any preceding aspect.

In yet another aspect, the invention provides a DNA library containing variant fiber genes and a selectable marker, where each variant fiber gene is flanked by lox sites, and contains a mutation that disrupts binding to a coxsackievirus-adenovirus receptor (CAR).

In yet another aspect, the invention provides a library of adenovirus clones, each of which contains a variant fiber gene and a selectable marker, where each variant fiber gene is flanked by lox sites and contains a mutation that disrupts binding to CAR.

In yet another aspect, the invention provides a library of infectious adenoviral particles generated by co-transforming a population of cells expressing Cre-recombinase with linearized shuttle plasmids, each containing a selectable marker, and transfer plasmids, each containing a variant capsid-displayed adenoviral gene flanked by lox sites, where the variant capsid-displayed adenoviral gene contains a mutation relative to the native adenoviral gene sequence and recombining the variant capsid-displayed adenoviral gene and the negatively selectable marker to generate an adenovirus expressing a modified capsid-displayed adenoviral polypeptide, each of which displays on its capsid a modified fiber polypeptide and a mutation that disrupts binding to CAR. In one embodiment, each variant fiber gene contains a mutation (e.g., a point mutation, an insertion, or a deletion). In one embodiment, the insertion is of a heterologous nucleic acid segment. In another embodiment, the heterologous nucleic acid segment is inserted at the HI-loop of the fiber polypeptide. In yet another embodiment, the mutation that disrupts binding to CAR is a deletion of fiber $T_{489}AYT_{492}$. In another embodiment, the library is a plasmid library. In another embodiment, the library contains $10^2$-$10^9$ plasmid clones. In another embodiment, the library contains $10^2$-$10^7$ adenovirus clones.

In yet another aspect, the invention provides a population of cells containing a library of any of previous aspect. In one embodiment, the cells are mammalian cells or are bacterial cells.

In yet another aspect, the invention provides a population of mammalian cells containing an adenoviral library, where each adenoviral clone contains a variant fiber gene and a selectable marker, where each variant fiber gene is flanked by lox sites, and contains a mutation that disrupts binding to a coxsackievirus-adenovirus receptor (CAR).

In yet another aspect, the invention provides a method of generating an adenoviral library, the method containing the steps of co-transforming a population of packaging cells expressing Cre-recombinase with linearized shuttle plasmids, each containing a selectable marker, and transfer plasmids, each containing a variant adenoviral gene encoding a modified capsid-displayed adenoviral polypeptide and a selectable marker, where each variant fiber gene is flanked by lox sites, and a mutation that disrupts binding to a coxsackievirus-adenovirus receptor (CAR); and recombining the variant adenoviral gene and the negatively selectable marker in the packaging cell to generate an adenovirus containing a modified capsid-displayed adenoviral polypeptide.

In yet another aspect, the invention provides a method of generating an adenoviral library, the method involves the steps of co-transforming a population of packaging cells expressing Cre-recombinase with linearized shuttle plasmids, each containing a selectable marker, and transfer plasmids, each containing a variant fiber gene and a selectable marker, where each variant fiber gene is flanked by lox sites, and a mutation that disrupts binding to a coxsackievirus-adenovirus receptor (CAR); and recombining the variant fiber gene and the negatively selectable marker in the packaging cell to generate an adenovirus containing a capsid expressing a modified fiber polypeptide.

In yet another aspect, the invention provides a method for expressing a desired product in a cell, the method containing infecting a cell with an adenovirus expressing a modified capsid-displayed adenoviral polypeptide identified according to the method of a previous aspect, where the adenovirus further contains a nucleic acid molecule encoding a desired product.

In yet another aspect, the invention provides a method for expressing a desired product in a cell, the method involves infecting a cell with an adenovirus containing a modified fiber gene identified according to the method of a previous aspect, where the adenovirus further contains a nucleic acid molecule encoding a desired product (e.g., a polypeptide, polypeptides, or fragments thereof, a nucleic acid molecule, an aptamer, a siRNA, an antisense nucleic acid molecule, or an shRNA). In one embodiment, the product is a polypeptide (e.g., a therapeutic or diagnostic polypeptide). In another embodiment, the desired diagnostic polypeptide is useful in imaging. In another embodiment, the diagnostic polypeptide contains a detectable reporter, or is a herpes thymidine kinase polypeptide, or a sodium iodide symporter. In another embodiment, the nucleic acid segment is under control of a promoter (e.g., a tissue specific promoter).

In yet another aspect, the invention provides an adenovirus particle containing a modified fiber gene flanked by two lox sites, where the fiber gene contains a heterologous nucleic acid segment encoding an integrin targeting peptide.

In yet another aspect, the invention provides an isolated vector containing the sequence of AdTrack-FBR2-A2, A3, or A4.

In yet another aspect, the invention provides a host cell infected with an adenovirus particle of a previous aspect or an adenovirus containing a modified fiber polypeptide encoded by a vector of a previous aspect.

In yet another aspect, the invention provides a method of detecting a cell or tissue infected with a re-targeted adenoviral vector, the method involves administering to a subject an adenoviral vector encoding a modified fiber polypeptide identified according to the method of a previous aspect, and further encoding a desired diagnostic product (e.g., a nucleic acid molecule encoding the diagnostic product inserted in the E1 cassette). In one embodiment, the desired diagnostic product identifies a neoplasia, a virus infection, or other pathological condition. In another embodiment, the diagnostic product is a herpes thymidine kinase or sodium iodide symporter. In another embodiment, the diagnostic product provides for the accumulation of a radiolabel or other detectable agent in an infected cell or tissue. In another embodiment, the diagnostic product provides for the imaging of a neoplasia, viral location or replicative activity.

In yet another aspect, the invention provides a pharmaceutical composition for the identification of an adenoviral-infected cell, the composition containing an effective amount of an adenoviral vector encoding a modified fiber polypeptide identified according to the method of claim 1 and a desired diagnostic product. In one embodiment, the diagnostic product is herpes thymidine kinase or a sodium iodide symporter that provides for the accumulation of a detectable agent. In another embodiment, the agent is visualized using SPECT or PET. In another embodiment, the agent includes a radionuclide that is iodine-$^{123}$I, $^{124}$I, $^{125}$I, or $^{131}$I.

In yet another aspect, the invention provides an in vivo method of identifying a modified capsid-displayed adenoviral polypeptide, the method involving contacting a subject with an adenoviral library generated by co-transforming a population of cells expressing Cre-recombinase with linearized shuttle plasmids, each containing a selectable marker, and transfer plasmids, each containing a variant capsid-displayed adenoviral gene flanked by lox sites, where the variant capsid-displayed adenoviral gene contains a mutation relative to the native adenoviral gene sequence and recombining the variant capsid-displayed adenoviral gene and the negatively selectable marker to generate an adenovirus expressing a modified capsid-displayed adenoviral polypeptide; identifying an adenovirus expressing a modified capsid-displayed adenoviral polypeptide that increases adenovirus binding to a cell of the subject relative to a wild-type adenovirus; and isolating the variant capsid-displayed adenoviral gene, thereby identifying a modified capsid-displayed adenoviral polypeptide that re-targets an adenovirus.

In yet another aspect, the invention provides a in vivo method of identifying a nucleic acid sequence encoding a modified fiber polypeptide that re-targets an adenovirus, the method involves contacting a subject with an adenoviral library generated by co-transforming a population of cells expressing Cre-recombinase with linearized shuttle plasmids, each containing a selectable marker, and transfer plasmids, each containing a variant fiber gene flanked by lox sites, and a mutation that disrupts binding to a coxsackievirus-adenovirus receptor (CAR), and recombining the variant fiber gene and the negatively selectable marker to generate an adenovirus expressing a modified fiber polypeptide; identifying a CAR-independent adenovirus infection of a cell of the subject; amplifying the variant fiber gene from the infected cell; isolating the variant fiber gene in a rescue vector by co-transforming a CRE expressing bacterial cell with a rescue plasmid containing a nucleic acid sequence encoding a negatively selectable marker flanked by lox sites and a transfer plasmid, containing a variant fiber gene flanked by lox sites, and recombining the variant fiber gene and the negatively selectable marker to generate a rescue plasmid containing the variant fiber gene; and characterizing the variant fiber gene, thereby identifying a modified fiber polypeptide that re-targets an adenovirus.

In various embodiments of any of the above aspects, the modified adenoviral or fiber polypeptide contains a mutation (e.g., a point mutation, an insertion, or a deletion). In other embodiments of the above aspects, the is of an amino acid sequence containing 5, 6, 7, 8, 9, 10, 15, 20, 25, 50, 75, 100, 125, 150, 175, or 200 amino acids. In other embodiments, the modified adenoviral or fiber polypeptide is a chimeric polypeptide, such a chimeric polypeptide that contains one or more amino acid sequences derived from one or more adenovirus serotypes, from one or more non-adenoviral polypeptides, from a random amino acid sequence, or from a rationally designed peptide insert. In other embodiments, any of the above aspects further include a characterizing step that involves assaying biodistribution or clearance of the modified adenoviral polypeptide or fiber polypeptide. In various embodiments, the characterizing step involves sequencing the modified adenoviral polypeptide or fiber polypeptide, or a fragment thereof. In other embodiments, the modified adenoviral polypeptide, variant fiber gene, or nucleic acid molecule of interest contains a heterologous nucleic acid segment. In other embodiments, the heterologous nucleic acid segment encodes a peptide that is inserted in the Fiber HI loop region. In another embodiment, the negatively selectable marker is SacB. In still other embodiments, the lox sites are any one or more of Lox m2/66, Lox 71, Lox m2/71 and Lox 66. In still other embodiments, the selectable marker is kanamycin or ampicillin. In still other embodiments, the method further involves selecting recombinant adenoviral vectors using the selectable marker. In still other embodiments, the cell is a bacterial cell (e.g., an E. coli cell) or is a mammalian cell (e.g., human, rodent). In still other embodiments, the shuttle plasmid contains a resistance gene and a nucleic acid segment encoding a desired product. In still other embodiments, the product is one or more of a polypeptide, polypeptides, or fragments thereof, a nucleic acid molecule, an aptamer, a siRNA, an antisense nucleic acid molecule, or an shRNA. In other embodiments, the desired polypeptide is a therapeutic or diagnostic polypeptide. In other embodiments of the above aspects, the transfer plasmid is constructed by: co-transforming a donor plasmid and an acceptor plasmid into a cell expressing Cre recombinase; where the acceptor plasmid contains a nucleic acid segment encoding a negatively selectable marker flanked by lox sites, and a first selectable marker; and the donor plasmid contains a nucleic acid segment encoding the fiber gene flanked by lox sites and a second selectable marker, thereby allowing for recombination of the fiber gene and the negatively selectable marker. In still other embodiments, the lox sites are incompatible (e.g., are mutated to result in unidirectional recombination). In still other embodiments, the negatively selectable marker is SacB.

The invention provides screening methods utilizing an adenoviral vector system that facilitates the identification of capsid-displayed modified fiber polypeptides that mediate viral re-targeting. Other features and advantages of the invention will be apparent from the detailed description, and from the claims.

DEFINITIONS

As used herein the term "acceptor plasmid" is intended to mean a plasmid containing a negatively selectable marker flanked by lox sites and a selectable marker, e.g., ampicillin, located between RecA homologous recombination sites. The negatively selectable marker can be, for example, SacB. An exemplary acceptor plasmid is referred to as pFex herein.

As used herein, the term "adenovirus" or "adenoviral particle" is used to include any and all viruses that can be categorized as an adenovirus, including any adenovirus that infects a human or an animal, including all groups, subgroups, and serotypes. Depending upon the context reference to "adenovirus" can include adenoviral vectors. There are at least 51 serotypes of Adenovirus that classified into several subgroups. For example, subgroup A includes adenovirus serotypes 12, 18, and 31. Subgroup C includes adenovirus serotypes 1, 2, 5, and 6. Subgroup D includes adenovirus serotype 8, 9, 10, 13, 15, 17, 19, 20, 22-30, 32, 33, 36-39, and 42-49. Subgroup E includes adenovirus serotype 4. Subgroup F includes adenovirus serotypes 40 and 41. These latter two serotypes have a long and a short fiber protein. Thus, as used herein an adenovirus or adenovirus particle is a packaged vector or genome.

An "adenovirus vector" or "adenoviral vector" (used interchangeably) is a term well understood in the art and generally comprises a polynucleotide comprising all or a portion of an adenovirus genome. As used herein, "adenovirus" refers to the virus itself or derivatives thereof. The term covers all serotypes and subtypes and both naturally occurring and recombinant forms, except where otherwise indicated. An adenoviral vector of the present invention can be in any of several forms, including, but not limited to, naked DNA; an adenoviral vector encapsulated in an adenovirus coat; packaged in another viral or viral-like form (such as herpes simplex virus and AAV); encapsulated in a liposome; complexed with polylysine or other biocompatible polymer; complexed with synthetic polycationic molecules; conjugated with transferrin; complexed with compounds such as PEG to immunologically "mask" the molecule and/or increase half-life, or conjugated to a non-viral protein. An adenoviral vector of this invention may be in the form of any of the delivery vehicles described herein. Such vectors are one embodiment of the invention. Preferably, the polynucleotide is DNA.

As used herein, "capsid-displayed adenoviral polypeptide" includes an adenoviral encoded polypeptide that is expressed on the adenoviral capsid. Preferably, the capsid-displayed adenoviral polypeptide mediates re-targeting.

As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides. For purposes of this invention, adenovirus vectors are replication-competent, conditionally replicative (i.e., replicative only in cancer cells or tissues, or replicative only in the context of a tissue specific promoter), or are replication incompetent in a target cell. In specific embodiments, the virus is replication incompetent due to the replacement of the E1 region with CMV-GFP. Such a virus can replicate in a "packaging cell" which provides E1 in trans.

As used herein the term "diagnostic product" encompasses a polypeptide that provides for the visualization or detection of a cell, tissue, or organ infected by an adenoviral vector of the invention. Such detection may be in vivo or in vitro.

As used herein the term "donor plasmid" is intended to mean a plasmid containing a donor gene flanked on either side by lox sites. In exemplary embodiments of the invention the donor gene is a fiber gene, or fragment thereof. However, one skilled in the art would understand that other genes can be used in place of fiber. For example, another gene that encodes a cell surface recognition protein can be used in place of fiber. Also, a nucleic acid molecule encoding a toxin can be used in place of fiber. In order to select for the transfer plasmid, the donor plasmid has a different selectable marker than the acceptor plasmid. In exemplary embodiments, the donor plasmid has ampicillin, kanamycin, or blastocidin resistance. Exemplary donor plasmids are referred to as RP-Fib, RPuc-Fib, and Rblast-Fib herein.

As used herein, the term "heterologous polynucleotide" means a polynucleotide derived from a biological source other than the biological source of the sequences flanking the heterologous polynucleotide. In one embodiment, the heterologous polynucleotide encodes a random peptide. In another embodiment, the heterologous polynucleotide is derived from an adenovirus or other virus family of a different strain or of a different species than the sequences flanking the heterologous polynucleotide. The heterologous polynucleotide can encode a polypeptide, such as a toxin or a therapeutic or diagnostic protein. The heterologous polynucleotide can contain regulatory regions, such as a promoter regions, such as a promoter active in specific cells or tissue, for example, tumor tissue as found in oncolytic adenoviruses. Alternatively, the heterologous polynucleotide encodes a polypeptide and contains a regulatory region, such as a promoter region operably linked to the coding region.

As used herein the term "lox sites" is intended to mean a nucleic acid sequence that the Cre recombinase recognizes. The canonical lox site is the loxP site. Lox sites are 34 nucleotides in length and have a 13 base pair inverted repeat separated by an 8 base pair spacer (see FIG. 1). Wild-type lox sites are unaltered following recombination thereby allowing for a reversible reaction. The instant invention uses "incompatible" lox sites which have a mutation such that intrageneic recombination, i.e. recombination within a plasmid which can result in deletion or inversion of flanked nucleic acid, can not occur. Exemplary mutations include those to the spacer that result in non-functional lox sites following recombination (see FIGS. 2A-B). The instant invention also applies "half-mutant" lox sites, which when correctly recombined, produce one fully mutant lox site and one wild type lox site, resulting in a non-functional lox site, thus preventing the reverse reaction. Specific exemplary incompatible lox sites for uni-directional insertion include the Lox m2/66 and Lox 71 on the donor fragment and Lox m2/71 with Lox66 on the acceptor fragment (see, for example, Langer, S. J. et al. (2002) *Nucleic Acid Research* 20:3067-77).

As used herein the term "modified fiber polypeptide" is intended to mean a fiber polypeptide comprising at least one alteration relative to a wild-type fiber amino acid sequence (e.g., GenBank Accession number P03275). Such alteration includes a point mutation, insertion, or deletion. In one embodiment, an insertion is of at least about 5, 6, 7, 8, 9, 10, 20, 30, 40, 50 or more amino acids. In another embodiment, the "modified fiber polypeptide" encodes a rationally designed chimera of adenovirus and other heterologous polynucleotide sequences. The "modified fiber polypeptide" can also encode a polypeptide which enhances viral infection for a specific tissue, such as a receptor ligand or a functional portion of an antibody.

As used herein the term "nucleic acid molecule encoding fiber" is intended to mean a nucleic acid segment encoding viral capsid protein that is responsible for mediating high-affinity attachment of adenovirus to a target cell. The amino acid sequence of fiber is available as GenBank Accession number P03275, and is further described by Hierisse, J., et al. (1981) Nucleic Acids Res. 9:4023-4042. In specific embodiments, the fiber gene used in the methods and compositions of the invention can be a functional fragment of the fiber protein, i.e., a fragment that retains the ability to allow the attachment of a virus to a cell.

As used herein, a packaging cell line is a cell line that is able to package adenoviral genomes or modified genomes to produce viral particles. It can provide a missing gene product or its equivalent. Thus, packaging cells can provide complementing functions for the genes deleted in an adenoviral genome (e.g., the nucleic acids encoding modified fiber proteins) and are able to package the adenoviral genomes into the adenovirus particle. The production of such particles require that the genome be replicated and that those proteins necessary for assembling an infectious virus are produced. The particles also can require certain proteins necessary for the maturation of the viral particle. Such proteins can be provided by the vector or by the packaging cell.

The term "plasmid" denotes an extrachromosomal circular DNA capable of autonomous replication in a given cell. The range of suitable plasmids is very large. Preferably, the plasmid is designed for amplification in bacteria and for expression in an eukaryotic target cell. Such plasmids can be purchased from a variety of manufacturers. Exemplary plasmids include but are not limited to those derived from pBR322 (Gibco BRL), pUC (Gibco BRL), pBluescript (Stratagene), pREP4, pCEP4 (Invitrogene), pCI (Promega) and p Poly (Lathe et al., Gene 57 (1987), 193-201). Plasmids can also be engineered by standard molecular biology techniques (Sambrook et al., Laboratory Manual, Cold Spring Harbor Laboratory Press, Cold Spring Harbor (1989), N.Y.). It may also comprise a selection gene in order to select or to identify the transfected cells (e.g., by complementation of a cell auxotrophy or by antibiotic resistance), stabilizing elements (e.g., cer sequence; Summers and Sherrat, 1984, Cell 36, 1097-1103) or integrative elements (e.g., LTR viral sequences and transposons).

As used herein the term "shuttle plasmid" is intended to mean a plasmid comprising a unique restriction site between RecA homologous recombination sites and used to insert a desired nucleic acid molecule, i.e., a nucleic acid molecule encoding a desired product, into a recombinant adenoviral vector. The RecA homologous recombination sites can be, for example, Ad5 right and Ad5 left. In further embodiments, the shuttle plasmid may have a tissue specific promoter which controls the expression of the desired nucleic acid molecule. The shuttle plasmid also contains a majority of the viral genes necessary to form viral particles. However, the shuttle plasmid does not contain all necessary genes to form viral particles. An exemplary shuttle plasmid is referred to as pShuttle herein (FIGS. 30A-30P and 31A-31D).

As used herein, RecA mediated homologous recombination is used to exemplify enzyme mediated homologous recombination. Other enzymes capable of mediating homolgous recombination are known in the art and can be used to design the vectors of the invention, and can further be used in the methods of the invention. For example, homologous recombination enzymes are known in eukaryotes, e.g., Rad51, Rad57, Rad55 and DMC1, in Archaea, e.g., RadA and RadB, and in phage, e.g., vsX in phage T4. These enzymes and homologs and orthologs of these enzymes are envisioned for use in the methods of the present invention.

As used herein the term "transfer plasmid" is intended to mean the plasmid that results from the Cre mediated recombination of the donor plasmid and the acceptor plasmid. The transfer plasmid has the fiber gene, or other gene in the fiber location, inserted in place of the negatively selectable marker. Moreover, the transfer plasmid has RecA homologous recombination sites to allow for insertion of a desired nucleic acid molecule by RecA mediated homologous recombination with the shuttle plasmid. The transfer plasmid also has a selectable marker, i.e., ampicillin located between the RecA homologous recombination sites. The RecA homologous recombination sites can be, for example, Ad5 tight and Ad5 left. An exemplary transfer plasmid is referred to as pFex-Fib herein.

As used herein the term "shuttle-acceptor plasmid" is intended to mean the recombination product of RecA mediated recombination of a shuttle plasmid and an acceptor plasmid. The shuttle-acceptor plasmids of the invention comprise a negatively selectable marker located between two lox sites, a resistance marker, and a nucleic acid molecule encoding a desired product. An exemplary shuttle-acceptor plasmid is referred to as pShuttle-Fex herein.

In one embodiment, the "desired product" in use in the present invention, encodes a gene product of therapeutic or diagnostic interest. In one embodiment, a "desired product" can have a therapeutic or protective activity when administered appropriately to a patient, especially a patient suffering from a disease or illness condition or who should be protected against this disease or condition. Such a therapeutic or protective activity can be correlated to a beneficial effect on the course of a symptom of said disease or said condition. It is within the reach of the man skilled in the art to select a gene encoding an appropriate gene product of therapeutic interest, depending on the disease or condition to be treated. In a general manner, his choice may be based on the results previously obtained, so that he can reasonably expect, without undue experimentation, i.e., other than practicing the invention as claimed, to obtain such therapeutic properties.

Alternatively, the desired product is useful as a diagnostic. In one embodiment, a vector of the invention is engineered with the herpes simplex 1 (HSV1) thymidine kinase (TK) gene to monitor cells targeted with the adenoviral vectors described herein using radiolabeled nucleoside analogues. HSV1 TK genes are known in the art, and are described, for example, in U.S. Patent Publication No. 20020042139; also in the following publications: Wigler, et al., 1977, Cell 11:223; Ram et al., (1993) Cancer Research, 53, 83-88; Culver et al., (1992), Science, 256, 1550-1552 Vile et al., Cancer Res., 53:3860-64, 1993; Moolten et al., J. Natl. Cancer Inst., 82(4):297-300, 1990; Wagner et al., Nucleotide sequence of the thymidine kinase gene of herpes simplex virus type 1. Proc. Natl. Acad. Sci. USA, 78:1441-45, 1981; each of which is incorporated herein by reference. In another embodiment, a vector of the invention is engineered with a sodium iodide symporter, which provides for the accumulation of radiolabelled iodide. The following scientific references describe such symporters: Arturi et al., J. Clin. Endocr. Metab. 83: 2493-2496, 1998; Caturegli et al., Proc. Nat. Acad. Sci. 97: 1719-1724, 2000; Cho et al., J. Clin. Endocr. Metab. 85: 2936-2943, 2000; Couch et al., J. Pediat. 106: 950-953, 1985; Dai et al., Nature 379: 458-460, 1996; Fujiwara et al., Nature Genet. 16: 124-125, 1997; Fujiwara et al., J. Clin. Endocr. Metab. 83: 2940-2943, 1998; Kosugi et al., J. Clin. Endocr. Metab. 84: 3248-3253, 1999; Kosugi et al., J. Clin. Endocr. Metab. 83: 3373-3376, 1998; Kosugi et al., J. Clin. Endocr. Metab. 83: 4123-4129, 1998; Lazar et al., J. Clin, Endocr. Metab. 84: 3228-3234, 1999; Levy et al., FEBS Lett. 429: 36-40, 1998; Matsuda et al., J. Clin. Endocr. Metab. 82: 3966-3971, 1997; Ohmori et al., Molec. Endocr. 12: 727-736, 1998; Pohlenz et al., Biochem. Biophys. Res. Commun. 240: 488-491, 1997; Pohlenz et al., J. Clin. Invest. 101: 1028-1035, 1998; Smanik et al., Biochem. Biophys. Res. Commun. 226: 339-345, 1996; Smanik et al., Endocrinology 138: 3555-3558, 1997; Spitzweg et al., J. Clin Endocr. Metab. 84: 4178-4184, 1999; Venkataraman et al., J. Clin. Endocr. Metab. 84: 2449-2457, 1999. Accordingly vectors of the invention are useful for the radioimaging of targeted cell types. In one embodiment, a replication-incompetent virus is used to transduce the human sodium iodide symporter gene or HSV1 TK gene into a neoplastic cells under the control of a promoter that directs expression of the gene in the transduced cell type. The adenovirus mediates expression of the transgene. Radiolabeled nucleoside accumulation can be used to image the neoplastic cell. If desired, human sodium iodide symporter expression may be combined with therapeutic doses of 131I to suppress tumor growth. The gene of interest can be used to image an infected cell or tissue by optical, magnetic resonance, or nuclear imaging techniques. In other embodiments, the desired product is useful as an imaging reporter that provides for the detection of viral location and replicative activity. If desired, a nucleic acid molecule encoding a desired product having therapeutic or diagnostic utility is inserted into the adenoviral E1 cassette or in any other region that provides for expression of the desired product.

As used herein the term "de-target" refers to an adenovirus comprising a modification that reduces the level or biological activity of one or more polypeptides that typically mediates adenoviral infection of a cell. An example of a de-targeted adenovirus is an adenovirus comprising a mutation that reduces the level or biological activity of CAR (e.g., CAR ablated Fiber (ΔTAYT))

As used herein the term "variant fiber gene" is intended to mean a fiber gene that encodes a modified fiber polypeptide.

As used herein the term "re-targets" is intended to mean that an adenoviral vector of the invention infects (or re-targets) a cell type that is only negligibly infected, if at all, by a wild-type adenovirus. Such re-targeted infection is at least about 5%, 10%, 15%, 25%, 50%, or even 75% greater than an infection caused by a wild-type virus. Such re-targeting can also reduce binding and infection rates of alternate cell types, leading to improved biodistribution and reduced viral sequestration in non-target tissues. In particular embodiments, the re-targeted adenovirus infects a stem cell, dendritic cell, or other cell type resistant to adenoviral infection.

In the context of the invention, the desired product can be homologous or heterologous to the host cell into which it is introduced. Advantageously, it encodes a polypeptide, a ribozyme or anti-sense RNA, RNAi, an aptamer or the like. The term "polypeptide" is to be understood as any translational product of a polynucleotide whatever its size is, and includes polypeptides having as few as 7 residues (peptides), but more typically proteins. In addition, it may be from any origin (prokaryotes, lower or higher eukaryotes, plant, virus etc). It may be a native polypeptide, a variant, a chimeric polypeptide having no counterpart in nature or fragments thereof. Advantageously, the gene of interest in use in the present invention encodes at least one polypeptide that can compensate for one or more defective or deficient cellular proteins in an animal or a human organism, or that acts through toxic effects to limit or remove harmful cells from the body. A suitable polypeptide may also be immunity conferring and acts as an antigen to provoke a humoral or a cellular response, or both.

The regulatory elements controlling the expression of the desired gene may further comprise additional elements, such as promoters, including constitutive, conditional, and tissue specific promoters, enhancers, exon/intron sequences, targeting sequences, transport sequences, secretion signal sequences, nuclear localization signal sequences, IRES, polyA transcription termination sequences, tripartite leader sequences, sequences involved in replication or integration. These elements have been reported in the literature and can be readily obtained by those skilled in the art.

The terms "polynucleotide" and "nucleic acid", used interchangeably herein, refer to a polymeric form of nucleotides of any length, either ribonucleotides or deoxyribonucleotides. These terms include a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracyl, other sugars and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support. Preferably, the polynucleotide is DNA. As used herein, "DNA" includes not only bases A, T, C, and G, but also includes any of their analogs or modified forms of these bases, such as methylated nucleotides, internucleotide modifications such as uncharged linkages and thioates, use of sugar analogs, and modified and/or alternative backbone structures, such as polyamides.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/ PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

BRIEF DESCRIPTION OF THE DRAWINGS

FIGS. 2A-2B depict various lox sequences. FIG. 2A depicts lox sequences (SEQ ID NOS 15-18, respectively) with half-site mutations in italics. FIG. 2B depicts spacer sequences with mutations in italics.

FIG. 14A shows that the large viral plasmid vector pFex has two regions for accepting transgene cassettes, the Amp-resistant-E1-region cassette and the SacB-Fiber-region cassette. The Fiber-region-cassette can be recombined before (bottom panel) or after E1-region-cassette recombination (top panel). E1 cassettes are recombined through homologous recombination of adenovirus left-hand and right-hand homology regions in RecA positive BJ5183 coli. Recombinant plasmids are selected according to the newly acquired resistance cassette. On the other hand, Fiber cassettes are recombined through half-mutant lox site (see legend: Green=wild type half site, Red=mutant half site, Black and Grey represent non-compatible spacers) recombination in Cre recombinase expressing coli. Non-compatible spacers (grey center versus black center) prevent intragenic recombination. The resulting recombinant plasmids are selected by growth on sucrose containing plates. Following recombination, the donor plasmid product contains fully mutant lox sites (red circles), where the resulting recombinant vector contains fully wild type lox sites (green circles); therefore preventing any further recombination between the shuttles and viral vectors. The final resulting vectors are linearized and transfected into mammalian packaging cells to create viral particles. FIG. 14B. Fiber gene cassettes can be directly shuttled into adenoviral genomes in mammalian cells. E1-cassette-containing pFex vectors, such as AdTrack-pFex, can be pseudotyped (packaged in cells that express wild type Fiber) and used to infect packaging cell lines that express Cre recombinase. Transfection of infected cells with a Fiber-gene shuttle results in site specific incorporation of the Fiber-cassette into replicative adenovirus. Only following recombination into a viral genome can the modified Fiber gene be expressed. The resulting recombinant virus will be packaged in the newly synthesized modified-Fiber capsids and amplified in other cell lines, such as 911-S111.

FIGS. 15A-15D show E1 and Fiber Cassette Exchange in Plasmid Vectors. FIG. 15A is an agarose gel showing PacI restriction digestion of parental vector, pFex, and resulting recombinant vectors pAdTrack-Fex and pAdTrack-Luc-Fex following E1 cassette exchange in BJ5183 E. coli. The corresponding E1 Cassettes contain an additional PacI site which results in the diagnostic 4.6 Kb band (arrow). FIG. 15B is a photograph of an agarose gel showing PCR across a single lox site of 294cre clones demonstrates the presence of Fiber containing pFex vectors in the recombination specific PCR (5'-primer within Fiber gene and 3'-primer within pFex). The Shuttle Control does not contain lox sites and therefore does not recombine with pFex. On the other hand, PCR within the pFex vector demonstrates presence of the "acceptor" pFex in both RP-Fib and Shuttle control samples. A PCR water control was included to detect PCR contamination. FIG. 15C shows the results of an XhoI restriction digest of 12 mini-preps randomly screened for the presence of the desired Fiber-containing clone following Fiber cassette exchange into pFex. The Fiber gene contains an additional XhoI site, which generates the diagnostic 3.6 Kb product (arrow). 100% of the screened clones contained the desired plasmid product. FIG. 15D shows the efficiency of fiber plasmid exchange in *E. coli*.

FIG. 16A shows a viral burst comparison of pFex derived and ADEASY™ derived virus, both containing wild type Fiber, which demonstrates equal replication and spreading rate as indicated by GFP positive viral burst size. FIG. 16B is a Western blot showing equal PFU of purified adenovirus containing wild type Fiber (AdTrack-WTFib), CAR ablated Fiber (ΔTAYT), or CAR ablated and RGD4C re-targeted Fiber (ΔTAYT-RGD). Samples were boiled and evaluated by Western Blotting (top gel). Similar Fiber quantities and appropriate size are demonstrated. Viral DNA of equal PFU of purified adenovirus was also subjected to PCR to evaluate content, size, and homogeneity of the Fiber-HI loop region (lower two gels). The larger Fiber-PCR band of AdTrack-RGD4C-2 (ΔTAYT-RGD) is caused by the peptide encoding region. AdTrack-FBR2 (ΔTAYT) and AdTrack-WTFib (Wild Type) do not contain recombinant HI loop peptides and therefore have identical size HI loop products. Hexon PCR was included as a reference control (FIG. 16C). PC-3 and PC3-CAR prostate cancer cells were infected with 100 MOI of Wild Type, CAR-ablated (ΔTAYT), and CAR-ablated and integrin re-targeted (ΔTAYT-RGD) GFP-expressing adenovirus. Infected cells were identified by GFP positive fluorescent microscopy. As predicted, ΔTAYT mutation completely de-targeted virus and inclusion of the integrin targeting peptide, RGD4C, restored viral infection in a CAR independent manner.

FIG. 19A shows a photomicrograph of 293 cells transfected with two separate anti-CAR siRNAs, a negative control siRNA, or non-transfected (UNT). 72 hours after transfection, cells were infected with each virus at an MOI of 1. Infected GFP positive cells were visible the following day by fluorescent microscopy (6×) at equal exposure times. The infection rate of adenoviruses with wild type Fiber were reduced by over 50% with both anti-CAR siRNAs. CAR knockdown had no effect on infected cell numbers in CAR-detargeted and peptide re-targeted viruses. FIG. 19B is a photomicrograph of PC-3 and the CAR over-expressing subline, PC3-CAR, which was infected with each virus at an MOI of 10. Infected GFP positive cells were visible the following day by fluorescent microscopy (6×) at equal exposure times. The infection rate of adenoviruses with wild type fiber increased several fold in the CAR over-expressing line. However, there was no visible increase in infected cell number in CAR-detargeted and peptide re-targeted viruses.

FIG. 21A shows that 293 cells were transfected with two separate anti-CAR siRNAs, a negative control siRNA, or non-transfected. 72 hours after transfection, cells were infected with each virus at an MOI of 10. Cell infection rate was quantified by fluorescence intensity on the BMG FLUOROstar fluorometer. Both anti-CAR siRNAs reduced infection by wild type fiber by over 50%. Each condition was performed in triplicate and error bars reflect standard error of the mean. FIG. 21B shows that PC-3 and the CAR over-expressing PC3-CAR cells were infected with each virus at an MOI of 100. Cell infection rate was quantified by fluorescence intensity on the BMG FLUO-ROstar fluorometer. CAR over-expression enhanced wild type infection by 26 fold. CAR over-expression did not enhance the infection rate of any CAR de-targeted or peptide re-targeted viruses. Each sample was completed in triplicate and error bars reflect standard error of the mean.

FIG. 22A is a plasmid map of the pFex "acceptor" vector. FIG. 22B shows a plasmid map of the RPuc-FBR1 "donor" vector. This ampicillin resistant vector is used for Fiber gene exchange into a Kanamycin resistant pFex vector which has already received an E1 gene cassette. FIG. 22C shows a plasmid map of the RP-FBR1 "donor" vector. This Kanamycin resistant vector is used for Fiber gene exchange into an ampicillin resistant pFex vector which has not yet received an E1 cassette.

FIG. 23 shows primers (SEQ ID NOS 24-53, respectively) for constructing and sequencing pFex.

FIG. 24 shows primers (SEQ ID NOS 54-57, 9-10, 58-64 and 64-66, respectively) for constructing and sequencing Fiber Shuttles

FIG. 29A-FIG. 29B show the sequence of RPuc-Rescue1.
FIG. 30A-FIG. 30P show the sequence of pShuttle-Fib.
FIG. 31A-FIG. 31D show the sequence of pShuttle.
FIG. 32A-FIG. 32B show the sequence of RP-Fib.
FIG. 33A-FIG. 33B show the sequence of RPucFib.
FIG. 34A-FIG. 34C show the sequence of RP-Blast-Fib.
FIG. 35A-FIG. 35N show the sequence of pFex.
FIG. 36 shows the sequence of a nucleic acid molecule encoding an exemplary modified Fiber sequence, AdTrack-RGD4C-2.

DETAILED DESCRIPTION OF THE INVENTION

Figure 1:
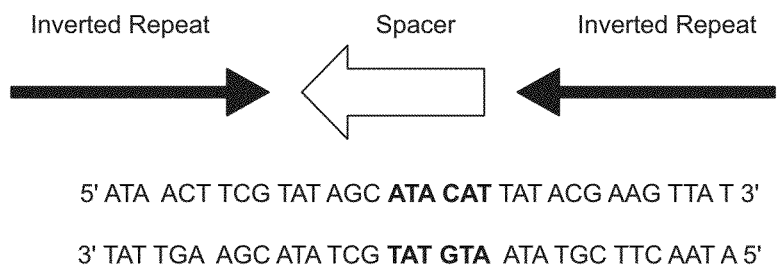
FIG. 1 is a schematic representation of a lox site showing two inverted repeats (SEQ ID NO: 15) separated by a spacer region.

The invention features compositions and methods for screening a capsid-displayed modified adenoviral polypeptide library utilizing an adenoviral vector system to identify modified adenoviral polypeptides that provide for re-targeted viral infection, and the therapeutic and/or diagnostic use of the retargeted viral vectors.

The invention utilizes an adenoviral vector system for generating Fiber-modified adenoviruses. The invention is based, at least in part, on the discovery of methods of using these vectors to shuttle modified Fiber genes into adenoviral plasmids in *E. coli* or into replicating adenovirus genomes in mammalian cells. The efficiency and sensitivity are such that Fiber-gene libraries can be generated and screened. Capsid-displayed adenoviral peptide libraries have long been sought, but a number of obstacles have hampered progress toward this goal. These obstacles include the large size of the viral genome, the low efficiency of converting plasmid-based genomes into packaged adenovirus, and the fact that library amplification is hampered by the ability of two (or more) virus to co-infect one cell. The present invention provides a novel vector system, termed "pFex" that overcomes these obstacles. The invention is based, at least in part, on the observation that using pFex, modified Fiber genes are recombined into the natural genetic locus of adenovirus through unidirectional Cre-lox recombination; modified-Fiber genes are directly shuttled into replicating viral genomes in mammalian cells. The "acceptor" vector does not contain the fiber gene, and therefore does not propagate until it has received a "donor" fiber gene. This methodology overcomes the low efficiency of transfecting large viral genomes and bypasses the need to transition to functional virus. Thus, with a Fiber-shuttle library, large numbers of fiber-modified adenovirus are generated and evaluated simultaneously. Finally, successful Fiber genes can be rescued from virus and recombined back into shuttle plasmids, avoiding the need to propagate mixed viral pools. As reported herein, this system has successfully been used to screen a capsid-displayed peptide library for re-targeted viral infection.

Adenovirus Technology

Decades of study of adenovirus biology have resulted in a detailed picture of the viral life cycle and the functions of the majority of viral proteins. The genome of the most commonly used human adenovirus (serotype 5) consists of a linear, 36 kb, double-stranded DNA molecule. Both strands are transcribed and nearly all transcripts are heavily spliced. Viral transcription units are conventionally referred to as early (E1, E2, E3 and E4) and late, depending on their temporal expression relative to the onset of viral DNA replication. The high density and complexity of the viral transcription units poses problems for recombinant manipulation, which is therefore usually restricted to specific regions, particularly E1, E2A, E3, and E4. In most recombinant vectors, transgenes are introduced in place of E1 or E3, the former supplied exogenously. The E1 deletion renders the viruses defective for replication and incapable of producing infectious viral particles in target cells; the E3 region encodes proteins involved in evading host immunity, and is dispensable for viral production per se.

Two approaches have traditionally been used to generate recombinant adenoviruses. The first involves direct ligation of DNA fragments of the adenoviral genome to restriction endonuclease fragments containing a transgene. The low efficiency of large fragment ligations and the scarcity of unique restriction sites have made this approach technically challenging. The second and more widely used method involves homologous recombination in mammalian cells capable of complementing defective adenoviruses ("packaging lines"). Homologous recombination results in a defective adenovirus which can replicate in the packaging line (e.g., 293 or 911 cells) which supplies the missing gene products (e.g., E1). The desired recombinants are identified by screening individual plaques generated in a lawn of packaging cells. The low efficiency of homologous recombination, the need for repeated rounds of plaque purification, and the long times required for completion of the viral production process have hampered more widespread use of adenoviral vector technology.

The present invention provides an adenoviral vector system that comprises an adenoviral vector, termed pFex, that facilitates the recombination of modified Fiber genes into the natural genetic locus of an adenovirus through uni-directional Cre-lox recombination. Modified-Fiber genes can be directly shuttled into replicating viral genomes in mammalian cells. The "acceptor" vector does not contain the fiber gene, and therefore does not propagate until it has received a "donor" fiber gene. This methodology overcomes the low efficiency of transfecting large viral genomes and bypasses the need to transition to functional virus. Thus, with a Fiber-shuttle library, large numbers of fiber-modified adenovirus are generated and evaluated simultaneously. Finally, successful Fiber genes can be rescued from virus and recombined back into shuttle plasmids, avoiding the need to propagate mixed viral pools. This selection pathway can be done in an iterative manner so that several selection "rounds" result in a desired product.

A key step in the generation of adenoviral plasmids according to the present invention is the co-transformation of bacteria with precursor DNA vectors. Transformation is the introduction of DNA into a bacterial cell. Transformation can be carried out by a number of techniques known in the art. Such methods include but are not limited to electroporation (exposure of a cell suspension to an electrical field), the use of calcium phosphate solutions, and the use of lipids to package the DNA and fuse with the cell membrane. Co-transformation refers to the introduction of two different species of DNA molecule into the same cell.

The plasmid desirably comprises one or more desired product. In addition, segments of DNA consisting of adenoviral sequences flank the desired product to promote homologous recombination with other nucleic acid molecules to ultimately produce an adenoviral vector.

The adenoviral vector typically contains most of the adenoviral genome. The adenoviral vector may also contain a bacterial origin of replication. Portions of the wild-type adenoviral genome may be deleted to permit insertion of desired products and the packaging of recombinant adenoviral vectors containing the desired genes.

The invention provides alternative methods for producing recombinant adenoviral vectors. The methods rely on two homologous recombination steps, one mediated by Cre and the other mediated by RecA. In alternate embodiments, the instant invention provides methods in which the Cre mediated recombination must precede the RecA recombination, methods in which the RecA mediated recombination must precede the Cre mediated recombination, and finally methods in which the order of recombination events in immaterial. The order of recombination events is dictated by the resistance genes on the precursor plasmids. For example, if the donor and shuttle plasmids have the same resistance gene, the Cre mediated recombination must be preformed first (see, for example, the schematic set forth in FIG. 4). In an alternate embodiment, if the donor and acceptor plasmids have the same resistance gene, the RecA mediated recombination must occur first (see, for example, the schematic set forth in FIG. 5). Lastly, if the donor has a different resistance gene than both the acceptor and shuttle plasmids, the order of recombination steps is at the discretion of the skilled artisan (for example, if the donor plasmid had blasticidin resistance as described in the examples).

In one embodiment, a Cre expressing cell is transformed with a donor and acceptor plasmid such that Cre mediated recombination results in the formation of a transfer plasmid. The donor plasmid contains a fiber gene, or other gene product to target the recombinant virus to a specific cell, flanked by lox sites. The acceptor plasmid has a negatively selectable marker, such as SacB, flanked by lox sites. In preferred embodiments of the invention, the lox sites are engineered, i.e., mutated, to result in irreversible, uni-directional recombination and to prevent intragenic recombination.

Cells containing the recombinant transfer plasmid are selected by growth in media containing a substrate for the negatively selectable marker and an antibiotic for which the resulting transfer plasmid carries a resistance gene. In exemplary embodiments, the negatively selectable gene is SacB and the antibiotic resistance is to ampicillin, and cells containing the recombinant transfer plasmid are selected by growth in media containing sucrose and ampicillin. Once cells containing transfer plasmids are isolated, the transfer plasmids can be isolated and transformed into a RecA expressing cell with linear shuttle plasmids. Linear shuttle plasmids are formed by digesting shuttle plasmids with one or more restriction enzymes. In one embodiment, the shuttle plasmid is linearized using a restriction enzyme that has a single restriction site in the plasmid. Alternatively, shuttle plasmids may not be linearized prior to introducing them into a cell for recombination. Recombinant adenoviral vectors formed as a result of RecA mediated recombination are selected by growing cells in the presence of an antibiotic which the recombinant adenoviral vectors carry a resistance gene against. This resistance gene was originally contained on the shuttle plasmid and is integrated into the recombinant viral vector during RecA mediated recombination. A schematic of this embodiment is set forth in FIG. 4.

In an alternate embodiment, the recombinant viral vectors are produced by transforming a cell expressing RecA with a linear shuttle plasmid and an acceptor plasmid. Cells containing a shuttle-acceptor plasmid are selected in media containing an antibiotic to which the resulting shuttle-acceptor plasmid confers resistance. Recombinant shuttle-acceptor plasmids are isolated and transformed into a cell expressing Cre along with a donor plasmid. Recombinant adenoviral vectors are selected using by growing cells in media containing a substrate for the negatively selectable marker and an antibiotic which recombinant adenoviral vectors carry a resistance gene against. This resistance gene was originally contained on the donor plasmid and is integrated into the recombinant viral vector during Cre mediated recombination. A schematic of this embodiment is set forth in FIG. 18.

In other embodiments, the Cre-recombinase mediate exchange is not limited to bacteria or plasmids. For example, fiberless acceptor plasmids can be packaged into working virus through complementary cell lines that express fiber protein (a process known as psuedotyping). These pseudotyped acceptor plasmids can then be used to infect Cre expressing cells, e.g., mammalian cells such as 293cre57, that have been transfected with fiber exchange vectors, i.e. donor vectors. Cell lysate and supernatant are then harvested and used to infect a non-Cre expressing packaging line, immediately generating a recombinant adenovirus.

Adenoviral particles can be prepared according to any conventional technique in the field of the art, such as homologous recombination in a permissive cell line (e.g., as described in Graham and Prevect, 1991, Methods in Molecular Biology, Vol 7, Gene Transfer and Expression Protocols; Ed E. J. Murray, The Human Press Inc, Clinton, N.J.) or in *Escherichia coli* (as described in WO96/17070). Propagation is advantageously performed in a complementing cell line or in the presence of a helper virus providing complementation in trans. "Complementing" or "complementation" denotes that the capability to encode and/or express functions that are defective in the vector but necessary for generating viable viral particles. The cell lines 293 (Graham et al., 1977, J. Gen. Virol. 36, 59-72) and PERC6 (Fallaux et al., 1998, Human Gene Therapy 9, 1909-1917) are commonly used to complement the E1 function. Other cell lines have been engineered to complement doubly defective vectors (Yeh et al., 1996, J. Virol. 70, 559-565; Krougliak and Graham, 1995, Human Gene Ther. 6, 1575-1586; Wang et al., 1995, Gene Ther. 2, 775-783; Lusky et al., 1998, J. Virol. 72, 2022-2033; EP919627 and WO97/04119). The adenoviral particles can be recovered from the culture supernatant but also from the cells after lysis and optionally further purified according to standard techniques (e.g., chromatography, ultracentrifugation, as described in WO96/27677, WO98/00524 and WO98/26048). Furthermore, the virions may be amplified by successive passage in a permissive cell in order to generate a high titer viral stock that may be used in the preparation of clinical lots.

The recombinant adenovirus vector generated as described above may be used to transfect mammalian cells. Techniques for transfection are well known. Available techniques include but are not limited to electroporation, the use of calcium chloride, and packaging of the vector together with lipid for fusion with the cells of interest. Cells may be transfected with the vector either in vitro or in vivo. The design of the recombinant adenoviral vector may place specific constraints on cells to be transfected. If production of viral particles is desired, a special packaging cell must be used that produces the adenoviral gene products which the adenoviral vector lacks. Which packaging cells are employed to replicate the virus will depend on the composition of the adenoviral vector used. The adenoviral vector may have specific portions of the adenoviral genome deleted, in order to make room for the desired gene in the recombinant vector. Suitable deletions which may be used include those of all or part of adenoviral transcription units E1, E3, and E4. The packaging cells preferably stably express the adenoviral proteins coded by the deleted transcription units. Techniques are known in the art for stably transfecting a cell line with whichever adenoviral sequences are required, i.e., by incorporation of the genes into the cell's genome. If virus particle production is not required, then packaging cell lines need not be used. For example, if cells are to express the desired product, production of viral particles need not be achieved. Thus for in vivo gene therapy, the recipient cells need not be able to complement the defective viruses.

Genes encoding a detectable marker may be present in adenoviral vector to allow for detection of the recombinant vector once produced. Preferably, a marker is used which is easy to monitor. More preferably a marker is used which can be detected even when present at very low levels. Use of a detectable marker permits monitoring of the transfection process. In an exemplary embodiment the detectable marker is β-galactosidase or green fluorescent protein (GFP). Detection of GFP can be achieved, for example, by fluorescence microscopy of cultured cells.

Genes encoding a selectable product can also be used as linked markers to the desired product. A selectable product is necessary for growth under a particular set of conditions. Thus it can be used to selectively grow only those cells that have been transformed or transfected. A preferred selectable product is an antibiotic resistance enzyme, such as those for ampicillin, kanamycin, or blastocidin.

The adenoviral vector of the invention can also be used to produce a pseudotyped viral particle, i.e., a viral particle that contains one or more structural genes that are not derived from the adenoviral genome. The viral vectors described herein can be made by recombination in intact viral genomes thereby producing pseudotyped virus.

Cell type-specific targeting may be achieved with vectors derived from viruses having a broad host range by the modification of viral surface proteins. For example, the specificity of infection of adenoviruses is determined by the attachment to cellular receptors present at the surface of permissive cells. In this regard, the fiber gene is exemplified throughout the instant application. However, those of skill in the art will recognize that many other genes can be used in place of fiber to achieve cell-type specific targeting. For example, penton plays a critical role in cellular attachment (Defer et al. J. Virol. 64 (1990) 3661-3673). Thus, cell targeting of adenoviruses can be carried out by genetic modification of a viral gene, e.g., fiber and/or penton, to generate modified proteins capable of specific interaction with unique cell surface polypeptides. Examples of such modifications are described in literature (for example in Wickam et al., 1997, J. Virol. 71, 8221-8229; Amberg et al., 1997, Virol. 227, 239-244; Michael et al., 1995, Gene Therapy 2, 660-668; WO94/10323). Moreover, a exemplary penton mutant is described herein and called pFex-p* (mutation D342E). Desirably, a modified Fiber, modified penton, modified capsid-displayed polypeptide, or other amino acid sequence is used to re-target the virus, such that it mediates infection of a cell type of interest and reduces infection or clearance of non-target cells.

The present invention also provides a host cell comprising an adenoviral vector of the invention, a polynucleotide or an expression vector as defined in connection with the use of the invention or infected by a viral particle of the invention. The vector may be inserted into the cellular genome or not (episome). A host cell may be unique type of cells or a group of different types of cells and encompass cultured cell lines, primary cells and proliferative cells, with a special preference for cells of human origin.

Shuttle Library and Screening Methods

The invention further provides DNA libraries, libraries of viral clones and libraries of infectious viral particles and methods of generating and screening these libraries. In particular, the invention provides a capsid-displayed peptide library that is particularly useful for the identification of peptides capable of mediating re-targeted viral infection. In particular, the invention provides a Fiber-shuttle library comprising large numbers of adenovirus that contain modified fiber genes. The methods of the invention involve generating an "acceptor" vector as a packaged and infective virus that genetically lacks the fiber gene; then transferring the Fiber peptide library from a shuttle vector into infected adenoviral genomes in mammalian cells. The Fiber protein is only expressed following successful gene transfer, thus only recombinant virus will properly package and propagate.

Figure 5:
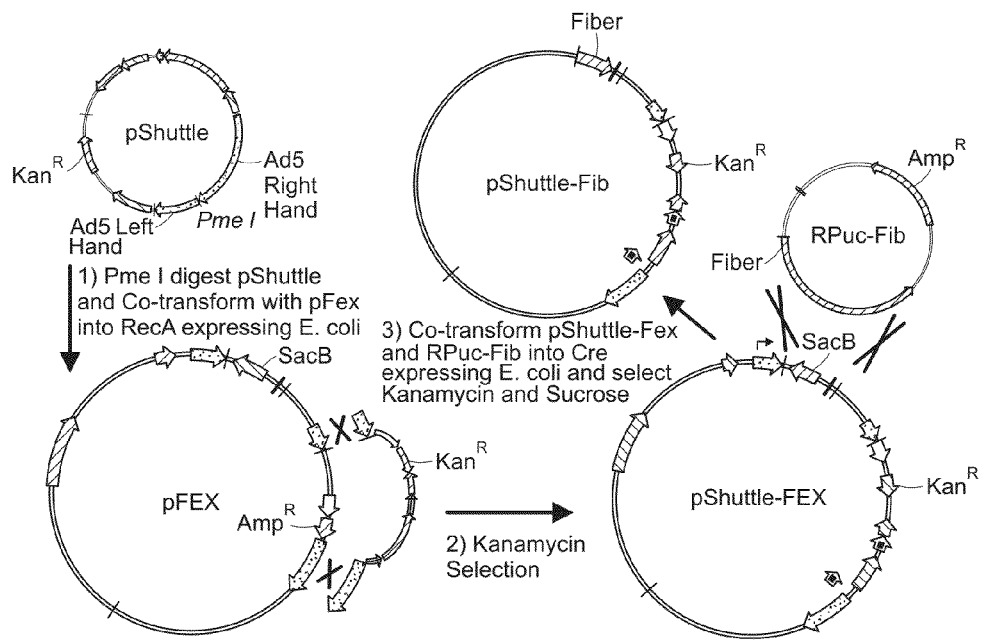
FIG. 5 is a schematic of Rec A recombination followed by pFex fiber exchange. The pshuttle-Fib is the completed adenoviral vector. This vector can be digested with Pac I and transfected into a desired cell line to create virus.
Figure 28:
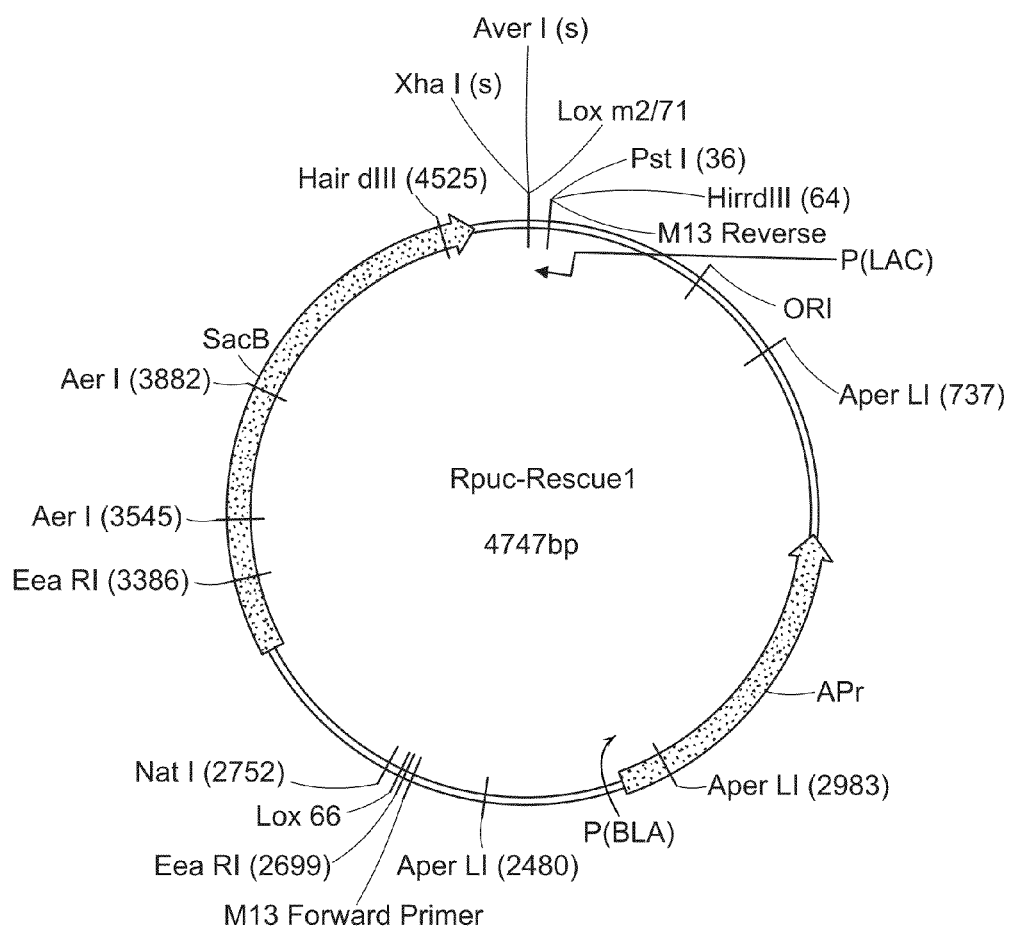
FIG. 28 shows the RPucRescue vector map.

Importantly, the invention provides a system, termed the pFex Rescue system (FIG. 18) that allows successful clones to be rescued from infected cells by PCR and recombined back into a RPuc-Rescue plasmid (FIGS. 28 and 29A and 29B), thereby avoiding the negative effects associated with amplifying a viral pool. This step can be used to rescue not only individual plaques, but may also be applied to a population of cells infected with a viral pool. The resulting rescue plasmids produce working Fiber shuttles which can be sequenced, applied to generate a new viral clone, or applied as a pool to a second round of library selection (FIG. 5).

The adenoviral library described herein can be screened to select for modified Fiber polypeptides. In one embodiment, the library comprises Fiber-displayed peptides (e.g., amino acid sequences comprising 6, 7, 8, 9, 10, 11, 12, 13, 14, 15, 16, 17, 18, 19, 20, 25, 30, 35, 40, or 50 amino acids in length) to identify adenoviruses that infect cells in a CAR independent manner. In another embodiment, the modified Fiber polypeptide is a mutant Fiber polypeptide (e.g., a point mutation, insertion, or deletion). Fiber mutations are generated using any method known in the art. In one embodiment, sexual PCR is used under error prone conditions to generate Fiber mutations or generate various chimeric fibers and then to reassemble DNA sequences, thereby simulating genetic recombination. Methods of the invention are then used to identify mutant Fiber sequences having the desired re-targeting activity. In another embodiment, chimeras of Fiber sequence and other non-adenoviral targeting ligands, such as antibody fragments or receptor ligands, are assembled to generate a library of possible re-targeted virus.

Adenovirus fiber polypeptides to be screened can be derived from an adenovirus of human or non-human origin. For example, non-human adenoviruses can include, for example, canine, avian, bovine, murine, ovine, porcine or simian origin. In other embodiments, the modified Fiber polypeptide is a chimeric polypeptide. A chimeric adenovirus fiber comprises fragments of diverse origins. For example, a chimeric fiber may be obtained by replacing part of a native fiber polypeptide with an equivalent part of an adenoviral fiber of another serotype. In certain embodiments, the fiber is derived from a human adenovirus (e.g., serotype C type 2 or 5 adenoviruses. The Ad2 fiber contains about 580 amino acids (aa), which sequence is disclosed, for example, by Heriss et al. Nucleic Acid Res. 9:4023-42 (1981), the disclosure of which is incorporated by reference herein). The Ad5 fiber contains about 582 amino acids. Its sequence is reported by Chroboczek et al. (Virology 161:549-54 (1987), the disclosure of which is incorporated by reference herein). In certain other embodiments, the adenovirus fiber can originate from an animal adenovirus, such as a bovine adenovirus (e.g., the BAV-3 strain) (see, e.g., PCT publication WO 95/16048). The fiber can optionally include other modifications as compared to the native sequence. In various embodiments, a Fiber polypeptide comprises 25, 50, 100, 200, 300, 400, or even 500 amino acid sequences from a non-human adenovirus or an adenovirus of another serotype.

Libraries of the invention are used for identifying viral particles that have been retargeted to a desired cell type. Libraries of the invention may also be used for identifying viral particles that bind or infect an undesirable cell line at a reduced rate. This retargeting can be done to increase or restrict the range of cells the adenoviral particle infects compared to a wild-type virus. The retargeting allows for a particular cell type to be specifically infected by the viral particle. Such specific targeting is clinically useful because it allows the viral particle to infect and deliver a therapeutic gene to specific target cells, thereby reducing adverse side effects associated with indiscriminate delivery. In one embodiment, a Fiber-displayed peptide that retargets an adenovirus to a cell of interest in selected in a single round of screening. If desired, additional rounds of biopanning are carried out to select for peptides which not only infect the target cell, but also minimize interference with fiber protein folding and capsid assembly (FIG. 5).

In one embodiment, the mutant fiber has reduced affinity for its native cellular receptor. A "native cellular receptor" refers to a cellular receptor normally bound by the unmutated adenovirus fiber. A mutant fiber can have an affinity that is reduced by about 100-fold, about 50 fold, about 10 fold, about 5 fold of, or that is about the same as, the affinity or avidity of the wild-type fiber for the native cellular receptor. In some embodiments, a modified fiber polypeptide includes a ligand for a different cellular receptor, other than the native cellular receptor. The term "ligand" refers to an entity capable of recognizing and binding, typically with a high affinity, a cell surface molecule different from the native cellular receptor.

The ligand can be, for example, an antibody, a peptide, a hormone, a polypeptide, a sugar, or any other moiety capable of mediating binding to a desired cell type. The term "antibody" comprises monoclonal antibodies, antibody fragments (e.g., Fab, F(ab)$_2$) single-chain antibodies (scFv), and heavy chain antibodies. (See generally, Harlow and Lane, Using Antibodies, A Laboratory Manual, Cold Spring Harbor Laboratory, New York (1999), the disclosure of which is incorporated by reference herein.) The target for the ligand cellular receptor can be expressed or exposed at the surface of the target cell (e.g., a cell surface marker, receptor, antigenic peptide presented by histocompatibility antigens, or the like). The addition of a ligand makes it possible to confer a new tropism toward one or more specific cell types carrying at their surface a target molecule recognized by the ligand. In certain embodiments, the regions for interaction with the natural cellular receptor can be deleted completely or partly and replaced with a ligand specific for a cell surface protein of the target cell type.

Preferably, a modified fiber polypeptide enhances biodistribution or immune response evasion. A modified fiber polypeptide having "improved biodistribution" is one that targets an adenovirus to a tissue of interest more effectively than a wild-type fiber polypeptide. Biodistribution is compared using any method known in the art. In one example, a test subject (e.g., rodent, primate) is systemically injected with an adenoviral pool expressing modified capsid-displayed adenoviral polypeptides. Subsequently, the level of adenovirus present in a tissue of interest is compared to the level present in a control animal that received a wild-type capsid-displayed adenoviral polypeptide or a de-targeted capsid-displayed adenoviral polypeptide. In one embodiment, the level of adenovirus re-targeted to the tissue of interest is compared using a detectable reporter (e.g., GFP, β-galactosidase, herpes thymidine kinase, immunoassay, or radioassay). In another embodiment, the level of adenovirus re-targeted to the tissue of interest is compared using quantitative PCR to detect, for example, the modified capsid-displayed adenoviral polypeptide in the tissue of interest. An increase in the level of modified capsid-displayed adenoviral polypeptide present in the tissue of interest relative to the level present in a corresponding tissue of a control animal that received wild-type or de-targeted adenovirus identifies a modified capsid-displayed adenoviral polypeptide having enhanced biodistribution. In one embodiment, a modified fiber polypeptide comprises a mutation in the shaft region that alters biodistribution and/or viral clearance. Such mutations may arise from rational design or may be identified according to a method of the invention.

Alternatively, a modified capsid-displayed adenoviral polypeptide having reduced clearance (e.g., reduced immune clearance, liver clearance) is identified by characterizing viral pharmacokinetics and distribution using any method known in the art. In one example, a test subject (e.g., rodent, primate) is systemically injected with an adenoviral pool expressing modified capsid-displayed adenoviral polypeptides. Subsequently, the level of adenovirus present in the blood stream or liver of the subject is compared to the level present in a control subject that received a wild-type or de-targeted adenovirus. A increase in the level of virus present in the blood stream or a reduction of the level of virus present in the liver identifies a modified capsid-displayed adenoviral polypeptide having desirably reduced clearance.

The methods described herein are useful to identify CAR-independent adenovirus that target virtually any cell type of interest. In one embodiment, a natural CAR-mediated infection pathway is disrupted, for example, through FG loop mutation ($\Delta T_{489}AYT_{492}$) (Roelvink et al., Science, 286, 1568-1571). CAR de-targeted viruses may be redirected to bind and infect cells of interest by inserting into a capsid displayed protein, such as fiber, a peptide having a known binding activity (e.g., an integrin-binding peptide RGD4C (CDCRGDCFC) (SEQ ID NO: 14) into the Fiber HI-loop), a random peptide library, or a rationally designed library of peptides to be screened.

Peptides may be inserted virtually any where in the fiber polypeptide or other capsid displayed polypeptide. In one embodiment, an adenovirus library is generated and screened, wherein a nucleic acid molecule encoding an amino acid sequence is cloned into a HI-loop of a CAR-ablated Fiber shuttle (e.g., RPuc-FBR2). The resulting plasmid library is used to transfect a CRE-expressing cell, which is infected with pseudotyped pAdTrack-Fex, and the recombinant virus pool is subsequently harvested. The viruses are used to infect a cell or tissue of interest to isolate infectious viral units or non-replicating viruses. The rate of infection of the recombinant virus is then compared to the infection rate of the wild-type (e.g., RPuc-WTFib) and of a CAR-ablated Fiber shuttle, or other negative control sample (e.g., N541S) were included in this experiment for reference purposes.

The viral burst can be quantified after infection, and individual plaques can be isolated and amplified. In parallel, PCR amplification of the floxed Fiber cassette is also cared out. The resulting PCR product is recombined using RPuc-Rescue, an acceptor plasmid that contains half-mutant lox sites flanking a negative marker gene (e.g., SacB). The Fiber gene is recombined into RPuc-Rescue in CRRE-expressing E. coli and recombinant clones are selected for growth in sucrose containing media or plates. The cloned Fiber gene is then characterized, for example, by sequencing. If desired, the cloned Fiber gene is further modified, or recombined with pFex viral genomes to create a subsequent virus.

Pharmaceutical Compositions

The present invention provides compositions, e.g., pharmaceutical compositions, comprising as an agent an adenoviral vector according to the invention, a polynucleotide or an expression vector as described in connection with the use of the invention, a host cell or a viral particle according to the invention or prepared according to the method of the invention.

The composition according to the invention may be manufactured in a conventional manner for a variety of modes of administration including systemic, topical and local administration. Referring to systemic administration, injection is preferred, e.g., intravenous, intraperitoneal, intraprostatic, intragastric, subcutaneous, intracardiac, intraarterial, intracoronary, intravascular, intraarterial, intramuscular, intrathecal, intratumoral, intranasal, intrapulmonary or intratracheal routes. Local administration include aerosolization instillation and oral routes of administration. The administration may take place in a single dose or a dose repeated one or several times after a certain time interval. The appropriate administration route and dosage vary in accordance with various parameters, for example, with the individual, the condition or disease to be treated, the stage to which it has progressed, the need for prevention or therapy and the gene of interest to be transferred. As an indication, a composition based on viral particles may be formulated in the form of doses of between $10^4$ and $10^{14}$ iu (infectious unit), advantageously between $10^5$ and $10^{13}$ in and preferably between $10^6$ and $10^{12}$ iu. The titer may be determined by conventional techniques. The doses of DNA vector are preferably comprised between 0.01 and 10 mg/kg, and more especially between 0.5 and 2 mg/kg. The composition of the invention can be in various forms, e.g., solid (powder, lyophilized form) or liquid (e.g., aqueous).

In a preferred embodiment, the composition comprises a pharmaceutically acceptable carrier, allowing its use in a method for the therapeutic treatment of humans or animals. In this particular case, the carrier is preferably a pharmaceutically suitable injectable carrier or diluent which is non-toxic to a human or animal organism at the dosage and concentration employed (for examples, see Remington's Pharmaceutical Sciences, 16.sup.th ed. 1980, Mack Publishing Co). It is preferably isotonic, hypotonic or weakly hypertonic and has a relatively low ionic strength, such as provided by a sucrose solution. Furthermore, it may contain any relevant solvents, aqueous or partly aqueous liquid carriers comprising sterile, pyrogen-free water, dispersion media, coatings, and equivalents, or diluents (e.g., Tris-HCl, acetate, phosphate), emulsifiers, solubilizers, excipients or adjuvants. The pH of the composition is suitably adjusted and buffered in order to be appropriate for use in humans or animals. Representative examples of carriers or diluents for an injectable composition include water, isotonic saline solutions which are preferably buffered at a physiological pH (such as phosphate buffered saline, Tris buffered saline, mannitol, dextrose, glycerol containing or not polypeptides or proteins such as human serum albumin). For example, such a composition may comprise 10 mg/ml mannitol, 1 mg/ml HSA, 20 mM Tris pH 7.2 and 150 mM NaCl.

In addition, the composition according to the present invention may include one or more stabilizing substance(s), such as lipids (e.g., cationic lipids, liposomes, lipids as described in WO98/44143; Felgner et al., 1987, Proc. West. Pharmacol. Soc. 32, 115-121; Hodgson and Solaiman, 1996, Nature Biotechnology 14, 339-342; Remy et al., 1994, Bioconjugate Chemistry 5, 647-654), nuclease inhibitors, hydrogel, hyaluronidase (WO98/53853), collagenase, polymers, chelating agents (EP890362), in order to preserve its degradation within the animal/human body and/or improve delivery into the host cell. Such substances may be used alone or in combination (e.g., cationic and neutral lipids). It may also comprise substances susceptible to facilitate gene transfer for special applications, such as a gel complex of polylysine and lactose facilitating delivery by intraarterial route (Midoux et al., 1993, Nucleic Acid Res. 21, 871-878) or poloxamer 407 (Pastore, 1994, Circulation 90, I-517). It has also be shown that adenovirus proteins are capable of destabilizing endosomes and enhancing the uptake of DNA into cells. The mixture of adenoviruses to solutions containing a lipid-complexed plasmid vector or the binding of DNA to polylysine covalently attached to adenoviruses using protein cross-linking agents may substantially improve the uptake and expression of the vector (Curiel et al., 1992, Am. J. Respir. Cell. Mol. Biol. 6, 247-252).

The present invention also provides the use of an adenoviral vector according to the invention, a polynucleotide or an expression vector, as described in connection with the use according to the invention, a viral particle or a host cell according to the invention for the preparation of a medicament intended for gene transfer, preferably into a human or animal body. Within the scope of the present invention, "gene transfer" has to be understood as a method for introducing any gene of interest into a cell. Thus, it also includes immunotherapy that relates to the introduction of a potentially antigenic epitope into a cell to induce an immune response which can be cellular or humoral or both.

Methods of Delivery

The invention also provides methods of delivering an adenoviral vector comprising a polypeptide identified according to a method described herein to a subject. For this purpose, the adenoviral vector, the polynucleotide and expression vector or the viral particle of the present invention may be delivered in vivo to the human or animal organism by specific delivery means adapted to the pathology to be treated. For example, a balloon catheter or a stent coated with the adenoviral vector, the expression vector carrying the polynucleotide or the viral particle may be employed to efficiently reach the cardiovascular system (as described in Riessen et al., 1993, Hum Gene Ther. 4, 749-758; Feldman and Steg, 1996, Medecine/Science 12, 47-55). It is also possible to deliver said therapeutic agents by direct administration, e.g., intravenously, in an accessible tumor, in the lungs by aerosolization and the like. Alternatively, one may employ eukaryotic host cells that have been engineered ex vivo to contain the adenoviral vector, the expression vector carrying the polynucleotide or the viral particle according to the invention. Methods for introducing such elements into an eukaryotic cell are well known to those skilled in the art and include microinjection of minute amounts of DNA into the nucleus of a cell (Capechi et al., 1980, Cell 22, 479-488), transfection with $CaPO_4$ (Chen and Okayama, 1987, Mol. Cell Biol. 7, 2745-2752), electroporation (Chu et al., 1987, Nucleic Acid Res. 15, 1311-1326), lipofection/liposome fusion (Felgner et al., 1987, Proc. Natl. Acad. Sci. USA 84, 7413-7417) and particle bombardement (Yang et al., 1990, Proc. Natl. Acad. Sci. USA 87, 9568-9572). The graft of engineered cells is also possible in the context of the present invention (Lynch et al, 1992, Proc. Natl. Acad. Sci. USA 89, 1138-1142).

The present invention also relates to a method for the treatment of a human or animal organism, comprising administering to said organism a therapeutically effective amount of an adenoviral vector of the invention, the polynucleotide or expression vector as described in connection with the use according to the invention, a viral particle or an eukaryotic cell according to the invention.

A "therapeutically effective amount" is a dose sufficient for the alleviation of one or more symptoms normally associated with the disease or condition desired to be treated. When prophylactic use is concerned, this term means a dose sufficient to prevent or to delay the establishment of a disease or condition.

The method of the present invention can be used for preventive purposes, imaging purposes, and for therapeutic applications relative to the diseases or conditions listed above. The present method is particularly useful to prevent or reduce the establishment of an inflammatory response following administration of a conventional gene-therapy vector. It is to be understood that the present method can be carried out by any of a variety of approaches. Advantageously, the vector, viral particle, cell or the pharmaceutical composition of the invention can be administered directly in vivo by any conventional and physiologically acceptable administration route, for example by intravenous injection, by direct injection into an accessible tumor or by means of an appropriate catheter into the vascular system, etc. Alternatively, the ex vivo approach may also be adopted which consists of introducing the adenoviral vector, the polynucleotide or the viral particle according to the invention into cells, growing the transfected/infected cells in vitro and then reintroducing them into the patient to be treated.

Diagnostic Imaging

The invention provides for the detection of cells and/or tissues, including neoplastic cells, expressing a desired product (e.g., desired diagnostic product, such as the herpes thymidine kinase or sodium iodide symporter) encoded by an adenoviral vector of the invention. The ability to image cell or tumor metabolism in vivo has broad application as exemplified by the increasing clinical use of positron emission tomography with [$^{18}$F]fluorodeoxyglucose (FDG-PET). Of course, the specificity of such scans for tumor tissue is limited insofar as many tissues as well as malignant ones rapidly metabolize glucose. Thus brain, cardiac muscle, and foci of inflammation all yield signal with FDG-PET imaging. The language "effective amount for imaging" of a compound is the amount necessary or sufficient to provide a signal sufficient to visualize the presence or absence of a neoplasm. Neoplasms or other adenoviral infected tissues may be imaged using any method know in the art or described herein, e.g., planar gamma imaging, single photon emission computed tomography (SPECT) and positron emission tomography (PET). The effective amount can vary depending on such factors as the size and weight of the subject, the type of illness, or the particular compound. For example, the choice of the compound can affect what constitutes an "effective amount for imaging". One of ordinary skill in the art would be able to study the factors contained herein and make the determination regarding the effective amount of the compound without undue experimentation. Imaging can allow for the detection of the presence and/or location of the imaging agent bound, for example, to a thymidine kinase or transported, for example, by a sodium iodide symporter. Presence can include below the level of detection or not present, and the location can include none.

In one embodiment, the invention provides vectors, including vectors that encode a desired diagnostic product, such as a herpes thymidine kinase polypeptide or sodium iodide symporter and produce a detectable signal that can used to obtain an image of a subject (e.g., a cell or tissue of a subject) and determine the presence and location of the transgene (e.g., the encoded thymidine kinase or sodium idodide symporter) in a subject. Thymidine kinases and sodium iodide symporters are particularly well suited for the methods of the invention because they provide for the accumulation of radionuclides in cells expressing a vector of the invention.

Imaging Techniques

Generally, imaging techniques involve administering a compound to a subject that can be detected externally to the subject. Images are generated by virtue of differences in the spatial distribution of the imaging agents which accumulate in various locations in a subject. The methods of the present invention, the imaging techniques rely on the compounds being preferentially bound or accumulated in a subject, e.g., viral thymidine kinase and sodium iodide symporter. The spatial distribution of the imaging agent accumulated in a subject, e.g., tumor volume, may be measured using any suitable means, for example, planar gamma imaging, single photon emission computed tomography (SPECT) and positron emission tomography (PET). Alternatively, imaging techniques that detect fluorescence may be used in the methods of the invention.

Exemplary compounds useful in the methods of the invention include 2'-fluoro-2'deoxy-1-beta-D-arabinofuranosyl-5-iodo-uracil ([$^{125}$I]-FIAU), 2'-fluoro-2'deoxy-1-beta-D-arabinofuranosyl-5-iodo-uracil ([$^{124}$I]-FIAU), 9-(4-$^{18}$F-fluoro-3-[hydroxymethyl]butyl)guanine ([$^{18}$F]-FHBG), (18)F-1-(2'-deoxy-2'-fluoro-beta-d-arabinofuranosyl)thymine ([$^{18}$F]-FMAU), $^{18}$F-2'-fluoro-2'deoxy-1beta-D-arabinofuranosyl-5-ethyl-uracil ([$^{18}$F]-FEAU) and 1-(2'-deoxy-2'-fluoro-beta-D-arabinofuranosyl)-5-[$^{18}$F] iodouracil ([$^{18}$F]-FIAU).

In specific embodiments, the invention provides nucleoside analogs, such as 1-(2'-deoxy-2'-fluoro-β-D-arabinofuranosyl)-5-iodouracil (FIAU), which are described, for example, in U.S. Pat. No. 4,211,773, as an antiviral and an antitumor agent. Whether the substrate is for imaging or for therapy merely depends on the radionuclide used, e.g., iodine-$^{123}$, $^{124}$ or $^{125}$ for imaging vs. iodine-$^{131}$ or astatine-$^{211}$ for therapy. The nucleoside analogs are labeled with a radioisotope, e.g., a radioisotope of iodine, fluorine, yttrium, bismuth, or astatine. In another embodiment, the nucleoside analogs may be fluorescent. Preferred radiolabeled compounds of the invention are nucleoside analogs that are easily synthesized and limited in vivo catabolism. Compounds such as those described in U.S. Pat. Nos. 5,879,661 and 6,331,287 can be used with the methods of the invention. Among the most commonly used positron-emitting nuclides in PET are $^{11}$C, $^{13}$N, $^{15}$O, and $^{18}$F. Isotopes that decay by electron capture and/or β or γ emission are used in SPECT, and include, for example, $^{123}$I and $^{124}$I.

In other embodiments utilizing the sodium iodide symporter, administration of labeled, including radiolabelled iodine, results in transport of the labeled iodine into the cell bearing the sodium idodide symporter, which can then be localized and measured using standard imaging techniques. The system is particularly useful for monitoring the location of adenoviral transgenes and tissue-specific distribution of the adenoviral gene product.

The methods of the invention include PET. Specifically, imaging is carried out by scanning the entire patient, or a particular region of the patient using the detection system, and detecting the signal, e.g., the radioisotope signal. The detected signal is then converted into an image. The resultant images should be read by an experienced observer, such as, for example, a physician. The foregoing process is referred to herein as "imaging" the patient. The precise timing of the imaging will be dependant upon such factors as the clearance rate of the compound administered, as will be readily apparent to those skilled in the art. Once an image has been obtained, one of skill in the art will be able to determine the location of the compound. Using this information, the artisan can determine, for example, if a tumor is present, the extent of the tumor, or the efficacy of treatment which the subject is undergoing. Images obtained at different time points, e.g., 12, 24, 36, 48 or more, hours apart are particularly useful in determining the efficacy of treatment.

The ability to image cell or tumor metabolism in vivo has broad application as exemplified by the increasing clinical use of positron emission tomography with [$^{18}$F]fluorodeoxyglucose (FDG-PET). Of course, the specificity of such scans for tumor tissue is limited insofar as many tissues as well as malignant ones rapidly metabolize glucose. Thus brain, cardiac muscle, and foci of inflammation all yield signals with FDG-PET imaging. The language "effective amount for imaging" of a compound is the amount necessary or sufficient to provide a signal sufficient to visualize the presence or absence of a neoplasm. Neoplasms may be imaged using any method know in the art or described herein, e.g., planar gamma imaging, single photon emission computed tomography (SPECT) and positron emission tomography (PET). The effective amount can vary depending on such factors as the size and weight of the subject, the type of illness, or the particular compound. For example, the choice of the compound can affect what constitutes an "effective amount for imaging". One of ordinary skill in the art would be able to study the factors contained herein and make the determination regarding the effective amount of the compound without undue experimentation. Imaging can allow for the detection of the presence and/or location of the imaging agent bound, for example, to a thymidine kinase, or of an agent transported by a sodium iodide symporter. Presence can include below the level of detection or not present, and the location can include none. Thymidine kinase binding compounds for use in the methods of the invention are provided for example in WO2006/002142, incorporated herein by reference.

Kits

A kit according to the invention comprises one or more of the described plasmids, e.g., a shuttle plasmid, a transfer plasmid, a donor plasmid, and/or an acceptor plasmid, useful in the generation of recombinant adenoviral vectors. A user of the kit may insert one or more desired genes into the shuttle plasmid using, for example, a restriction endonuclease and a DNA ligase. The kit may also comprise a packaging cell line for producing virus particles from the defective adenoviral vector and/or the recombinant adenoviral vectors produced containing the desired product. The kit may also comprise bacterial cells which can be used for co-transformation. Preferably the bacterial cells are homologous-recombination proficient and highly competent to receive transforming DNA. Typically, each kit component is separately packaged to avoid premature mixing. Further, all individually packaged components are provided in a box or other container which holds the other components. Instructions for making a recombinant adenovirus vector according to the methods disclosed herein may also be included in the kit. Reference to instructions may also be provided in the kit, for example to a text or webpage.

Kits may also contain the recombinant adenoviral vectors, or viral particles, produced by the methods of the invention and instructions for the administration of the vectors or viral particles to a subject for therapeutic or preventative purposes.

Host Cells

The present invention also provides a host cell comprising an adenoviral vector of the invention, a polynucleotide or an expression vector as defined in connection with the use of the invention or infected by a viral particle of the invention. The vector may be inserted into the cellular genome or not (episome). A host cell may be unique type of cells or a group of different types of cells and encompass cultured cell lines, primary cells and proliferative cells, with a special preference for cells of human origin.

The present invention also provides compositions, e.g., pharmaceutical compositions, comprising as an agent an adenoviral vector according to the invention, a polynucleotide or an expression vector as described in connection with the use of the invention, a host cell or a viral particle according to the invention or prepared according to the method of the invention.

The composition according to the invention may be manufactured in a conventional manner for a variety of modes of administration including systemic, topical and local administration. Referring to systemic administration, injection is preferred, e.g., intravenous, intraperitoneal, intragastric, subcutaneous, intracardiac, intraarterial, intracoronary, intravascular, intraarterial, intramuscular, intrathecal, intratumoral, intranasal, intrapulmonary or intratracheal routes. Local administration include aerosolization instillation and oral routes of administration. The administration may take place in a single dose or a dose repeated one or several times after a certain time interval. The appropriate administration route and dosage vary in accordance with various parameters, for example, with the individual, the condition or disease to be treated, the stage to which it has progressed, the need for prevention or therapy and the gene of interest to be transferred. As an indication, a composition based on viral particles may be formulated in the form of doses of between $10^4$ and $10^{14}$ iu (infectious unit), advantageously between $10^5$ and $10^{13}$ iu and preferably between $10^6$ and $10^{12}$ iu. The titer may be determined by conventional techniques. The doses of DNA vector are preferably comprised between 0.01 and 10 mg/kg, and more especially between 0.5 and 2 mg/kg. The composition of the invention can be in various forms, e.g., solid (powder, lyophilized form) or liquid (e.g., aqueous).

In a preferred embodiment, the composition comprises a pharmaceutically acceptable carrier, allowing its use in a method for the therapeutic treatment of humans or animals. In this particular case, the carrier is preferably a pharmaceutically suitable injectable carrier or diluent which is non-toxic to a human or animal organism at the dosage and concentration employed (for examples, see Remington's Pharmaceutical Sciences, 16.sup.th ed. 1980, Mack Publishing Co). It is preferably isotonic, hypotonic or weakly hypertonic and has a relatively low ionic strength, such as provided by a sucrose solution. Furthermore, it may contain any relevant solvents, aqueous or partly aqueous liquid carriers comprising sterile, pyrogen-free water, dispersion media, coatings, and equivalents, or diluents (e.g., Tris-HCl, acetate, phosphate), emulsifiers, solubilizers, excipients or adjuvants. The pH of the composition is suitably adjusted and buffered in order to be appropriate for use in humans or animals. Representative examples of carriers or diluents for an injectable composition include water, isotonic saline solutions which are preferably buffered at a physiological pH (such as phosphate buffered saline, Tris buffered saline, mannitol, dextrose, glycerol containing or not polypeptides or proteins such as human serum albumin). For example, such a composition may comprise 11 mg/ml mannitol, 1 mg/ml HSA, 20 mM Tris pH 7.2 and 150 mM NaCl.

In addition, the composition according to the present invention may include one or more stabilizing substance(s), such as lipids (e.g., cationic lipids, liposomes, lipids as described in WO98/44143; Felgner et al., 1987, Proc. West. Pharmacol. Soc. 32, 115-121; Hodgson and Solaiman, 1996, Nature Biotechnology 14, 339-342; Remy et al., 1994, Bioconjugate Chemistry 5, 647-654), nuclease inhibitors, hydrogel, hyaluronidase (WO98/53853), collagenase, polymers, chelating agents (EP890362), in order to preserve its degradation within the animal/human body and/or improve delivery into the host cell. Such substances may be used alone or in combination (e.g., cationic and neutral lipids). It may also comprise substances susceptible to facilitate gene transfer for special applications, such as a gel complex of polylysine and lactose facilitating delivery by intraarterial route (Midoux et al., 1993, Nucleic Acid Res. 21, 871-878) or poloxamer 407 (Pastore, 1994, Circulation 90, 1-517). It has also be shown that adenovirus proteins are capable of destabilizing endosomes and enhancing the uptake of DNA into cells. The mixture of adenoviruses to solutions containing a lipid-complexed plasmid vector or the binding of DNA to polylysine covalently attached to adenoviruses using protein cross-linking agents may substantially improve the uptake and expression of the vector (Curiel et al., 1992, Am. J. Respir. Cell. Mol. Biol. 6, 247-252).

The present invention also provides the use of an adenoviral vector according to the invention, a polynucleotide or an expression vector, as described in connection with the use according to the invention, a viral particle or a host cell according to the invention for the preparation of a medicament intended for gene transfer, preferably into a human or animal body. Within the scope of the present invention, "gene transfer" has to be understood as a method for introducing any gene of interest into a cell. Thus, it also includes immunotherapy that relates to the introduction of a potentially antigenic epitope into a cell to induce an immune response which can be cellular or humoral or both.

For this purpose, the adenoviral vector, the polynucleotide and expression vector or the viral particle of the present invention may be delivered in vivo to the human or animal organism by specific delivery means adapted to the pathology to be treated. For example, a balloon catheter or a stent coated with the adenoviral vector, the expression vector carrying the polynucleotide or the viral particle may be employed to efficiently reach the cardiovascular system (as described in Riessen et al., 1993, Hum Gene Ther. 4, 749-758; Feldman and Steg, 1996, Medecine/Science 12, 47-55). It is also possible to deliver said therapeutic agents by direct administration, e.g., intravenously, in an accessible tumor, in the lungs by aerosolization and the like. Alternatively, one may employ eukaryotic host cells that have been engineered ex vivo to contain the adenoviral vector, the expression vector carrying the polynucleotide or the viral particle according to the invention. Methods for introducing such elements into an eukaryotic cell are well known to those skilled in the art and include microinjection of minute amounts of DNA into the nucleus of a cell (Capechi et al., 1980, Cell 22, 479-488), transfection with CaPO.sub.4 (Chen and Okayama, 1987, Mol. Cell Biol. 7, 2745-2752), electroporation (Chu et al., 1987, Nucleic Acid Res. 15, 1311-1326), lipofection/liposome fusion (Felgner et al., 1987, Proc. Natl. Acad. Sci. USA 84, 7413-7417) and particle bombardement (Yang et al., 1990, Proc. Natl. Acad. Sci. USA 87, 9568-9572). The graft of engineered cells is also possible in the context of the present invention (Lynch et al, 1992, Proc. Natl. Acad. Sci. USA 89, 1138-1142).

The present invention also relates to a method for the treatment of a human or animal organism, comprising administering to said organism a therapeutically effective amount of an adenoviral vector of the invention, the polynucleotide or expression vector as described in connection with the use according to the invention, a viral particle or an eukaryotic cell according to the invention.

A "therapeutically effective amount" is a dose sufficient for the alleviation of one or more symptoms normally associated with the disease or condition desired to be treated. When prophylactic use is concerned, this term means a dose sufficient to prevent or to delay the establishment of a disease or condition.

The method of the present invention can be used for preventive purposes and for therapeutic applications relative to the diseases or conditions listed above. The present method is particularly useful to prevent or reduce the establishment of an inflammatory response following administration of a conventional gene-therapy vector. It is to be understood that the present method can be carried out by any of a variety of approaches. Advantageously, the vector, viral particle, cell or the pharmaceutical composition of the invention can be administered directly in vivo by any conventional and physiologically acceptable administration route, for example by intravenous injection, by direct injection into an accessible tumor or by means of an appropriate catheter into the vascular system, etc. Alternatively, the ex vivo approach may also be adopted which consists of introducing the adenoviral vector, the polynucleotide or the viral particle according to the invention into cells, growing the transfected/infected cells in vitro and then reintroducing them into the patient to be treated.

The present invention provides methods of treating disease and/or disorders or symptoms thereof which comprise administering a therapeutically effective amount of an adenoviral composition containing a capsid displayed re-targeting peptide and a desired therapeutic polypeptide to a subject (e.g., a mammal such as a human). Thus, one embodiment is a method of treating a subject suffering from or susceptible to a disease or disorder or symptom thereof susceptible to treatment with the therapeutic polypeptide. The method includes the step of administering to the mammal a therapeutic amount of an amount of a compound herein sufficient to treat the disease or disorder or symptom thereof, under conditions such that the disease or disorder is treated.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

The therapeutic methods of the invention (which include prophylactic treatment) in general comprise administration of a therapeutically effective amount of the compounds herein, such as a compound of the formulae herein to a subject (e.g., animal, human) in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like).

In one embodiment, the invention provides a method of monitoring treatment progress. The method includes the step of determining a level of diagnostic marker (Marker) (e.g., any target delineated herein modulated by a compound herein, a protein or indicator thereof, etc.) or diagnostic measurement (e.g., screen, assay) in a subject suffering from or susceptible to a disorder or symptoms thereof associated with a disorder amenable to treatment with a therapeutic polypeptide, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1

Vector Strategy

The Cre recombinase from bacteriophage P1 is an enzyme which mediates the excision and integration of DNA based on specific sequence binding sites (lox) through stepwise cleavage and ligation involving Holiday Junction intermediates (Ghosh, K. and Van Duyne, G. D. (2002) *Methods*, 28: 374-383). Though nearly 100 related tyrosine recombinases have been identified by sequence homology, Cre recombinase is among the best studied. Lox binding sites are 34 base pairs in length, but are solely sufficient to target Cre binding and recombination with the corresponding Lox sites. The canonical Lox site is the LoxP site. It has a 13 bp inverted repeat and an 8 bp spacer (FIG. 1). The 8 bp spacer is asymmetrical and hence has orientation (actual direction of arrow is arbitrary).

Two-loxP sites flanking a gene are called "floxing". If a gene is floxed by two identical sites facing the same direction, it will be deleted with Cre recombinase. If a gene is floxed by Lox sites facing opposite directions, it will be reversed in its orientation with Cre recombinase. If two separate genes are floxed by identical sites, the genes may be exchanged with Cre recombinase. This is known as recombinase mediated cassette exchange (RMCE). Because the lox sites remain unaltered following recombination, these reactions are reversible or bidirectional.

In order to maximize gene replacement, without favoring spontaneous excision, two Lox sites have to be used which are incompatible. This can be accomplished by mutating the spacer (FIG. 2B). In addition, half site mutations in the inverted repeat section can lead to a unidirectional recombination event by resulting in a non-functional lox site following recombination (FIG. 2A). By combining these two methods, a highly efficient unidirectional gene replacement can be achieved (Langer, S. J. et al. (2002) *Nucleic Acids Res,* 30: 3067-3077).

Figure 3:
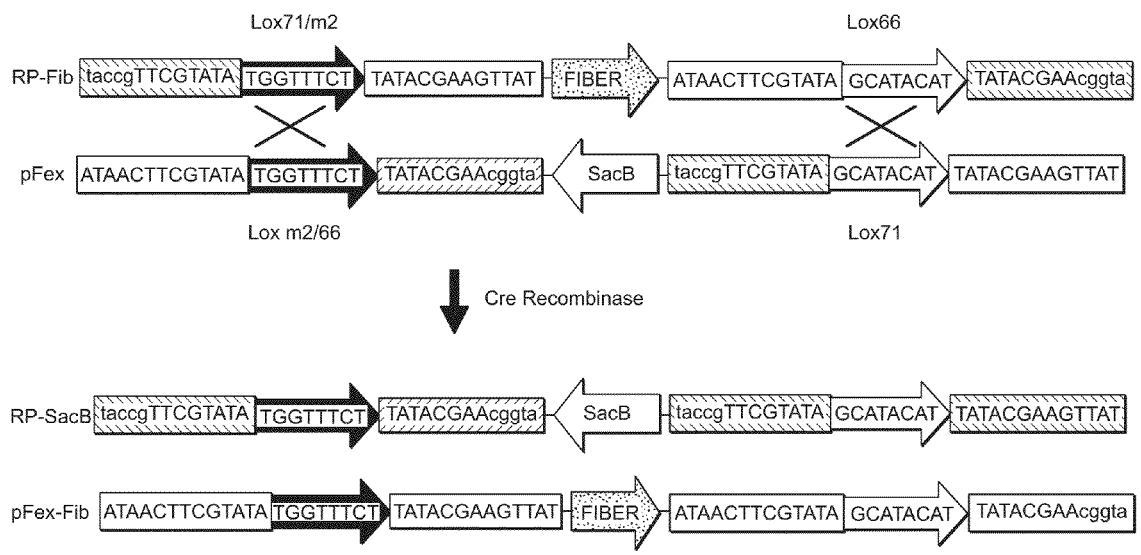
FIG. 3 is a schematic depicting two non-compatible spacer sequences (black arrows) that force gene exchange rather than excision. The reaction of two half-mutant lox sites (shaded with mutations in lower case) results in a dually mutated lox site (PR-SacB) and a unidirectional reaction. The sequences disclosed in FIG. 3 are SEQ ID NOS 19-22, 17-18, 23 and 15, respectively.
Figure 22A:
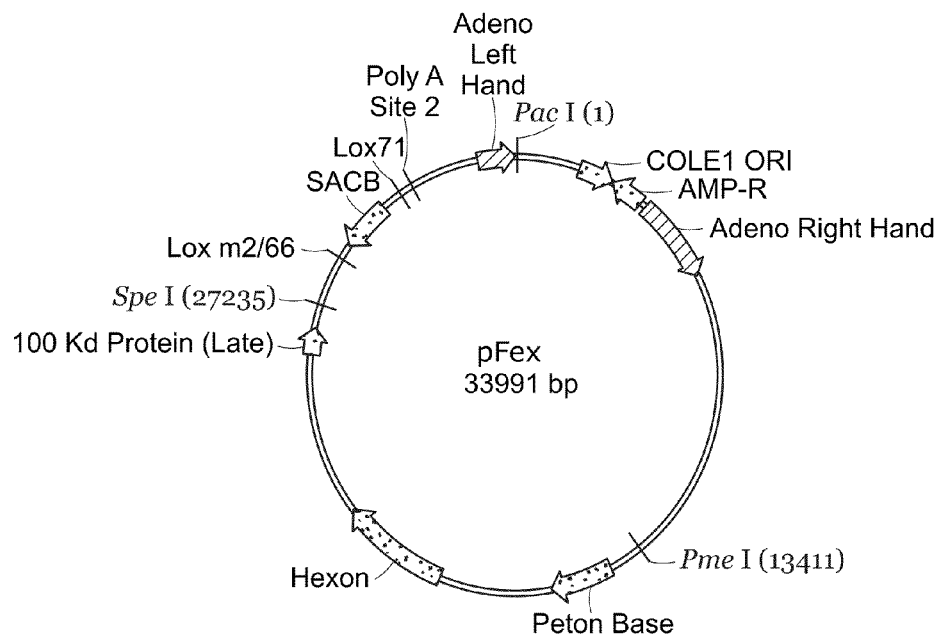
FIGS. 22A-22C show plasmid maps.

This invention applies Cre recombinase and half mutant lox sites with incompatible spacers to uni-directionally exchange modified targeting genes into the fiber region of adenoviral vectors. As delineated by Langer et al, the use of a Lox m2/66 and Lox 71 on the donor fragment; and a Lox m2/71 with Lox 66 on the acceptor fragment results in a unidirectional gene exchange with maintained orientation and lack of alternative recombination events (Langer, supra). Here the acceptor vector, pFEX (FIG. 22A), has a Lox m2/66 3' of the SacB gene and a Lox 71 on the 5'-side. When induced by media containing 5% sucrose, SacB is lethal in a wide range of Gram negative bacteria, and thus permits selection for loss of the vector (Quandt, J. and Hynes, M. F. (1993) *Gene,* 127: 15-21). The donor vector, RP-Fib (FIGS. 32A and 32B), contains a lox m2/71 site 5' of the Fiber gene and a Lox 66 site on the 3'-side (FIG. 3). The combination of the unidirectional recombination with a negative selectable marker results in extremely high numbers of desired recombinants. The system is directly compatible with the existing ADEASY™ system. The acceptor vector, named pFex, is similar to ADEASY™-1, but it has the fiber gene replaced with a floxed negative selectable marker, the SacB gene. The smaller donor vector, RP-Fib, contains a modified fiber gene, which is also floxed. Several variations of the smaller donor include a unique BspEI site in the HI loop for the incorporation of targeting ligands and/or a mutation in the receptor binding region of fiber. Additionally, the donor contains many convenient restriction enzyme recognition sites so genes other than fiber can be efficiently shuttled into pFex. The numerous shuttle vectors are described in detail below.

Using the described system, the fiber gene can be transferred into pFex either before (FIG. 4) or after (FIG. 5) the recombination with the E1 shuttle vector. Two separate fiber shuttle scaffolds have been constructed for either transfer stage. RP-Fib, which is kanamycin resistant, is applied for recombination prior to the E1 shuttle recombination (FIG. 4), and RPuc-Fib (FIGS. 33A and 33B), which is ampicillin resistant, is applied for recombination after the E1 shuttle recombination. To increase the efficiency of the E1 shuttle recombination, pFex stable *E. coli* called bFex, can be used to overcome limitations in large plasmid transformation efficiency. This option is available for any pFex vector, after fiber exchange, if multiple E1 variations are needed. Both recombination pathways result in the same product, which can then be linearized with Pac I digestion, and transfected into a mammalian cell packaging cell line, such as 293-HEK, for the creation of virus. A third fiber shuttle, RP-Blast-Fib (FIGS. 34A-34C), has been designed to allow for blasticidin selection at either stage of recombination.

Example 2

Figure 6:
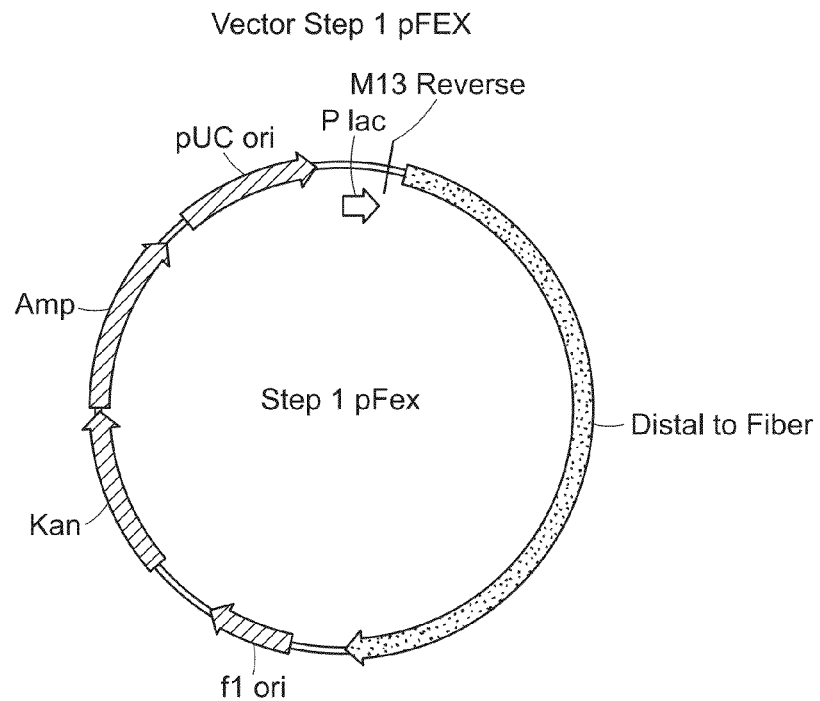
FIG. 6 is a schematic depicting step 1 of pFex assembly.

Design and Methods for Producing pFex Components pFex was assembled through several steps. First, a segment called 'distal to fiber Age I' was created by PCR amplification of the adenovirus serotype 5 genome with primers AdE-Dist 5' and AdE-Dist 3' (FIG. 23). This product was then cloned into the TOPO-TA vector pCR-2.1, using TA cloning, to produce the vector Step 1 pFex (FIG. 6).

Figure 7:
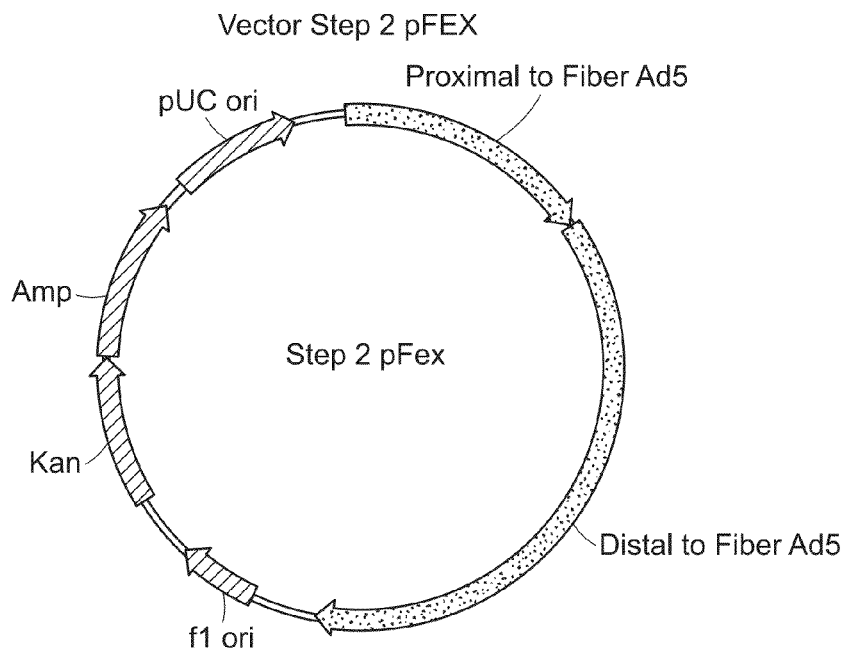
FIG. 7 is a schematic depicting step 2 of pFex assembly.

Second, a segment called 'proximal to fiber' was created by PCR amplification of the adenovirus serotype 5 genome with primers loxmve1 and loxmve2 (FIG. 23). This product was then cloned into Step 1 pFex using the Spe I and Age I restriction sites. The resulting vector is Step 2 pFex (FIG. 7).

Figure 8:
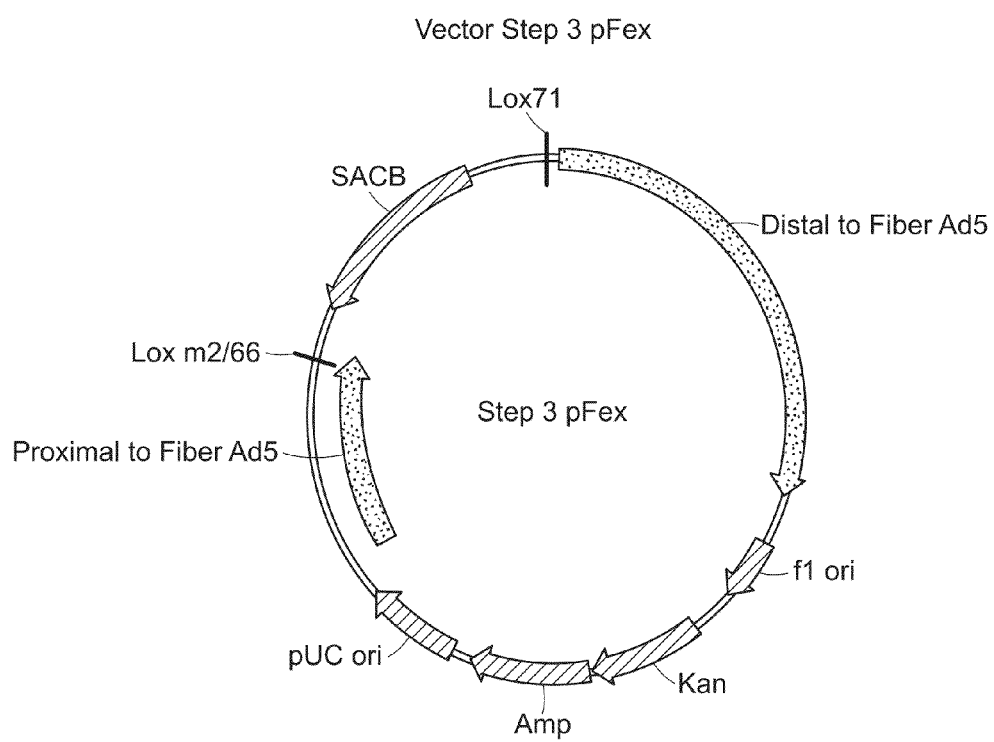
FIG. 8 is a schematic depicting step 3 of pFex assembly.

The SacB gene was isolated from the vector pAJ200 using the Bgl II and Pvu I restriction sites. Next, the two half mutant lox sites, lox m2/66 and lox 71, were added by ligation with self annealed linkers 5' lox m2/66 and 3' lox m2/66, and 5' lox 71, and 3' lox 71, respectively (FIG. 23). The resulting floxed SacB gene was then subcloned into Step 2 pFex to create Step 3 pFex (FIG. 8).

Figure 9:
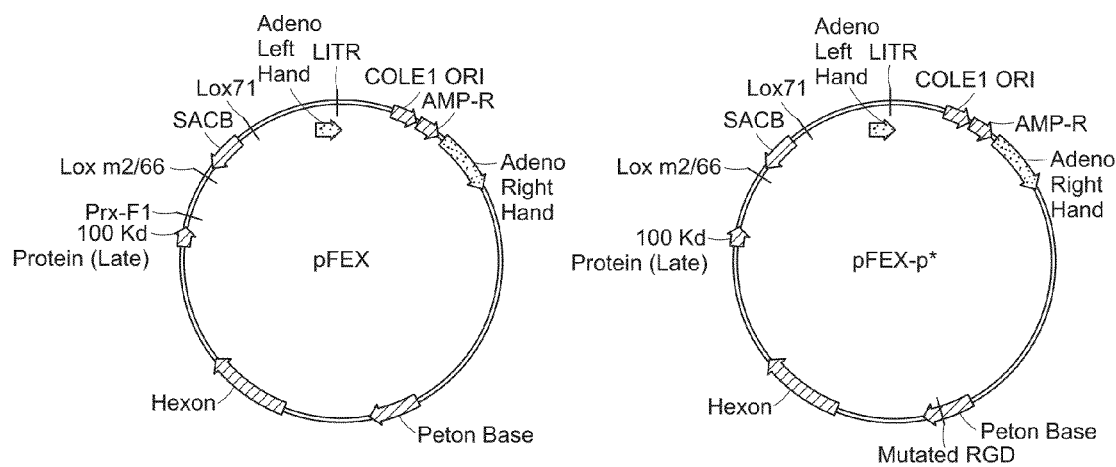
FIG. 9 is a schematic showing vectors pFex and pFex-p*.

Finally, the modified ADEASY™ segment containing SacB in place of fiber was removed with a double digest of SpeI and PacI. This product was then exchanged for the pre-existing region of fiber in pADEASY™-1. The final vector construct is called pFEX (FIG. 9). The final product was verified by sequencing using primers pFEXfor01-11 and pFEXrev01-11 (FIG. 23). Finally, a second version of pFEX, termed pFEX-p*, contains a mutation in the integrin binding domain of the penton gene, where RGD is mutated to RGE (FIG. 9).

Figure 11:
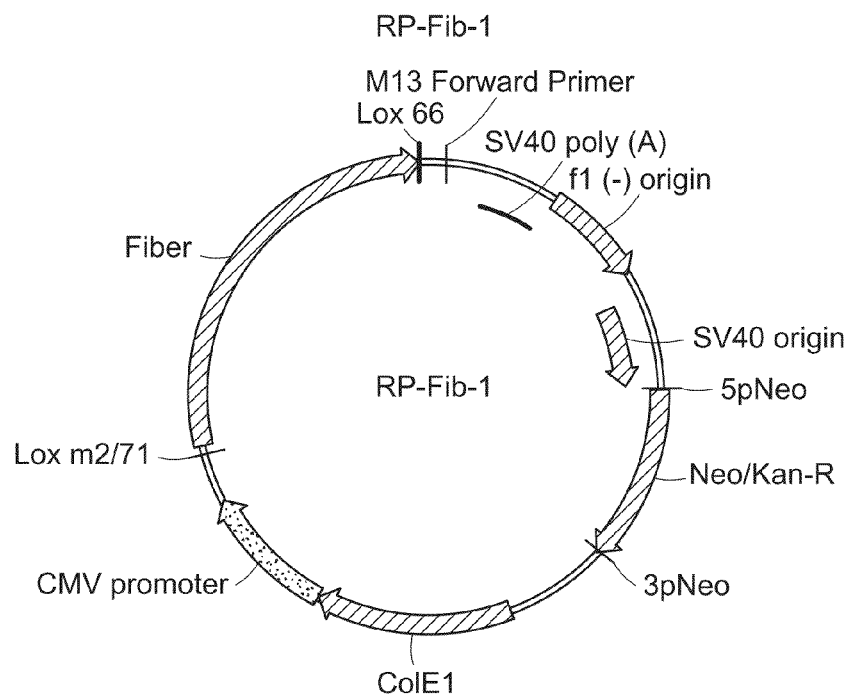
FIG. 11 is a schematic of RP-Fib-1.

The fiber shuttle vectors were also constructed in a stepwise manner. An existing adenovirus serotype 5 fiber vector, pBK-CMV-Fiber, was first digested with the restriction enzymes Spe I and Xho I. The linkers S-lox m2/71-X5 and S-lox m2/71-X5 (FIG. 24) were self annealed and then inserted into the vector at these sites, creating Step 1 Fiber Shuttle Lox m2/71 (FIG. 23). This product was then digested with restriction enzymes Acc65 I and Not I, and the linkers N-Lox 66-A-5 and N-Lox 66-A-3 (FIG. 24), were then ligated into this site. The final product was named RP-Fib (FIG. 24). Finally, the tripartite leader splice acceptor site was inserted downstream of the lox m2/71 site by annealing the primers splce1 (TCGAGAACTATCTTCATGTTGTT-GCA-GATGAAGCGCGCAAGACCGTCTGAA-GATACCTTCAACCCCGTGTATCCATATG ACACG-GAAA) (SEQ ID NO: 9) and splce 2 (CCGGTTTCCGTGTCATATGGATACACGGGG-TTGAAGGTATCTTCAGACGGTCT-TGCGCGCTTCATCTGCAACAACATGAAGATAGTT C) (SEQ ID NO: 10) and cloning this into XhoI/AgeI sites of all fiber shuttle vectors. All of the described RP-Fib vectors have a mutated fiber gene that contains a unique BspEI site in the gene's HI loop for the incorporation of targeting peptide sequences (FIG. 11). Additionally, some vectors have a mutated fiber gene were the coding region for $T_{489}AYT_{492}$, a known Coxsackie and Adenovirus Receptor (CAR) binding site, has been deleted (Roelvink, P. W. et al. 1999) *Science*, 286: 1568-1571).

Figure 4:
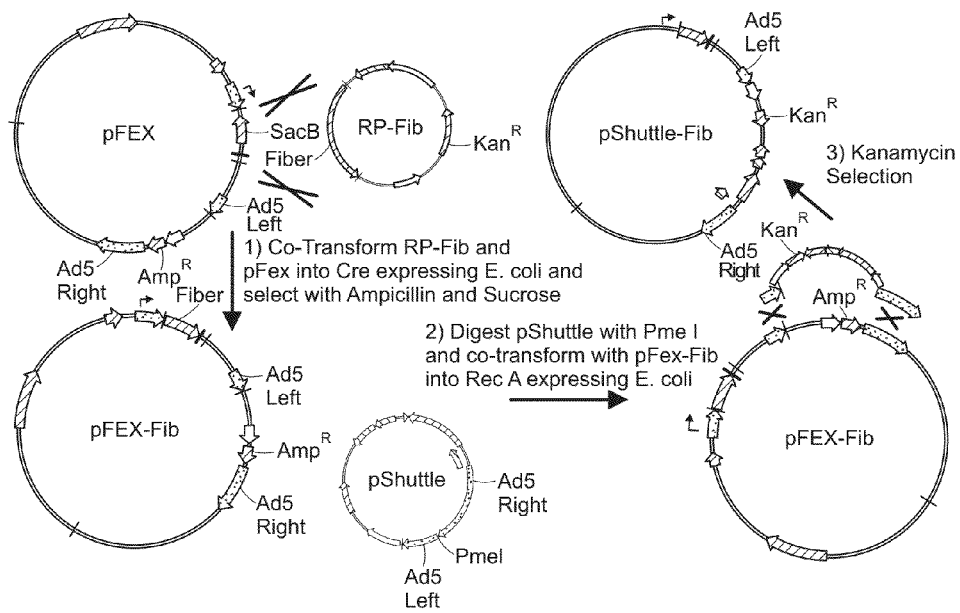
FIG. 4 is a schematic of pFex fiber exchange followed by RecA recombination resulting in pShuffle-Fib, an adenoviral vector. This vector can be digested with Pac I and transfected into a desired cell line to create virus.
Figure 12:
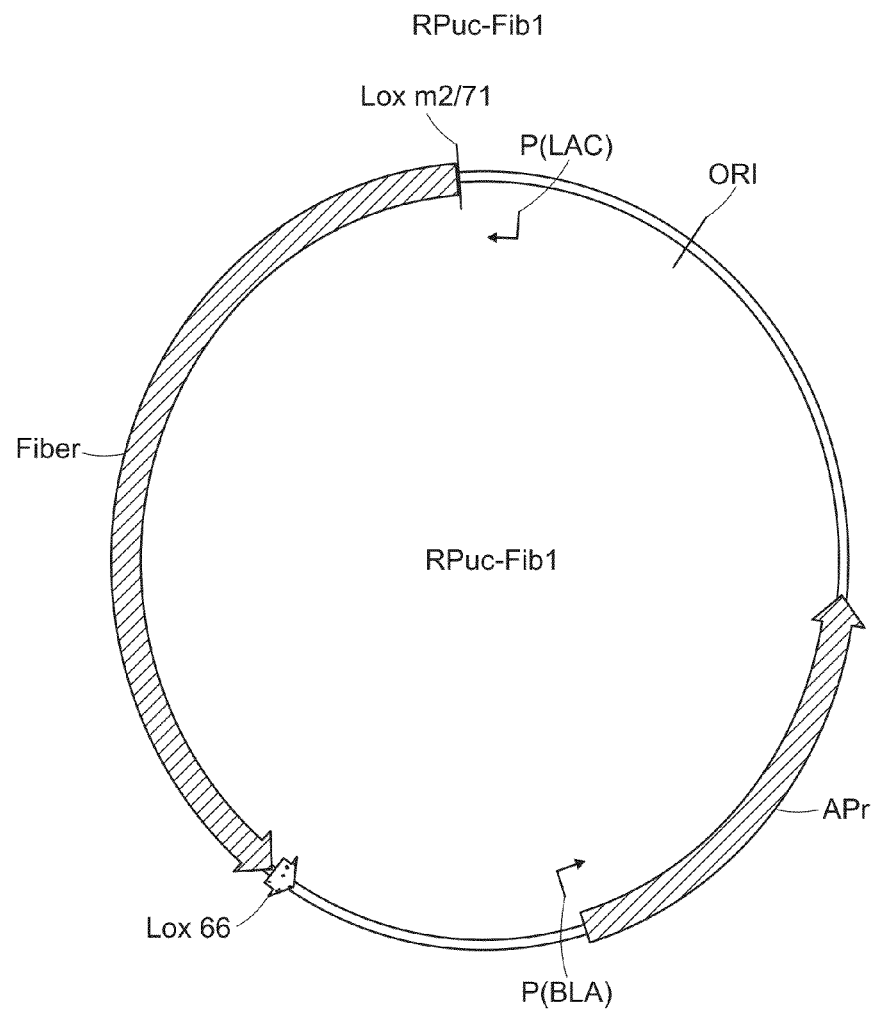
FIG. 12 is a schematic of RPuc-Fib-1.

All RP-Fib vectors contain genes encoding kanamycin resistance. A separate set of vectors, RPuc-Fib, contain the same floxed fiber genes; however, the vector base is pUC-19, which is ampicillin resistant (FIG. 12). These two separate selection antibiotics allow for fiber gene exchange to occur at multiple steps (FIGS. 4 & 5).

Example 3

Design of the Vector System

A novel vector system was generated for modifying the Fiber-gene region of the widely applied Adenovirus vector, pADEASY™-1 (He et al., *Proc Natl Acad Sci USA*, 95, 2509-2514). The vector system, outlined in FIG. 14, applies an "acceptor" vector, pFex, and Fiber "donor" vectors, RP-FBR or RPuc-FBR (depending on required antibiotic). The pFex acceptor vector is a modified version of ADEASY™-1, where the Fiber gene and upstream tripartite leader (TPL) splice-acceptor-site (Ad5 nucleotides 31,023-32,768) have been replaced with the *Bacillus subtilis* (SacB) gene. SacB imparts negative selectivity to bacteria grown in 5% sucrose and thus offers a means to negatively select against non-recombined acceptor vectors (Pierce et al., *Proc Natl Acad Sci USA*, 89, 2056-206). Correspondingly, the donor vectors contain the modified fiber gene, TPL splice acceptor site, and regions for additional transgene incorporation. Both donor and acceptor gene cassettes are flanked by non-compatible half-mutant lox sites. As delineated by Langer et al., the use of these specialized lox sites results in a unidirectional gene exchange with maintained orientation and lack of alternative recombination events (Langer et al., *Nucleic Acids Res*, 30, 3067-3077). In the presence of Cre Recombinase the Fiber gene cassette replaces SacB, placing Fiber in the natural location of the adenovirus genome. By including the natural TPL splice acceptor sequence in the fiber shuttles, upstream lox sites are not included in the final spliced Fiber transcript.

Example 4

Fiber Gene Exchange in *E. coli* and Mammalian Cells

Figure 14A:
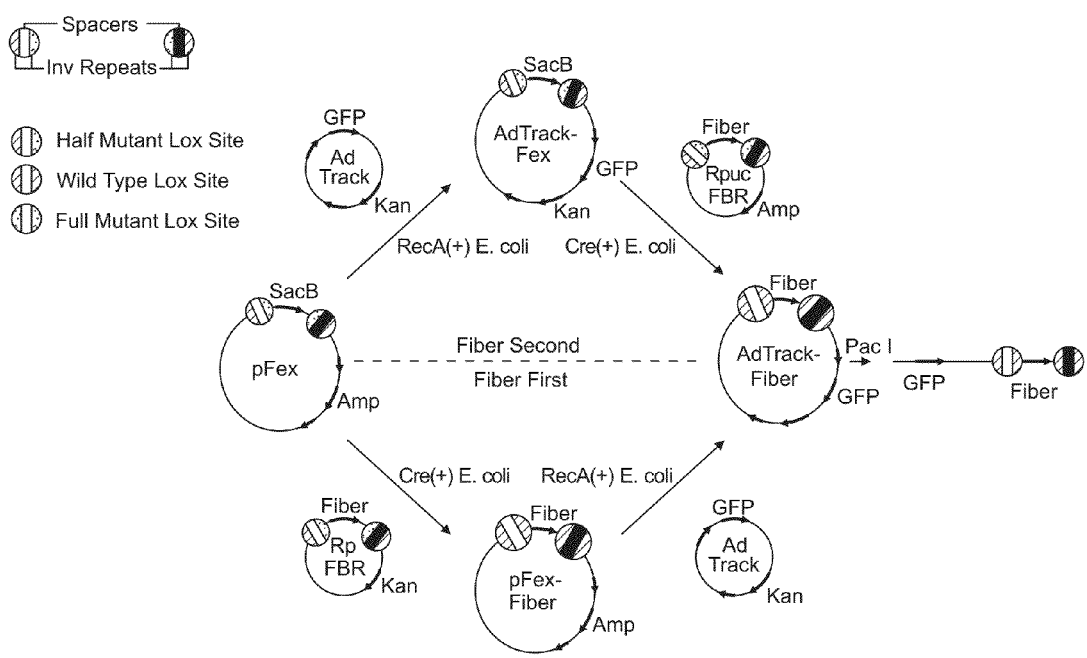
FIGS. 14A and 14B are schematic diagrams illustrating methods for site-specifically transferring modified Fiber gene cassettes into adenoviral plasmid vectors or replicating viral genomes in mammalian cells through uni-directional Cre-lox mediated recombination.
Figure 14B:
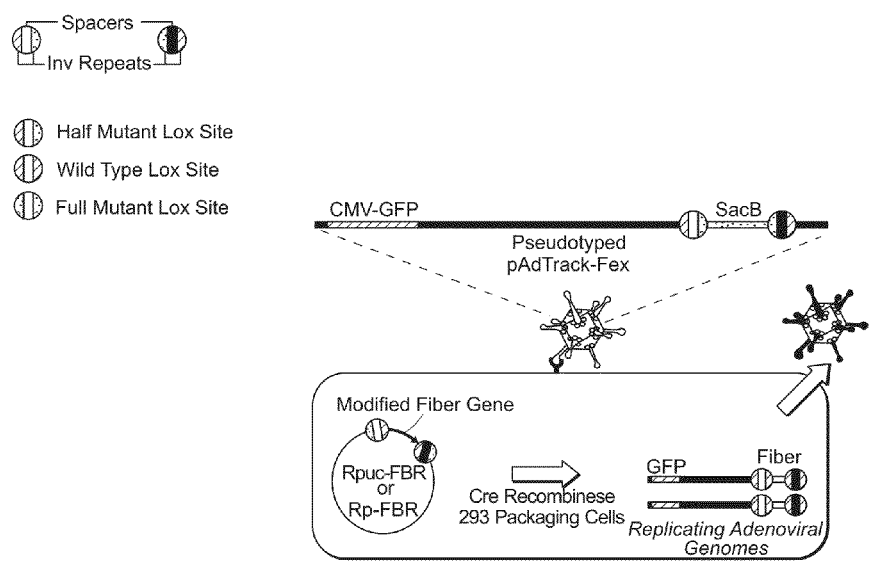

The vector system is flexible, allowing one to shuttle Fiber-cassettes into adenoviral plasmids in *E. coli* or replicating adenovirus genomes in mammalian cells (FIGS. 14A & 14B, respectively). When generating recombinant adenoviral plasmids, the modified-fiber cassette can be recombined from the smaller fiber-shuttle vectors (RP-FBR or RPuc-FBR) into the larger viral genomic plasmid vector (pFex) either before or after incorporation of a modified E1 gene cassette. For example, if a single E1 cassette is to be tested with multiple Fiber modifications, one can first generate E1-pFex (FIG. 14A, top), followed by recombination with different Fiber-shuttles. Alternatively, if a single Fiber modification is to be studied in the background of multiple E1 cassettes, one can generate a pFex-Fiber (FIG. 14A, bottom), followed by recombination with different E1 cassettes. pFex is compatible with all ADEASY™-based E1 shuttle vectors.

E1 region shuttles are recombined into pFex through traditional RecA mediated homologous recombination in *E. coli*, such as BJ5183 (FIG. 15A). Efficiency of this step can be enhanced by generating stable pFex containing BJ5183 coli, as has been shown with the AdEasier method (Zeng et al., *Biotechniques*, 31, 260-262). Fiber cassette insertion, on the other hand, is completed in 294cre *E. coli* by temperature-induced expression of Cre recombinase (Buchholz et al., *Nucleic Acids Res*, 24, 3118-3119). The desired Modified-Fiber clones can be selected through appropriate antibiotic resistance and growth on plates containing 5% sucrose, which negatively selects against SacB-containing parent vectors. If desired, the recombinant colonies can be confirmed in 294cre *E. coli* by colony PCR (FIG. 15B). Plasmid-based efficiency of Fiber gene exchange with this system is considerably better than previously reported RecA mediated fiber gene recombinations. With pFex, often 100% of screened clones contain the fiber of interest (FIG. 15C). Further, the efficiency is such that a few thousand clones can be generated in a small volume reaction (FIG. 15D).

In addition to plasmid gene exchange, the pFex system allows modified-Fiber cassettes to be transferred directly and site specifically into mature pFex-based viral genomes. To achieve this, pFex vectors are pseudotyped (packaged in cells that express wild type Fiber) and used to infect a Cre recombinase expressing mammalian cell that has been transfected with a fiber-shuttle plasmid (FIG. 14B). The modified-Fiber gene is only expressed following recombination into the genome of a replicating pFex virus. Thus, only the desired recombinant virus will propagate (see FIG. 17, viral burst). This methodology was used to generate numerous infective adenoviruses (Tables 1 & 2), including a library of adenoviruses displaying various peptides in the Fiber HI-loop.

TABLE 1

ADEASY™ and pFex derived vectors

| Name | Parent vector | E1 cassette | Fiber cassette | PFU/ml | VP/ml |
|---|---|---|---|---|---|
| AdTrack-AdEasy[a] | pAdEasy-1 | CMV-GFP | — | $2.2 \times 10^9$ | $4 \times 10^{11}$ |
| AdTrack-WTFib[a] | pFex | CMV-GFP | Wild Type Fiber | $1.7 \times 10^9$ | $1.9 \times 10^{12}$ |
| AdTrack-FBR2[b] | pFex | CMV-GFP | ΔTAYT | $1.8 \times 10$ | $2.4 \times 10^{11}$ |
| AdTrack-RGD4C-2[b] | pFex | CMV-GFP | ΔTAYT + RGD4C | $3.0 \times 10^7$ | $4.9 \times 10^{11}$ |

[a]Virus amplified, purified and titered simultaneously (equal time and volumes at all steps).
[b]Titer determined on 911-S11 cells.

TABLE 2

Peptide library and selected recombinant viruses (SEQ ID NOS 11-13)

| Name | E1 cassette | CAR binding | Fiber cassette | PFU/ml |
|---|---|---|---|---|
| AdTrack-FBR2-6X | CMV-GFP | ΔTAYT | XXXXXX | — |
| AdTrack-FBR2-A2 | CMV-GFP | ΔTAYT | TGEKGG | $1.6 \times 10^5$ |
| AdTrack-FBR2-A3 | CMV-GFP | ΔTAYT | GGAAGA | $1.4 \times 10^6$ |
| AdTrack-FBR2-A4 | CMV-GFP | ΔTAYT | GGGDRG | $1.6 \times 10^6$ |

Titer determined on 911-S11 cells, X-refers to randomized peptide sequence.

Example 5 pFex Derived Adenovirus

Figure 16A:
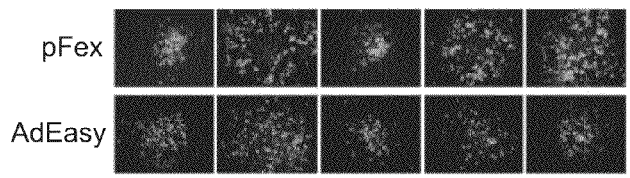
FIGS. 16A-16C show an evaluation of adenovirus generated by the pFex system.

The modifications of the pFex vector do not impart any negative effects on viral propagation. To confirm this pFex vectors were used to generate a virus containing wild type Adenovirus Serotype 5 (Ad5) Fiber using the cellular recombination method outlined in FIG. 14B. The resulting virus, AdTrack-WTFib, is identical to the traditionally generated AdTrack-ADEASY™ virus, except for the incorporated lox sites. Both viruses were simultaneously amplified, purified, and titered to observe any differences. Both viruses produced identical infectious titers (PFU) (Table 1). Viral packaging and spread through viral burst assays. Specifically, 293 cells were infected with each virus at Multiplicity of Infection (MOI) less than 1 and evaluated for viral replication and spread by burst size. Viral bursts were visualized at early stages by GFP fluorescent microscopy and five randomly selected bursts from each sample were measured (longest point diameter). AdTrack-ADEASY™ and AdTrack-WTFib had identical burst size, indicating little to no difference between ADEASY™ versus pFex derived virus (FIG. 16A). The incorporated lox sites in pFex had no significant inhibitory impact on viral lifecycle or production.

Figure 16B:
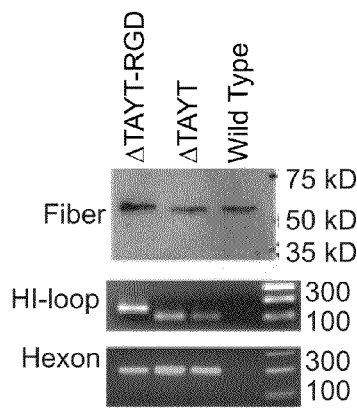
Figure 16C:
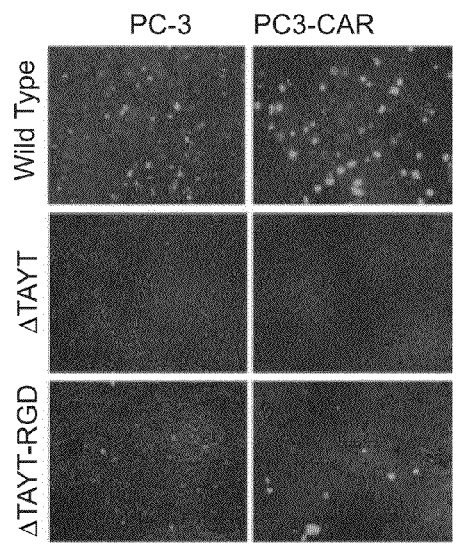

The pFex system was used to generate previously characterized tropism-modified adenovirus for proof of principal. First, the natural CAR-mediated infection pathway was ablated through FG loop mutation ($\Delta T_{489}AYT_{492}$) (Roelvink et al., *Science*, 286, 1568-1571). These CAR de-targeted viruses (referred to as ΔTAYT) were then redirected to bind and infect cells via integrins by inserting the cysteine-constrained, integrin-binding peptide RGD4C (CDCRGDCFC) (SEQ ID NO: 14) into the Fiber HI-loop (Koivunen et al., *Biotechnology* (NY), 13, 265-270). Purified particles of these two viruses, AdTrack-FBR2 (ΔTAYT) and AdTrack-RGD4C-2 (FIG. 36) (ΔTAYT-RGD) contain only the desired recombinant Fiber DNA and recombinant Fiber protein at expected size and proportions (FIG. 16B). 911-S11 cells, which contain an anti-Fiber pseudoreceptor (van Beusechem et al., *J Virol*, 76, 2753-2762), were used to propagate and titer these CAR-ablated vectors. In cell infection assays, Fiber FG loop mutation predictably ablates CAR mediated infection of PC-3 and PC3-CAR prostate cancer cell lines (FIG. 16C). The incorporation of the integrin targeting peptide expectedly provides an alternative infection pathway for both cell lines. Notably, the CAR over-expressing cell line, PC3-CAR, was infected by wild type Fiber adenovirus (AdTrack-WTFib) at a higher rate than the parental PC-3 cell line, which is known to express lower levels of CAR (Okegawa et al., *Cancer Res*, 60, 5031-5036). On the other hand the CAR de-targeted and integrin re-targeted virus (ΔTAYT-RGD) infected both PC-3 and PC3-CAR cell lines with equal efficiency. Though integrin re-targeted infection is low when compared to wild type fiber in this cell line (~5%), such vectors are valuable for infecting cancer cells which often lack CAR expression (Wickham et al., (1995) *Gene Ther*, 2, 750-756). These results confirm previous reports of FG loop de-targeting and the subsequent re-targeted infection through capsid-displayed integrin-binding peptides (Wickham et al., (1997) *J Virol*, 71, 8221-8229; Mizuguchi et al., (2002) *Gene Ther*, 9, 769-776.

Example 6

Efficiency and Sensitivity of Generating Modified Adenovirus with pFex

Cre-lox recombination offers a means to site specifically recombine gene cassettes into large vectors, including cellular genomes. However, in traditional Cre-lox recombination, the symmetric lox site remains unchanged following recombination. Thus, the reactant and product are identical and the reverse reaction occurs with equal efficiency. Langer et al. have overcome this limitation by designing half-mutant lox sites which, after recombination, produce a unique and non-functional product in the donor vector, rendering the reaction uni-directional (Langer et al., (2002) *Nucleic Acids Res,* 30, 3067-3077). The application of this uni-directional cassette exchange theoretically provides added efficacy by preventing any reverse recombination over time.

Figure 26:
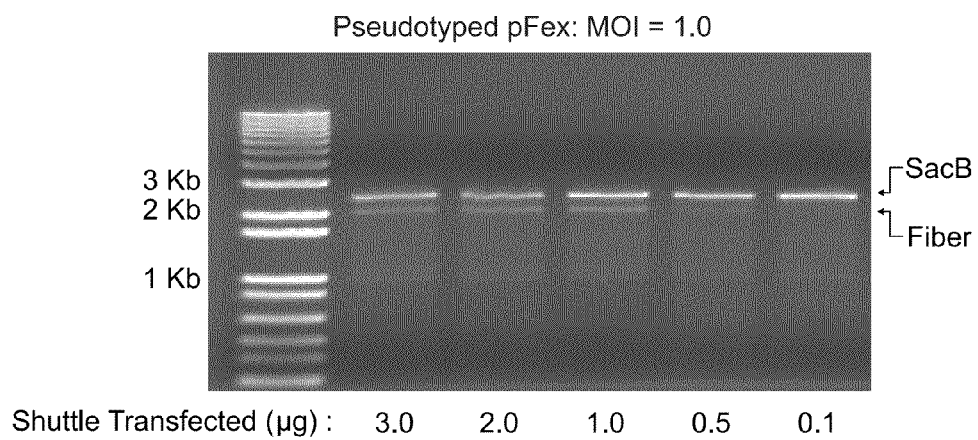
FIG. 26 shows PCR products in an evaluation of shuttle-vector amounts on gene exchange. Transgene exchange was determine by PCR amplification of the fiber gene region from resulting viral pools. Non-recombinant virus contains SacB where recombinant virus contains Fiber.

In vitro evaluation of gene exchange efficiency was evaluated with four separate Fiber shuttle vectors. In this plasmid based gene exchange, numerous Fiber gene cassettes were recombined into the 34 Kb pFex plasmid, producing approximately 1800 recombinant clones per milliliter of transformation culture in the absence of detectable background (FIG. 26). While this efficiency could be easily scaled to generate a large diversity plasmid library, direct translation to active adenoviral particles is unrealistic. Therefore, the true value of the system is best evaluated by the ability to generate recombinant infectious virus.

Figure 17:
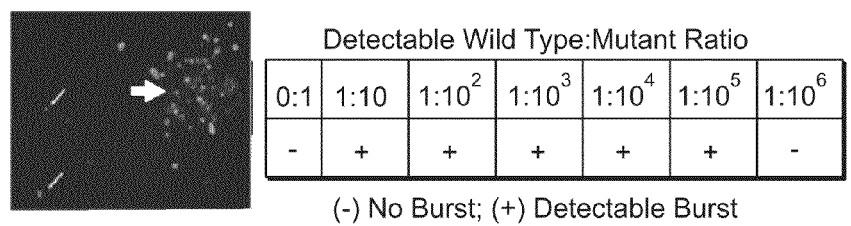
FIG. 17 shows the efficiency and sensitivity of Fiber gene exchange. Serial dilution mixing experiments demonstrate Fiber-cassette exchange sensitivity. Fiber shuttle RPuc-WT-Fib was serially diluted from 1:10 to 1:1,000,000 and mixed into a constant amount of mutant Rpuc-Fib1R1 (N541S) plasmid. This plasmid mix was recombined into AdTrack-pFex genomes by transfection into 293cre57 cells infected with pseudotyped AdTrack-Fex at an MOI of 1. Cell lysates were used to infect 293 cells, which were then overlayed by agar. Recombinant AdTrack-WTFib viruses were identified by viral burst (open block arrow). At least a single viral burst was detectable in dilutions of 1:10,000 to 1:100,000 wild type fiber shuttle, indicating a sensitivity of 0.01-0.001%. Some non-spreading viral infections were present (small arrows), indicating infection by AdTrack-pFex or AdTrack-N541S which was pseudotyped in cells co-inhabited by AdTrack-WTFib viral genomes. Fiber N541S alone control (0:1) was unable to create any viral bursts.

To evaluate the efficiency of exchanging modified fiber genes into viral genomes in mammalian cells (FIG. 14B) serial dilution mixing experiments were performed using a wild type fiber shuttle (Rpuc-WTFib) and a non-infective fiber mutant (N541S) shuttle. Recombinant AdTrack-WTFib virus produces GFP positive viral bursts visible by fluorescent microscopy in agar overlayed 293 cells (FIG. 17, large arrow), where AdTrack-N541S is non-infective. The wild type Fiber shuttle was serially diluted (1:10 to 1:1,000,000) and mixed into a constant amount of mutant fiber shuttle, and the resulting plasmid mixes were transfected into 293cre57 cells which were simultaneously infected with pseudotyped AdTrack-Fex virus (MOI=1). Five days after transfection and infection, recombinant viral pools were harvested and applied to 293 cells with agar overlay in order to determine the sensitivity of detecting spreading AdTrack-WTFib virus (as indicated by a GFP positive viral burst). This is the most stringent assay possible as adenovirus with Fiber N541S mutation do not produce infective virus particles. Therefore, this mutant fiber protein will potentially hybridize and compete with the wild type fiber in a co-infected or co-transfected cell. A sensitivity of 0.01-0.001% was determined by finding at least one viral burst in ratios of 1 WTFib shuttle to 10,000 or 100,000 Fiber-N541S mutant shuttles (FIG. 17). This success is unprecedented for Fiber gene exchange and suggests that Fiber-peptide adenovirus libraries can be simultaneously generated and screened for the ability to create infective and spreading virus.

Example 7

Adenoviral Peptide Library Screen for Re-Targeted Infection

A low diversity fiber-displayed hexapeptide adenovirus library was generated and screened (Table 2). A random peptide cassette was cloned into the HI-loop of the CAR-ablated (ΔTAYT) Fiber shuttle, RPuc-FBR2. The resulting plasmid library (RPuc-FBR2-6X) produced ~16,000 plasmid clones, reflecting the maximum diversity. One million 293cre57 cells were transfected with 3 µg of RPuc-FBR2-6X and infected with pseudotyped pAdTrack-Fex (MOI of 1). Five days later, the recombinant virus pool was harvested. 293 cells were then infected to identify CAR-independent viral plaques. Both positive (RPuc-WTFib) and negative (N541S) control samples were included in this experiment for reference purposes.

Figure 18:
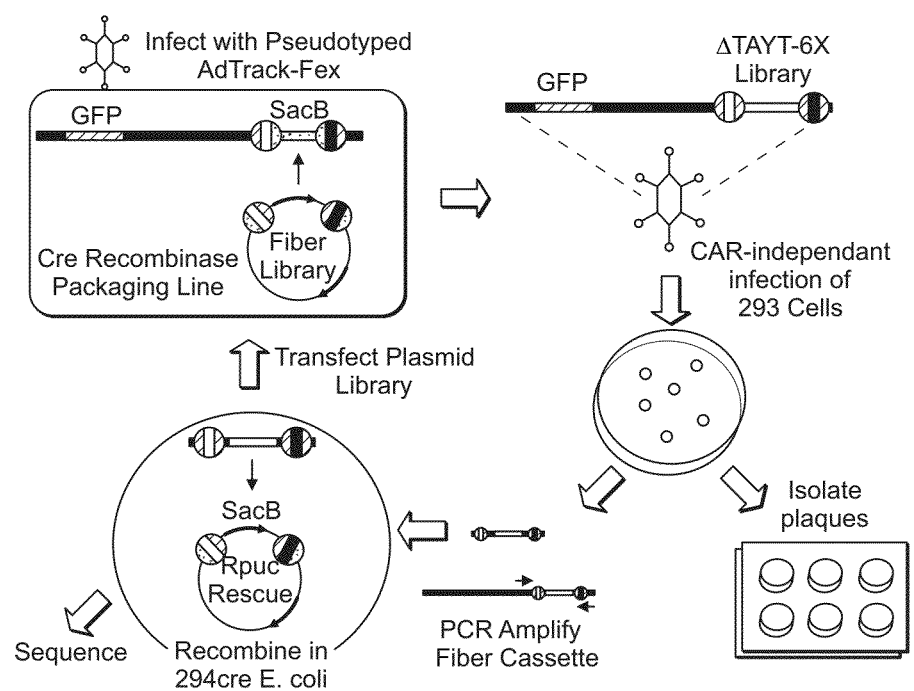
FIG. 18 is a schematic diagram showing an exemplary strategy used for generating, selecting, and rescuing adenoviral peptide libraries. Clockwise from top left: CAR-ablated Fiber-peptide library cassettes are uni-directionally shuttled into Fiber-less pFex viral genomes in 293cre57 cells. Some of the resulting CAR de-targeted and peptide re-targeted viruses infect the target cells. Resulting viral plaques can be isolated and amplified. Alternatively, the floxed Fiber cassette can be amplified by PCR (either from the plaques or from the pool of infected cells) and recombined with RPuc-Rescue in 294cre *E. coli*. Growth in appropriate antibiotics and 5% sucrose selects new fiber-shuttles that are directly applicable to sequencing, farther modification, or recombination to generate new virus in plasmid or viral form.

Viral burst from each sample were quantified 48 hours post infection. In comparison to the wild type control, the FBR2-6X library produced approximately 0.075% the number of bursts. There were no infected cells bursts in the negative (N541S) control. Individual plaques were randomly isolated and amplified in 24-well plates. Aliquots were taken for PCR amplification of the floxed Fiber cassette. The resulting PCR product was then recombined with RPuc-Rescue, an acceptor plasmid that contains half-mutant lox sites flanking a SacB gene for sucrose selection, in 294cre *E. coli* (FIG. 18). Once recombined into RPuc-Rescue, the cloned Fiber gene is available for sequencing, further modification, or recombination with pFex viral genomes to create a subsequent virus.

Figure 19A:
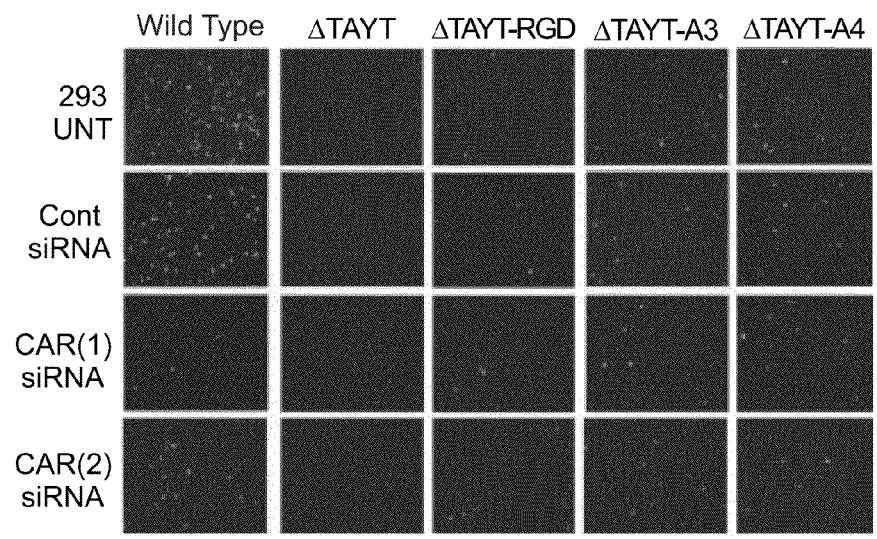
FIGS. 19A and 19B show CAR-independent infection by selected re-targeted adenovirus.
Figure 19B:
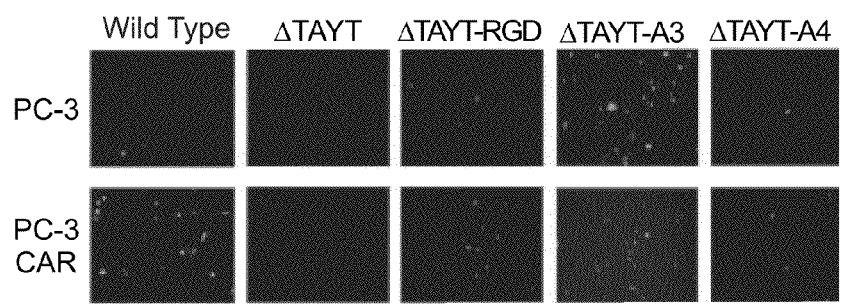
Figure 20:
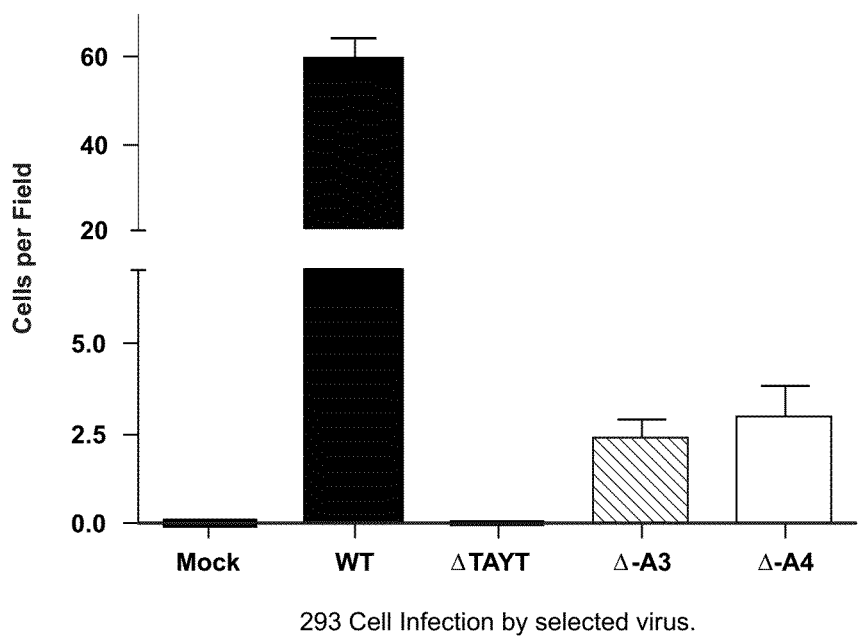
FIG. 20 is a graph showing 293 Cell infection by selected virus.
Figure 21A:
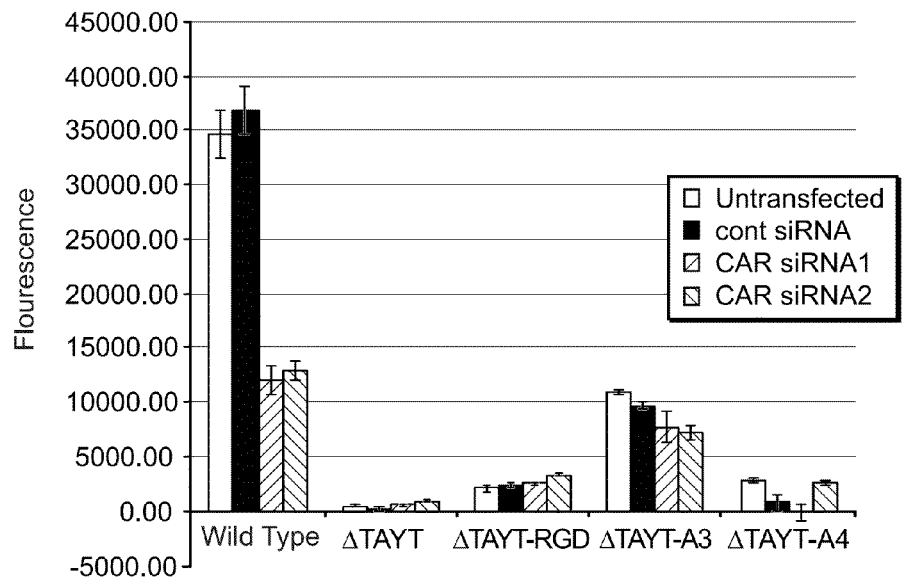
FIGS. 21A and 21B are graphs showing a quantification of CAR dependent and independent infection.
Figure 21B:
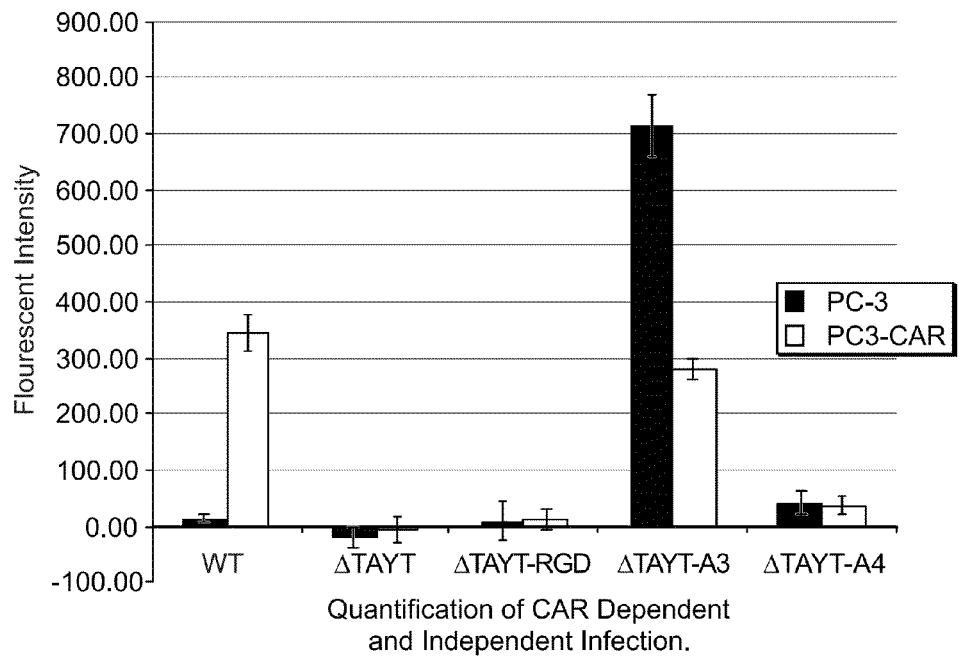

Three plaques from the hexapeptide library were cloned and sequenced to identify three unique peptides (Table 2). These clones were amplified, purified, titered, and evaluated for re-targeting ability in comparison to CAR ablated virus. Adenovirus AdTrack-FBR2-A2 (ΔTAYT-A2) was poorly propagated in 293 cells, possibly due to peptide inhibition during packaging. The two remaining viruses, FBR2-A3 and FBR-2A4, do propagate and are capable of re-targeting adenoviral infection to 293 cells (FIG. 20). To evaluate if this infection was CAR-independent, CAR protein levels were knocked down by transfecting 293 cells with two separate anti-CAR siRNAs. CAR-specific knock-down by both siRNAs reduced wild-type fiber infection by over 50%, but did not reduce the number of infected A3, A4, or RGD peptide re-targeted viruses (FIG. 19A). This infection rate was also quantified by fluorometer (FIG. 20). Further, the infection rates of these viruses was evaluated in PC-3 and the CAR over-expressing subline, PC3-CAR. Wild-type adenovirus infected PC3-CAR cells with 26 fold better efficiency than the low CAR expressing PC-3 parental cell line. However, CAR over-expression did not enhance the infection rate of the A3, A4, or ROD peptide re-targeted virus (FIG. 199B and FIG. 21B). Notably, the infection rate of the A3 re-targeted virus was superior to the RGD re-targeted virus in both cell lines. These experiments indicate that the ligand for FBR2-A3 and FBR2-A4 viruses is expressed in both 293 cells and PC-3 prostate cancer cells. The sequences of these peptides are provided at Table 2.

The fiber capsid protein is responsible for the initial interaction between the virus and the cell, through high affinity binding with the cellular receptor, CAR (Bergelson et al., (1997) *Science,* 275, 1320-1323; Tomko et al., (1997) *Proc Natl Acad Sci USA,* 94, 3352-3356), followed by internalization, which is triggered by viral penton base interaction with cellular integrins (Wickham et al., (1993) *Cell,* 73, 309-319). The fiber gene is the fifth and last gene in the Major Late Transcriptional Unit (MLTU), an approximately 29 Kb, multiple open reading frame (ORF) transcript expressed late in the viral lifecycle (Nevins et al., *J Virol,* 25, 811-823). Alternative splicing of the MLTU links each ORF with a 5'-leader for preferential translation and a 3'-polyadenylation site (Berget et al., (1977) *Proc Natl Acad Sci USA,* 74, 3171-3175; Chow et al., (1977) *Cell,* 12, 1-8; Ziff et al., (1978) *Cell,* 15, 1463-1475. When designing fiber-gene modified virus, one must avoid interrupting splice donor and acceptor sites because they cannot only affect fiber, but also other ORF in the MLTU. Apart from splicing, modification of the fiber coding region can also negatively affect fiber protein folding, trimerization, assembly into the virus, and therefore viral production. The HI-loop, a serotype variable region, is an accepted site for incorporating targeting motifs while still allowing successful viral propagation Krasnykh et al., *J Virol,* 72, 1844-1852.

However, each ligand is unique and may affect fiber differently (Belousova et al., (2002) *J Virol,* 76, 8621-8631). Additionally, incorporation of a targeting peptide into the fiber protein backbone may interfere with the ability of the peptide to bind its ligand. Therefore, rigorous evaluation of each re-targeted virus is required to confirm that they have no deleterious effects on viral production or peptide-ligand binding. Because of these potential problems, and the time and effort required to make genetically re-targeted virus, there was a significant risk of failure in pursuing these projects using conventional screening methods.

For this reason, adenoviral-display peptide libraries have been a significant yet difficult goal in adenoviral biotechnology. While high diversity libraries can be generated in plasmid form, transformation to a packaged adenovirus library is difficult due to inefficiencies in transfecting the large viral genome and low rates of conversion to a packaged and infective adenovirus. For example, most protocols recommend transfection of 2-5 micrograms of linearized adenoviral plasmid DNA ($\sim 5 \times 10^{10}$-$1 \times 10^{11}$ plasmid particles) into $2 \times 10^6$ 293 cells to obtain full infection within 7-10 days. This corresponds to an MOI of 50,000. On the other hand, infection with an MOI of 1 will generally provide full infection in less than half the time. Therefore, the efficiency of viral production is several logs better with infection when compared to transfection. While it is notable that conjugation of terminal protein complex (TPC) can improve the conversion rate of viral DNA into packaged adenoviral particles by a few logs, this efficiency is still far below that of natural viral infection. Here a methodology to produce fiber peptide libraries by applying the large "acceptor" vector as a packaged and infective virus that genetically lacks the fiber gene is described. The Fiber peptide library is then transferred from a small, more easily transfected shuttle, into infected adenoviral genomes in mammalian cells. The Fiber protein is only expressed following successful gene transfer, thus only recombinant virus will properly package and propagate. This step overcomes the major limitation of converting the large linearized viral plasmid genome into a packageable and infectious adenovirus particle.

Through serial dilution mixing experiments with this system, libraries of at least $10^5$ can be generated and screened to identify successfully propagating virus (FIG. 17). These studies, completed in 6 well dishes, can be easily expanded to increase the applicable diversity. Moreover, the applicable diversity may be improved by transfecting smaller amounts of the shuttle plasmid library (to achieve a low plasmid copy number per cell) during library generation. This could potentially minimize the number of chimeric viruses formed during this first step. Later, during library selection and amplification, there is the possibility of co-infection by a neighboring virus. The resulting co-infection would create chimeric viruses, potentially inhibiting the propagation of a successful clone. With the pFex Rescue system (FIG. 18), successful clones can be rescued from infected cells by PCR and recombined back into the RPuc-Rescue plasmid. This step, while applied to individual plaques in our screen, can also be applied to a population of cells infected with a viral pool. With this methodology, one can avoid the negative effects associated with amplifying a viral pool. The resulting rescue plasmids produce working Fiber shuttles which can be sequenced, applied to generate a new viral clone, or applied as a pool to a second round of library selection (FIG. 18).

Here, a single round of selection was applied to a moderately diverse library of 16,000 potential Fiber-displayed hexapeptides to identify adenoviruses which infect cells in a CAR independent manner. With a projected three amino acid diversity of 8,000 ($20^3$=8,000), this library should contain at least one integrin targeting RGD motif, currently one of the best peptide motifs for retargeting adenoviruses to CAR-deficient cells. One of the selected peptides, A3, redirects infection of de-targeted viruses to 293, PC-3, and PC3-CAR cells at higher levels than the widely applied integrin targeting peptide, RGD4C. The selected retargeting peptides, like RGD and other peptides, appear to reduce the overall output of infectious viruses (PFU). However, it is possible that additional rounds of biopanning may select for peptides which not only infect the target cell, but also minimize interference with fiber protein folding and capsid assembly (i.e. —more favorable Viral Particle to PFU ratios). The pFex system can be used in this way to generate and screen higher diversity libraries through iterative selection rounds, as shown in FIG. 5, to identify CAR-independent adenovirus to most any cell type.

Example 8

Optimization of Gene Transfer

Figure 25:
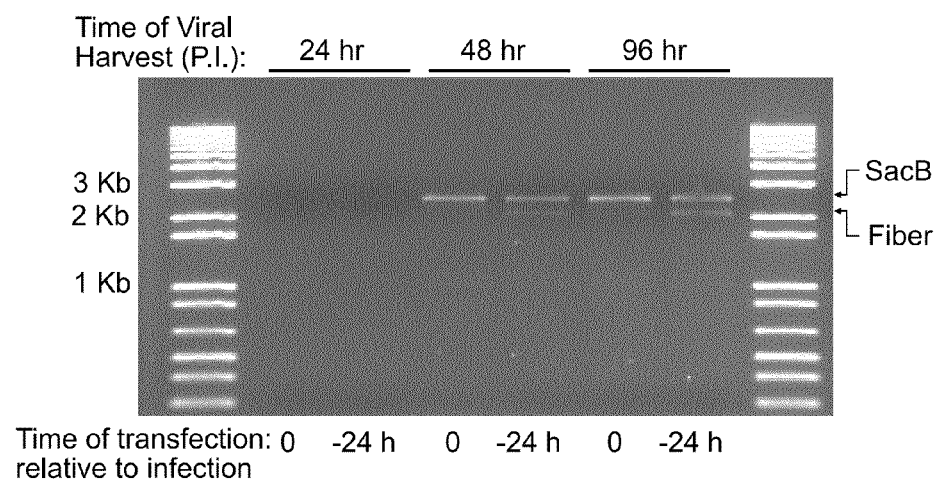
FIG. 25 shows PCR products in an evaluation of transfection time and viral harvest for effective Fiber gene transfer. Virus was harvested at designated time points and transgene determine by PCR amplification of the fiber gene region. Non-recombinant virus contains SacB and recombinant virus contains Fiber.

Further studies have been completed to optimize the efficiency of gene transfer between the shuttle plasmids and the pseudotyped viral genome when generating viral libraries. It was found that transfection of the shuttle plasmid 24 hours prior to infection produced a higher fraction of Fiber-gene containing virus. Further, it was found that the viral library should be harvested 3-4 days after recombination (FIG. 25).

Serial dilution studies were also completed to identify the minimal amount of fiber-shuttle needed for effective fiber gene exchange into the pseudotyped genome. The results found that 1.0 micrograms is the minimal amount of shuttle plasmid needed for efficient transgene exchange (FIG. 26). The application of this minimum amount of shuttle-plasmid should reduce the possibility of generating two separate recombinant virus within the same cell.

Figure 27:
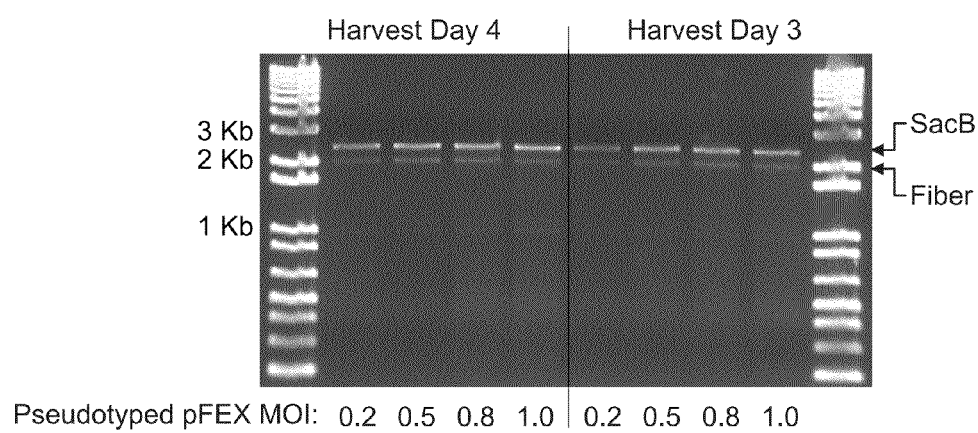
FIG. 27 shows PCR products in an evaluation of acceptor virus MOI on recombination efficiency. Transgene exchange was determine by PCR amplification of the fiber gene region. Non-recombinant virus contain SacB where recombinant virus contain Fiber.

Finally, serial dilutions of the acceptor virus were studied to identify the minimum applicable multiplicity of infection (MOI) for efficient gene exchange. The application of lower viral titers will theoretically reduce the chance of producing two separate recombinant viruses in one cell. Gene exchange was efficient with 0.5-1.0 MOI of virus (FIG. 27).

Cells and Culture.

293 (Quantum Biotech), FBJ, and 293cre57 cells were maintained in Dulbecco's MEM (DMEM) with 10% FBS. 911-S11 cells were maintained in DMEM with 5% FBS and 200 µg/ml G418. 911-S11 cells express a previously characterized membrane-bound anti-Fiber single chain antibody as a pseudo-receptor (van Beusechem et al., *J Virol,* 76, 2753-2762). DPL-37 cells were maintained in DMEM with 10% FBS and 10 mM MgCl$_2$. PC-3 cells were obtained from ATCC (Manassas, Va.) and maintained in RPMI medium supplemented with 10% FBS. PC3-CAR was provided by Dr. Hsieh (Okegawa (2000) *Cancer Res,* 60, 5031-5036). All medias were supplemented with Ciprofloxacin Hydrochloride 5 µg/ml (US Biological, Swampscott, Mass.), and Gentamicin 50 µg/ml (Quality Biological Inc., Gaithersburg, Md.). All cells were maintained at 37° C. in an atmosphere containing 5% CO2.

Generation of Plasmid Vectors.

The pFex plasmid was assembled through several steps. First, 'distal to fiber AgeI' was created by PCR amplification and cloning with primers AdE-Dist 5' and AdE-Dist 3' (FIG. 12) into pCR-2.1 to produce the vector 'Step 1 pFex'. Second, 'proximal to fiber' was created by PCR amplification with primers loxmve1 and loxmve2 and subcloning into 'Step 1 pFex' using the SpeI and AgeI. The resulting vector is 'Step 2 pFex' (FIG. 7).

The SacB gene was isolated from pAJ200 using the BglII and PvuI restriction sites. Next, the two half mutant lox sites, lox m2/66 and lox 71, were added by ligation with self annealed linkers 5' lox m2/66 and 3' lox m2/66, and 5' lox 71 and 3' lox 71, respectively (FIG. 12). The resulting floxed SacB gene was then subcloned into Step 2 pFex to create 'Step 3 pFex' (FIG. 8).

Finally, the modified segment was subcloned into pADEASY™-1 with SpeI and PacI, replacing the pre-existing region. The final vector construct is called pFEX (FIG. 9) and was verified by sequencing using primers pFEXfor01-11 and pFEXrev01-11 (FIG. 12). Primers used for constructing and sequencing pFex are shown in FIG. 23. Finally, a second version of pFEX, termed pFEX-p*, contains a mutation in the integrin binding domain of the penton gene, where RGD is mutated to RGE (FIG. 9).

Figure 10:
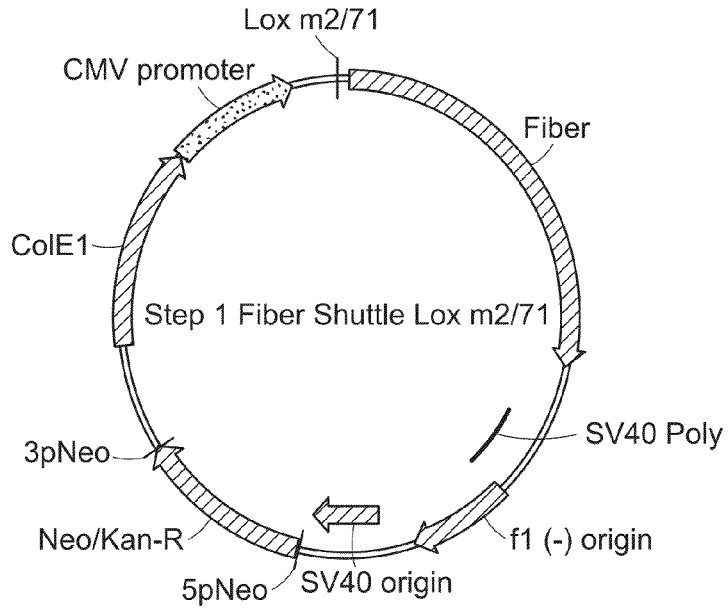
FIG. 10 is a schematic depicting Fiber Shuttle Lox m2/71.
Figure 13A:
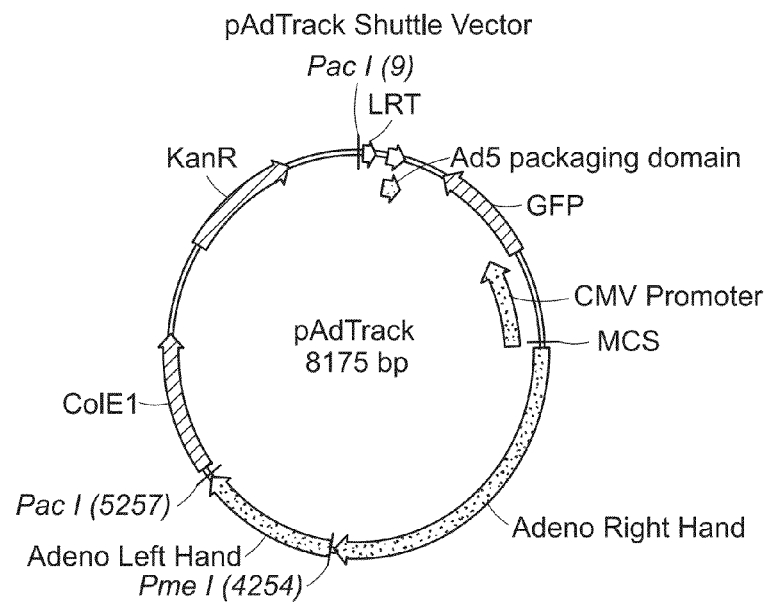
FIGS. 13A and 13B are schematics of a pAdTrack shuttle vector and RPuc-WTFib, respectively.
Figure 13B:
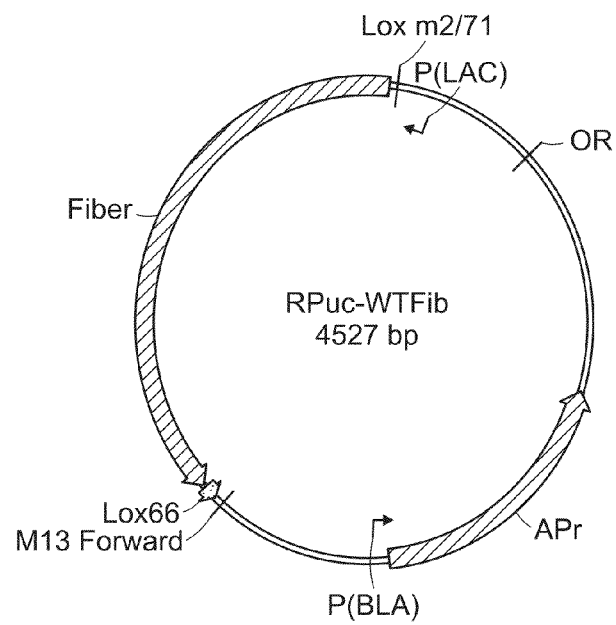

Fiber shuttle vectors were also constructed in a stepwise manner. Primers used for constructing and sequencing Fiber shuttle are shown in FIG. 24. pBK-CMV-Fiber (a generous gift from Drew Pardoll and Sara Pai, Johns Hopkins) contained three mutations, A32665T, A32667C (which created a unique BspEI site in the Fiber-HI loop), and A32651G (N541S ablative mutation). Adenovirus containing the Fiber N541S mutation are unable to infect or propagate (FIG. 4, far left column 0:1 (WT:N541S) produces no viral bursts or plaques). pBK-CMV-Fiber was digested with the SpeI and XhoI and the linkers S-lox m2/71-X5 and S-lox m2/71-X3 (FIG. 13) were self annealed and ligated into the vector creating 'Step 1 Fiber Shuttle Lox m2/71' (FIG. 10). The linkers N-Lox 66-A-5 and N-Lox 66-A-3 were then subcloned into this vector by Acc65I and NotI, making 'RP-Fib1' (FIG. 11) The tripartite leader (TPL) splice acceptor site was subcloned downstream of the lox m2/71 site with linkers splce1 (TC-GAGAACTATCTTCATGTTGTT-GCAGATGAAGCGCG-CAAGACCGTCTGAAGATACCTTCAAC-CCCGTGTATCCATATG ACACGGAAA) (SEQ ID NO: 9) and splce 2 (CCGGTTTCCGTGTCATATGGATA-CACGGGG-TTGAAGGTATCTTCAGACGGTCT-TGCGCGCTTCATCTGCAACAACATGAAGATAGTT C) (SEQ. ID NO: 10) creating RP-Fib1R1. For CAR ablated vectors, pBK-CMV-TAYT-Fiber (ΔAd5 nucleotides 32506-32518, amino acids T$_{489}$AYT$_{492}$; Roelvink, P. W. et al. (1999) Science 286:1568-1571) was subcloned into shuttle through XhoI/NotI, creating 'RP-Fib2'.

Figure 22B:
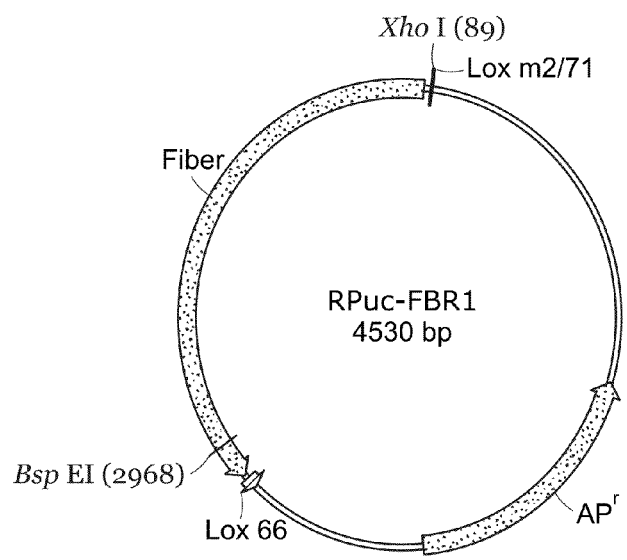
Figure 22C:
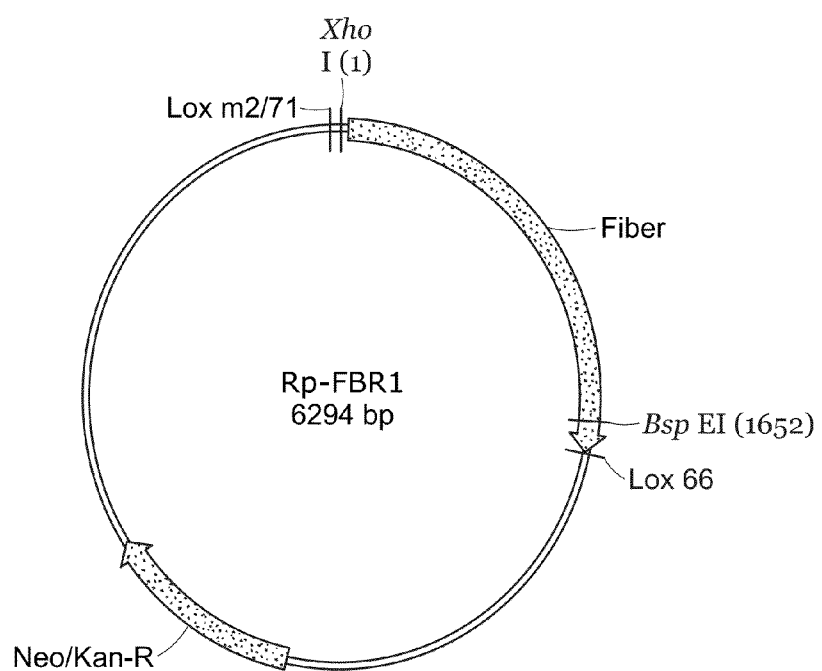

The TPL splice acceptor was cloned as above creating 'RP-Fib2R1'. Finally, plasmids RP-FBR1 and RP-FBR2 were generated by reverting the A32651G (N541S) mutation to wild type with primers 5FBR-537REP and 3FBR-537REP and BglII and BspEI subcloning. To generate Ampicillin resistant versions, the floxed cassettes were subcloned into Puc19 through KpnI and SpeI, creating RPuc-Fib1, RPuc-Fib2, RPuc-Fib1R1, RPuc-Fib2R1, RPuc-FBr1, and RPuc-FBR2 (FIG. 12; FIGS. 22B, 22C).

RPuc-RGD4C-2, was created in two steps. First, annealed primers 5N-Dir and 3N-Dir (5'N-Dir: [Phos] CCGGCGAAT-TCGCAGGTGGTGGTGGTGGTT (SEQ ID NO: 62) 3'N-Dir: [Phos] CCGGAACCACCACCACCACCTGCGAAT-TCG (SEQ ID NO: 63)) were subcloned into the HI-loop BspeI site. Linkers 5'RGD and 3'RGD (5'RGD: [P]AAT-TGGGAAGAGGTGACACCCCT (SEQ ID NO: 64) 3'RGD: [P]CCGGAGGGGGTGTCACCTCTTCCC (SEQ ID NO: 67)) were then annealed and subcloned into the vector. RPuc-WTFib and RP-WTFib, were generated with primers WTFibFix-1 and WTFibFix-2 and subcloning through NcoI and NoI. RPuc-Rescue was generated by PCR amplification of SacB with primers Not-SacB (AATTGCGGC-CGCCACTATTATTTAGT-GAAATGAGATATTA) (SEQ ID NO: 68) and Xho-SacB (ATCTCGAGAGAAGTGATG-CACTTTGATATCGACCCAAG) (SEQ ID NO: 69) and subsequent cloning into RPuc-FBR1, replacing Fiber with SacB.

All Fiber shuttle vectors were sequenced with primers M13 forward, M13 Reverse, Fiber-S2 and Fiber-S3.

Generation and Evaluation of Adenovirus Through Plasmid Based Recombination.

pAdTrack (FIG. 13), was recombined with the pFex plasmid vector either before or after Fiber-region recombination in BJ5183 *E. coli* either by co-electroporation or by first generating a stable pFex-based BJ51823 *coli* followed by electroporation of the AdTrack shuttle vector (He et al., (1998) Proc Natl Acad Sci USA, 95, 2509-2514; Zeng et al., (2001) Biotechniques, 31, 260-262). Recombinant vectors were propagated in DH5α. For Fiber-region recombination, 10 ng of pFex was transformed with the 10 ng Fiber-shuttle vector into 40 µl of electrocompetent 294cre *coil* (Gene Bridges GmbH, Dresden, Germany) in a 0.2 cm cuvette at 2.5 KV, 200 ohms, and 25 µFd (BioRad Gene Pulser). Following electroporation, samples were resuspended in 1.0 ml SOC broth, incubated at 42° C. for 20 minutes, and then shook vertically (225 rpm) at 37° C. for 1 hour. Recombinant plasmids were selected on appropriate antibiotic LB agar plates containing 5-7% sucrose. Clones were amplified, mini-prepped, and the resulting plasmid electroporated into DH5α *coli*. In some cases, PCR was applied prior to DH5α transformation to detect the presence of recombinant clones (see "recombination specific PCR" below and FIG. 2B). Recombinant plasmids were screened by XhoI restriction mapping and confirmed by DNA sequencing. Viral plasmid products were linearized by PacI digestion and transfected into the desired packaging lines (293 or 911-S11). Viruses were step amplified to 5×150 mm² flasks and then purified by commercial adenovirus purification kit (Adenopure™, Puresyn, Inc., Malvern, Pa.). Benzonase was used in the purification process. Resulting viruses were titered by Adeno-X™ Rapid Titer Kit (BD Biosciences). The correct splicing pattern upstream of the recombinant fiber gene was confirmed by reverse transcription of total RNA harvested from infected cells (Trizol, Invitrogen), followed by PCR amplification with primers Fib-RT1 (ACAAACUCUUCGCGGUCUUU) (SEQ ID NO: 70) and Fib-RT2 (UAUCUUCAGACGGUCU-UGCG) (SEQ ID NO: 71), TOPO-TA cloning (pCR-21-TOPO, InVitrogen), and sequencing. These results confirmed natural linkage of the TPL to the Fiber coding region.

Recombination Specific PCR.

Colony PCR was applied to confirm recombination of the Fiber gene into pFex. Primers Fiber-S2 and pFexrev07 produce a 1.6 Kb product that is specific for fiber containing clones (FIG. 2B). Note the PCR product size depends on the content of the Fiber gene cassette. PCR primers pFexfor08 and pFex rev02 were used for positive controls. Clones positive by these assays were then mini-prepped and transformed into the more stable DH5α *E. coli*.

Efficiency of Plasmid Based Recombination.

294cre *E. coli* were electroporated with 50 ng of pFex plasmid and 10-fold molar excess fiber-shuttle. Cells were heat shocked for 20 minutes and grown for 2 hours 37 C, 225 rpm. Clones were quantified on LB+50 ug/ml Kan for pFex containing colonies, LB+100 ug/ml Amp for fiber-shuttle colonies, and LB+7% Sucrose+50 ug/ml Kan as colonies per milliliter of growth medium.

Generation and Evaluation of Adenovirus Through Mammalian Cell Based Recombination.

The Fiber-less pAdTrack-Fex plasmid was pseudotyped by PacI digestion and transfection into the Fiber-gene expressing FBJ cell line (a generous gift of Dr. David Johns, Johns Hopkins). Pseudotyped AdTrack-Fex virus was amplified, purified, and titered as described above. For Fiber gene recombination, approximately $10^6$ 293cre57 cells (15) (a generous gift of Dr. Stephen Langer, University of Colorado) were transfected with 2 μg of Fiber-shuttle shuttle plasmid through magnet assisted transfection (MATra-A, IBA, St. Louis, Mo.) in a 6 well plate, immediately followed by infection with pseudotyped AdTrack-Fex (MOI=1). 3-5 days after transfection and infection, cells were harvested by scraping and virus eluted by 3-4 freeze/thaw cycles. The resulting supernatant was then used to infect 293 or 911-S11 cells.

Evaluation of Purified Adenoviral Particles.

$10^6$ Plaque Forming Units (PFU) of each purified adenovirus were boiled in Laemmli buffer for western blot analysis. Blots were probed with 4D2 Anti-Fiber antibody (Abcam, Cambridge, Mass.), anti-mouse IgG-HRP (Sigma, St. Louis, Mo.), and developed by ECL-Plus HRP detection assay (GE Healthcare). For PCR detection, $10^5$ PFU was boiled and DNA subjected to Hexon (primers Ad5Hexon sense: ATG-GCTACCCCTTCGATGAT (SEQ ID NO: 72) and Ad5Hexon antisense: GATGAACCGCAGCGTCAAAC (SEQ ID NO: 73); 207 bp product) and Fiber HI-loop (primers HIFlnk: TTCATTAATGTAGTTGTGGC (SEQ ID NO: 74) and knlFIH: ACCATTACACTAAACGGTAC (SEQ ID NO: 75); 101 bp for Wild Type and CAR ablated (ΔTAYT) vectors and 140 bp for RGD4C vectors) PCR. PCR products were separated on agarose gel and stained with Ethidium Bromide.

Serial Dilution Experiments.

As described above, RPuc-WTFib was serially diluted from 1:10 to 1:1,000,000 and mixed into a total of 3 μg of Rpuc-Fib1R1 (N541S). A negative control of N541S alone was also included. Shuttle dilutions were transfected into 293cre57 cells and immediately infected with pseudotyped AdTrack-Fex (MOI=1). Five days later, recombinant virus was harvested and used to infect 293 cells in 100 mm plates (2-5 hours). Cells were overlayed with noble agar and viral bursts allowed to form for 3-7 days. Only RPuc-WTFib recombinant virus form GFP-positive viral bursts (as in FIG. 4, box arrow). Some pFex or N541S virus are infectious by complementation; however, these virus fail to spread and only appear to occupy a single cell (FIG. 4, small arrows). The number of viral bursts were counted for each dilution to determine the sensitivity of detecting a single working Fiber-shuttle plasmid in the background of extensive mutant Fiber shuttles.

Tropism Studies.

Four separate tropism studies were performed. First, $5 \times 10^5$ PC-3 and PC3-CAR cells were infected with AdTrack-WT-Fib, AdTrack-FBR2, or AdTrack-RGD4C-FBR2 at MOI's of 100 for two hours in 6 well dishes. Infected cells were visualized 48-72 hours post infection by fluorescent and light microscopy. Collected images were overlayed to demonstrate number of cells infected and non-infected. In a second study, clones from the library selection, and CAR ablated and Wild type controls, were used to infect 293 cells (24 hours after plating) with an MOI of 0.1. Ten fields of GFP positive infected cells were counted 24 hours after infection and results plotted as percent infected cells relative to Wild Type Fiber control. Finally, experiments investigating CAR-independent infection were performed in 96 well plate format. For anti-CAR siRNA experiments, $1 \times 10^4$ 293 cells were plated and transfected with 5 nM of siRNA (Hs_CXADR_10 HP siRNA, Hs_CXADR_11 HP siRNA, All-Stars negative control siRNA, or untransfected using HiPerfect Transfection Reagent (Qiagen, Valencia, Calif.). 72 hours after transfection, cells were infected with adenovirus (MOI=1 & 10) for 2 hours as triplicate samples. For CAR over-expression experiments, $1 \times 10^4$ PC-3 or PC3-CAR cells were plated in 96 well plates. Cells were infected the next day with each adenovirus (MOI=10 & 100) for 2 hours in triplicate samples. For both studies, infection was quantified at 24-48 hours post-infection by fluorescent microscopy (6×, equal exposure rates and processing) and fluorescent intensity (FLUOROstar Optima BMG fluorometer). Statistical significance was determined by student's T-Test.

Adenoviral Peptide Library.

Primers for the random hexapeptide library, Bsp-Lib and Rnd-ext (BSP-Lib: TGGAGTTGTGTCTCCG-GANNNNNNNNNNNNNNNNNNNTCCGGAT-TCCTGTGTACCGC T (SEQ ID NO: 76); Rnd-ext: 5AGCG-GTACACAGGAATCCGGA (SEQ ID NO: 77)) were annealed and incubated with Klenow polymerase. Biotinylated primers Lib001 (Biotin-AGCGGTACACA-GGAATCC (SEQ ID NO: 78)) and Lib002 (Biotin-TG-GAGTTGTGTCTCCGGA (SEQ ID NO: 79)) were then used for PCR amplification, and the resulting product was digested with BspEI. Flanking digestion products and uncut product were removed with streptavidin magnetic beads (New England Biolabs). The resulting library fragment was subcloned into RPuc-FBR2. Ligation conditions were optimized and large scale electroporation to DH5α was used to generate approximately 16,000 clones of the RPuc-FBR2-6X library. To generate library virus, $10^6$ 293cre57 cells were transfected with 3 μg of RPuc-FBR2-6X and infected with pseudotyped pAdTrack-Fex (MOI=1). Five days later, cells and media were harvested, freeze-thawed, and the lysate was used to infect 293 cells on 100 mm plates. Infections were overlayed with agar and viral infection visualized by fluorescent microscopy. Both positive (RPuc-WTFib) and negative (N541S) shuttles were included for reference. Viral bursts were counted 48 hours after infection and plaques isolated at later time points in 293 cells. Aliquots of viral lysate were treated with proteinase K, boiled, and used to PCR amplify the foxed fiber region (FF01: TGTTCCTGTCCATCCG-CACCCACTATCTTCATGTTG (SEQ ID NO: 80) and FF02: AGGACTGTGTACTCTGTGTGTTGGGAGG-GAGGTGGCA (SEQ ID NO: 81)). The resulting PCR product was recombined with RPuc-Rescue in 294cre E. coli as described in the above "plasmid based recombination" section. Selected fiber clones were confirmed by restriction mapping and sequencing.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference. The disclosure of the present application may be related to disclosures present in PCT/US2006/010025 and U.S. Pat. No. 5,922,576, which are hereby incorporated by reference in their entirety.

What is claimed is:

1. A method of generating an adenoviral library, the method comprising the steps of:
   (a) preparing a plasmid library comprising:
      i) providing a plurality of transfer vectors, wherein each transfer vector comprises a fiber gene flanked by lox sites; and
      ii) inserting into each fiber gene a random oligonucleotide, thereby producing a variant fiber gene;
   (b) introducing the plasmid library into mammalian cells expressing Cre recombinase;
   (c) infecting the mammalian cells with a plurality of adenoviruses, wherein each adenovirus comprises an acceptor vector that lacks a fiber gene and a marker flanked by lox sites; and
   (d) allowing recombination of the variant fiber genes into the acceptor vectors, thereby generating an adenoviral library comprising the variant fiber genes.

2. The method of claim 1, wherein the plasmid library is introduced into the mammalian cells by transformation, and wherein the lox sites in the acceptor vector are positioned at the natural genetic locus of a fiber gene in the adenovirus genome.

3. The method of claim 1, wherein the plasmid library is introduced into the mammalian cells by transfection, and wherein the lox sites in the acceptor vector are positioned at the natural genetic locus of a fiber gene in the adenovirus genome.

4. The method of claim 1, wherein the lox sites are incompatible.

5. The method of claim 1, wherein the lox sites are mutated to result in unidirectional recombination.

6. The method of claim 3, wherein the acceptor vector comprises a SacB negatively selectable marker.

7. The method of claim 1, wherein the lox sites are selected from the group consisting of Lox m2/66, Lox 71, Lox m2/71 and Lox 66.

8. The method of claim 1, wherein the variant fiber gene comprises a mutation.

9. The method of claim 8, wherein the mutation is a point mutation, an insertion, or a deletion.

10. The method of claim 9, wherein the insertion is of a heterologous nucleic acid segment.

11. The method of claim 10, wherein the variant fiber gene encodes a chimeric fiber polypeptide.

12. The method of claim 1, wherein the variant fiber gene further comprises a mutation that disrupts binding to CAR.

13. The method of claim 12, wherein the mutation is a $T_{489}AYT_{492}$ deletion.

* * * * *

SEQUENCE LISTING

<160> NUMBER OF SEQ ID NOS: 81

<210> SEQ ID NO 1
<211> LENGTH: 37941
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1254)..(1259)
<223> OTHER INFORMATION: a, c, g, t, unknown or other
<220> FEATURE:
<221> NAME/KEY: modified_base
<222> LOCATION: (2797)..(2863)
<223> OTHER INFORMATION: a, c, g, t, unknown or other
<220> FEATURE:
<221> NAME/KEY: modified_base
<222> LOCATION: (2872)..(2874)
<223> OTHER INFORMATION: a, c, g, t, unknown or other
<220> FEATURE:
<221> NAME/KEY: modified_base
<222> LOCATION: (3215)..(3217)
<223> OTHER INFORMATION: a, c, g, t, unknown or other
<220> FEATURE:
<221> NAME/KEY: modified_base
<222> LOCATION: (4805)..(4807)
<223> OTHER INFORMATION: a, c, g, t, unknown or other
<220> FEATURE:
<221> NAME/KEY: modified_base
<222> LOCATION: (4864)..(4866)
<223> OTHER INFORMATION: a, c, g, t, unknown or other
<220> FEATURE:
<221> NAME/KEY: modified_base
<222> LOCATION: (36237)..(36239)
<223> OTHER INFORMATION: a, c, g, t, unknown or other

<400> SEQUENCE: 1
gcgctcttcc gcttcctcgc tcactgactc gctgcgctcg gtcgttcggc tgcggcgagc      60
ggtatcagct cactcaaagg cggtaatacg gttatccaca gaatcagggg ataacgcagg     120
aaagaacatg tgagcaaaag gccagcaaaa ggccaggaac cgtaaaaagg ccgcgttgct     180
ggcgtttttc cataggctcc gcccccctga cgagcatcac aaaaatcgac gctcaagtca     240
gaggtggcga aacccgacag gactataaag ataccaggcg tttccccctg gaagctccct     300
cgtgcgctct cctgttccga ccctgccgct taccggatac ctgtccgcct ttctcccttc     360
gggaagcgtg gcgctttctc atagctcacg ctgtaggtat ctcagttcgg tgtaggtcgt     420
tcgctccaag ctgggctgtg tgcacgaacc ccccgttcag cccgaccgct gcgccttatc     480
cggtaactat cgtcttgagt ccaacccggt aagacacgac ttatcgccac tggcagcagc     540
cactggtaac aggattagca gagcgaggta tgtaggcggt gctacagagt tcttgaagtg     600
gtggcctaac tacggctaca ctagaaggac agtatttggt atctgcgctc tgctgaagcc     660
agttaccttc ggaaaaagag ttggtagctc ttgatccggc aaacaaacca ccgctggtag     720
cggtggtttt tttgtttgca agcagcagat tacgcgcaga aaaaaggat ctcaagaaga     780 tcctttgatc ttttctacgg ggtctgacgc tcagtggaac gaaaactcac gttaagggat     840
tttggtcatg agattatcaa aaaggatctt cacctagatc cttttaaatt aaaaatgaag     900
ttttaaatca atctaaagta tatatgagta aacttggtct gacagttacc aatgcttaat     960
cagtgaggca cctatctcag cgatctgtct atttcgttca tccatagttg cctgactccc    1020
cgtcgtgtag ataactacga tacgggaggg cttaccatct ggccccagtg ctgcaatgat    1080

```
accgcgagac ccacgctcac cggctccaga tttatcagca ataaaccagc cagccggaag    1140
ggccgagcgc agaagtggtc ctgcaacttt atccgcctcc atccagtcta ttaattgttg    1200 ccggaagct  agagtaagta gttcgccagt taatagtttg cgcaacgttg ttgnnnnnna    1260
aaaaggatct tcacctagat ccttttcacg tagaaagcca gtccgcagaa acggtgctga    1320
ccccggatga atgtcagcta ctgggctatc tggacaaggg aaaacgcaag cgcaaagaga    1380
aagcaggtag cttgcagtgg gcttacatgg cgatagctag actgggcggt tttatggaca    1440
gcaagcgaac cggaattgcc agctggggcg ccctctggta aggttgggaa gccctgcaaa    1500
gtaaactgga tggcttttctc gccgccaagg atctgatggc gcaggggatc aagctctgat    1560
caagagacag gatgaggatc gtttcgcatg attgaacaag atggattgca cgcaggttct    1620
ccggccgctt gggtggagag gctattcggc tatgactggg cacaacagac aatcggctgc    1680
tctgatgccg ccgtgttccg gctgtcagcg caggggcgcc cggttctttt tgtcaagacc    1740
gacctgtccg gtgccctgaa tgaactgcaa gacgaggcag cgcggctatc gtggctggcc    1800
acgacgggcg ttccttgcgc agctgtgctc gacgttgtca ctgaagcggg aagggactgg    1860
ctgctattgg gcgaagtgcc ggggcaggat ctcctgtcat ctcaccttgc tcctgccgag    1920
aaagtatcca tcatggctga tgcaatgcgg cggctgcata cgcttgatcc ggctacctgc    1980
ccattcgacc accaagcgaa acatcgcatc gagcgagcac gtactcggat ggaagccggt    2040
cttgtcgatc aggatgatct ggacgaagag catcaggggc tcgcgccagc cgaactgttc    2100
gccaggctca aggcgagcat gcccgacggc gaggatctcg tcgtgaccca tggcgatgcc    2160
tgcttgccga atatcatggt ggaaaatggc cgcttttctg gattcatcga ctgtggccgg    2220
ctgggtgtgg cggaccgcta tcaggacata gcgttggcta cccgtgatat tgctgaagag    2280
cttggcggcg aatgggctga ccgcttcctc gtgctttacg gtatcgccgc tcccgattcg    2340
cagcgcatcg ccttctatcg ccttcttgac gagttcttct gaattttgtt aaaattttg    2400 ttaaatcagc tcatttttta accataggc cgaaatcggc aacatccctt ataaatcaaa    2460
agaatagacc gcgatagggt tgagtgttgt tccagtttgg aacaagagtc cactattaaa    2520
gaacgtggac tccaacgtca aagggcgaaa aaccgtctat cagggcgatg gcccactacg    2580
tgaaccatca cccaaatcaa gttttttgcg gtcgaggtgc cgtaaagctc taaatcggaa    2640
ccctaaaggg agcccccgat ttagagcttg acggggaaag ccggcgaacg tggcgagaaa    2700
ggaagggaag aaagcgaaag gagcgggcgc tagggcgctg gcaagtgtag cggtcacgct    2760
gcgcgtaacc accacacccg cgcgcttaat gcgccgnnnn nnnnnnnnnn nnnnnnnnnn    2820
nnnnnnnnnn nnnnnnnnnn nnnnnnnnnn nnnnnnnnnn nnnttaatta annntcccctt    2880 ccagctctct gccccttttg gattgaagcc aatatgataa tgaggggtg gagtttgtga    2940 cgtggcgcgg ggcgtgggaa cggggcgggt gacgtagtag tgtggcggaa gtgtgatgtt    3000
gcaagtgtgg cggaacacat gtaagcgacg gatgtggcaa aagtgacgtt tttggtgtgc    3060
gccggtgtac acaggaagtg acaattttcg cgcggtttta ggcggatgtt gtagtaaatt    3120
tgggcgtaac cgagtaagat ttggccattt tcgcgggaaa actgaataag aggaagtgaa    3180
atctgaataa ttttgtgtta ctcatagcgc gtaannncgc gttaagatac attgatgagt    3240
ttggacaaac cacaactaga atgcagtgaa aaaaatgctt tatttgtgaa atttgtgatg    3300
ctattgcttt atttgtaacc attataagct gcaataaaca agttaacaac aacaattgca    3360
ttcattttat gtttcaggtt caggggagg tgtgggaggt tttttaaagc aagtaaaacc    3420
```

```
tctacaaatg tggtatggct gattatgatc agttatctag atccggtgga tctgagtccg   3480
gacttgtaca gctcgtccat gccgagagtg atcccggcgg cggtcacgaa ctccagcagg   3540
accatgtgat cgcgcttctc gttggggtct ttgctcaggg cggactgggt gctcaggtag   3600
tggttgtcgg gcagcagcac ggggccgtcg ccgatggggg tgttctgctg gtagtggtcg   3660
gcgagctgca cgctgccgtc ctcgatgttg tggcggatct tgaagttcac cttgatgccg   3720
ttcttctgct tgtcggccat gatatagacg ttgtggctgt tgtagttgta ctccagcttg   3780
tgccccagga tgttgccgtc ctccttgaag tcgatgccct tcagctcgat gcggttcacc   3840
agggtgtcgc cctcgaactt cacctcggcg cgggtcttgt agttgccgtc gtccttgaag   3900
aagatggtgc gctcctggac gtagccttcg ggcatggcgg acttgaagaa gtcgtgctgc   3960
ttcatgtggt cggggtagcg gctgaagcac tgcacgccgt aggtcagggt ggtcacgagg   4020
gtgggccagg gcacgggcag cttgccggtg gtgcagatga acttcagggt cagcttgccg   4080
taggtggcat cgccctcgcc ctcgccggac acgctgaact tgtggccgtt tacgtcgccg   4140
tccagctcga ccaggatggg caccaccccg gtgaacagcc cctcgccctt gctcaccatg   4200
gtggcgaccg gtagcgctag cggatctgac ggttcactaa accagctctg cttatataga   4260
cctcccaccg tacacgccta ccgcccattt gcgtcaatgg ggcggagttg ttacgacatt   4320
ttggaaagtc ccgttgattt tggtgccaaa acaaactccc attgacgtca atggggtgga   4380
gacttggaaa tccccgtgag tcaaaccgct atccacgccc attgatgtac tgccaaaacc   4440
gcatcaccat ggtaatagcg atgactaata cgtagatgta ctgccaagta ggaaagtccc   4500
ataaggtcat gtactgggca taatgccagg cgggccattt accgtcattg acgtcaatag   4560
ggggcgtact tggcatatga tacacttgat gtactgccaa gtgggcagtt taccgtaaat   4620
actccaccca ttgacgtcaa tggaaagtcc ctattggcgt tactatggga acatacgtca   4680
ttattgacgt caatgggcgg gggtcgttgg gcggtcagcc aggcgggcca tttaccgtaa   4740
gttatgtaac gcggaactcc atatatgggc tatgaactaa tgaccccgta attgattact   4800
attannncta gcagatctgg taccgtcgac gcggccgcga tatcctcgag aagctttcta   4860
gagnnntaag ggtgggaaag aatatataag gtggggtct tatgtagttt tgtatctgtt   4920
ttgcagcagc cgccgccgcc atgagcacca actcgtttga tggaagcatt gtgagctcat   4980
atttgacaac gcgcatgccc ccatgggccg gggtgcgtca gaatgtgatg ggctccagca   5040
ttgatggtcg ccccgtcctg cccgcaaact ctactacctt gacctacgag accgtgtctg   5100
gaacgccgtt ggagactgca gcctccgccg ccgcttcagc cgctgcagcc accgcccgcg   5160
ggattgtgac tgactttgct ttcctgagcc cgcttgcaag cagtgcagct tcccgttcat   5220
ccgcccgcga tgacaagttg acggctcttt tggcacaatt ggattctttg acccgggaac   5280
ttaatgtcgt ttctcagcag ctgttggatc tgcgccagca ggtttctgcc ctgaaggctt   5340
cctcccctcc caatgcggtt taaaacataa ataaaaaacc agactctgtt tggatttgga   5400
tcaagcaagt gtcttgctgt ctttatttag gggttttgcg cgcgcggtag gcccgggacc   5460
agcggtctcg gtcgttgagg gtcctgtgta ttttttccag gacgtggtaa aggtgactct   5520
ggatgttcag atacatgggc ataagcccgt ctctggggtg gaggtagcac cactgcagag   5580
cttcatgctg cggggtggtg ttgtagatga tccagtcgta gcaggagcgc tgggcgtggt   5640
gcctaaaaat gtcttttcagt agcaagctga ttgccagggg caggcccttg gtgtaagtgt   5700
ttacaaagcg gttaagctgg gatgggtgca tacgtgggga tatgagatgc atcttggact   5760
gtattttttag gttggctatg ttcccagcca tatccctccg gggattcatg ttgtgcagaa   5820
```

```
ccaccagcac agtgtatccg gtgcacttgg gaaatttgtc atgtagctta gaaggaaatg    5880
cgtggaagaa cttggagacg cccttgtgac ctccaagatt ttccatgcat tcgtccataa    5940
tgatggcaat gggcccacgg gcggcggcct gggcgaagat atttctggga tcactaacgt    6000
catagttgtg ttccaggatg agatcgtcat aggccatttt tacaaagcgc gggcggaggg    6060
tgccagactg cggtataatg gttccatccg gcccaggggc gtagttaccc tcacagattt    6120
gcatttccca cgctttgagt tcagatgggg ggatcatgtc tacctgcggg gcgatgaaga    6180
aaacggtttc cggggtaggg gagatcagct gggaagaaag caggttcctg agcagctgcg    6240
acttaccgca gccggtgggc ccgtaaatca cacctattac cgggtgcaac tggtagttaa    6300
gagagctgca gctgccgtca tccctgagca ggggggccac ttcgttaagc atgtccctga    6360
ctcgcatgtt ttccctgacc aaatccgcca gaaggcgctc gccgcccagc gatagcagtt    6420
cttgcaagga agcaaagttt ttcaacggtt tgagaccgtc cgccgtaggc atgcttttga    6480
gcgtttgacc aagcagttcc aggcggtccc acagctcggt cacctgctct acggcatctc    6540
gatccagcat atctcctcgt ttcgcgggtt ggggcggctt tcgctgtacg gcagtagtcg    6600
gtgctcgtcc agacgggcca gggtcatgtc tttccacggg cgcagggtcc tcgtcagcgt    6660
agtctgggtc acggtgaagg ggtgcgctcc gggctgcgcg ctggccaggg tgcgcttgag    6720
gctggtcctg ctggtgctga agcgctgccg gtcttcgccc tgcgcgtcgg ccaggtagca    6780
tttgaccatg gtgtcatagt ccagcccctc cgcggcgtgg cccttggcgc gcagcttgcc    6840
cttggaggag cgccgcacg agggcagtg cagactttg agggcgtaga gcttgggcgc    6900
gagaaatacc gattccgggg agtaggcatc cgcgccgcag gccccgcaga cggtctcgca    6960
ttccacgagc caggtgagct ctggccgttc ggggtcaaaa accaggtttc ccccatgctt    7020
tttgatgcgt ttcttacctc tggtttccat gagccggtgt ccacgctcgg tgacgaaaag    7080
gctgtccgtg tccccgtata cagactactt gagaggcctg tcctcgagcg gtgttccgcg    7140
gtcctcctcg tatagaaact cggaccactc tgagacaaag gctcgcgtcc aggccagcac    7200
gaaggaggct aagtgggagg ggtagcggtc gttgtccact aggggtgtcca ctcgctccag    7260
ggtgtgaaga cacatgtcgc cctcttcggc atcaaggaag gtgattggtt tgtaggtgta    7320
ggccacgtga ccgggtgttc ctgaaggggg gctataaaag ggggtgggg gcgcgttcgtc    7380
ctcactctct tccgcatcgc tgtctgcgag gccagctgt tggggtgagt actccctctg    7440
aaaagcgggc atgacttctg cgctaagatt gtcagtttcc aaaaacgagg aggatttgat    7500
attcacctgg cccgcggtga tgcctttgag ggtggccgca tccatctggt cagaaaagac    7560
aatcttttg ttgtcaagct tggtggcaaa cgacccgtag agggcgttgg acagcaactt    7620
ggcgatggag cgcagggttt ggttttgtc gcgatcggcg cgctccttgg ccgcgatgtt    7680
tagctgcacg tattcgcgcg caacgcaccg ccattcggga aagacggtgg tgcgctcgtc    7740
gggcaccagg tgcacgcgcc aaccgcggtt gtgcagggtg acaaggtcaa cgctggtggc    7800
tacctctccg cgtaggcgct cgttggtcca gcagaggcgg ccgcccttgc gcgagcagaa    7860
tggcggtagg gggtctagct gcgtctcgtc cgggggtct gcgtccacgg taaagacccc    7920
gggcagcagg cgcgcgtcga agtagtctat cttgcatcct tgcaagtcta gcgcctgctg    7980
ccatgcgcgg gcggcaagcg cgcgctcgta tgggttgagt gggggacccc atggcatggg    8040
gtgggtgagc gcggaggcgt acatgccgca aatgtcgtaa acgtagaggg gctctctgag    8100
tattccaaga tatgtagggt agcatcttcc accgcggatg ctggcgcgca cgtaatcgta    8160
```

```
tagttcgtgc gagggagcga ggaggtcggg accgaggttg ctacgggcgg gctgctctgc    8220
tcggaagact atctgcctga agatggcatg tgagttggat gatatggttg gacgctggaa    8280
gacgttgaag ctggcgtctg tgagacctac cgcgtcacgc acgaaggagg cgtaggagtc    8340
gcgcagcttg ttgaccagct cggcggtgac ctgcacgtct agggcgcagt agtccagggt    8400
ttccttgatg atgtcatact tatcctgtcc cttttttttc cacagctcgc ggttgaggac    8460
aaactcttcg cggtctttcc agtactcttg gatcggaaac ccgtcggcct ccgaacggta    8520
agagcctagc atgtagaact ggttgacggc ctggtaggcg cagcatccct tttctacggg    8580
tagcgcgtat gcctgcgcgg ccttccggag cgaggtgtgg gtgagcgcaa aggtgtccct    8640
gaccatgact ttgaggtact ggtatttgaa gtcagtgtcg tcgcatccgc cctgctccca    8700
gagcaaaaag tccgtgcgct ttttggaacg cggatttggc agggcgaagg tgacatcgtt    8760
gaagagtatc tttcccgcgc gaggcataaa gttgcgtgtg atgcggaagg gtcccggcac    8820
ctcggaacgg ttgttaatta cctgggcggc gagcacgatc tcgtcaaagc cgttgatgtt    8880
gtggcccaca atgtaaagtt ccaagaagcg cgggatgccc ttgatggaag gcaattttt    8940 aagttcctcg taggtgagct cttcagggga gctgagcccg tgctctgaaa gggcccagtc    9000
tgcaagatga gggttggaag cgacgaatga gctccacagg tcacgggcca ttagcatttg    9060
caggtggtcg cgaaaggtcc taaactggcg acctatggcc atttttcctg gggtgatgca    9120
gtagaaggta agcgggtctt gttcccagcg gtcccatcca aggttcgcgg ctaggtctcg    9180
cgcggcagtc actagaggct catctccgcc gaacttcatg accagcatga agggcacgag    9240
ctgcttccca aaggccccca tccaagtata ggtctctaca tcgtaggtga caaagagacg    9300
ctcggtgcga ggatgcgagc cgatcgggaa gaactggatc tcccgccacc aattggagga    9360
gtggctattg atgtggtgaa agtagaagtc cctgcgacgg gccgaacact cgtgctggct    9420
tttgtaaaaa cgtgcgcagt actggcagcg gtgcacgggc tgtacatcct gcacgaggtt    9480
gacctgacga ccgcgcacaa ggaagcagag tgggaatttg agcccctcgc ctggcgggtt    9540
tggctggtgg tcttctactt cggctgcttg tccttgaccg tctggctgct cgaggggagt    9600
tacggtggat cggaccacca cgccgcgcga gcccaaagtc cagatgtccg cgcgcggcgg    9660
tcggagcttg atgacaacat cgcgcagatg ggagctgtcc atggtctgga gctcccgcgg    9720
cgtcaggtca ggcgggagct cctgcaggtt tacctcgcat agacgggtca gggcgcgggc    9780
tagatccagg tgatacctaa tttccagggg ctggttggtg gcggcgtcga tggcttgcaa    9840
gaggccgcat ccccgcggcg cgactacggt accgcgcggc gggcggtggg ccgcgggggt    9900
gtccttggat gatgcatcta aaagcggtga cgcgggcgag ccccggagg taggggggc    9960 tccggacccg ccgggagagg gggcaggggc acgtcggcgc cgcgcgcggg caggagctgg   10020
tgctgcgcgc gtaggttgct ggcgaacgcg acgacgcggc ggttgatctc ctgaatctgg   10080
cgcctctgcg tgaagacgac gggcccggtg agcttgagcc tgaaagagag ttcgacagaa   10140
tcaatttcgg tgtcgttgac ggcggcctgg cgcaaaatct cctgcacgtc tcctgagttg   10200
tcttgatagg cgatctcggc catgaactgc tcgatctctt cctcctggag atctccgcgt   10260
ccggctcgct ccacggtggc ggcgaggtcg ttggaaatgc gggccatgag ctgcgagaag   10320
gcgttgaggc ctccctcgtt ccagacgcgg ctgtagacca cgccccttc ggcatcgcgg   10380 gcgcgcatga ccacctgcgc gagattgagc tccacgtgcc gggcgaagac ggcgtagttt   10440
cgcaggcgct gaaagaggta gttgagggtg gtggcggtgt gttctgccac gaagaagtac   10500
ataacccagc gtcgcaacgt ggattcgttg atatccccca aggcctcaag gcgctccatg   10560
```

```
gcctcgtaga agtccacggc gaagttgaaa aactgggagt tgcgcgccga cacggttaac    10620
tcctcctcca gaagacggat gagctcggcg acagtgtcgc gcacctcgcg ctcaaaggct    10680 acagggggcct cttcttcttc ttcaatctcc tcttccataa gggcctcccc ttcttcttct    10740
tctggcggcg gtgggggagg ggggacacgg cggcgacgac ggcgcaccgg gaggcggtcg    10800
acaaagcgct cgatcatctc cccgcggcga cggcgcatgg tctcggtgac ggcgcggccg    10860
ttctcgcggg ggcgcagttg gaagacgccg cccgtcatgt cccggttatg ggttggcggg    10920
gggctgccat gcggcaggga tacggcgcta acgatgcatc tcaacaattg ttgtgtaggt    10980
actccgccgc cgagggacct gagcgagtcc gcatcgaccg gatcggaaaa cctctcgaga    11040
aaggcgtcta accagtcaca gtcgcaaggt aggctgagca ccgtggcggg cggcagcggg    11100
cggcggtcgg ggttgtttct ggcggaggtg ctgctgatga tgtaattaaa gtaggcggtc    11160
ttgagacggc ggatggtcga cagaagcacc atgtccttgg gtccggcctg ctgaatgcgc    11220
aggcggtcgc ccatgcccca ggcttcgttt tgacatcggc gcaggtcttt gtagtagtct    11280
tgcatgagcc tttctaccgg cacttcttct tctccttcct cttgtcctgc atctcttgca    11340
tctatcgctg cggcggcggc ggagtttggc cgtaggtggc gccctcttcc tcccatgcgt    11400
gtgaccccga agcccctcat cggctgaagc agggctaggt cggcgacaac gcgctcggct    11460
aatatggcct gctgcacctg cgtgagggta gactggaagt catccatgtc cacaaagcgg    11520
tggtatgcgc ccgtgttgat ggtgtaagtg cagttggcca taacggacca gttaacggtc    11580
tggtgacccg gctgcgagag ctcggtgtac ctgagacgcg agtaagccct cgagtcaaat    11640
acgtagtcgt tgcaagtccg caccaggtac tggtatccca ccaaaaagtg cggcggcggc    11700
tggcggtaga ggggccagcg tagggtggcc ggggctccgg gggcgagatc ttccaacata    11760
aggcgatgat atccgtagat gtacctggac atccaggtga tgccggcggc ggtggtggag    11820
gcgcgcggaa agtcgcggac gcggttccag atgttgcgca gcggcaaaaa gtgctccatg    11880
gtcgggacgc tctggccggt caggcgcgcg caatcgttga cgctctaccg tgcaaaagga    11940
gagcctgtaa gcgggcactc ttccgtggtc tggtggataa attcgcaagg gtatcatggc    12000
ggacgaccgg ggttcgagcc ccgtatccgg ccgtccgccg tgatccatgc ggttaccgcc    12060
cgcgtgtcga acccaggtgt gcgacgtcag acaacggggg agtgctcctt ttggcttcct    12120
tccaggcgcg gcggctgctg cgctagcttt tttggccact ggccgcgcgc agcgtaagcg    12180
gttaggctgg aaagcgaaag cattaagtgg ctcgctccct gtagccggag ggttattttc    12240
caagggttga gtcgcgggac ccccggttcg agtctcggac cggccggact gcggcgaacg    12300
ggggtttgcc tccccgtcat gcaagacccc gcttgcaaat tcctccggaa acagggacga    12360
gccccttttt tgcttttccc agatgcatcc ggtgctgcgg cagatgcgcc ccctcctca    12420 gcagcggcaa gagcaagagc agcggcagac atgcagggca ccctcccctc ctcctaccgc    12480
gtcaggaggg gcgacatccg cggttgacgc ggcagcagat ggtgattacg aaccccgcg    12540 gcgccgggcc cggcactacc tggacttgga ggagggcgag ggcctggcgc ggctaggagc    12600
gccctctcct gagcggtacc caagggtgca gctgaagcgt gatacgcgtg aggcgtacgt    12660
gccgcggcag aacctgtttc gcgaccgcga gggagaggag cccgaggaga tgcgggatcg    12720
aaagttccac gcagggcgcg agctgcggca tggcctgaat cgcgagcggt tgctgcgcga    12780
ggaggacttt gagcccgacg cgcgaaccgg gattagtccc gcgcgcgcac acgtggcggc    12840
cgccgacctg gtaaccgcat acgagcagac ggtgaaccag gagattaact ttcaaaaaag    12900
```

```
ctttaacaac cacgtgcgta cgcttgtggc gcgcgaggag gtggctatag gactgatgca    12960
tctgtgggac tttgtaagcg cgctggagca aaacccaaat agcaagccgc tcatggcgca    13020
gctgttcctt atagtgcagc acagcaggga caacgaggca ttcagggatg cgctgctaaa    13080
catagtagag cccgagggcc gctggctgct cgatttgata aacatcctgc agagcatagt    13140
ggtgcaggag cgcagcttga gcctggctga caaggtggcc gccatcaact attccatgct    13200
tagcctgggc aagttttacg cccgcaagat ataccatacc ccttacgttc ccatagacaa    13260
ggaggtaaag atcgagggt tctacatgcg catggcgctg aaggtgctta ccttgagcga    13320
cgacctgggc gtttatcgca acgagcgcat ccacaaggcc gtgagcgtga gccggcggcg    13380
cgagctcagc gaccgcgagc tgatgcacag cctgcaaagg gccctggctg gcacgggcag    13440
cggcgataga gaggccgagt cctactttga cgcgggcgct gacctgcgct gggccccaag    13500
ccgacgcgcc ctggaggcag ctggggccgg acctgggctg gcggtggcac ccgcgcgcgc    13560
tggcaacgtc ggcggcgtgg aggaatatga cgaggacgat gagtacgagc cagaggacgg    13620
cgagtactaa gcggtgatgt ttctgatcag atgatgcaag acgaacgga cccggcggtg    13680 cgggcggcgc tgcagagcca gccgtccggc cttaactcca cggacgactg cgccaggtc    13740 atggaccgca tcatgtcgct gactgcgcgc aatcctgacg cgttccggca gcagccgcag    13800
gccaaccggc tctccgcaat tctggaagcg gtggtcccgg cgcgcgcaaa ccccacgcac    13860
gagaaggtgc tggcgatcgt aaacgcgctg gccgaaaaca gggccatccg gcccgacgag    13920
gccggcctgg tctacgacgc gctgcttcag cgcgtggctc gttacaacag cggcaacgtg    13980
cagaccaacc tggaccggct ggtggggat gtgcgcgagg ccgtggcgca gcgtgagcgc    14040
gcgcagcagc agggcaacct gggctccatg gttgcactaa acgccttcct gagtacacag    14100
cccgccaacg tgccgcgggg acaggaggac tacaccaact tgtgagcgc actgcggcta    14160 atggtgactg agacaccgca aagtgaggtg taccagtctg ggccagacta tttttcccag    14220
accagtagac aaggcctgca gaccgtaaac ctgagccagg cttcaaaaa cttgcagggg    14280 ctgtgggggg tgcgggctcc cacaggcgac cgcgcgaccg tgtctagctt gctgacgccc    14340
aactcgcgct tgttgctgct gctaatagcg cccttcacgg acagtggcag cgtgtcccgg    14400
gacacatacc taggtcactt gctgacactg taccgcgagg ccataggtca ggcgcatgtg    14460
gacgagcata cttttccagga gattacaagt gtcagccgcg cgctgggca ggaggacacg    14520 ggcagcctgg aggcaacct aaaactacctg ctgaccaacc ggcggcagaa gatcccctcg    14580
ttgcacagtt taaacagcga ggaggagcgc attttgcgct acgtcagca gagcgtgagc    14640 cttaacctga tgcgcgacgg ggtaacgccc agcgtggcgc tggacatgac cgcgcgcaac    14700
atggaaccgg gcatgtatgc ctcaaacgg ccgtttatca accgcctaat ggactacttg    14760
catcgcgcgg ccgccgtgaa ccccgagtat ttcaccaatg ccatcttgaa cccgcactgg    14820
ctaccgcccc ctggttttcta caccggggga ttcgaggtgc ccgagggtaa cgatggattc    14880
ctctgggacg acatagacga cagcgtgttt tccccgcaac cgcagaccct gctagagttg    14940
caacagcgcg agcaggcaga ggcggcgctg cgaaaggaaa gcttccgcag gccaagcagc    15000
ttgtccgatc taggcgctgc ggccccgcgg tcagatgcta gtagcccatt tccaagcttg    15060
atagggtctc ttaccagcac tcgcaccacc cgcccgcgcc tgctgggcga ggaggagtac    15120
ctaaacaact cgctgctgca gccgcagcgc gaaaaaaacc tgcctccggc atttcccaac    15180
aacgggatag agagcctagt ggacaagatg agtagatgga agacgtacgc gcaggagcac    15240
agggacgtgc caggcccgcg cccgcccacc cgtcgtcaaa ggcacgaccg tcagcgggt    15300
```

```
ctggtgtggg aggacgatga ctcggcagac gacagcagcg tcctggattt gggagggagt   15360
ggcaacccgt ttgcgcacct tcgcccagg ctggggagaa tgttttaaaa aaaaaaaagc    15420
atgatgcaaa ataaaaaact caccaaggcc atggcaccga gcgttggttt tcttgtattc   15480
cccttagtat gcggcgcgcg gcgatgtatg aggaaggtcc tcctccctcc tacgagagtg   15540
tggtgagcgc ggcgccagtg gcggcggcgc tgggttctcc cttcgatgct ccctggacc    15600
cgccgtttgt gcctccgcgg tacctgcggc ctaccggggg gagaaacagc atccgttact   15660
ctgagttggc acccctattc gacaccaccc gtgtgtacct ggtggacaac aagtcaacgg   15720
atgtggcatc cctgaactac cagaacgacc acagcaactt tctgaccacg gtcattcaaa   15780
acaatgacta cagcccgggg gaggcaagca cacagaccat caatcttgac gaccggtcgc   15840
actgggcgg cgacctgaaa accatcctgc ataccaacat gccaaatgtg aacgagttca    15900
tgtttaccaa taagtttaag gcgcgggtga tggtgtcgcg cttgcctact aaggacaatc   15960
aggtggagct gaaatacgag tgggtggagt tcacgctgcc cgagggcaac tactccgaga   16020
ccatgaccat agaccttatg aacaacgcga tcgtggagca ctacttgaaa gtgggcagac   16080
agaacggggt tctggaaagc gacatcgggg taaagtttga cacccgcaac ttcagactgg   16140
ggtttgaccc cgtcactggt cttgtcatgc ctggggtata tacaaacgaa gccttccatc   16200
cagacatcat tttgctgcca ggatgcgggg tggacttcac ccacagccgc ctgagcaact   16260
tgttgggcat ccgcaagcgg caaccttcc aggagggctt taggatcacc tacgatgatc    16320
tggagggtgg taacattccc gcactgttgg atgtggacgc ctaccaggcg agcttgaaag   16380
atgacaccga acagggcggg ggtggcgcag gcggcagcaa cagcagtggc agcggcgcgg   16440
aagagaactc caacgcggca gccgcggcaa tgcagccggt ggaggacatg aacgatcatg   16500
ccattcgcgg cgacaccttt gccacacggg ctgaggagaa gcgcgctgag gccgaagcag   16560
cggccgaagc tgccgccccc gctgcgcaac ccgaggtcga gaagcctcag aagaaaccgg   16620
tgatcaaacc cctgacagag gacagcaaga acgcagtta caacctaata agcaatgaca   16680
gcaccttcac ccagtaccgc agctggtacc ttgcatacaa ctacggcgac cctcagaccg   16740
gaatccgctc atggaccctg ctttgcactc ctgacgtaac ctgcggctcg gagcaggtct   16800
actggtcgtt gccagacatg atgcaagacc ccgtgacctt ccgctccacg cgccagatca   16860
gcaactttcc ggtggtgggc gccgagctgt gcccgtgca ctccaagagc ttctacaacg    16920
accaggccgt ctactcccaa ctcatccgcc agtttacctc tctgacccac gtgttcaatc   16980
gctttcccga gaaccagatt ttggcgcgcc cgccagcccc caccatcacc accgtcagtg   17040
aaaacgttcc tgctctcaca gatcacggga cgctaccgct gcgcaacagc atcggaggag   17100
tccagcgagt gaccattact gacgccgac gccgcacctg cccctacgtt tacaaggccc    17160
tgggcatagt ctcgccgcgc gtcctatcga gccgcacttt ttgagcaagc atgtccatcc   17220
ttatatcgcc cagcaataac acaggctggg gcctgcgctt cccaagcaag atgtttggcg   17280
gggccaagaa gcgctccgac caacacccag tgcgcgtgcg cgggcactac cgcgcgccct   17340
ggggcgcgca caaacgcggc cgcactgggc gcaccaccgt cgatgacgcc atcgacgcgg   17400
tggtggagga ggcgcgcaac tacacgccca cgccgccacc agtgtccaca gtggacgcgg   17460
ccattcagac cgtggtgcgc ggagcccggc gctatgctaa aatgaagaga cggcggaggc   17520
gcgtagcacg tcgccaccgc cgccgacccg gcactgccgc ccaacgcgcg cggcggccc    17580
tgcttaaccg cgcacgtcgc accggccgac gggcggccat gcgggccgct cgaaggctgg   17640
```

```
ccgcgggtat tgtcactgtg ccccccaggt ccaggcgacg agcggccgcc gcagcagccg   17700
cggccattag tgctatgact cagggtcgca ggggcaacgt gtattgggtg cgcgactcgg   17760
ttagcggcct gcgcgtgccc gtgcgcaccc gcccccgcg caactagatt gcaagaaaaa    17820
actacttaga ctcgtactgt tgtatgtatc cagcggcggc ggcgcgcaac gaagctatgt   17880
ccaagcgcaa aatcaaagaa gagatgctcc aggtcatcgc gccggagatc tatggccccc   17940
cgaagaagga agagcaggat tacaagcccc gaaagctaaa gcgggtcaaa agaaaaaga    18000 aagatgatga tgatgaactt gacgacgagg tggaactgct gcacgctacc gcgcccaggc   18060
gacgggtaca gtggaaaggt cgacgcgtaa aacgtgtttt gcgacccggc accaccgtag   18120
tctttacgcc cggtgagcgc tccacccgca cctacaagcg cgtgtatgat gaggtgtacg   18180
gcgacgagga cctgcttgag caggccaacg agcgcctcgg ggagtttgcc tacgaaaagc   18240
ggcataagga catgctggcg ttgccgctgg acagggcaa cccaacacct agcctaaagc    18300
ccgtaacact gcagcaggtg ctgccccgcgc ttgcaccgtc cgaagaaaag cgcggcctaa   18360
agcgcgagtc tggtgacttg gcacccaccg tgcagctgat ggtacccaag cgccagcgac   18420
tggaagatgt cttggaaaaa atgaccgtgg aacctgggct ggagcccgag gtccgcgtgc   18480
ggccaatcaa gcaggtggcg ccgggactgg gcgtgcagac cgtggacgtt cagataccca   18540
ctaccagtag caccagtatt gccaccgcca cagagggcat ggagacacaa acgtccccgg   18600
ttgcctcagc ggtggcggat gccgcggtgc aggcggtcgc tgcggccgcg tccaagacct   18660
ctacggaggt gcaaacggac ccgtggatgt ttcgcgtttc agccccccgg cgcccgcgcg   18720
gttcgaggaa gtacgcgcc gccagcgcgc tactgcccga atatgcccta catccttcca    18780
ttgcgcctac ccccggctat cgtggctaca cctaccgccc cagaagacga gcaactaccc   18840
gacgccgaac caccactgga acccgccgcc gccgtcgccg tcgccagccc gtgctggccc   18900
cgatttccgt gcgcagggtg gctcgcgaag gaggcaggac cctggtgctg ccaacagcgc   18960
gctaccaccc cagcatcgtt taaaagccgg tctttgtggt tcttgcagat atggccctca   19020
cctgccgcct ccgtttcccg gtgccgggat tccgaggaag aatgcaccgt aggagggca    19080 tggccggcca cggcctgacg ggcggcatgc gtcgtgcgca ccaccggcgg cggcgcgcgt   19140
cgcaccgtcg catgcgcggc ggtatcctgc ccctccttat tccactgatc gccgcggcga   19200
ttggcgccgt gccggaatt gcatccgtgg ccttgcaggc gcagagacac tgattaaaaa    19260
caagttgcat gtggaaaaat caaaataaaa agtctggact ctcacgctcg cttggtcctg   19320
taactatttt gtagaatgga agacatcaac tttgcgtctc tggccccgcg cacggctcg    19380 cgcccgttca tgggaaactg gcaagatatc ggcaccagca atatgagcgg tggcgccttc   19440
agctggggct cgctgtggag cggcattaaa aatttcggtt ccaccgttaa gaactatggc   19500
agcaaggcct ggaacagcag cacaggccag atgctgaggg ataagttgaa agagcaaaat   19560
ttccaacaaa aggtggtaga tggcctggcc tctggcatta gcggggtggt ggacctggcc   19620
aaccaggcag tgcaaaataa gattaacagt aagcttgatc cccgccctcc cgtagaggag   19680
cctccaccgg ccgtggagac agtgtctcca gaggggcgtg gcgaaaagcg tccgcgcccc   19740
gacagggaag aaactctggt gacgcaaata gacgagcctc cctcgtacga ggaggcacta   19800
aagcaaggcc tgcccaccac ccgtcccatc gcgcccatgg ctaccggagt gctgggccag   19860
cacacacccg taacgctgga cctgcctccc cccgccgaca cccagcagaa acctgtgctg   19920
ccaggcccga ccgccgttgt tgtaacccgt cctagccgcg cgtccctgcg ccgcgccgcc   19980
agcggtccgc gatcgttgcg gcccgtagcc agtggcaact ggcaaagcac actgaacagc   20040
```

```
atcgtgggtc tgggggtgca atccctgaag cgccgacgat gcttctgaat agctaacgtg    20100
tcgtatgtgt gtcatgtatg cgtccatgtc gccgccagag gagctgctga gccgccgcgc    20160
gcccgctttc caagatggct acccccttcga tgatgccgca gtggtcttac atgcacatct    20220
cgggccagga cgcctcggag tacctgagcc ccgggctggt gcagtttgcc cgcgccaccg    20280
agacgtactt cagcctgaat aacaagttta gaaaccccac ggtggcgcct acgcacgacg    20340
tgaccacaga ccggtcccag cgtttgacgc tgcggttcat ccctgtggac cgtgaggata    20400
ctgcgtactc gtacaaggcg cggttcaccc tagctgtggg tgataaccgt gtgctggaca    20460
tggcttccac gtactttgac atccgcgcg tgctggacag gggccctact tttaagccct    20520
actctggcac tgcctacaac gccctggctc caagggtgc cccaaatcct tgcgaatggg    20580
atgaagctgc tactgctctt gaaataaacc tagaagaaga ggacgatgac aacgaagacg    20640
aagtagacga gcaagctgag cagcaaaaaa ctcacgtatt tgggcaggcg ccttattctg    20700
gtataaatat tacaaaggag ggtattcaaa taggtgtcga aggtcaaaca cctaaatatg    20760
ccgataaaac atttcaacct gaacctcaaa taggagaatc tcagtggtac gaaactgaaa    20820
ttaatcatgc agctgggaga gtccttaaaa agactacccc aatgaaacca tgttacggtt    20880
catatgcaaa acccacaaat gaaaatggag ggcaaggcat tcttgtaaag caacaaaatg    20940
gaaagctaga aagtcaagtg gaaatgcaat ttttctcaac tactgaggcg accgcaggca    21000
atggtgataa cttgactcct aaagtggtat tgtacagtga agatgtagat atagaaaccc    21060
cagacactca tatttcttac atgcccacta ttaaggaagg taactcacga gaactaatgg    21120
gccaacaatc tatgcccaac aggcctaatt acattgcttt tagggacaat tttattggtc    21180
taatgtatta caacagcacg ggtaatatgg gtgttctggc gggccaagca tcgcagttga    21240
atgctgttgt agatttgcaa gacagaaaca cagagctttc ataccagctt ttgcttgatt    21300
ccattggtga tagaaccagg tactttttcta tgtggaatca ggctgttgac agctatgatc    21360
cagatgttag aattattgaa aatcatggaa ctgaagatga acttccaaat tactgctttc    21420
cactgggagg tgtgattaat acagagactc ttaccaaggt aaaacctaaa acaggtcagg    21480
aaaatggatg ggaaaaagat gctacagaat tttcagataa aaatgaaata agagttggaa    21540
ataattttgc catggaaatc aatctaaatg ccaacctgtg gagaaatttc ctgtactcca    21600
acatagcgct gtatttgccc gacaagctaa agtacagtcc ttccaacgta aaaatttctg    21660
ataacccaaa cacctacgac tacatgaaca agcgagtggt ggctcccggg ttagtggact    21720
gctacattaa ccttggagca cgctggtccc ttgactatat ggacaacgtc aacccattta    21780
accaccaccg caatgctggc ctgcgctacc gctcaatgtt gctgggcaat ggtcgctatg    21840
tgcccttcca catccaggtg cctcagaagt tctttgccat taaaaacctc cttctcctgc    21900
cgggctcata cacctacgag tggaacttca ggaaggatgt taacatggtt ctgcagagct    21960
ccctaggaaa tgacctaagg gttgacggag ccagcattaa gtttgatagc atttgccttt    22020
acgccacctt cttccccatg gcccacaaca ccgcctccac gcttgaggcc atgcttagaa    22080
acgacaccaa cgaccagtcc tttaacgact atctctccgc cgccaacatg ctctacccta    22140
tacccgccaa cgctaccaac gtgcccatat ccatcccctc ccgcaactgg gcggctttcc    22200
gcggctgggc cttcacgcgc cttaagacta aggaaacccc atcactgggc tcgggctacg    22260
acccttatta cacctactct ggctctatac cctaccctaga tggaaccttt acctcaacc    22320
acacctttaa gaaggtggcc attacctttg actcttctgt cagctggcct ggcaatgacc    22380
```

```
gcctgcttac ccccaacgag tttgaaatta agcgctcagt tgacggggag ggttacaacg    22440
ttgcccagtg taacatgacc aaagactggt tcctggtaca aatgctagct aactacaaca    22500
ttggctacca gggcttctat atcccagaga gctacaagga ccgcatgtac tccttcttta    22560
gaaacttcca gcccatgagc cgtcaggtgg tggatgatac taaatacaag gactaccaac    22620
aggtgggcat cctacaccaa cacaacaact ctggatttgt tggctacctt gcccccacca    22680
tgcgcgaagg acaggcctac cctgctaact tcccctatcc gcttataggc aagaccgcag    22740
ttgacagcat tacccagaaa aagtttcttt gcgatcgcac cctttggcgc atcccattct    22800
ccagtaactt tatgtccatg ggcgcactca cagacctggg ccaaaacctt ctctacgcca    22860
actccgccca cgcgctagac atgacttttg aggtggatcc catggacgag cccacccttc    22920
tttatgtttt gtttgaagtc tttgacgtgg tccgtgtgca ccggccgcac cgcggcgtca    22980
tcgaaaccgt gtacctgcgc acgcccttct cggccggcaa cgccacaaca taagaagca    23040 agcaacatca acaacagctg ccgccatggg ctccagtgag caggaactga agccattgt    23100 caaagatctt ggttgtgggc catattttt gggcacctat gacaagcgct ttccaggctt    23160
tgtttctcca cacaagctcg cctgcgccat agtcaatacg gccggtcgcg agactggggg    23220
cgtacactgg atggcctttg cctggaaccc gcactcaaaa acatgctacc tctttgagcc    23280
ctttggcttt tctgaccagc gactcaagca ggtttaccag tttgagtacg agtcactcct    23340
gcgccgtagc gccattgctt cttcccccga ccgctgtata acgctggaaa agtccaccca    23400
aagcgtacag gggcccaact cggccgcctg tggactattc tgctgcatgt ttctccacgc    23460
ctttgccaac tggcccccaaa ctcccatgga tcacaacccc accatgaacc ttattaccgg    23520
ggtacccaac tccatgctca acagtcccca ggtacagccc accctgcgtc gcaaccagga    23580
acagctctac agcttcctgg agcgccactc gccctacttc cgcagccaca gtgcgcagat    23640
taggagcgcc acttcttttt gtcacttgaa aaacatgtaa aaataatgta ctagagacac    23700
tttcaataaa ggcaaatgct tttatttgta cactctcggg tgattattta cccccaccct    23760
tgccgtctgc gccgtttaaa aatcaaaggg gttctgccgc gcatcgctat gcgccactgg    23820
cagggacacg ttgcgatact ggtgtttagt gctccactta aactcaggca caaccatccg    23880
cggcagctcg gtgaagtttt cactccacag gctgcgcacc atcaccaacg cgtttagcag    23940
gtcgggcgcc gatatcttga agtcgcagtt ggggcctccg ccctgcgcgc gcgagttgcg    24000
atacacaggg ttgcagcact ggaacactat cagcgccggg tggtgcacgc tggccagcac    24060
gctcttgtcg gagatcagat ccgcgtccag gtcctccgcg ttgctcaggg cgaacggagt    24120
caactttggt agctgccttc ccaaaaaggg gcgcgtgccca ggctttgagt tgcactcgca    24180
ccgtagtggc atcaaaaggt gaccgtgccc ggtctgggcg ttaggataca gcgcctgcat    24240
aaaagccttg atctgcttaa aagccacctg agcctttgcg ccttcagaga gaacatgcc    24300 gcaagacttg ccggaaaact gattggccgg acaggccgcg tcgtgcacgc agcaccttgc    24360
gtcggtgttg gagatctgca ccacatttcg gccccaccgg ttcttcacga tcttggcctt    24420
gctagactgc tccttcagcg cgcgctgccc gttttcgctc gtcacatcca tttcaatcac    24480
gtgctcctta tttatcataa tgcttccgtg tagacactta agctcgcctt cgatctcagc    24540
gcagcggtgc agccacaacg cgcagcccgt gggctcgtga tgcttgtagg tcacctctgc    24600
aaacgactgc aggtacgcct gcaggaatcg ccccatcatc gtcacaaagg tcttgttgct    24660
ggtgaaggtc agctgcaacc cgcggtgctc ctcgttcagc caggtcttgc atacggccgc    24720
cagagcttcc acttggtcag gcagtagttt gaagttcgcc tttagatcgt tatccacgtg    24780
```

```
gtacttgtcc atcagcgcgc gcgcagcctc catgcccttc tcccacgcag acacgatcgg   24840
cacactcagc gggttcatca ccgtaatttc actttccgct tcgctgggct cttcctcttc   24900
ctcttgcgtc cgcataccac gcgccactgg gtcgtcttca ttcagccgcc gcactgtgcg   24960
cttacctcct ttgccatgct tgattagcac cggtgggttg ctgaaaccca ccatttgtag   25020
cgccacatct tctcttctt cctcgctgtc cacgattacc tctggtgatg gcgggcgctc   25080
gggcttggga aagggcgct tcttttttctt cttgggcgca atggccaaat ccgccgccga   25140
ggtcgatggc cgcgggctgg gtgtgcgcgg caccagcgcg tcttgtgatg agtcttcctc   25200
gtcctcggac tcgatacgcc gcctcatccg cttttttggg ggcgcccggg gaggcggcgg   25260
cgacggggac ggggacgaca cgtcctccat ggttggggga cgtcgcgccg caccgcgtcc   25320
gcgctcgggg gtggtttcgc gctgctcctc ttcccgactg gccatttcct tctcctatag   25380
gcagaaaaag atcatggagt cagtcgagaa gaaggacagc ctaaccgccc cctctgagtt   25440
cgccaccacc gcctccaccg atgccgccaa cgcgcctacc accttccccg tcgaggcacc   25500
cccgcttgag gaggaggaag tgattatcga gcaggaccca ggttttgtaa gcgaagacga   25560
cgaggaccgc tcagtaccaa cagaggataa aaagcaagac caggacaacg cagaggcaaa   25620
cgaggaacaa gtcgggcggg gggacgaaag gcatggcgac tacctagatg tgggagacga   25680
cgtgctgttg aagcatctgc agcgccagtg cgccattatc tgcgacgcgt tgcaagagcg   25740
cagcgatgtg cccctcgcca tagcggatgt cagccttgcc tacgaacgcc acctattctc   25800
accgcgcgta cccccccaaac gccaagaaaa cggcacatgc gagcccaacc cgcgcctcaa   25860
cttctacccc gtatttgccg tgccagaggt gcttgccacc tatcacatct tttccaaaa    25920 ctgcaagata cccctatcct gccgtgccaa ccgcagccga gcggacaagc agctggcctt   25980
gcggcagggc gctgtcatac ctgatatcgc ctcgctcaac gaagtgccaa aaatctttga   26040
gggtcttgga cgcgacgaga agcgcgcggc aaacgctctg caacaggaaa acagcgaaaa   26100
tgaaagtcac tctggagtgt tggtggaact cgagggtgac aacgcgcgcc tagccgtact   26160
aaaacgcagc atcgaggtca cccactttgc ctacccggca cttaacctac cccccaaggt   26220
catgagcaca gtcatgagtg agctgatcgt gcgccgtgcg cagcccctgg agagggatgc   26280
aaatttgcaa gaacaaacag aggagggcct acccgcagtt ggcgacgagc agctagcgcg   26340
ctggcttcaa acgcgcgagc ctgccgactt ggaggagcga cgcaaactaa tgatggccgc   26400
agtgctcgtt accgtggagc ttgagtgcat gcagcggttc tttgctgacc cggagatgca   26460
gcgcaagcta gaggaaacat tgcactacac ctttcgacag ggctacgtac gccaggcctg   26520
caagatctcc aacgtggagc tctgcaacct ggtctcctac cttggaattt tgcacgaaaa   26580
ccgccttggg caaaacgtgc ttcattccac gctcaagggc gaggcgcgcc gcgactacgt   26640
ccgcgactgc gtttacttat ttctctatgct acacctggcag acggccatgg gcgtttggca   26700
gcagtgcttg gaggagtgca acctcaagga gctgcagaaa ctgctaaagc aaaacttgaa   26760
ggacctatgg acggccttca acgagcgctc cgtggccgcg cacctggcgg acatcatttt   26820
ccccgaacgc ctgcttaaaa ccctgcaaca gggtctgcca gacttcacca gtcaaagcat   26880
gttgcagaac tttaggaact ttatcctaga gcgctcagga atcttgcccg ccacctgctg   26940
tgcacttcct agcgactttg tgccattaa gtaccgcgaa tgccctccgc cgctttgggg   27000
ccactgctac cttctgcagc tagccaacta ccttgcctac cactctgaca taatggaaga   27060
cgtgagcggt gacggtctac tggagtgtca ctgtcgctgc aacctatgca cccgcaccg   27120
```

```
ctccctggtt tgcaattcgc agctgcttaa cgaaagtcaa attatcggta cctttgagct   27180
gcagggtccc tcgcctgacg aaaagtccgc ggctccgggg ttgaaactca ctccggggct   27240
gtggacgtcg gcttaccttc gcaaatttgt acctgaggac taccacgccc acgagattag   27300
gttctacgaa gaccaatccc gcccgccaaa tgcggagctt accgcctgcg tcattaccca   27360
gggccacatt cttggccaat tgcaagccat caacaaagcc cgccaagagt ttctgctacg   27420
aaagggacgg ggggtttact tggaccccca gtccggcgag gagctcaacc caatcccccc   27480
gccgccgcag ccctatcagc agcagccgcg ggcccttgct tcccaggatg cacccaaaa    27540 agaagctgca gctgccgccg ccacccacgg acgaggagga atactgggac agtcaggcag   27600
aggaggtttt ggacgaggag gaggaggaca tgatggaaga ctgggagagc ctagacgagg   27660
aagcttccga ggtcgaagag gtgtcagacg aaacaccgtc accctcggtc gcattcccct   27720
cgccggcgcc ccagaaatcg gcaaccggtt ccagcatggc tacaacctcc gctcctcagg   27780
cgccgccggc actgcccgtt cgccgaccca accgtagatg ggacaccact ggaaccaggg   27840
ccggtaagtc caagcagccg ccgccgttag cccaagagca caacagcgc caaggctacc    27900 gctcatggcg cgggcacaag aacgccatag ttgcttgctt gcaagactgt ggggcaaca    27960 tctccttcgc ccgccgcttt cttctctacc atcacgcgt ggccttcccc cgtaacatcc     28020
tgcattacta ccgtcatctc tacagcccat actgcaccgg cggcagcggc agcggcagca   28080
acagcagcgc ccacacagaa gcaaaggcga ccggatagca agactctgac aaagcccaag   28140
aaatccacag cggcggcagc agcaggagga ggagcgctgc gtctggcgcc caacgaaccc   28200
gtatcgaccc gcgagcttag aaacaggatt tttcccactc tgtatgctat atttcaacag   28260
agcaggggcc aagaacaaga gctgaaaata aaaaacaggt ctctgcgatc cctcacccgc   28320
agctgcctgt atcacaaaag cgaagatcag cttcggcgca cgctggaaga gcgcggaggct   28380 ctcttcagta aatactgcgc gctgactctt aaggactagt ttcgcgccct ttctcaaatt    28440
taagcgcgaa aactacgtca tctccagcgg ccacacccgg cgccagcacc tgtcgtcagc    28500
gccattatga gcaaggaaat tcccacgccc tacatgtgga gttaccagcc acaaatggga   28560
cttgcggctg gagctgccca agactactca acccgaataa actacatgag cgcgggaccc   28620
cacatgatat cccgggtcaa cggaatccgc gcccaccgaa accgaattct cttggaacag   28680
gcggctatta ccaccacacc tcgtaataac cttaatcccc gtagttggcc cgctgccctg   28740
gtgtaccagg aaagtcccgc tcccaccact gtggtacttc ccagagacgc ccaggccgaa   28800
gttcagatga ctaactcagg ggcgcagctt gcgggcggct ttcgtcacag ggtgcggtcg   28860
cccgggcagg gtataactca cctgacaatc agagggcgag gtattcagct caacgacgag   28920
tcggtgagct cctcgcttgg tctccgtccg gacgggacat ttcagatcgg cggcgccggc    28980
cgtccttcat tcacgcctcg tcaggcaatc ctaactctgc agacctcgtc tctgagccg     29040 cgctctggag gcattggaac tctgcaattt attgaggagt ttgtgccatc ggtctacttt    29100
aaccccttct cgggacctcc cggccactat ccggatcaat ttattcctaa ctttgacgcg   29160
gtaaaggact cggcggacgg ctacgactga atgttaagtg gagaggcaga gcaactgcgc   29220
ctgaaacacc tggtccactg tcgccgccac aagtgctttg cccgcgactc cggtgagttt   29280
tgctactttg aattgcccga ggatcatatc gagggccgg cgcacggcgt ccggcttacc     29340
gcccagggag agcttgcccg tagcctgatt cgggagttta cccagcgccc cctgctagtt   29400
gagcgggaca ggggaccctg tgttctcact gtgatttgca actgtcctaa ccttggatta   29460
catcaagatc ctctagttat aactagagta cccggggatc ttattccctt taactaataa   29520
```

```
aaaaaaataa taaagcatca cttacttaaa atcagttagc aaatttctgt ccagtttatt  29580
cagcagcacc tccttgccct cctcccagct ctggtattgc agcttcctcc tggctgcaaa  29640
ctttctccac aatctaaatg gaatgtcagt ttcctcctgt tcctgtccat ccgcacccac  29700
cggtataact tcgtatatgg tttcttatac gaacggtaca agaacaagag ctgaaaataa  29760
aaaacaggtc tctgcgatcc ctcacccgca gctgcctgta tcacaaaagc gaagatcagc  29820
ttcggcgcac gctggaagac gcggaggctc tcttcagtaa atactgcgcg ctgactctta  29880
aggactagtt tcgcgccctt tctcaaattt aagcgcgaaa actacgtcat ctccagcggc  29940
cacacccggc gccagcacct gtcgtcagcg ccattatgag caaggaaatt cccacgccct  30000
acatgtggag ttaccagcca caaatgggac ttgcggctgg agctgcccaa gactactcaa  30060
cccgaataaa ctacatgagc gcgggacccc acatgatatc ccgggtcaac ggaatccgcg  30120
cccaccgaaa ccgaattctc ttggaacagg cggctattac caccacacct cgtaataacc  30180
ttaatccccg tagttggccc gctgcccctgg tgtaccagga aagtcccgct cccaccactg  30240
tggtacttcc cagagacgcc caggccgaag ttcagatgac taactcaggg gcgcagcttg  30300
cgggcggctt tcgtcacagg gtgcggtcgc ccgggcaggg tataactcac ctgacaatca  30360
gagggcgagg tattcagctc aacgacgagt cggtgagctc ctcgcttggt ctccgtccgg  30420
acgggacatt tcagatcggc ggcgccggcc gtccttcatt cacgcctcgt caggcaatcc  30480
taactctgca gacctcgtcc tctgagccgc gctctggagg cattggaact ctgcaattta  30540
ttgaggagtt tgtgccatcg gtctacttta accccttctc gggacctccc ggccactatc  30600
cggatcaatt tattcctaac tttgacgcgg taaaggactc ggcggacggc tacgactgaa  30660
tgttaagtgg agaggcagag caactgcgcc tgaaacacct ggtccactgt cgccgccaca  30720
agtgctttgc ccgcgactcc ggtgagtttt gctactttga attgcccgag gatcatatcg  30780
agggcccggc gcacggcgtc cggcttaccg cccaggagga gcttgcccgt agcctgattc  30840
gggagtttac ccagcgcccc ctgctagttg agcgggacag gggaccctgt gttctcactg  30900
tgatttgcaa ctgtcctaac cttggattac atcaagatcc tctagttata actagagtac  30960
ccggggatct tattccctt aactaataaa aaaaaataat aaagcatcac ttacttaaaa  31020
tcagttagca aatttctgtc cagtttattc agcagcacct ccttgccctc ctcccagctc  31080
tggtattgca gcttcctcct ggctgcaaac tttctccaca atctaaatgg aatgtcagtt  31140
tcctcctgtt cctgtccatc cgcacccact atcttcatgt tgttgcagat accggtataa  31200
cttcgtatat ggtttcttat acgaagttat ctcgagaact atcttcatgt tgttgcagat  31260
gaagcgcgca agaccgtctg aagataccttt caaccccgtg tatccatatg acacggaaac  31320
cggtcctcca actgtgcctt ttcttactcc tcccttttgta tccccaatg ggtttcaaga  31380
gagtcccct ggggtactct ctttgcgcct atccgaacct ctagttacct ccaatggcat  31440
gcttgcgctc aaaatgggca acggcctctc tctggacgag gccggcaacc ttacctccca  31500
aaatgtaacc actgtgagcc cacctctcaa aaaaccaag tcaaacataa acctggaaat  31560
atctgcaccc ctcacagtta cctcagaagc cctaactgtg gctgccgccg cacctctaat  31620
ggtcgcgggc aacacactca ccatgcaatc acaggccccg ctaaccgtgc acgactccaa  31680
acttagcatt gccacccaag gaccctcac agtgtcagaa ggaaagctag ccctgcaaac  31740
atcaggcccc ctcaccacca ccgatagcag tacccttact atcactgcct cacccctct  31800
aactactgcc actggtagct tgggcattga cttgaaagag cccatttata cacaaaatgg  31860
```

```
aaaactagga ctaaagtacg gggctccttt gcatgtaaca gacgacctaa acactttgac    31920
cgtagcaact ggtccaggtg tgactattaa taatacttcc ttgcaaacta aagttactgg    31980
agccttgggt tttgattcac aaggcaatat gcaacttaat gtagcaggag gactaaggat    32040
tgattctcaa aacagacgcc ttatacttga tgttagttat ccgtttgatg ctcaaaacca    32100
actaaatcta agactaggac agggccctct ttttataaac tcagcccaca acttggatat    32160
taactcaaac aaaggccttt acttgtttac agcttcaaac aattccaaaa agcttgaggt    32220
taacctaagc actgccaagg ggttgatgtt tgacgctaca gccatagcca ttaatgcagg    32280
agatgggctt gaatttggtt cacctaatgc accaaacaca aatcccctca aaacaaaaat    32340
tggccatggc ctagaatttg attcaaacaa ggctatggtt cctaaactag gaactggcct    32400
tagttttgac agcacaggtg ccattacagt aggaaacaaa aataatgata agctaacttt    32460
gtggaccaca ccagctccat ctcctaactg tagactaaat gcagagaaag atgctaaact    32520
cactttggtc ttaacaaaat gtggcagtca aatacttgct acagtttcag ttttggctgt    32580
taaaggcagt ttggctccaa tatctggaac agttcaaagt gctcatctta ttataagatt    32640
tgacgaaaat ggagtgctac taaacaattc cttcctggac ccagaatatt ggaactttag    32700
aaatggagat cttactgaag gcacagccta tacaaacgct gttggattta tgcctaacct    32760
atcagcttat ccaaaatctc acggtaaaac tgccaaaagt aacattgtca gtcaagttta    32820
cttaaacgga gacaaaacta aacctgtaac actaaccatt acactaagcg gtacacagga    32880
atccggagac acaactccaa gtgcatactc tatgtcattt tcatgggact ggtctggcca    32940
caactacatt aatgaaatat ttgccacatc ctcttacact ttttcataca ttgcccaaga    33000
ataaagaagc ggccgcataa cttcgtatag catacattat acgaagttat accggtatac    33060
attgcccaag aataaagaat cgtttgtgtt atgtttcaac gtgtttattt ttcaattgca    33120
gaaaatttca agtcattttt cattcagtag tatagcccca ccaccacata gcttatacag    33180
atcaccgtac cttaatcaaa ctcacagaac cctagtattc aacctgccac ctccctccca    33240
acacacagag tacacagtcc tttctccccg gctggcctta aaaagcatca tatcatgggt    33300
aacagacata ttcttaggtg ttatattcca cacggttttcc tgtcgagcca aacgctcatc    33360
agtgatatta ataaactccc cgggcagctc acttaagttc atgtcgctgt ccagctgctg    33420
agccacaggc tgctgtccaa cttgcggttg cttaacgggc ggcgaaggag aagtccacgc    33480
ctacatgggg gtagagtcat aatcgtgcat caggataggg cggtggtgct gcagcagcgc    33540
gcgaataaac tgctgccgcc gccgctccgt cctgcaggaa tacaacatgg cagtggtctc    33600
ctcagcgatg attcgcaccg cccgcagcat aaggcgcctt gtcctccggg cacagcagcg    33660
caccctgatc tcacttaaat cagcacagta actgcagcac agcaccacaa tattgttcaa    33720
aatcccacag tgcaaggcgc tgtatccaaa gctcatggcg gggaccacag aacccacgtg    33780
gccatcatac cacaagcgca ggtagattaa gtggcgaccc ctcataaaca cgctggacat    33840
aaacattacc tcttttggca tgttgtaatt caccacctcc cggtaccata taaacctctg    33900
attaaacatg gcgccatcca ccaccatcct aaaccagctg gccaaaacct gcccgccggc    33960
tatacactgc agggaaccgg gactggaaca atgacagtgg agagcccagg actcgtaacc    34020
atggatcatc atgctcgtca tgatatcaat gttggcacaa cacaggcaca cgtgcataca    34080
cttcctcagg attacaagct cctcccgcgt tagaaccata tcccagggaa caacccattc    34140
ctgaatcagc gtaaatccca cactgcaggg aagacctcgc acgtaactca cgttgtgcat    34200
tgtcaaagtg ttacattcgg gcagcagcgg atgatcctcc agtatggtag cgcgggtttc    34260
```

-continued

```
tgtctcaaaa ggaggtagac gatccctact gtacggagtg cgccgagaca accgagatcg    34320
tgttggtcgt agtgtcatgc caaatggaac gccggacgta gtcatatttc ctgaagcaaa    34380
accaggtgcg ggcgtgacaa acagatctgc gtctccggtc tcgccgctta gatcgctctg    34440
tgtagtagtt gtagtatatc cactctctca aagcatccag gcgcccctg gcttcgggtt    34500 ctatgtaaac tccttcatgc gccgctgccc tgataacatc caccaccgca gaataagcca    34560
cacccagcca acctacacat tcgttctgcg agtcacacac gggaggagcg ggaagagctg    34620
gaagaaccat gtttttttt ttattccaaa agattatcca aaacctcaaa atgaagatct    34680
attaagtgaa cgcgctcccc tccggtggcg tggtcaaact ctacagccaa agaacagata    34740
atggcatttg taagatgttg cacaatggct tccaaaaggc aaacggccct cacgtccaag    34800
tggacgtaaa ggctaaaccc ttcagggtga atctcctcta taaacattcc agcaccttca    34860
accatgccca ataattctc atctcgccac cttctcaata tatctctaag caaatcccga    34920
atattaagtc cggccattgt aaaaatctgc tccagagcgc cctccacctt cagcctcaag    34980
cagcgaatca tgattgcaaa aattcaggtt cctcacagac ctgtataaga ttcaaaagcg    35040
gaacattaac aaaaataccg cgatcccgta ggtcccttcg cagggccagc tgaacataat    35100
cgtgcaggtc tgcacggacc agcgcggcca cttccccgcc aggaaccttg acaaaagaac    35160
ccacactgat tatgacacgc atactcggag ctatgctaac cagcgtagcc ccgatgtaag    35220
ctttgttgca tgggcggcga tataaaatgc aaggtgctgc tcaaaaaatc aggcaaagcc    35280
tcgcgcaaaa aagaaagcac atcgtagtca tgctcatgca gataaaggca ggtaagctcc    35340
ggaaccacca cagaaaaaga caccattttt ctctcaaaca tgtctgcggg tttctgcata    35400
aacacaaaat aaaataacaa aaaaacattt aaacattaga agcctgtctt acaacaggaa    35460
aaacaaccct tataagcata agacggacta cggccatgcc ggcgtgaccg taaaaaaact    35520
ggtcaccgtg attaaaaagc accaccgaca gctcctcggt catgtccgga gtcataatgt    35580
aagactcggt aaacacatca ggttgattca tcggtcagtg ctaaaaagcg accgaaatag    35640
cccgggggaa tacatacccg caggcgtaga gacaacatta cagccccat aggaggtata    35700 acaaaattaa taggagagaa aaacacataa acacctgaaa aaccctcctg cctaggcaaa    35760
atagcaccct cccgctccag aacaacatac agcgcttcac agcggcagcc taacagtcag    35820
ccttaccagt aaaaaagaaa acctattaaa aaaacaccac tcgacacggc accagctcaa    35880
tcagtcacag tgtaaaaaag ggccaagtgc agagcgagta tatataggac taaaaaatga    35940
cgtaacggtt aaagtccaca aaaaacaccc agaaaaccgc acgcgaacct acgcccagaa    36000
acgaaagcca aaaaacccac aacttcctca aatcgtcact tccgttttcc cacgttacgt    36060
aacttcccat tttaagaaaa ctacaattcc caacacatac aagttactcc gccctaaaac    36120
ctacgtcacc cgccccgttc ccacgccccg cgccacgtca caaactccac cccctcatta    36180
tcatattggc ttcaatccaa aataaggtat attattgatg atttaattaa ggatccnnnc    36240
ctgtcctcga ccgatgccct tgagagcctt caacccagtc agctccttcc ggtgggcgcg    36300
gggcatgact atcgtcgccg cacttatgac tgtcttcttt atcatgcaac tcgtaggaca    36360
ggtgccggca gcgctctggg tcattttcgg cgaggaccgc tttcgctgga gcgcgacgat    36420
gatcggcctg tcgcttgcgg tattcggaat cttgcacgcc ctcgctcaag ccttcgtcac    36480
tggtcccgcc accaaacgtt tcggcgagaa gcaggccatt atcgccggca tggcggccga    36540
cgcgctgggc tacgtcttgc tggcgttcgc gacgcgaggc tggatggcct tccccattat    36600
```

```
gattcttctc gcttccggcg gcatcgggat gcccgcgttg caggccatgc tgtccaggca    36660
ggtagatgac gaccatcagg gacagcttca aggatcgctc gcggctctta ccagcctaac    36720
ttcgatcact ggaccgctga tcgtcacggc gatttatgcc gcctcggcga gcacatggaa    36780
cgggttggca tggattgtag cgccgccct ataccttgtc tgcctcccg cgttgcgtcg    36840 cggtgcatgg agccgggcca cctcgacctg aatggaagcc ggcggcacct cgctaacgga    36900
ttcaccactc caagaattgg agccaatcaa ttcttgcgga gaactgtgaa tgcgcaaacc    36960 aaccccttggc agaacatatc catcgcgtcc gccatctcca gcagccgcac gcggcgcatc    37020
tcgggcagcg ttgggtcctg gccacgggtg cgcatgatcg tgctcctgtc gttgaggacc    37080
cggctaggct ggcggggttg ccttactggt tagcagaatg aatcaccgat acgcgagcga    37140
acgtgaagcg actgctgctg caaaacgtct gcgacctgag caacaacatg aatggtcttc    37200
ggtttccgtg tttcgtaaag tctggaaacg cggaagtcag cgccctgcac cattatgttc    37260
cggatctgca tcgcaggatg ctgctggcta ccctgtggaa cacctacatc tgtattaacg    37320
aagcgctggc attgaccctg agtgattttt ctctggtccc gccgcatcca taccgccagt    37380
tgtttaccct cacaacgttc cagtaaccgg gcatgttcat catcagtaac ccgtatcgtg    37440
agcatcctct ctcgtttcat cggtatcatt accccccatga acagaaattc ccccttacac    37500
ggaggcatca agtgaccaaa caggaaaaaa ccgcccttaa catggcccgc tttatcagaa    37560
gccagacatt aacgcttctg gagaaactca acgagctgga cgcggatgaa caggcagaca    37620
tctgtgaatc gcttcacgac cacgctgatg agctttaccg cagctgcctc gcgcgtttcg    37680
gtgatgacgg tgaaaacctc tgacacatgc agctcccgga gacggtcaca gcttgtctgt    37740
aagcggatgc cgggagcaga caagcccgtc agggcgcgtc agcgggtgtt ggcgggtgtc    37800
ggggcgcagc catgacccag tcacgtagcg atagcggagt gtatactggc ttaactatgc    37860
ggcatcagag cagattgtac tgagagtgca ccatatgcgg tgtgaaatac cgcacagatg    37920
cgtaaggaga aaataccgca t                                              37941
```

<210> SEQ ID NO 2
<211> LENGTH: 8172
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (9)..(11)
<223> OTHER INFORMATION: a, c, g, t, unknown or other
<220> FEATURE:
<221> NAME/KEY: modified_base
<222> LOCATION: (352)..(354)
<223> OTHER INFORMATION: a, c, g, t, unknown or other
<220> FEATURE:
<221> NAME/KEY: modified_base
<222> LOCATION: (1942)..(1944)
<223> OTHER INFORMATION: a, c, g, t, unknown or other
<220> FEATURE:
<221> NAME/KEY: modified_base
<222> LOCATION: (2001)..(2003)
<223> OTHER INFORMATION: a, c, g, t, unknown or other
<220> FEATURE:
<221> NAME/KEY: modified_base
<222> LOCATION: (4244)..(4246)
<223> OTHER INFORMATION: a, c, g, t, unknown or other
<220> FEATURE:
<221> NAME/KEY: modified_base
<222> LOCATION: (4261)..(4263)
<223> OTHER INFORMATION: a, c, g, t, unknown or other
<220> FEATURE:

```
<221> NAME/KEY: modified_base
<222> LOCATION: (5246)..(5248)
<223> OTHER INFORMATION: a, c, g, t, unknown or other
<220> FEATURE:
<221> NAME/KEY: modified_base
<222> LOCATION: (5263)..(5265)
<223> OTHER INFORMATION: a, c, g, t, unknown or other
<220> FEATURE:
<221> NAME/KEY: modified_base
<222> LOCATION: (6566)..(6571)
<223> OTHER INFORMATION: a, c, g, t, unknown or other
<220> FEATURE:
<221> NAME/KEY: modified_base
<222> LOCATION: (8109)..(8172)
<223> OTHER INFORMATION: a, c, g, t, unknown or other

<400> SEQUENCE: 2
```

| | | | | | |
|---|---|---|---|---|---|
| ttaattaann | ntcccttcca | gctctctgcc | cctttggat | tgaagccaat | atgataatga | 60 |
| gggggtggag | tttgtgacgt | ggcgcgggc | gtgggaacgg | ggcgggtgac | gtagtagtgt | 120 |
| ggcggaagtg | tgatgttgca | agtgtggcgg | aacacatgta | agcgacggat | gtggcaaaag | 180 |
| tgacgttttt | ggtgtgcgcc | ggtgtacaca | ggaagtgaca | atttttcgcgc | ggttttaggc | 240 |
| ggatgttgta | gtaaatttgg | gcgtaaccga | gtaagatttg | gccatttttcg | cgggaaaact | 300 |
| gaataagagg | aagtgaaatc | tgaataattt | tgtgttactc | atagcgcgta | anncgcgtt | 360 |
| aagatacatt | gatgagtttg | gacaaaccac | aactagaatg | cagtgaaaaa | aatgctttat | 420 |
| ttgtgaaatt | tgtgatgcta | ttgctttatt | tgtaaccatt | ataagctgca | ataaacaagt | 480 |
| taacaacaac | aattgcattc | attttatgtt | tcaggttcag | ggggaggtgt | gggaggtttt | 540 |
| ttaaagcaag | taaaacctct | acaaatgtgg | tatggctgat | tatgatcagt | tatctagatc | 600 |
| cggtggatct | gagtccggac | ttgtacagct | cgtccatgcc | gagagtgatc | ccggcggcgg | 660 |
| tcacgaactc | cagcaggacc | atgtgatcgc | gcttctcgtt | ggggtctttg | ctcagggcgg | 720 |
| actgggtgct | caggtagtgg | ttgtcgggca | gcagcacggg | gccgtcgccg | atggggtgt | 780 |
| tctgctggta | gtggtcggcg | agctgcacg | tgccgtcctc | gatgttgtgg | cggatcttga | 840 |
| agttcacctt | gatgccgttc | ttctgcttgt | cggccatgat | atagacgttg | tggctgttgt | 900 |
| agttgtactc | cagcttgtgc | cccaggatgt | tgccgtcctc | cttgaagtcg | atgcccttca | 960 |
| gctcgatgcg | gttcaccagg | gtgtcgccct | cgaacttcac | ctcggcgcgg | gtcttgtagt | 1020 |
| tgccgtcgtc | cttgaagaag | atggtgcgct | cctggacgta | gccttcgggc | atggcggact | 1080 |
| tgaagaagtc | gtgctgcttc | atgtggtcgg | ggtagcggct | gaagcactgc | acgccgtagg | 1140 |
| tcagggtggt | cacgagggtg | ggccagggca | cgggcagctt | gccggtggtg | cagatgaact | 1200 |
| tcagggtcag | cttgccgtag | gtggcatcgc | cctcgccctc | gccggacacg | ctgaacttgt | 1260 |
| ggccgtttac | gtcgccgtcc | agctcgacca | ggatgggcac | caccccggtg | aacagctcct | 1320 |
| cgcccttgct | caccatggtg | gcgaccggta | gcgctagcgg | atctgacggt | tcactaaacc | 1380 |
| agctctgctt | atatagacct | cccaccgtac | acgcctaccg | cccatttgcg | tcaatggggc | 1440 |
| ggagttgtta | cgacattttg | gaaagtcccg | ttgattttgg | tgccaaaaca | aactcccatt | 1500 |
| gacgtcaatg | gggtggagac | ttggaaatcc | ccgtgagtca | aaccgctatc | cacgcccatt | 1560 |
| gatgtactgc | caaaaccgca | tcaccatggt | aatagcgatg | actaatacgt | agatgtactg | 1620 |
| ccaagtagga | aagtcccata | aggtcatgta | ctgggcataa | tgccaggcgg | gccatttacc | 1680 |
| gtcattgacg | tcaatagggg | gcgtacttgg | catatgatac | acttgatgta | ctgccaagtg | 1740 |
| ggcagtttac | cgtaaatact | ccacccattg | acgtcaatg | aaagtcccta | ttggcgttac | 1800 |
| tatgggaaca | tacgtcatta | ttgacgtcaa | tgggcggggg | tcgttgggcg | gtcagccagg | 1860 |

```
cgggccattt accgtaagtt atgtaacgcg gaactccata tatgggctat gaactaatga    1920
ccccgtaatt gattactatt annnctagca gatctggtac cgtcgacgcg gccgcgatat    1980
cctcgagaag ctttctagag nnntaagggt gggaaagaat atataaggtg ggggtcttat    2040
gtagttttgt atctgttttg cagcagccgc cgccgccatg agcaccaact cgtttgatgg    2100
aagcattgtg agctcatatt tgacaacgcg catgccccca tgggccgggg tgcgtcagaa    2160
tgtgatgggc tccagcattg atggtcgccc cgtcctgccc gcaaactcta ctaccttgac    2220
ctacgagacc gtgtctggaa cgccgttgga gactgcagcc tccgccgccg cttcagccgc    2280
tgcagccacc gcccgcggga ttgtgactga ctttgctttc ctgagcccgc ttgcaagcag    2340
tgcagcttcc cgttcatccg cccgcgatga caagttgacg gctcttttgg cacaattgga    2400
ttctttgacc cgggaactta atgtcgtttc tcagcagctg ttggatctgc gccagcaggt    2460
ttctgccctg aaggcttcct cccctcccaa tgcggtttaa acataaata aaaaaccaga    2520 ctctgtttgg atttgatca agcaagtgtc ttgctgtctt tatttagggg ttttgcgcgc    2580
gcggtaggcc cgggaccagc ggtctcggtc gttgagggtc ctgtgtattt tttccaggac    2640
gtggtaaagg tgactctgga tgttcagata catgggcata agcccgtctc tggggtggag    2700
gtagcaccac tgcagagctt catgctgcgg ggtggtgttg tagatgatcc agtcgtagca    2760
ggagcgctgg gcgtggtgcc taaaaatgtc tttcagtagc aagctgattg ccaggggcag    2820
gcccttggtg taagtgttta caaagcggtt aagctgggat gggtgcatac gtgggatat    2880 gagatgcatc ttggactgta tttttaggtt ggctatgttc ccagccatat ccctccgggg    2940
attcatgttg tgcagaacca ccagcacagt gtatccggtg cacttgggaa atttgtcatg    3000
tagcttagaa ggaaatgcgt ggaagaactt ggagacgccc ttgtgacctc caagattttc    3060
catgcattcg tccataatga tggcaatggg cccacgggcg gcggcctggg cgaagatatt    3120
tctgggatca ctaacgtcat agttgtgttc caggatgaga tcgtcatagg ccatttttac    3180
aaagcgcggg cggagggtgc cagactgcgg tataatggtt ccatccggcc caggggcgta    3240
gttaccctca cagatttgca tttcccacgc tttgagttca gatggggga tcatgtctac    3300 ctgcggggcg atgaagaaaa cggtttccgg ggtagggag atcagctggg aagaaagcag    3360
gttcctgagc agctgcgact taccgcagcc ggtgggcccg taaatcacac ctattaccgg    3420
gtgcaactgg tagttaagag agctgcagct gccgtcatcc ctgagcaggg gggccacttc    3480
gttaagcatg tccctgactc gcatgttttc cctgaccaaa tccgccagaa ggcgctcgcc    3540
gcccagcgat agcagttctt gcaaggaagc aaagttttc aacggtttga ccgtccgc    3600 cgtaggcatg cttttgagcg tttgaccaag cagttccagg cggtcccaca gctcggtcac    3660
ctgctctacg gcatctcgat ccagcatatc tcctcgtttc gcgggttggg gcggctttcg    3720
ctgtacggca gtagtcggtg ctcgtccaga cgggccaggg tcatgtcttt ccacgggcgc    3780
agggtcctcg tcagcgtagt ctgggtcacg gtgaagggt gcgctccggg ctgcgcgctg    3840
gccagggtgc gcttgaggct ggtcctgctg gtgctgaagc gctgccggtc ttcgccctgc    3900
gcgtcggcca ggtagcattt gaccatggtg tcatagtcca gccccccgc ggcgtggccc    3960 ttggcgcgca gcttgccctt ggaggaggcg ccgcacgagg ggcagtgcag acttttgagg    4020
gcgtagagct tgggcgcgag aaataccgat tccggggagt aggcatccgc gccgcaggcc    4080
ccgcagacgt tctcgcattc cacgagccag gtgagctctg gccgttcggg gtcaaaaacc    4140
aggtttcccc catgcttttt gatgcgtttc ttacctctgg tttccatgag ccggtgtcca    4200
```

```
cgctcggtga cgaaaaggct gtccgtgtcc ccgtatacag actnnngttt aaacgaattc    4260
nnntataaaa tgcaaggtgc tgctcaaaaa atcaggcaaa gcctcgcgca aaaagaaag     4320
cacatcgtag tcatgctcat gcagataaag gcaggtaagc tccggaacca ccacagaaaa    4380
agacaccatt tttctctcaa acatgtctgc gggtttctgc ataaacacaa aataaaataa    4440
caaaaaaaca tttaaacatt agaagcctgt cttacaacag gaaaaacaac ccttataagc    4500
ataagacgga ctacgccat gccggcgtga ccgtaaaaaa actggtcacc gtgattaaaa     4560
agcaccaccg acagctcctc ggtcatgtcc ggagtcataa tgtaagactc ggtaaacaca    4620
tcaggttgat tcatcggtca gtgctaaaaa gcgaccgaaa tagcccgggg aatacatac    4680
ccgcaggcgt agagacaaca ttacagcccc cataggaggt ataacaaaat taataggaga    4740
gaaaaacaca taaacacctg aaaaaccctc ctgcctaggc aaaatagcac cctcccgctc    4800
cagaacaaca tacagcgctt cacagcggca gcctaacagt cagccttacc agtaaaaaag    4860
aaaacctatt aaaaaacac cactcgacac ggcaccagct caatcagtca cagtgtaaaa     4920
aagggccaag tgcagagcga gtatatatag gactaaaaaa tgacgtaacg gttaaagtcc    4980
acaaaaaaca cccagaaaac cgcacgcgaa cctacgccca gaaacgaaag ccaaaaaacc    5040
cacaacttcc tcaaatcgtc acttccgttt tcccacgtta cgtaacttcc cattttaaga    5100
aaactacaat tcccaacaca tacaagttac tccgccctaa aacctacgtc acccgccccg    5160
ttcccacgcc ccgcgccacg tcacaaactc cacccccta ttatcatatt ggcttcaatc     5220
caaaataagg tatattattg atgatnnntt aattaaggat ccnnncggtg tgaaataccg    5280
cacagatgcg taaggagaaa ataccgcatc aggcgctctt ccgcttcctc gctcactgac    5340
tcgctgcgct cggtcgttcg gctgcggcga gcggtatcag ctcactcaaa ggcggtaata    5400
cggttatcca cagaatcagg ggataacgca ggaaagaaca tgtgagcaaa aggccagcaa    5460
aaggccagga accgtaaaaa ggccgcgttg ctggcgtttt tccataggct ccgcccccct    5520
gacgagcatc acaaaaatcg acgctcaagt cagaggtggc gaaacccgac aggactataa    5580
agataccagg cgtttccccc tggaagctcc ctcgtgcgct ctcctgttcc gaccctgccg    5640
cttaccggat acctgtccgc ctttctccct tcgggaagcg tggcgctttc tcatagctca    5700
cgctgtaggt atctcagttc ggtgtaggtc gttcgctcca agctgggctg tgtgcacgaa    5760
ccccccgttc agcccgaccg ctgcgcctta tccggtaact atcgtcttga gtccaacccg    5820
gtaagacacg acttatcgcc actggcagca gccactggta acaggattag cagagcgagg    5880
tatgtaggcg gtgctacaga gttcttgaag tggtggccta actacggcta cactagaagg    5940
acagtatttg gtatctgcgc tctgctgaag ccagttacct tcggaaaaag agttggtagc    6000
tcttgatccg gcaaacaaac caccgctggt agcggtggtt ttttgtttg caagcagcag     6060
attacgcgca gaaaaaaagg atctcaagaa gatcctttga tcttttctac ggggtctgac    6120
gctcagtgga acgaaaactc acgttaaggg attttggtca tgagattatc aaaaaggatc    6180
ttcacctaga tccttttaaa ttaaaaatga agttttaaat caatctaaag tatatatgag    6240
taaacttggt ctgacagtta ccaatgctta atcagtgagg cacctatctc agcgatctgt    6300
ctatttcgtt catccatagt tgcctgactc ccgtcgtgt agataactac gatacgggag     6360
ggcttaccat ctggccccag tgctgcaatg ataccgcgag acccacgctc accggctcca    6420
gatttatcag caataaacca gccagccgga agggccgagc gcagaagtgg tcctgcaact    6480
ttatccgcct ccatccagtc tattaattgt tgccgggaag ctagagtaag tagttcgcca    6540
gttaatagtt tgcgcaacgt tgttgnnnnn naaaaaggat cttcacctag atcctttca     6600
```

```
cgtagaaagc cagtccgcag aaacggtgct gaccccggat gaatgtcagc tactgggcta    6660
tctggacaag ggaaaacgca agcgcaaaga gaaagcaggt agcttgcagt gggcttacat    6720
ggcgatagct agactgggcg gttttatgga cagcaagcga accggaattg ccagctgggg    6780
cgccctctgg taaggttggg aagccctgca agtaaactg gatggctttc tcgccgccaa    6840
ggatctgatg gcgcagggga tcaagctctg atcaagagac aggatgagga tcgtttcgca    6900
tgattgaaca agatggattg cacgcaggtt ctccggccgc ttgggtggag aggctattcg    6960
gctatgactg ggcacaacag acaatcggct gctctgatgc cgccgtgttc cggctgtcag    7020
cgcaggggcg cccggttctt tttgtcaaga ccgacctgtc cggtgccctg aatgaactgc    7080
aagacgaggc agcgcggcta tcgtggctgg ccacgacggg cgttccttgc gcagctgtgc    7140
tcgacgttgt cactgaagcg ggaagggact ggctgctatt gggcgaagtg ccggggcagg    7200
atctcctgtc atctcacctt gctcctgccg agaaagtatc catcatggct gatgcaatgc    7260
ggcggctgca tacgcttgat ccggctacct gcccattcga ccaccaagcg aaacatcgca    7320
tcgagcgagc acgtactcgg atggaagccg gtcttgtcga tcaggatgat ctggacgaag    7380
agcatcaggg gctcgcgcca gccgaactgt tcgccaggct caaggcgagc atgcccgacg    7440
gcgaggatct cgtcgtgacc catggcgatg cctgcttgcc gaatatcatg gtggaaaatg    7500
gccgcttttc tggattcatc gactgtggcc ggctgggtgt ggcggaccgc tatcaggaca    7560
tagcgttggc tacccgtgat attgctgaag agcttggcgg cgaatgggct gaccgcttcc    7620
tcgtgcttta cggtatcgcc gctcccgatt cgcagcgcat cgccttctat cgccttcttg    7680
acgagttctt ctgaattttg ttaaaatttt tgttaaatca gctcattttt taaccaatag    7740
gccgaaatcg gcaacatccc ttataaatca aagaatagac cgcgataggt tgagtgtt    7800 gttccagttt ggaacaagag tccactatta agaacgtgg actccaacgt caagggcga    7860 aaaaccgtct atcagggcga tggcccacta cgtgaaccat cacccaaatc aagttttttg    7920
cggtcgaggt gccgtaaagc tctaaatcgg aaccctaaag ggagccccg atttagagct    7980 tgacggggaa agccggcgaa cgtggcgaga aggaaggga agaaagcgaa aggagcgggc    8040
gctagggcgc tggcaagtgt agcggtcacg ctgcgcgtaa ccaccacacc cgcgcgctta    8100
atgcgccgnn nnnnnnnnn nnnnnnnnn nnnnnnnnnn nnnnnnnnn nnnnnnnnn        8160 nnnnnnnnnn nn                                                        8172
```

<210> SEQ ID NO 3
<211> LENGTH: 4530
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
tcgagaacta tcttcatgtt gttgcagatg aagcgcgcaa gaccgtctga agataccttc     60
aaccccgtgt atccatatga cacggaaacc ggtcctccaa ctgtgccttt tcttactcct    120 cccttttgtat cccccaatgg gtttcaagag agtcccctg gggtactctc tttgcgccta    180
tccgaacctc tagttacctc caatggcatg cttgcgctca aaatgggcaa cggcctctct    240
ctggacgagg ccgcaaccct tacctcccaa aatgtaacca ctgtgagccc acctctcaaa    300
aaaaccaagt caaacataaa cctgaaaata tctgcacccc tcacagttac ctcagaagcc    360
ctaactgtgg ctgccgccgc acctctaatg gtcgcgggca acacactcac catgcaatca    420
```

```
caggccccgc taaccgtgca cgactccaaa cttagcattg ccacccaagg acccctcaca      480
gtgtcagaag gaaagctagc cctgcaaaca tcaggccccc tcaccaccac cgatagcagt      540
acccttacta tcactgcctc accccctcta actactgcca ctggtagctt gggcattgac      600
ttgaaagagc ccatttatac acaaaatgga aaactaggac taaagtacgg ggctcctttg      660
catgtaacag acgacctaaa cactttgacc gtagcaactg gtccaggtgt gactattaat      720
aatacttcct tgcaaactaa agttactgga gccttgggtt ttgattcaca aggcaatatg      780
caacttaatg tagcaggagg actaaggatt gattctcaaa acagacgcct tatacttgat      840
gttagttatc cgtttgatgc tcaaaaccaa ctaaatctaa gactaggaca gggccctctt      900
tttataaact cagcccacaa cttggatatt aactacaaca aaggccttta cttgtttaca      960
gcttcaaaca attccaaaaa gcttgaggtt aacctaagca ctgccaaggg gttgatgttt     1020
gacgctacag ccatagccat taatgcagga gatgggcttg aatttggttc acctaatgca     1080
ccaaacacaa atcccctcaa aacaaaaatt ggccatggcc tagaatttga ttcaaacaag     1140
gctatggttc ctaaactagg aactggcctt agttttgaca gcacaggtgc cattacagta     1200
ggaaacaaaa ataatgataa gctaactttg tggaccacac cagctccatc tcctaactgt     1260
agactaaatg cagagaaaga tgctaaactc actttggtct aacaaaatg tggcagtcaa     1320 atacttgcta cagtttcagt tttggctgtt aaaggcagtt tggctccaat atctggaaca     1380
gttcaaagtg ctcatcttat tataagattt gacgaaaatg gagtgctact aaacaattcc     1440
ttcctggacc cagaatattg gaactttaga aatggagatc ttactgaagg cacagcctat     1500
acaaacgctg ttggatttat gcctaaccta tcagcttatc caaaatctca cggtaaaact     1560 gccaaagta acattgtcag tcaagtttac ttaaacggag acaaaactaa acctgtaaca     1620
ctaaccatta cactaagcgg tacacaggaa tccggagaca caactccaag tgcatactct     1680
atgtcatttt catgggactg gtctggccac aactacatta tgaaatatt tgccacatcc     1740 tcttacactt tttcatacat tgcccaagaa taaagaagcg gccgcataac ttcgtatagc     1800
atacattata cgaacggtag gtaccgagct cgaattcact ggccgtcgtt ttacaacgtc     1860
gtgactggga aaaccctggc gttacccaac ttaatcgcct tgcagcacat ccccctttcg     1920
ccagctggcg taatagcgaa gaggcccgca ccgatcgccc ttcccaacag ttgcgcagcc     1980
tgaatggcga atggcgcctg atgcggtatt ttctccttac gcatctgtgc ggtatttcac     2040
accgcatatg gtgcactctc agtacaatct gctctgatgc cgcatagtta agccagcccc     2100
gacacccgcc aacacccgct gacgcgccct gacgggcttg tctgctcccg gcatccgctt     2160
acagacaagc tgtgaccgtc tccgggagct gcatgtgtca gaggttttca ccgtcatcac     2220
cgaaacgcgc gagacgaaag ggcctcgtga tacgcctatt tttataggtt aatgtcatga     2280
taataatggt ttcttagacg tcaggtggca cttttcgggg aaatgtgcgc ggaaccccta     2340
tttgtttatt tttctaaata cattcaaata tgtatccgct catgagacaa taaccctgat     2400
aaatgcttca ataatattga aaaggaaga gtatgagtat tcaacatttc cgtgtcgccc     2460
ttattccctt ttttgcggca ttttgccttc ctgttttgc tcacccagaa acgctggtga     2520
aagtaaaaga tgctgaagat cagttgggtg cacgagtggg ttacatcgaa ctggatctca     2580
acagcggtaa gatccttgag agttttcgcc ccgaagaacg ttttccaatg atgagcactt     2640
ttaaagttct gctatgtggc gcggtattat cccgtattga cgccgggcaa gagcaactcg     2700
gtcgccgcat acactattct cagaatgact tggttgagta ctcaccagtc acagaaaagc     2760
```

-continued

| | |
|---|---|
| atcttacgga tggcatgaca gtaagagaat tatgcagtgc tgccataacc atgagtgata | 2820 |
| acactgcggc caacttactt ctgacaacga tcggaggacc gaaggagcta accgcttttt | 2880 |
| tgcacaacat gggggatcat gtaactcgcc ttgatcgttg ggaaccggag ctgaatgaag | 2940 |
| ccataccaaa cgacgagcgt gacaccacga tgcctgtagc aatggcaaca acgttgcgca | 3000 |
| aactattaac tggcgaacta cttactctag cttcccggca acaattaata gactggatgg | 3060 |
| aggcggataa agttgcagga ccacttctgc gctcggccct ccggctggc tggtttattg | 3120 |
| ctgataaatc tggagccggt gagcgtgggt ctcgcggtat cattgcagca ctggggccag | 3180 |
| atggtaagcc ctcccgtatc gtagttatct cacgacgggg gagtcaggca actatggatg | 3240 |
| aacgaaatag acagatcgct gagataggtg cctcactgat taagcattgg taactgtcag | 3300 |
| accaagttta ctcatatata ctttagattg atttaaaact tcatttttaa tttaaaagga | 3360 |
| tctaggtgaa gatcctttt gataatctca tgaccaaaat cccttaacgt gagttttcgt | 3420 |
| tccactgagc gtcagacccc gtagaaaaga tcaaaggatc ttcttgagat cctttttttc | 3480 |
| tgcgcgtaat ctgctgcttg caaacaaaaa aaccaccgct accagcggtg gtttgtttgc | 3540 |
| cggatcaaga gctaccaact cttttccga aggtaactgg cttcagcaga gcgcagatac | 3600 |
| caaatactgt ccttctagtg tagccgtagt taggccacca cttcaagaac tctgtagcac | 3660 |
| cgcctacata cctcgctctg ctaatcctgt taccagtggc tgctgccagt ggcgataagt | 3720 |
| cgtgtcttac cgggttggac tcaagacgat agttaccgga taaggcgcag cggtcgggct | 3780 |
| gaacggggg ttcgtgcaca gcccagctt ggagcgaac gacctacacc gaactgagat | 3840 |
| acctacagcg tgagctatga gaaagcgcca cgcttcccga aggagaaag gcggacaggt | 3900 |
| atccggtaag cggcagggtc ggaacaggag agcgcacgag ggagcttcca ggggaaacg | 3960 |
| cctggtatct ttatagtcct gtcgggtttc gccacctctg acttgagcgt cgatttttgt | 4020 |
| gatgctcgtc aggggggcgg agcctatgga aaaacgccag caacgcggcc ttttacggt | 4080 |
| tcctggcctt ttgctggcct tttgctcaca tgttctttcc tgcgttatcc cctgattctg | 4140 |
| tggataaccg tattaccgcc tttgagtgag ctgataccgc tcgccgcagc cgaacgaccg | 4200 |
| agcgcagcga gtcagtgagc gaggaagcgg aagagcgccc aatacgcaaa ccgcctctcc | 4260 |
| ccgcgcgttg gccgattcat taatgcagct ggcacgacag gtttcccgac tggaaagcgg | 4320 |
| gcagtgagcg caacgcaatt aatgtgagtt agctcactca ttaggcaccc caggctttac | 4380 |
| actttatgct tccggctcgt atgttgtgtg gaattgtgag cggataacaa tttcacacag | 4440 |
| gaaacagcta tgaccatgat tacgccaagc ttgcatgcct gcaggtcgac actagtaccg | 4500 |
| ttcgtatatg gtttcttata cgaagttatc | 4530 |

<210> SEQ ID NO 4
<211> LENGTH: 4530
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

| | |
|---|---|
| ccggtttccg tgtcatatgg atacacgggg ttgaaggtat cttcagacgg tcttgcgcgc | 60 |
| ttcatctgca acaacatgaa gatagttctc gagataactt cgtataagaa accatatacg | 120 |
| aacggtacta gtgtcgacct gcaggcatgc aagcttggcg taatcatggt catagctgtt | 180 |
| tcctgtgtga attgttatc cgctcacaat tccacacaac atacgagccg gaagcataaa | 240 |

```
gtgtaaagcc tggggtgcct aatgagtgag ctaactcaca ttaattgcgt tgcgctcact    300
gcccgctttc cagtcgggaa acctgtcgtg ccagctgcat taatgaatcg gccaacgcgc    360
ggggagaggc ggtttgcgta ttgggcgctc ttccgcttcc tcgctcactg actcgctgcg    420
ctcggtcgtt cggctgcggc gagcggtatc agctcactca aaggcggtaa tacggttatc    480
cacagaatca ggggataacg caggaaagaa catgtgagca aaaggccagc aaaaggccag    540
gaaccgtaaa aaggccgcgt tgctggcgtt tttccatagg ctccgccccc ctgacgagca    600
tcacaaaaat cgacgctcaa gtcagaggtg gcgaaacccg acaggactat aaagatacca    660
ggcgtttccc cctggaagct ccctcgtgcg ctctcctgtt ccgaccctgc cgcttaccgg    720
atacctgtcc gcctttctcc cttcgggaag cgtggcgctt tctcatagct cacgctgtag    780
gtatctcagt tcggtgtagg tcgttcgctc caagctgggc tgtgtgcacg aaccccccgt    840
tcagcccgac cgctgcgcct tatccggtaa ctatcgtctt gagtccaacc cggtaagaca    900
cgacttatcg ccactggcag cagccactgg taacaggatt agcagagcga ggtatgtagg    960
cggtgctaca gagttcttga agtggtggcc taactacggc tacactagaa ggacagtatt    1020
tggtatctgc gctctgctga agccagttac cttcggaaaa agagttggta gctcttgatc    1080
cggcaaacaa accaccgctg gtagcggtgg ttttttttgtt tgcaagcagc agattacgcg    1140
cagaaaaaaa ggatctcaag aagatccttt gatcttttct acggggtctg acgctcagtg    1200
gaacgaaaac tcacgttaag ggattttggt catgagatta tcaaaaagga tcttcaccta    1260 gatccttttta aattaaaaat gaagttttaa atcaatctaa agtatatatg agtaaacttg    1320
gtctgacagt taccaatgct taatcagtga ggcacctatc tcagcgatct gtctatttcg    1380
ttcatccata gttgcctgac tccccgtcgt gtagataact acgatacggg agggcttacc    1440
atctggcccc agtgctgcaa tgataccgcg agacccacgc tcaccggctc cagatttatc    1500
agcaataaac cagccagccg aagggccga gcgcagaagt ggtcctgcaa ctttatccgc    1560
ctccatccag tctattaatt gttgccggga agctagagta agtagttcgc cagttaatag    1620
tttgcgcaac gttgttgcca ttgctacagg catcgtggtg tcacgctcgt cgtttggtat    1680
ggcttcattc agctccggtt cccaacgatc aaggcgagtt acatgatccc ccatgttgtg    1740
caaaaaagcg gttagctcct tcggtcctcc gatcgttgtc agaagtaagt tggccgcagt    1800
gttatcactc atggttatgg cagcactgca taattctctt actgtcatgc catccgtaag    1860
atgcttttct gtgactggtg agtactcaac caagtcattc tgagaatagt gtatgcggcg    1920
accgagttgc tcttgcccgg cgtcaatacg ggataatacc gcgccacata gcagaacttt    1980
aaaagtgctc atcattggaa aacgttcttc ggggcgaaaa ctctcaagga tcttaccgct    2040
gttgagatcc agttcgatgt aacccactcg tgcacccaac tgatcttcag catcttttac    2100
tttcaccagc gtttctgggt gagcaaaaac aggaaggcaa aatgccgcaa aaaagggaat    2160
aagggcgaca cggaaatgtt gaatactcat actcttcctt tttcaatatt attgaagcat    2220
ttatcagggt tattgtctca tgagcggata catatttgaa tgtatttaga aaaataaaca    2280
aataggggtt ccgcgcacat ttccccgaaa agtgccacct gacgtctaag aaaccattat    2340
tatcatgaca ttaacctata aaaataggcg tatcacgagg ccctttcgtc tcgcgcgttt    2400
cggtgatgac ggtgaaaacc tctgacacat gcagctcccg gagacggtca gcttgtct     2460 gtaagcggat gccgggagca gacaagcccg tcagggcgcg tcagcgggtg ttggcgggtg    2520
tcggggctgg cttaactatg cggcatcaga gcagattgta ctgagagtgc accatatgcg    2580
gtgtgaaata ccgcacagat gcgtaaggag aaaataccgc atcaggcgcc attcgccatt    2640
```

```
caggctgcgc aactgttggg aagggcgatc ggtgcgggcc tcttcgctat tacgccagct    2700
ggcgaaaggg ggatgtgctg caaggcgatt aagttgggta acgccagggt ttcccagtc    2760 acgacgttgt aaaacgacgg ccagtgaatt cgagctcggt acctaccgtt cgtataatgt    2820
atgctatacg aagttatgcg gccgcttctt tattcttggg caatgtatga aaaagtgtaa    2880
gaggatgtgg caaatatttc attaatgtag ttgtggccag accagtccca tgaaaatgac    2940
atagagtatg cacttggagt tgtgtctccg gattcctgtg taccgtttag tgtaatggtt    3000
agtgttacag gtttagtttt gtctccgttt aagtaaactt gactgacaat gttacttttg    3060
gcagttttac cgtgagattt tggataagct gataggttag gcataaatcc aacagcgttt    3120
gtataggctg tgccttcagt aagatctcca tttctaaagt tccaatattc tgggtccagg    3180
aaggaattgt ttagtagcac tccatttttcg tcaaatctta taataagatg agcactttga    3240
actgttccag atattggagc caaactgcct ttaacagcca aaactgaaac tgtagcaagt    3300
atttgactgc cacattttgt taagaccaaa gtgagtttag catctttctc tgcatttagt    3360
ctacagttag gagatggagc tggtgtggtc cacaaagtta gcttatcatt attttttgttt    3420 cctactgtaa tggcacctgt gctgtcaaaa ctaaggccag ttcctagttt aggaaccata    3480
gccttgtttg aatcaaattc taggccatgg ccaattttttg ttttgagggg atttgtgttt    3540
ggtgcattag gtgaaccaaa ttcaagccca tctcctgcat taatggctat ggctgtagcg    3600
tcaaacatca acccccttggc agtgcttagg ttaacctcaa gcttttttgga attgtttgaa    3660 gctgtaaaca gtaaaggcc tttgttgtag ttaatatcca agttgtgggc tgagttttata    3720 aaaagagggc cctgtcctag tcttagatttt agttggtttt gagcatcaaa cggataacta    3780
acatcaagta taaggcgtct gttttgagaa tcaatcctta gtcctcctgc tacattaagt    3840
tgcatattgc cttgtgaatc aaaacccaag gctccagtaa ctttagtttg caaggaagta    3900
ttattaatag tcacacctgg accagttgct acggtcaaag tgtttaggtc gtctgttaca    3960
tgcaaaggag ccccgtactt tagtcctagt tttccatttt gtgtataaat gggctctttc    4020
aagtcaatgc ccaagctacc agtggcagta gttagagggg gtgaggcagt gatagtaagg    4080
gtactgctat cggtggtggt gagggggcct gatgtttgca gggctagctt tccttctgac    4140
actgtgaggg gtccttgggt ggcaatgcta agtttggagt cgtgcacggt tagcggggcc    4200
tgtgattgca tggtgagtgt gttgcccgcg accattagag gtgcggcggc agccacagtt    4260
agggcttctg aggtaactgt gaggggtgca gatatttcca ggtttatgtt tgacttggtt    4320
tttttgagag gtgggctcac agtggttaca ttttgggagg taaggttgcc ggcctcgtcc    4380
agagagaggc cgttgcccat tttgagcgca agcatgccat tggaggtaac tagaggttcg    4440
gataggcgca aagagagtac cccagggggg actctcttgaa acccattggg ggatacaaag    4500
ggaggagtaa gaaaaggcac agttggagga                                     4530
```

<210> SEQ ID NO 5
<211> LENGTH: 5383
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

```
tcgagaacta tcttcatgtt gttgcagatg aagcgcgcaa gaccgtctga agataccttc     60
aaccccgtgt atccatatga cacggaaacc ggtcctccaa ctgtgccttt tcttactcct    120
```

```
cccttttgtat cccccaatgg gtttcaagag agtcccctg gggtactctc tttgcgccta    180
tccgaacctc tagttacctc caatggcatg cttgcgctca aaatgggcaa cggcctctct    240
ctggacgagg ccggcaacct tacctcccaa aatgtaacca ctgtgagccc acctctcaaa    300
aaaaccaagt caaacataaa cctgaaata tctgcacccc tcacagttac ctcagaagcc    360
ctaactgtgg ctgccgccgc acctctaatg tcgcgggca acacactcac catgcaatca    420
caggccccgc taaccgtgca cgactccaaa cttagcattg ccacccaagg accccctcaca    480 gtgtcagaag gaaagctagc cctgcaaaca tcaggccccc tcaccaccac cgatagcagt    540 accttacta tcactgcctc accccctcta actactgcca ctggtagctt gggcattgac    600
ttgaaagagc ccatttatac acaaaatgga aaactaggac taaagtacgg ggctcctttg    660
catgtaacag acgacctaaa cactttgacc gtagcaactg gtccaggtgt gactattaat    720
aatacttcct tgcaaactaa agttactgga gccttgggtt ttgattcaca aggcaatatg    780
caacttaatg tagcaggagg actaaggatt gattctcaaa acagacgcct tatacttgat    840
gttagttatc cgtttgatgc tcaaaaccaa ctaaatctaa gactaggaca gggccctctt    900
tttataaact cagcccacaa cttggatatt aactacaaca aaggcccttta cttgtttaca    960 gcttcaaaca attccaaaaa gcttgaggtt aacctaagca ctgccaaggg gttgatgttt    1020
gacgctacag ccatagccat taatgcagga gatgggcttg aatttggttc acctaatgca    1080
ccaaacacaa atcccctcaa aacaaaaatt ggccatggcc tagaatttga ttcaaacaag    1140
gctatggttc ctaaactagg aactggcctt agttttgaca gcacaggtgc cattacagta    1200
ggaaacaaaa ataatgataa gctaactttg tggaccacac cagctccatc tcctaactgt    1260
agactaaatg cagagaaaga tgctaaactc actttggtct taacaaaaatg tggcagtcaa    1320 atacttgcta cagtttcagt tttggctgtt aaaggcagtt tggctccaat atctggaaca    1380
gttcaaagtg ctcatcttat tataagattt gacgaaaatg gagtgctact aaacaattcc    1440
ttcctggacc cagaatattg gaactttaga aatggagatc ttactgaagg cacagcctat    1500
acaaacgctg ttggatttat gcctaaccta tcagcttatc caaaatctca cggtaaaact    1560
gccaaaagta acattgtcag tcaagtttac ttaaacggag acaaaactaa acctgtaaca    1620
ctaaccatta cactaagcgg tacacaggaa tccggagaca caactccaag tgcatactct    1680
atgtcatttt catgggactg gtctggccac aactacatta tgaaatatt tgccacatcc    1740 tcttacactt tttcatacat tgcccaagaa taaagaagcg gccgcataac ttcgtatagc    1800
atacattata cgaacggtag gtaccaggta agtgtaccca attcgcccta tagtgagtcg    1860
tattacaatt cactggccgt cgttttacaa cgcctgatgc ggtatttttct ccttacgcat    1920 ctgtgcggta tttcacaccg catatatggt gcactctcag tacaatctgc tctgatgccg    1980
catagttaag ccagccccga cacccgccaa cacccgctga cgcgccctga cgggcttgtc    2040
tgctcccggc atccgcttac agacaagctg tgaccgtctc cggagctgc atgtgtcaga    2100 ggttttcacc gtcatcaccg aaacgcgcga gacgaaaggg cctcgtgata cgcctatttt    2160
tataggttaa tgtcatgata taatggttt cttagacgtc aggtggcact tttcggggaa    2220
atgtgcgcgg aacccctatt tgtttatttt tctaaataca ttcaaatatg tatccgctca    2280
tgagacaata accctgataa atgcttcaat aatattgaaa aaggaagagt atgagtattc    2340
aacatttccg tgtcgccctt attccctttt ttgcggcatt ttgccttcct gttttttgctc    2400 acccagaaac gctggtgaaa gtaaaagatg ctgaagatca gttgggtgca cgagtgggtt    2460
```

```
acatcgaact ggatctcaac agcggtaaga tccttgagag ttttcgcccc gaagaacgtt    2520
ttccaatgat gagcactttt aaagttctgc tatgtggcgc ggtattatcc cgtattgacg    2580
ccgggcaaga gcaactcggt cgccgcatac actattctca gaatgacttg gttgagtact    2640
caccagtcac agaaaagcat cttacggatg gcatgacagt aagagaatta tgcagtgctg    2700
ccataaccat gagtgataac actgcggcca acttacttct gacaacgatc ggaggaccga    2760
aggagctaac cgcttttttg cacaacatgg ggatcatgt aactcgcctt gatcgttggg     2820
aaccggagct gaatgaagcc ataccaaacg acgagcgtga ccacgcgatg cctgtagcaa    2880
tggcaacaac gttgcgcaaa ctattaactg cgaactact tactctagct tcccggcaac     2940
aattaataga ctggatggag gcggataaag ttgcaggacc acttctgcgc tcggcccttc    3000
cggctggctg gtttattgct gataaatctg gagccggtga gcgtgggtct cgcggtatca    3060
ttgcagcact ggggccagat ggtaagccct cccgtatcgt agttatctac acgacgggga    3120
gtcaggcaac tatggatgaa cgaaatagac agatcgctga gataggtgcc tcactgatta    3180
agcattggta actgtcagac caagtttact catatatact ttagattgat ttaaaacttc     3240
atttttaatt taaaaggatc taggtgaaga tccttttga taatctcatg accaaaatcc      3300
cttaacgtga gttttcgttc cactgagcgt cagaccccgt agaaaagatc aaaggatctt    3360
cttgagatcc ttttttctg cgcgtaatct gctgcttgca acaaaaaaa ccaccgctac       3420 cagcggtggt ttgtttgccg gatcaagagc taccaactct ttttccgaag gtaactggct    3480
tcagcagagc gcagatacca atactgtcc ttctagtgta gccgtagtta ggccaccact     3540
tcaagaactc tgtagcaccg cctacatacc tcgctctgct aatcctgtta ccagtggctg    3600
ctgccagtgg cgataagtcg tgtcttaccg ggttggactc aagacgatag ttaccggata    3660
aggcgcagcg gtcgggctga acggggggtt cgtgcacaca gcccagcttg gagcgaacga    3720
cctacaccga actgagatac ctacagcgtg agcattgaga aagcgccacg ctcccgaag     3780 ggagaaaggc ggacaggtat ccggtaagcg gcagggtcgg aacaggagag cgcacgaggg    3840
agcttccagg gggaaacgcc tggtatcttt atagtcctgt cgggtttcgc cacctctgac    3900
ttgagcgtcg atttttgtga tgctcgtcag ggggcggag cctatggaaa aacgccagca     3960
acgcggcctt tttacggttc ctggcctttt gctggccttt tgctcacatg ctgggcccag    4020
ccggccagat ctgagctcgc ggccgcgata tcgctagctc gaggtccgtt acataactta    4080
cggtaaatgg cccgcctggc tgaccgccca acgaccccg cccattgacg tcaataatga     4140
cgtatgttcc catagtaacg ccaataggga cttt ccattg acgtcaatgg gtggagtatt   4200
tacggtaaac tgcccacttg gcagtacatc aagtgtatca tatgccaagt acgccccta    4260 ttgacgtcaa tgacggtaaa tggcccgcct ggcattatgc ccagtacatg accttatggg   4320
actttcctac ttggcagtac atctacgtat tagtcatcgc tattaccatg gtgatgcggt   4380
tttggcagta catcaatggg cgtggatagc ggtttgactc acggggattt ccaagtctcc   4440
accccattga cgtcaatggg agtttgtttt ggcaccaaaa tcaacgggac tttccaaaat   4500
gtcgtaacaa ctccgcccca ttgacgcaaa tgggcggtag cgtgtacgg tgggaggtct    4560 atataagcag agctcgttta gtgaaccgtc agatcgcctg gagacgccat ccacgctgtt   4620
ttgacctcca tagaagacac cgggaccgat ccagcctccg cggccgggaa cggtgcattg   4680
gaacggaccg tgttgacaat taatcatcgg catagtatat cggcatagta taatacgaca   4740
aggtgaggaa ctaaaccatg gccaagcctt tgtctcaaga agaatccacc ctcattgaaa   4800
gagcaacggc tacaatcaac agcatcccca tctctgaaga ctacagcgtc gccagcgcag   4860
```

```
ctctctctag cgacggccgc atcttcactg gtgtcaatgt atatcatttt actgggggac    4920
cttgtgcaga actcgtggtg ctgggcactg ctgctgctgc ggcagctggc aacctgactt    4980
gtatcgtcgc gatcggaaat gagaacaggg gcatcttgag ccctgcgga cggtgccgac    5040 aggtgcttct cgatctgcat cctgggatca aagccatagt gaaggacagt gatggacagc    5100
cgacggcagt tgggattcgt gaattgctgc cctctggtta tgtgtgggag ggctaagcac    5160
ttcgtggccg aggagcagga ctgacactcg acctcgaaac ttgtttattg cagcttataa    5220
tggttacaaa taaagcaata gcatcacaaa tttcacaaat aaagcatttt tttcactgca    5280
ttctagttgt ggtttgtcca aactcatcaa tgtatcttat catgtctgaa ttcccgggga    5340
tcctctagta ccgttcgtat atggtttctt atacgaagtt atc                      5383
```

<210> SEQ ID NO 6
<211> LENGTH: 33991
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<221> NAME/KEY: modified_base
<222> LOCATION: (10)..(12)
<223> OTHER INFORMATION: a, c, g, t, unknown or other
<220> FEATURE:
<221> NAME/KEY: modified_base
<222> LOCATION: (3655)..(3657)
<223> OTHER INFORMATION: a, c, g, t, unknown or other
<220> FEATURE:
<221> NAME/KEY: modified_base
<222> LOCATION: (3684)..(3686)
<223> OTHER INFORMATION: a, c, g, t, unknown or other

<400> SEQUENCE: 6

```
taaggatccn nncctgtcct cgaccgatgc ccttgagagc cttcaaccca gtcagctcct      60
tccggtgggc gcggggcatg actatcgtcg ccgcacttat gactgtcttc tttatcatgc     120
aactcgtagg acaggtgccg gcagcgctct gggtcatttt cggcgaggac cgctttcgct     180
ggagcgcgac gatgatcggc ctgtcgcttg cggtattcgg aatcttgcac gccctcgctc     240
aagccttcgt cactggtccc gccaccaaac gtttcggcga aagcaggcc attatcgccg     300 gcatggcggc cgacgcgctg ggctacgtct tgctggcgtt cgcgacgcga ggctggatgg     360
ccttccccat tatgattctt ctcgcttccg gcggcatcgg gatgcccgcg ttgcaggcca     420
tgctgtccag gcaggtagat gacgaccatc agggacagct tcaaggatcg ctcgcggctc     480
ttaccagcct aacttcgatc actggaccgc tgatcgtcac ggcgatttat gccgcctcgg     540
cgagcacatg gaacgggttg gcatggattg taggcgccgc cctataccct gtctgcctcc     600
ccgcgttgcg tcgcggtgca tggagccggg ccacctcgac ctgaatggaa gccggcggca     660
cctcgctaac ggattcacca ctccaagaat tggagccaat caattcttgc ggagaactgt     720
gaatgcgcaa accaacccct tgcagaacat atccatcgcg tccgccatct ccagcagccg     780
cacgcggcgc atctcgggca gcgttgggtc ctggccacgg gtgcgcatga tcgtgctcct     840
gtcgttgagg acccggctag gctggcgggg ttgccttact ggttagcaga atgaatcacc     900
gatacgcgag cgaacgtgaa gcgactgctg ctgcaaaacg tctgcgacct gagcaacaac     960
atgaatggtc ttcggtttcc gtgtttcgta aagtctggaa acgcggaagt cagcgccctg    1020
caccattatg ttccggatct gcatcgcagg atgctgctgg ctaccctgtg gaacacctac    1080
atctgtatta acgaagcgct ggcattgacc ctgagtgatt tttctctggt cccgccgcat    1140
```

-continued

```
ccataccgcc agttgtttac cctcacaacg ttccagtaac cgggcatgtt catcatcagt    1200
aacccgtatc gtgagcatcc tctctcgttt catcggtatc attaccccca tgaacagaaa    1260
ttccccctta cacggaggca tcaagtgacc aaacaggaaa aaaccgccct aacatggcc     1320 cgctttatca gaagccagac attaacgctt ctggagaaac tcaacgagct ggacgcggat    1380
gaacaggcag acatctgtga atcgcttcac gaccacgctg atgagcttta ccgcagctgc    1440
ctcgcgcgtt tcggtgatga cggtgaaaac ctctgacaca tgcagctccc ggagacggtc    1500
acagcttgtc tgtaagcgga tgccgggagc agacaagccc gtcagggcgc gtcagcgggt    1560
gttggcgggt gtcggggcgc agccatgacc cagtcacgta gcgatagcgg agtgtatact    1620
ggcttaacta tgcggcatca gagcagattg tactgagagt gcaccatatg cggtgtgaaa    1680
taccgcacag atgcgtaagg agaaaatacc gcatcaggcg ctcttccgct tcctcgctca    1740
ctgactcgct gcgctcggtc gttcggctgc ggcgagcggt atcagctcac tcaaaggcgg    1800
taatacggtt atccacagaa tcaggggata cgcaggaaa gaacatgtga gcaaaaggcc    1860
agcaaaaggc caggaaccgt aaaaaggccg cgttgctggc gtttttccat aggctccgcc    1920
cccctgacga gcatcacaaa aatcgacgct caagtcagag gtggcgaaac ccgacaggac    1980
tataaagata ccaggcgttt ccccctggaa gctccctcgt gcgctctcct gttccgaccc    2040
tgccgcttac cggatacctg tccgcctttc tcccttcggg aagcgtggcg ctttctcaat    2100
gctcacgctg taggtatctc agttcggtgt aggtcgttcg ctccaagctg ggctgtgtgc    2160
acgaaccccc cgttcagccc gaccgctgcg ccttatccgg taactatcgt cttgagtcca    2220
acccggtaag acacgactta tcgccactgg cagcagccac tggtaacagg attagcagag    2280
cgaggtatgt aggcggtgct acagagttct tgaagtggtg gcctaactac ggctacacta    2340
gaaggacagt atttggtatc tgcgctctgc tgaagccagt taccttcgga aaaagagttg    2400
gtagctcttg atccggcaaa caaaccaccg ctggtagcgg tggttttttt gtttgcaagc    2460
agcagattac gcgcagaaaa aaaggatctc aagaagatcc tttgatcttt tctacggggt    2520
ctgacgctca gtggaacgaa aactcacgtt aagggatttt ggtcatgaga ttatcaaaaa    2580
ggatcttcac ctagatcctt ttaaattaaa aatgaagttt taaatcaatc taagtatat    2640 atgagtaaac ttggtctgac agttaccaat gcttaatcag tgaggcacct atctcagcga    2700
tctgtctatt tcgttcatcc atagttgcct gactccccgt cgtgtagata actacgatac    2760
gggagggctt accatctggc cccagtgctg caatgatacc gcgagaccca cgctcaccgg    2820
ctccagattt atcagcaata aaccagccag ccggaagggc cgagcgcaga agtggtcctg    2880
caactttatc cgcctccatc cagtctatta attgttgccg ggaagctaga gtaagtagtt    2940
cgccagttaa tagtttgcgc aacgttgttg ccattgctgc aggcatcgtg gtgtcacgct    3000
cgtcgtttgg tatggcttca ttcagctccg gttcccaacg atcaaggcga gttacatgat    3060
cccccatgtt gtgcaaaaaa gcggttagct ccttcggtcc tccgatcgtt gtcagaagta    3120
agttggccgc agtgttatca ctcatggtta tggcagcact gcataattct cttactgtca    3180
tgccatccgt aagatgcttt tctgtgactg gtgagtactc aaccaagtca ttctgagaat    3240
agtgtatgcg gcgaccgagt tgctcttgcc cggcgtcaac acgggataat accgcgccac    3300
atagcagaac tttaaaagtg ctcatcattg gaaaacgttc ttcggggcga aaactctcaa    3360
ggatcttacc gctgttgaga tccagttcga tgtaacccac tcgtgcaccc aactgatctt    3420
cagcatcttt tactttcacc agcgtttctg ggtgagcaaa aacaggaagg caaaatgccg    3480
```

```
caaaaaaggg aataagggcg acacggaaat gttgaatact catactcttc cttttttcaat    3540
attattgaag catttatcag ggttattgtc tcatgagcgg atacatattt gaatgtattt    3600
agaaaaataa acaaataggg gttccgcgca catttccccg aaaagtgcca cctgnnngaa    3660
ttcgaatcta gtatcgattc gaannncta agggtgggaa agaatatata aggtgggggt     3720
cttatgtagt tttgtatctg ttttgcagca gccgccgccg ccatgagcac caactcgttt    3780
gatggaagca ttgtgagctc atatttgaca acgcgcatgc ccccatgggc cggggtgcgt    3840
cagaatgtga tgggctccag cattgatggt cgccccgtcc tgcccgcaaa ctctactacc    3900
ttgacctacg agaccgtgtc tggaacgccg ttggagactg cagcctccgc cgccgcttca    3960
gccgctgcag ccaccgcccg cgggattgtg actgactttg ctttcctgag cccgcttgca    4020
agcagtgcag cttcccgttc atccgcccgc gatgacaagt tgacggctct tttggcacaa    4080
ttggattctt tgacccggga acttaatgtc gtttctcagc agctgttgga tctgcgccag    4140
caggtttctg ccctgaaggc ttcctccccct cccaatgcgg tttaaaacat aaataaaaaa    4200
ccagactctg tttggatttg gatcaagcaa gtgtcttgct gtctttattt aggggttttg    4260
cgcgcgcggt aggcccggga ccagcggtct cggtcgttga gggtcctgtg tattttttcc    4320
aggacgtggt aaaggtgact ctggatgttc agatacatgg gcataagccc gtctctgggg    4380
tggaggtagc accactgcag agcttcatgc tgcggggtgg tgttgtagat gatccagtcg    4440
tagcaggagc gctgggcgtg gtgcctaaaa atgtctttca gtagcaagct gattgccagg    4500
ggcaggccct tggtgtaagt gtttacaaag cggttaagct gggatgggtg catacgtggg    4560
gatatgagat gcatcttgga ctgtattttt aggttggcta tgttcccagc catatccctc    4620
cggggattca tgttgtgcag aaccaccagc acagtgtatc cggtgcactt gggaaatttg    4680
tcatgtagct tagaaggaaa tgcgtggaag aacttggaga cgcccttgtg acctccaaga    4740
ttttccatgc attcgtccat aatgatggca atgggcccac gggcggcggc ctgggcgaag    4800
atatttctgg gatcactaac gtcatagttg tgttccagga tgagatcgtc ataggccatt    4860
tttacaaagc gcgggcggag ggtgccagac tgcggtataa tggttccatc cggcccaggg    4920
gcgtagttac cctcacagat ttgcatttcc cacgctttga gttcagatgg ggggatcatg    4980
tctacctgcg gggcgatgaa gaaaacggtt ccggggtag gggagatcag ctgggaagaa    5040
agcaggttcc tgagcagctg cgacttaccg cagccgtgg gcccgtaaat cacacctatt     5100
accgggtgca actggtagtt aagagagctg cagctgccgt catccctgag caggggggcc    5160
acttcgttaa gcatgtccct gactcgcatg ttttccctga ccaaatccgc cagaaggcgc    5220
tcgccgccca gcgatagcag ttcttgcaag gaagcaaagt ttttcaacgg tttgagaccg    5280
tccgccgtag gcatgctttt gagcgtttga ccaagcagtt ccaggcggtc ccacagctcg    5340
gtcacctgct ctacggcatc tcgatccagc atatctcctc gtttcgcggg ttggggcggc    5400
tttcgctgta cggcagtagt cggtgctcgt ccagacgggc cagggtcatg tctttccacg    5460
ggcgcagggt cctcgtcagc gtagtctggg tcacggtgaa ggggtgcgct ccgggctgcg    5520
cgctggccag ggtgcgcttg aggctggtcc tgctggtgct gaagcgctgc cggtcttcgc    5580
cctgcgcgtc ggccaggtag catttgacca tggtgtcata gtccagcccc tccgcggcgt    5640
ggcccttggc gcgcagcttg cccttggagg aggcgccgca cgaggggcag tgcagacttt    5700
tgagggcgta gagcttgggc gcgagaaata ccgattccgg ggagtaggca tccgcgccgc    5760
aggccccgca gacggtctcg cattccacga gccaggtgag ctctgccgt tcggggtcaa     5820
aaaccaggtt tcccccatgc ttttgatgc gtttcttacc tctggtttcc atgagccggt    5880
```

-continued

```
gtccacgctc ggtgacgaaa aggctgtccg tgtccccgta tacagacttg agaggcctgt    5940
cctcgagcgg tgttccgcgg tcctcctcgt atagaaactc ggaccactct gagacaaagg    6000
ctcgcgtcca ggccagcacg aaggaggcta agtgggaggg gtagcggtcg ttgtccacta    6060
gggggtccac tcgctccagg gtgtgaagac acatgtcgcc ctcttcggca tcaaggaagg    6120
tgattggttt gtaggtgtag gccacgtgac cgggtgttcc tgaagggggg ctataaaagg    6180
gggtgggggc gcgttcgtcc tcactctctt ccgcatcgct gtctgcgagg ccagctgtt    6240 ggggtgagta ctccctctga aaagcgggca tgacttctgc gctaagattg tcagtttcca    6300
aaaacgagga ggatttgata ttcacctggc ccgcggtgat gcctttgagg gtggccgcat    6360
ccatctggtc agaaaagaca atcttttttgt tgtcaagctt ggtggcaaac gacccgtaga    6420
gggcgttgga cagcaacttg gcgatggagc cagggtttg gttttttgtcg cgatcggcgc    6480 gctccttggc cgcgatgttt agctgcacgt attcgcgcgc aacgcaccgc cattcgggaa    6540
agacggtggt gcgctcgtcg ggcaccaggt gcacgcgcca accgcggttg tgcagggtga    6600
caaggtcaac gctggtggct acctctccgc gtaggcgctc gttggtccag cagaggcggc    6660
cgcccttgcg cgagcagaat ggcggtaggg ggtctagctg cgtctcgtcc gggggtctg    6720 cgtccacggt aaagaccccg ggcagcaggc gcgcgtcgaa gtagtctatc ttgcatcctt    6780
gcaagtctag cgcctgctgc catgcgcggg cggcaagcgc gcgctcgtat gggttgagtg    6840 ggggaccca tggcatgggg tgggtgagcg cggaggcgta catgccgcaa atgtcgtaaa    6900
cgtagagggg ctctctgagt attccaagat atgtagggta gcatcttcca ccgcggatgc    6960
tggcgcgcac gtaatcgtat agttcgtgcg agggagcgag gaggtcggga ccgaggttgc    7020
tacgggcggg ctgctctgct cggaagacta tctgcctgaa gatggcatgt gagttggatg    7080
atatggttgg acgctggaag acgttgaagc tggcgtctgt gagacctacc gcgtcacgca    7140
cgaaggaggc gtaggagtcg cgcagcttgt tgaccagctc ggcggtgacc tgcacgtcta    7200
gggcgcagta gtccagggtt tccttgatga tgtcatactt atcctgtccc ttttttttcc    7260
acagctcgcg gttgaggaca aactcttcgc ggtctttcca gtactcttgg atcggaaacc    7320
cgtcggcctc cgaacggtaa gagcctagca tgtagaactg gttgacggcc tggtaggcgc    7380
agcatccctt ttctacgggt agcgcgtatg cctgcgcggc cttccggagc gaggtgtggg    7440
tgagcgcaaa ggtgtccctg accatgactt tgaggtactg gtatttgaag tcagtgtcgt    7500
cgcatccgcc ctgctcccag agcaaaaagt ccgtgcgctt tttggaacgc ggatttggca    7560
gggcgaaggt gacatcgttg aagagtatct ttcccgcgcg aggcataaag ttgcgtgtga    7620
tgcggaaggg tcccggcacc tcggaacggt tgttaattac ctgggcggcg agcacgatct    7680
cgtcaaagcc gttgatgttg tggcccacaa tgtaaagttc caagaagcgc gggatgccct    7740
tgatggaagg caattttttta agttcctcgt aggtgagctc ttcagggag ctgagcccgt    7800 gctctgaaag ggcccagtct gcaagatgag ggttggaagc gacgaatgag ctccacaggt    7860
cacgggccat tagcatttgc aggtggtcgc gaaaggtcct aaactggcga cctatggcca    7920
ttttttctgg ggtgatgcag tagaaggtaa gcgggtcttg ttcccagcgg tcccatccaa    7980
ggttcgcggc taggtctcgc gcggcagtca ctagaggctc atctccgccg aacttcatga    8040
ccagcatgaa gggcacgagc tgcttcccaa aggcccccat ccaagtatag gtctctacat    8100
cgtaggtgac aaagagacgc tcggtgcgag gatgcgagcc gatcgggaag aactggatct    8160
cccgccacca attggaggag tggctattga gtgtggtgaaa gtagaagtcc ctgcgacggg    8220
```

```
ccgaacactc gtgctggctt ttgtaaaaac gtgcgcagta ctggcagcgg tgcacgggct    8280
gtacatcctg cacgaggttg acctgacgac cgcgcacaag gaagcagagt gggaatttga    8340 gccctcgcc tggcgggttt ggctggtggt cttctacttc ggctgcttgt ccttgaccgt    8400
ctggctgctc gaggggagtt acggtggatc ggaccaccac gccgcgcgag cccaaagtcc    8460
agatgtccgc gcgcggcggt cggagcttga tgacaacatc gcgcagatgg gagctgtcca    8520
tggtctggag ctcccgcggc gtcaggtcag gcgggagctc ctgcaggttt acctcgcata    8580
gacgggtcag ggcgcgggct agatccaggt gatacctaat ttccaggggc tggttggtgg    8640
cggcgtcgat ggcttgcaag aggccgcatc ccgcggcgc gactacggta ccgcgcggcg    8700
ggcggtgggc cgcgggggtg tccttggatg atgcatctaa aagcggtgac gcgggcgagc    8760
ccccggaggt agggggggct ccggaccgc cgggagaggg ggcaggggca cgtcggcgcc    8820
gcgcgcgggc aggagctggt gctgcgcgcg taggttgctg gcgaacgcga cgacgcggcg    8880
gttgatctcc tgaatctggc gcctctgcgt gaagacgacg ggcccggtga gcttgagcct    8940
gaaagagagt tcgacagaat caatttcggt gtcgttgacg gcggcctggc gcaaaatctc    9000
ctgcacgtct cctgagttgt cttgataggc gatctcggcc atgaactgct cgatctcttc    9060
ctcctggaga tctccgcgtc cggctcgctc acggtggcg gcgaggtcgt tggaaatgcg    9120
ggccatgagc tgcgagaagg cgttgaggcc tccctcgttc cagacgcggc tgtagaccac    9180
gcccccttcg gcatcgcggg cgcgcatgac cacctgcgcg agattgagct ccacgtgccg    9240
ggcgaagacg gcgtagtttc gcaggcgctg aaagaggtag ttgagggtgg tggcggtgtg    9300
ttctgccacg aagaagtaca taacccagcg tcgaacgtg gattcgttga tatcccccaa    9360
ggcctcaagg cgctccatgg cctcgtagaa gtccacggcg aagttgaaaa actgggagtt    9420
gcgcgccgac acgttaact cctcctccag aagacggatg agctcggcga cagtgtcgcg    9480
cacctcgcgc tcaaaggcta caggggcctc ttcttcttct tcaatctcct cttccataag    9540
ggcctcccct tcttcttctt ctggcggcgg tgggggaggg gggacacggc ggcgacgacg    9600
gcgcaccggg aggcggtcga caaagcgctc gatcatctcc ccgcggcgac ggcgcatggt    9660
ctcggtgacg gcgcggccgt tctcgcgggg gcgcagttgg aagacgccgc ccgtcatgtc    9720
ccggttatgg gttggcgggg ggctgccatg cggcagggat acggcgctaa cgatgcatct    9780
caacaattgt tgtgtaggta ctccgccgcc gagggacctg agcgagtccg catcgaccgg    9840
atcggaaaac ctctcgagaa aggcgtctaa ccagtcacag tcgcaaggta ggctgagcac    9900
cgtggcgggc ggcagcgggc ggcggtcggg gttgtttctg gcggaggtgc tgctgatgat    9960
gtaattaaag taggcggtct tgagacggcg gatggtcgac agaagcacca tgtccttggg    10020
tccggcctgc tgaatgcgca ggcggtcggc catgcccag gcttcgtttt gacatcggcg    10080
caggtctttg tagtagtctt gcatgagcct ttctaccggc acttcttctt ctccttcctc    10140
ttgtcctgca tctcttgcat ctatcgctgc ggcggcggcg gagtttggcc gtaggtggcg    10200
ccctcttcct cccatgcgtg tgaccccgaa gcccctcatc ggctgaagca gggctaggtc    10260
ggcgacaacg cgctcggcta atatggcctg ctgcacctgc gtgagggtag actggaagtc    10320
atccatgtcc acaaagcggt ggtatgcgcc cgtgttgatg gtgtaagtgc agttggccat    10380
aacggaccag ttaacggtct ggtgacccgg ctgcgagagc tcggtgtacc tgagacgcga    10440
gtaagccctc gagtcaaata cgtagtcgtt gcaagtccgc accaggtact ggtatcccac    10500 caaaagtgc ggcggcggct ggcggtagag gggccagcgt agggtggccg gggctccggg    10560
ggcgagatct tccaacataa ggcgatgata tccgtagatg tacctggaca tccaggtgat    10620
```

```
gccggcggcg gtggtggagg cgcgcggaaa gtcgcggacg cggttccaga tgttgcgcag    10680
cggcaaaaag tgctccatgg tcgggacgct ctggccggtc aggcgcgcgc aatcgttgac    10740
gctctaccgt gcaaaaggag agcctgtaag cgggcactct tccgtggtct ggtggataaa    10800
ttcgcaaggg tatcatggcg gacgaccggg gttcgagccc cgtatccggc cgtccgccgt    10860
gatccatgcg gttaccgccc gcgtgtcgaa cccaggtgtg cgacgtcaga aacggggga    10920 gtgctccttt tggcttcctt ccaggcgcgg cggctgctgc gctagctttt ttggccactg    10980
gccgcgcgca gcgtaagcgg ttaggctgga aagcgaaagc attaagtggc tcgctccctg    11040
tagccggagg gttattttcc aagggttgag tcgcgggacc cccggttcga gtctcggacc    11100
ggccggactg cggcgaacgg gggtttgcct ccccgtcatg caagaccccg cttgcaaatt    11160
cctccggaaa cagggacgag ccccttttttt gcttttccca gatgcatccg gtgctgcggc    11220
agatgcgccc ccctcctcag cagcggcaag agcaagagca gcggcagaca tgcagggcac    11280
cctcccctcc tcctaccgcg tcaggagggg cgacatccgc ggttgacgcg gcagcagatg    11340
gtgattacga accccgcgg cgccgggccc ggcactacct ggacttggag gagggcgagg    11400
gcctggcgcg gctaggagcg ccctctcctg agcggtaccc aagggtgcag ctgaagcgtg    11460
atacgcgtga ggcgtacgtg ccgcggcaga acctgtttcg cgaccgcgag ggagaggagc    11520
ccgaggagat gcgggatcga aagttccacg cagggcgcga gctgcggcat ggcctgaatc    11580
gcgagcggtt gctgcgcgag gaggactttg agcccgacgc gcgaaccggg attagtcccg    11640
cgcgcgcaca cgtggcggcc gccgacctgg taaccgcata cgagcagacg gtgaaccagg    11700
agattaactt tcaaaaaagc tttaacaacc acgtgcgtac gcttgtggcg cgcgaggagg    11760
tggctatagg actgatgcat ctgtgggact ttgtaagcgc gctggagcaa aacccaaata    11820
gcaagccgct catggcgcag ctgttcctta tagtgcagca cagcagggac aacgaggcat    11880
tcagggatgc gctgctaaac atagtagagc ccgagggccg ctggctgctc gatttgataa    11940
acatcctgca gagcatagtg gtgcaggagc gcagcttgag cctggctgac aaggtggccg    12000
ccatcaacta ttccatgctt agcctgggca agtttttacgc ccgcaagata taccatacccc    12060 cttacgttcc catagacaag gaggtaaaga tcgaggggtt ctacatgcgc atggcgctga    12120
aggtgcttac cttgagcgac gacctgggcg tttatcgcaa cgagcgcatc cacaaggccg    12180
tgagcgtgag ccggcggcgc gagctcagcg accgcgagct gatgcacagc ctgcaaaggg    12240
ccctggctgg cacgggcagc ggcgatagag aggccgagtc ctactttgac gcgggcgctg    12300
acctgcgctg ggccccaagc cgacgcgccc tggaggcagc tggggccgga cctgggctgg    12360
cggtggcacc cgcgcgcgct ggcaacgtcg gcggcgtgga ggaatatgac gaggacgatg    12420
agtacgagcc agaggacggc gagtactaag cggtgatgtt tctgatcaga tgatgcaaga    12480
cgcaacggac ccggcggtgc gggcggcgct gcagagccag ccgtccggcc ttaactccac    12540
ggacgactgg cgccaggtca tggaccgcat catgtcgctg actgcgcgca atcctgacgc    12600
gttccggcag cagccgcagg ccaaccggct ctccgcaatt ctggaagcgg tggtcccggc    12660
gcgcgcaaac cccacgcacg agaaggtgct ggcgatcgta aacgcgctgg ccgaaaacag    12720
ggccatccgg cccgacgagg ccggcctggt ctacgacgcg ctgcttcagc gcgtggctcg    12780
ttacaacagc ggcaacgtgc agaccaacct ggaccggctg gtgggggatg tgcgcgaggc    12840
cgtggcgcag cgtgagcgcg cgcagcagca gggcaacctg ggctccatgg ttgcactaaa    12900
cgccttcctg agtacacagc ccgccaacgt gccgcgggga caggaggact acaccaactt    12960
```

```
tgtgagcgca ctgcggctaa tggtgactga gacaccgcaa agtgaggtgt accagtctgg   13020
gccagactat ttttttccaga ccagtagaca aggcctgcag accgtaaacc tgagccaggc   13080
tttcaaaaac ttgcagggggc tgtgggggggt gcgggctccc acaggcgacc gcgcgaccgt   13140
gtctagcttg ctgacgccca actcgcgcct gttgctgctg ctaatagcgc ccttcacgga   13200
cagtggcagc gtgtcccggg acacatacct aggtcacttg ctgacactgt accgcgaggc   13260
cataggtcag gcgcatgtgg acgagcatac tttccaggag attacaagtg tcagccgcgc   13320
gctggggcag gaggacacgg gcagcctgga ggcaaccta aactacctgc tgaccaaccg   13380
gcggcagaag atcccctcgt tgcacagttt aaacagcgag gaggagcgca ttttgcgcta   13440
cgtgcagcag agcgtgagcc ttaacctgat gcgcgacggg gtaacgccca gcgtggcgct   13500
ggacatgacc gcgcgcaaca tggaaccggg catgtatgcc tcaaaccggc cgtttatcaa   13560
ccgcctaatg gactacttgc atcgcgcggc cgccgtgaac cccgagtatt tcaccaatgc   13620
catcttgaac ccgcactggc taccgccccc tggtttctac accgggggat tcgaggtgcc   13680
cgagggtaac gatggattcc tctgggacga catagacgca agcgtgtttt ccccgcaacc   13740
gcagaccctg ctagagttgc aacagcgcga gcaggcagag gcggcgctgc gaaaggaaag   13800
cttccgcagg ccaagcagct tgtccgatct aggcgctgcg gccccgcggt cagatgctag   13860
tagcccattt ccaagcttga tagggtctct taccagcact cgcaccaccc gcccgcgcct   13920
gctgggcgag gaggagtacc taaacaactc gctgctgcag ccgcagcgcg aaaaaaacct   13980
gcctccggca tttcccaaca acgggataga gagcctagtg gacaagatga gtagatggaa   14040
gacgtacgcg caggagcaca gggacgtgcc aggcccgcgc ccgcccaccc gtcgtcaaag   14100
gcacgaccgt cagcggggtc tggtgtggga ggacgatgac tcggcagacg acagcagcgt   14160
cctggatttg ggagggagtg gcaacccgtt tgcgcacctt cgccccaggc tggggagaat   14220
gttttaaaaa aaaaaaagca tgatgcaaaa taaaaaactc accaaggcca tggcaccgag   14280
cgttggtttt cttgtattcc ccttagtatg cggcgcgcgg cgatgtatga ggaaggtcct   14340
cctccctcct acgagagtgt ggtgagcgcg gcgccagtgg cggcggcgct gggttctccc   14400
ttcgatgctc ccctggaccc gccgtttgtg cctccgcgt acctgcggcc taccgggggg   14460
agaaacagca tccgttactc tgagttggca cccctattcg acaccacccg tgtgtacctg   14520
gtggacaaca agtcaacgga tgtggcatcc ctgaactacc agaacgacca cagcaacttt   14580
ctgaccacgg tcattcaaaa caatgactac agcccggggg aggcaagcac acagaccatc   14640
aatcttgacg accggtcgca ctggggcggc gacctgaaaa ccatcctgca taccaacatg   14700
ccaaatgtga acgagttcat gtttaccaat aagtttaagg cgcgggtgat ggtgtcgcgc   14760
ttgcctacta aggacaatca ggtggagctg aaatacgagt gggtggagtt cacgctgccc   14820
gagggcaact actccgagac catgaccata gaccttatga acaacgcgat cgtggagcac   14880
tacttgaaag tgggcagaca gaacgggggtt ctggaaagcg catcgggggt aaagtttgac   14940
acccgcaact tcagactggg gtttgacccc gtcactggtc ttgtcatgcc tggggtatat   15000
acaaacgaag ccttccatcc agacatcatt ttgctgccag gatgcggggt ggacttcacc   15060
cacagccgcc tgagcaactt gttgggcatc cgcaagcggc aacccttcca ggagggcttt   15120
aggatcacct acgatgatct ggagggtggt aacattcccg cactgttgga tgtggacgcc   15180
taccaggcga gcttgaaaga tgacaccgaa cagggcgggg gtggcgcagg cggcagcaac   15240
agcagtggca gcgcgcgcgga agagaactcc aacgcggcag ccgcggcaat gcagccggtg   15300
gaggacatga acgatcatgc cattcgcggc gacacctttg ccacacgggc tgaggagaag   15360
```

```
cgcgctgagg ccgaagcagc ggccgaagct gccgccccg  ctgcgcaacc cgaggtcgag    15420
aagcctcaga agaaaccggt gatcaaaccc ctgacagagg acagcaagaa acgcagttac    15480
aacctaataa gcaatgacag caccttcacc cagtaccgca gctggtacct tgcatacaac    15540 tacgcgacc  ctcagaccgg aatccgctca tggaccctgc tttgcactcc tgacgtaacc    15600
tgcggctcgg agcaggtcta ctggtcgttg ccagacatga tgcaagaccc cgtgaccttc    15660
cgctccacgc gccagatcag caactttccg gtggtgggcg ccgagctgtt gcccgtgcac    15720
tccaagagct tctacaacga ccaggccgtc tactcccaac tcatccgcca gtttacctct    15780
ctgacccacg tgttcaatcg ctttcccgag aaccagattt ggcgcgccc  gccagccccc    15840 accatcacca ccgtcagtga aaacgttcct gctctcacag atcacgggac gctaccgctg    15900
cgcaacagca tcggaggagt ccagcgagtg accattactg acgccagacg ccgcacctgc    15960
ccctacgttt acaaggccct gggcatagtc tcgccgcgcg tcctatcgag ccgcactttt    16020
tgagcaagca tgtccatcct tatatcgccc agcaataaca caggctgggg cctgcgcttc    16080
ccaagcaaga tgtttggcgg ggccaagaag cgctccgacc aacacccagt gcgcgtgcgc    16140
gggcactacc gcgcgccctg gggcgcgcac aaacgcggcc gcactgggcg caccaccgtc    16200
gatgacgcca tcgacgcggt ggtggaggag gcgcgcaact acacgcccac gccgccacca    16260
gtgtccacag tggacgcggc cattcagacc gtggtgcgcg gagcccggcg ctatgctaaa    16320
atgaagagac ggcggaggcg cgtagcacgt cgccaccgcc gccgacccgg cactgccgcc    16380
caacgcgcgg cggcggccct gcttaaccgc gcacgtcgca ccggccgacg ggcggccatg    16440
cgggccgctc gaaggctggc cgcgggtatt gtcactgtgc ccccaggtc  caggcgacga    16500 gcggccgccg cagcagccgc ggccattagt gctatgactc agggtcgcag gggcaacgtg    16560
tattgggtgc gcgactcggt tagcggcctg cgcgtgcccg tgcgcacccg ccccccgcgc    16620
aactagattg caagaaaaaa ctacttagac tcgtactgtt gtatgtatcc agcggcggcg    16680
gcgcgcaacg aagctatgtc caagcgcaaa atcaaagaag gatgctcca  ggtcatcgcg    16740 ccggagatct atggccccc  gaagaaggaa gagcaggatt acaagccccg aaagctaaag    16800
cgggtcaaaa agaaaagaa  agatgatgat gatgaacttg acgacgaggt ggaactgctg    16860
cacgctaccg cgcccaggcg acgggtacag tggaaaggtc gacgcgtaaa acgtgttttg    16920 cgaccccggca ccaccgtagt ctttacgccc ggtgagcgct ccacccgcac ctacaagcgc    16980
gtgtatgatg aggtgtacgg cgacgaggac ctgcttgagc aggccaacga gcgcctcggg    17040
gagtttgcct acgaaagcg  gcataaggac atgctggcgt tgccgctgga cgagggcaac    17100
ccaacaccta gcctaaagcc cgtaacactg cagcaggtgc tgcccgcgct tgcaccgtcc    17160
gaagaaaagc gcggcctaaa gcgcgagtct ggtgacttgg cacccaccgt gcagctgatg    17220
gtacccaagc gccagcgact ggaagatgtc ttggaaaaaa tgaccgtgga acctgggctg    17280
gagcccgagg tccgcgtgcg gccaatcaag caggtggcgc cggactggg  cgtgcagacc    17340 gtggacgttc agatacccac taccagtagc accagtattg ccaccgccac agagggcatg    17400
gagacacaaa cgtccccggt tgcctcagcg gtggcggatg ccgcggtgca ggcggtcgct    17460
gcggccgcgt ccaagacctc tacggagtg  caaacgacc  cgtggatgtt tcgcgtttca    17520
gccccccggc gcccgcgcgg ttcgaggaag tacggcgccg ccagcgcgct actgcccgaa    17580
tatgccctac atccttccat tgcgcctacc ccggctatc  gtggctacac ctaccgcccc    17640
agaagacgag caactacccg acgccgaacc accactggaa cccgccgccg ccgtcgccgt    17700
```

```
cgccagcccg tgctggcccc gatttccgtg cgcagggtgg ctcgcgaagg aggcaggacc   17760
ctggtgctgc caacagcgcg ctaccacccc agcatcgttt aaaagccggt ctttgtggtt   17820
cttgcagata tggccctcac ctgccgcctc cgtttcccgg tgccgggatt ccgaggaaga   17880
atgcaccgta ggaggggcat ggccggccac ggcctgacgg gcggcatgcg tcgtgcgcac   17940
caccggcggc ggcgcgcgtc gcaccgtcgc atgcgcggcg gtatcctgcc cctccttatt   18000
ccactgatcg ccgcggcgat tggcgccgtg cccggaattg catccgtggc cttgcaggcg   18060
cagagacact gattaaaaac aagttgcatg tggaaaaatc aaaataaaaa gtctggactc   18120
tcacgctcgc ttggtcctgt aactattttg tagaatggaa gacatcaact ttgcgtctct   18180
ggccccgcga cacggctcgc gcccgttcat gggaaactgg caagatatcg gcaccagcaa   18240
tatgagcggt ggcgccttca gctgggctc gctgtggagc ggcattaaaa atttcggttc   18300
caccgttaag aactatggca gcaaggcctg gaacagcagc acaggccaga tgctgaggga   18360
taagttgaaa gagcaaaatt tccaacaaaa ggtggtagat ggcctggcct ctggcattag   18420
cggggtggtg gacctggcca accaggcagt gcaaaataag attaacagta agcttgatcc   18480
ccgccctccc gtagaggagc ctccaccggc cgtggagaca gtgtctccag aggggcgtgg   18540
cgaaaagcgt ccgcgccccg acagggaaga aactctggtg acgcaaatag acgagcctcc   18600
ctcgtacgag gaggcactaa agcaaggcct gcccaccacc cgtcccatcg cgcccatggc   18660
taccggagtg ctgggccagc acacaccccgt aacgctggac ctgcctcccc ccgccgacac   18720
ccagcagaaa cctgtgctgc caggcccgac cgccgttgtt gtaacccgtc ctagccgcgc   18780
gtccctgcgc cgcgccgcca gcggtccgcg atcgttgcgg cccgtagcca gtggcaactg   18840
gcaaagcaca ctgaacagca tcgtgggtct gggggtgcaa tccctgaagc gccgacgatg   18900
cttctgaata gctaacgtgt cgtatgtgtg tcatgtatgc gtccatgtcg ccgccagagg   18960
agctgctgag ccgccgcgcg cccgctttcc aagatggcta ccccttcgat gatgccgcag   19020
tggtcttaca tgcacatctc gggccaggac gcctcggagt acctgagccc cgggctggtg   19080
cagtttgccc gcgccaccga dacgtacttc agcctgaata acaagtttag aaaccccacg   19140
gtggcgccta cgcacgacgt gaccacagac cggtcccagc gtttgacgct gcggttcatc   19200
cctgtggacc gtgaggatac tgcgtactcg tacaaggcgc ggttcacccct agctgtgggt   19260 gataaccgtg tgctggacat ggcttccacg tactttgaca tccgcggcgt gctggacagg   19320
ggccctactt ttaagcccta ctctggcact gcctacaacg ccctggctcc caagggtgcc   19380
ccaaatcctt gcgaatggga tgaagctgct actgctcttg aaataaacct agaagaagag   19440
gacgatgaca acgaagacga agtagacgag caagctgagc agcaaaaaac tcacgtattt   19500
gggcaggcgc cttattctgg tataaatatt acaaaggagg gtattcaaat aggtgtcgaa   19560
ggtcaaacac ctaaatatgc cgataaaaca tttcaacctg aacctcaaat aggagaatct   19620
cagtggtacg aaactgaaat taatcatgca gctgggagag tccttaaaaa gactacccca   19680
atgaaaccat gttacggttc atatgcaaaa cccacaaatg aaaatggagg caaggcatt   19740 cttgtaaagc aacaaatgg aaagctagaa agtcaagtgg aaatgcaatt tttctcaact   19800
actgaggcga ccgcaggcaa tggtgataac ttgactccta aagtggtatt gtacagtgaa   19860
gatgtagata tagaaacccc agacactcat atttcttaca tgcccactat taggaaggt   19920 aactcacgag aactaatggg ccaacaatct atgcccaaca ggcctaatta cattgctttt   19980
agggacaatt ttattggtct aatgtattac aacagcacgg gtaatatggg tgttctggcg   20040
ggccaagcat cgcagttgaa tgctgttgta gatttgcaag acagaaacac agagctttca   20100
```

```
taccagctttt tgcttgattc cattggtgat agaaccaggt acttttctat gtggaatcag    20160
gctgttgaca gctatgatcc agatgttaga attattgaaa atcatggaac tgaagatgaa    20220
cttccaaatt actgctttcc actgggaggt gtgattaata cagagactct taccaaggta    20280
aaacctaaaa caggtcagga aaatggatgg gaaaaagatg ctacagaatt ttcagataaa    20340
aatgaaataa gagttggaaa taattttgcc atggaaatca atctaaatgc caacctgtgg    20400
agaaatttcc tgtactccaa catagcgctg tatttgcccg acaagctaaa gtacagtcct    20460
tccaacgtaa aaatttctga taacccaaac acctacgact acatgaacaa gcgagtggtg    20520
gctcccgggt tagtggactg ctacattaac cttggagcac gctggtccct tgactatatg    20580
gacaacgtca acccatttaa ccaccaccgc aatgctggcc tgcgctaccg ctcaatgttg    20640
ctgggcaatg gtcgctatgt gcccttccac atccaggtgc ctcagaagtt ctttgccatt    20700
aaaaacctcc ttctcctgcc gggctcatac acctacgagt ggaacttcag gaaggatgtt    20760
aacatggttc tgcagagctc cctaggaaat gacctaaggg ttgacggagc cagcattaag    20820
tttgatagca tttgccttta cgccaccttc ttccccatgg cccacaacac cgcctccacg    20880
cttgaggcca tgcttagaaa cgacaccaac gaccagtcct ttaacgacta tctctccgcc    20940
gccaacatgc tctaccctat acccgccaac gctaccaacg tgcccatatc catcccctcc    21000
cgcaactggg cggctttccg cggctgggcc ttcacgcgcc ttaagactaa ggaaacccca    21060
tcactgggct cgggctacga cccttattac acctactctg gctctatacc ctacctagat    21120 ggaaccttt acctcaacca cacctttaag aaggtggcca ttacctttga ctcttctgtc    21180
agctggcctg gcaatgaccg cctgcttacc cccaacgagt ttgaaattaa gcgctcagtt    21240
gacggggagg gttacaacgt tgcccagtgt aacatgacca aagactggtt cctggtacaa    21300
atgctagcta actacaacat tggctaccag ggcttctata tcccagagag ctacaaggac    21360
cgcatgtact ccttctttag aaacttccag cccatgagcc gtcaggtggt ggatgatact    21420
aaatacaagg actaccaaca ggtgggcatc ctacaccaac acaacaactc tggatttgtt    21480
ggctaccttg cccccaccat gcgcgaagga caggcctacc ctgctaactt cccctatccg    21540
cttataggca agaccgcagt tgacagcatt acccagaaaa agtttcttg cgatcgcacc    21600 ctttggcgca tcccattctc cagtaacttt atgtccatgg gcgcactcac agacctgggc    21660
caaaaccttc tctacgccaa ctccgcccac gcgctagaca tgactttga ggtggatccc    21720 atggacgagc ccaccttct ttatgttttg tttgaagtct tgacgtggt ccgtgtgcac    21780 cggccgcacc gcggcgtcat cgaaaccgtg tacctgcgca cgcccttctc ggccggcaac    21840
gccacaacat aaagaagcaa gcaacatcaa caacagctgc cgccatgggc tccagtgagc    21900
aggaactgaa agccattgtc aaagatcttg ttgtgtgggc atattttttg ggcacctatg    21960
acaagcgctt tccaggcttt gtttctccac acaagctcgc ctgcgccata gtcaatacgg    22020
ccggtcgcga gactggggc gtacactgga tggcctttgc ctggaacccg cactcaaaaa    22080
catgctacct ctttgagccc tttggctttt ctgaccagcg actcaagcag gtttaccagt    22140
ttgagtacga gtcactcctg cgccgtagcg ccattgcttc ttcccccgac cgctgtataa    22200
cgctggaaaa gtcacccaa agcgtacagg ggcccaactc ggccgcctgt ggactattct    22260
gctgcatgtt tctccacgcc tttgccaact ggccccaaac tcccatggat cacaaccca    22320 ccatgaacct tattaccggg gtacccaact ccatgctcaa cagtccccag gtacagccca    22380
ccctgcgtcg caaccaggaa cagctctaca gcttcctgga gcgccactcg ccctacttcc    22440
```

```
gcagccacag tgcgcagatt aggagcgcca cttctttttg tcacttgaaa aacatgtaaa    22500
aataatgtac tagagacact ttcaataaag gcaaatgctt ttatttgtac actctcgggt    22560
gattatttac ccccacccct tgccgtctgcg ccgtttaaaa atcaaagggg ttctgccgcg    22620
catcgctatg cgccactggc agggacacgt tgcgatactg gtgtttagtg ctccacttaa    22680
actcaggcac aaccatccgc ggcagctcgg tgaagttttc actccacagg ctgcgcacca    22740
tcaccaacgc gtttagcagg tcgggcgccg atatcttgaa gtcgcagttg ggcctccgc    22800 cctgcgcgcg cgagttgcga tacacagggt tgcagcactg gaacactatc agcgccgggt    22860
ggtgcacgct ggccagcacg ctcttgtcgg agatcagatc cgcgtccagg tcctccgcgt    22920
tgctcagggc gaacggagtc aactttggta gctgccttcc caaaagggc gcgtgcccag    22980 gctttgagtt gcactcgcac cgtagtggca tcaaaaggtg accgtgcccg gtctgggcgt    23040
taggatacag cgcctgcata aaagccttga tctgcttaaa agccacctga gcctttgcgc    23100
cttcagagaa gaacatgccg caagacttgc cggaaaactg attggccgga caggccgcgt    23160
cgtgcacgca gcaccttgcg tcggtgttgg agatctgcac cacatttcgg ccccaccggt    23220
tcttcacgat cttggccttg ctagactgct ccttcagcgc gcgctgcccg ttttcgctcg    23280
tcacatccat ttcaatcacg tgctcctat ttatcataat gcttccgtgt agacacttaa    23340
gctcgccttc gatctcagcg cagcggtgca gccacaacgc gcagcccgtg ggctcgtgat    23400
gcttgtaggt cacctctgca aacgactgca ggtacgcctg caggaatcgc ccatcatcg    23460 tcacaaaggt cttgttgctg gtgaaggtca gctgcaaccc gcggtgctcc tcgttcagcc    23520
aggtcttgca tacggccgcc agagcttcca cttggtcagg cagtagtttg aagttcgcct    23580
ttagatcgtt atccacgtgg tacttgtcca tcagcgcgcg cgcagcctcc atgcccttct    23640
cccacgcaga cacgatcggc acactcagcg ggttcatcac cgtaatttca ctttccgctt    23700
cgctgggctc ttcctcttcc tcttgcgtcc gcataccacg cgccactggg tcgtcttcat    23760
tcagccgccg cactgtgcgc ttacctcctt tgccatgctt gattagcacc ggtgggttgc    23820
tgaaacccac catttgtagc gccacatctt ctctttcttc ctcgctgtcc acgattacct    23880
ctggtgatgg cgggcgctcg ggcttgggag aagggcgctt cttttttcttc ttgggcgcaa    23940 tggccaaatc cgccgccgag gtcgatggcc gcgggctggg tgtgcgcggc accagcgcgt    24000
cttgtgatga gtcttcctcg tcctcggact cgatacgccg cctcatccgc tttttttgggg    24060 gcgcccgggg aggcggcggc gacggggacg gggacgacac gtcctccatg gttgggggac    24120
gtcgcgccgc accgcgtccg cgctcggggg tggtttcgcg ctgctcctct tcccgactgg    24180
ccatttcctt ctcctatagg cagaaaaaga tcatggagtc agtcgagaag aaggacagcc    24240
taaccgcccc ctctgagttc gccaccaccg cctccaccga tgccgccaac gcgcctacca    24300
ccttccccgt cgaggcaccc ccgcttgagg aggaggaagt gattatcgag caggacccag    24360
gttttgtaag cgaagacgac gaggaccgct cagtaccaac agaggataaa aagcaagacc    24420
aggacaacgc agaggcaaac gaggaacaag tcgggcgggg ggacgaaagg catggcgact    24480
acctagatgt gggagacgac gtgctgttga agcatctgca gcgccagtgc gccattatct    24540
gcgacgcgtt gcaagagcgc agcgatgtgc ccctcgccat agcggatgtc agccttgcct    24600
acgaacgcca cctattctca ccgcgcgtac cccccaaacg ccaagaaaac ggcacatgcg    24660
agcccaaccc gcgcctcaac ttctaccccg tatttgccgt gccagaggtg cttgccacct    24720
atcacatctt tttccaaaac tgcaagatac ccctatcctg ccgtgccaac cgcagccgag    24780
cggacaagca gctggccttg cggcagggcg ctgtcatacc tgatatcgcc tcgctcaacg    24840
```

```
aagtgccaaa aatctttgag ggtcttggac gcgacgagaa gcgcgcggca aacgctctgc   24900
aacaggaaaa cagcgaaaat gaaagtcact ctggagtgtt ggtggaactc gagggtgaca   24960
acgcgcgcct agccgtacta aaacgcagca tcgaggtcac ccactttgcc tacccggcac   25020
ttaacctacc cccaaggtc atgagcacag tcatgagtga gctgatcgtg cgccgtcgcg    25080
agcccctgga gagggatgca aatttgcaag aacaaacaga ggagggccta cccgcagttg   25140
gcgacgagca gctagcgcgc tggcttcaaa cgcgcgagcc tgccgacttg gaggagcgac   25200
gcaaactaat gatggccgca gtgctcgtta ccgtggagct tgagtgcatg cagcggttct   25260
ttgctgaccc ggagatgcag cgcaagctag aggaaacatt gcactacacc tttcgacagg   25320
gctacgtacg ccaggcctgc aagatctcca acgtggagct ctgcaacctg gtctcctacc   25380
ttggaatttt gcacgaaaac cgccttgggc aaaacgtgct tcattccacg ctcaagggcg   25440
aggcgcgccg cgactacgtc cgcgactgcg tttacttatt tctatgctac acctggcaga   25500
cggccatggg cgtttggcag cagtgcttgg aggagtgcaa cctcaaggag ctgcagaaac   25560
tgctaaagca aaacttgaag gacctatgga cggccttcaa cgagcgctcc gtggccgcgc   25620
acctggcgga catcattttc cccgaacgcc tgcttaaaac cctgcaacag gtctgccag   25680 acttcaccag tcaaagcatg ttgcagaact ttaggaactt tatcctagag cgctcaggaa   25740
tcttgcccgc cacctgctgt gcacttccta gcgactttgt gcccattaag taccgcgaat   25800
gccctccgcc gctttggggc cactgctacc ttctgcagct agccaactac cttgcctacc   25860
actctgacat aatggaagac gtgagcggtg acggtctact ggagtgtcac tgtcgctgca   25920
acctatgcac cccgcaccgc tccctggttt gcaattcgca gctgcttaac gaaagtcaaa   25980
ttatcggtac ctttgagctg cagggtccct cgcctgacga aaagtccgcg gctccggggt   26040
tgaaactcac tccggggctg tggacgtcgg cttaccttcg caaatttgta cctgaggact   26100
accacgccca cgagattagg ttctacgaag accaatcccg cccgccaaat gcggagctta   26160
ccgcctgcgt cattacccag ggccacattc ttggccaatt gcaagccatc aacaaagccc   26220
gccaagagtt tctgctacga aagggacggg gggtttactt ggaccccag tccggcgagg    26280 agctcaaccc aatccccccg ccgccgcagc cctatcagca gcagccgcgg gcccttgctt   26340
cccaggatgg cacccaaaaa gaagctgcag ctgccgccgc cacccacgga cgaggaggaa   26400
tactgggaca gtcaggcaga ggaggttttg gacgaggagg aggaggacat gatggaagac   26460
tgggagagcc tagacgagga agcttccgag gtcgaagagg tgtcagacga aacaccgtca   26520
ccctcggtcg cattcccctc gccggcgccc cagaaatcgg caaccggttc cagcatggct   26580
acaacctccg ctcctcaggc gccgccggca ctgcccgttc gccgacccaa ccgtagatgg   26640
gacaccactg gaaccagggc cggtaagtcc aagcagccgc cgccgttagc caagagcaa    26700 caacagcgcc aaggctaccg ctcatggcgc gggcacaaga acgccatagt tgcttgcttg   26760
caagactgtg ggggcaacat ctccttcgcc cgccgctttc ttctctacca tcacggcgtg   26820
gccttccccc gtaacatcct gcattactac cgtcatctct acagcccata ctgcaccggc   26880
ggcagcggca gcggcagcaa cagcagcggc cacacagaag caaaggcgac cggatagcaa   26940
gactctgaca aagcccaaga aatccacagc ggcggcagca gcaggaggag gagcgctgcg   27000
tctggcgccc aacgaacccg tatcgacccg cgagcttaga aacaggattt ttcccactct   27060
gtatgctata tttcaacaga gcaggggcca agaacaagag ctgaaaataa aaacaggtc    27120 tctgcgatcc ctcacccgca gctgcctgta tcacaaaagc gaagatcagc ttcggcgcac   27180
```

```
gctggaagac gcggaggctc tcttcagtaa atactgcgcg ctgactctta aggactagtt    27240
tcgcgccctt tctcaaattt aagcgcgaaa actacgtcat ctccagcggc cacacccggc    27300
gccagcacct gtcgtcagcg ccattatgag caaggaaatt cccacgccct acatgtggag    27360
ttaccagcca caaatgggac ttgcggctgg agctgcccaa gactactcaa cccgaataaa    27420
ctacatgagc gcgggacccc acatgatatc ccgggtcaac ggaatccgcg cccaccgaaa    27480
ccgaattctc ttggaacagg cggctattac caccacacct cgtaataacc ttaatccccg    27540
tagttggccc gctgccctgg tgtaccagga aagtcccgct cccaccactg tggtacttcc    27600
cagagacgcc caggccgaag ttcagatgac taactcaggg gcgcagcttg cgggcggctt    27660
tcgtcacagg gtgcggtcgc ccgggcaggg tataactcac ctgacaatca gagggcgagg    27720
tattcagctc aacgacgagt cggtgagctc ctcgcttggt ctccgtccgg acgggacatt    27780
tcagatcggc ggcgccggcc gtccttcatt cacgcctcgt caggcaatcc taactctgca    27840
gacctcgtcc tctgagccgc gctctggagg cattggaact ctgcaattta ttgaggagtt    27900
tgtgccatcg gtctacttta acccttctc gggacctccc ggccactatc cggatcaatt    27960
tattcctaac tttgacgcgg taaaggactc ggcggacggc tacgactgaa tgttaagtgg    28020
agaggcagag caactgcgcc tgaaacacct ggtccactgt cgccgccaca agtgctttgc    28080
ccgcgactcc ggtgagtttt gctactttga attgcccgag gatcatatcg agggcccggc    28140
gcacggcgtc cggcttaccg cccagggaga gcttgcccgt agcctgattc gggagtttac    28200
ccagcgcccc ctgctagttg agcgggacag gggaccctgt gttctcactg tgatttgcaa    28260
ctgtcctaac cttggattac atcaagatcc tctagtttata actagagtac ccggggatct    28320
tattcccttt aactaataaa aaaaaataat aaagcatcac ttacttaaaa tcagttagca    28380
aatttctgtc cagtttattc agcagcacct ccttgccctc ctcccagctc tggtattgca    28440
gcttcctcct ggctgcaaac tttctccaca atctaaatgg aatgtcagtt tcctcctgtt    28500
cctgtccatc cgcacccacc ggtataactt cgtatatgtt tcttatacg aacggtagat    28560
ctatatctat gatctcgcag tctccggcga gcaccggagg cagggcattg ccaccgcgct    28620
catcaatctc ctcaagcatg aggccaacgc gcttggtgct tatgtgatct acgtgcaagc    28680
agattacggt gacgatcccg cagtggctct ctatacaaag ttgggcatac gggaagaagt    28740
gatgcacttt gatatcgacc caagtaccgc cacctaacaa ttcgttcaag ccagatcgg    28800
cttcccggcc gcggagttgt tcggtaaatt gtcacaacgc cgcggccatc ggcattttct    28860
tttgcgtttt tatttgttaa ctgttaattg tccttgttca aggatgctgt ctttgacaac    28920
agatgttttc ttgcctttga tgttcagcag gaagcttggc gcaaacgttg attgtttgtc    28980
tgcgtagaat cctctgtttg tcatatagct tgtaatcacc acgacattgt ttcctttcgc    29040
ttgaggtaca gcgaagtgtg agtaagtaaa ggttacatcg ttaggatcaa gatccatttt    29100
taacacaagg ccagttttgt tcagcggctt gtatgggcca gttaaagaat tagaaacata    29160
accaagcatg taaatatcgt tagacgaaat gccgtcaatc gtcattttg atccgcggga    29220
gtcagtgaac aggtaccatt tgccgttcat tttaaagacg ttcgcgcgtt caatttcatc    29280
tgttactgtg ttagatgcaa tcagcggttt catcacttt ttcagtgtgt aatcatcgtt    29340
tagctcaatc ataccgagag cgccgttttgc taactcagcc gtgcgttttt tatcgctttg    29400
cagaagtttt tgactttctt gacggaagaa tgatgtgctt ttgccatagt atgctttgtt    29460
aaataaagat tcttcgcctt ggtagccatc ttcagttcca gtgtttgctt caaatactaa    29520
gtatttgtgg cctttatctt ctacgtagtg aggatctctc agcgtatggt tgtcgcctga    29580
```

```
gctgtagttg ccttcatcga tgaactgctg tacattttga tacgtttttc cgtcaccgtc   29640
aaagattgat ttataatcct ctacaccgtt gatgttcaaa gagctgtctg atgctgatac   29700
gttaacttgt gcagttgtca gtgtttgttt gccgtaatgt ttaccggaga atcagtgta    29760 gaataaacgg attttttccgt cagatgtaaa tgtggctgaa cctgaccatt cttgtgtttg  29820
gtcttttagg atagaatcat ttgcatcgaa tttgtcgctg tctttaaaga cgcggccagc   29880 gttttttccag ctgtcaatag aagtttcgcc gactttttga tagaacatgt aaatcgatgt  29940
gtcatccgca ttttttaggat ctccggctaa tgcaaagacg atgtggtagc cgcgatagtt  30000
tgcgacagtg ccgtcagcgt tttgtaatgg ccagctgtcc caaacgtcca ggccttttgc   30060
agaagagata tttttaattg tggacgaatc gaattcagga acttgatatt tttcatttttt  30120 ttgctgttca gggatttgca gcatatcatg gcgtgtaata tgggaaatgc cgtatgtttc   30180
cttatatggc ttttggttcg tttctttcgc aaacgcttga gttgcgcctc ctgccagcag   30240
tgcggtagta aaggttaata ctgttgcttg ttttgcaaac ttttttgatgt tcatcgttca   30300 tgtctccttt tttatgtact gtgttagcgg tctgcttctt ccagccctcc tgtttgaaga   30360
tggcaagtta gttacgcaca ataaaaaaag acctaaaata tgtaagggggt gacgccaaag   30420 tatacacttt gccctttaca cattttaggt cttgcctgct ttatcagtaa caaacccgcg   30480
cgatttactt ttcgacctca ttctattaga ctctcgtttg gattgcaact ggtctatttt   30540
cctcttttgt ttgatagaaa atcataaaag gatttgcaga ctacgggcct aaagaactaa   30600
aaaatctatc tgtttctttt cattctctgt atttttttata gtttctgttg catgggcata   30660
aagttgcctt tttaatcaca attcagaaaa tatcataata tctcatttca ctaaataata   30720
gtgaacggca ggtatatgtg atgggttaaa aaggatcgat cctctagcta gagtcgatcg   30780
taccgttcgt atagcataca ttatacgaag ttataccggt atacattgcc caagaataaa   30840
gaatcgtttg tgttatgttt caacgtgttt attttttcaat tgcagaaaat ttcaagtcat   30900
ttttcattca gtagtatagc cccaccacca catagcttat acagatcacc gtaccttaat   30960
caaactcaca gaaccctagt attcaacctg ccacctccct cccaacacac agagtacaca   31020 gtccttttctc cccggctggc cttaaaaagc atcatatcat gggtaacaga catattctta   31080
ggtgttatat tccacacggt ttcctgtcga gccaaacgct catcagtgat attaataaac   31140
tccccgggca gctcacttaa gttcatgtcg ctgtccagct gctgagccac aggctgctgt   31200
ccaacttgcg gttgcttaac gggcggcgaa ggagaagtcc acgcctacat gggggtagag   31260
tcataatcgt gcatcaggat agggcggtgg tgctgcagca gcgcgcgaat aaactgctgc   31320
cgccgccgct ccgtcctgca ggaatacaac atggcagtgg tctcctcagc gatgattcgc   31380
accgcccgca gcataaggcg ccttgtcctc cgggcacagc agcgcaccct gatctcactt   31440
aaatcagcac agtaactgca gcacagcacc acaatattgt tcaaaatccc acagtgcaag   31500
gcgctgtatc caaagctcat ggcggggacc acagaaccca cgtggccatc ataccacaag   31560
cgcaggtaga ttaagtggcg acccctcata acacgctgg acataaacat tacctctttt    31620
ggcatgttgt aattcaccac ctcccggtac catataaacc tctgattaaa catggcgcca   31680
tccaccacca tcctaaacca gctggccaaa acctgcccgc cggctataca ctgcagggaa   31740
ccgggactgg aacaatgaca gtggagagcc caggactcgt aaccatggat catcatgctc   31800
gtcatgatat caatgttggc acaacacagg cacacgtgca tacacttcct caggattaca   31860
agctcctccc gcgttagaac catatcccag ggaacaaccc attcctgaat cagcgtaaat   31920
```

```
cccacactgc agggaagacc tcgcacgtaa ctcacgttgt gcattgtcaa agtgttacat   31980
tcgggcagca gcggatgatc ctccagtatg gtagcgcggg tttctgtctc aaaaggaggt   32040
agacgatccc tactgtacgg agtgcgccga gacaaccgag atcgtgttgg tcgtagtgtc   32100
atgccaaatg gaacgccgga cgtagtcata tttcctgaag caaaaccagg tgcgggcgtg   32160
acaaacagat ctgcgtctcc ggtctcgccg cttagatcgc tctgtgtagt agttgtagta   32220
tatccactct ctcaaagcat ccaggcgccc cctggcttcg ggttctatgt aaactccttc   32280
atgcgccgct gccctgataa catccaccac cgcagaataa gccacaccca gccaacctac   32340
acattcgttc tgcgagtcac acacgggagg agcgggaaga gctggaagaa ccatgttttt   32400 tttttttattc caaaagatta tccaaaacct caaaatgaag atctattaag tgaacgcgct   32460
cccctccggt ggcgtggtca aactctacag ccaaagaaca gataatggca tttgtaagat   32520
gttgcacaat ggcttccaaa aggcaaacgg ccctcacgtc caagtggacg taaaggctaa   32580
acccttcagg gtgaatctcc tctataaaca ttccagcacc ttcaaccatg cccaaataat   32640
tctcatctcg ccaccttctc aatatatctc taagcaaatc ccgaatatta agtccggcca   32700
ttgtaaaaat ctgctccaga gcgccctcca ccttcagcct caagcagcga atcatgattg   32760
caaaaattca ggttcctcac agacctgtat aagattcaaa agcggaacat taacaaaaat   32820
accgcgatcc cgtaggtccc ttcgcagggc cagctgaaca taatcgtgca ggtctgcacg   32880
gaccagcgcg gccacttccc cgccaggaac cttgacaaaa gaacccacac tgattatgac   32940
acgcatactc ggagctatgc taaccagcgt agccccgatg taagctttgt tgcatgggcg   33000
gcgatataaa atgcaaggtg ctgctcaaaa aatcaggcaa agcctcgcgc aaaaaagaaa   33060
gcacatcgta gtcatgctca tgcagataaa ggcaggtaag ctccggaacc accacagaaa   33120 aagcaccat ttttctctca aacatgtctg cgggtttctg cataaacaca aaataaaata   33180
acaaaaaaac atttaaacat tagaagcctg tcttacaaca ggaaaaacaa cccttataag   33240
cataagacgg actacggcca tgccggcgtg accgtaaaaa aactggtcac cgtgattaaa   33300
aagcaccacc gacagctcct cggtcatgtc cggagtcata atgtaagact cggtaaacac   33360
atcaggttga ttcatcggtc agtgctaaaa agcgaccgaa atagcccggg ggaatacata   33420
cccgcaggcg tagagacaac attacagccc ccataggagg tataacaaaa ttaataggag   33480
agaaaaacac ataaacacct gaaaaaccct cctgcctagg caaaatagca ccctcccgct   33540
ccagaacaac atacagcgct tcacagcggc agcctaacag tcagccttac cagtaaaaaa   33600
gaaaacctat taaaaaaaca ccactcgaca cggcaccagc tcaatcagtc acagtgtaaa   33660
aaagggccaa gtgcagagcg agtatatata ggactaaaaa atgacgtaac ggttaaagtc   33720
cacaaaaaac acccagaaaa ccgcacgcga acctacgccc agaaacgaaa gccaaaaaac   33780
ccacaacttc ctcaaatcgt cacttccgtt ttcccacgtt acgtaacttc ccattttaag   33840
aaaactacaa ttcccaacac atacaagtta ctccgcccta aaacctacgt cacccgcccc   33900
gttcccacgc cccgcgccac gtcacaaact ccaccccctc attatcatat tggcttcaat   33960
ccaaaataag gtatattatt gatgatttaa t                                 33991
```

<210> SEQ ID NO 7
<211> LENGTH: 4747
<212> TYPE: DNA
<213> ORGANISM: Artificial Sequence
<220> FEATURE:
<223> OTHER INFORMATION: Description of Artificial Sequence: Synthetic primer

```
<400> SEQUENCE: 7
tcgagataac ttcgtataag aaaccatata cgaacggtac tagtgtcgac ctgcaggcat     60
gcaagcttgg cgtaatcatg gtcatagctg tttcctgtgt gaaattgtta tccgctcaca    120
attccacaca acatacgagc cggaagcata agtgtaaag cctggggtgc ctaatgagtg     180
agctaactca cattaattgc gttgcgctca ctgcccgctt tccagtcggg aaacctgtcg    240
tgccagctgc attaatgaat cggccaacgc gcggggagag gcggtttgcg tattgggcgc    300
tcttccgctt cctcgctcac tgactcgctg cgctcggtcg ttcggctgcg gcgagcggta    360
tcagctcact caaaggcggt aatacggtta ccacagaat cagggggataa cgcaggaaag    420
aacatgtgag caaaaggcca gcaaaaggcc aggaaccgta aaaaggccgc gttgctggcg    480
ttttttccata ggctccgccc ccctgacgag catcacaaaa atcgacgctc aagtcagagg    540
tggcgaaacc cgacaggact ataaagatac caggcgtttc ccctggaag ctccctcgtg     600
cgctctcctg ttccgaccct gccgcttacc ggatacctgt ccgcctttct cccttcggga    660
agcgtggcgc tttctcatag ctcacgctgt aggtatctca gttcggtgta ggtcgttcgc    720
tccaagctgg gctgtgtgca cgaaccccc gttcagcccg accgctgcgc cttatccggt     780
aactatcgtc ttgagtccaa cccggtaaga cacgacttat cgccactggc agcagccact    840
ggtaacagga ttagcagagc gaggtatgta ggcggtgcta cagagttctt gaagtggtgg    900
cctaactacg gctacactag aaggacagta tttggtatct gcgctctgct gaagccagtt    960
accttcggaa aaagagttgg tagctcttga tccggcaaac aaaccaccgc tggtagcggt   1020
ggttttttg tttgcaagca gcagattacg cgcagaaaaa aaggatctca agaagatcct   1080
ttgatcttt ctacggggtc tgacgctcag tggaacgaaa actcacgtta agggattttg    1140
gtcatgagat tatcaaaaag gatcttcacc tagatccttt taaattaaaa atgaagtttt    1200
aaatcaatct aaagtatata tgagtaaact tggtctgaca gttaccaatg cttaatcagt    1260
gaggcaccta tctcagcgat ctgtctattt cgttcatcca tagttgcctg actccccgtc    1320
gtgtagataa ctacgatacg ggagggctta ccatctggcc ccagtgctgc aatgataccg    1380
cgagacccac gctcaccggc tccagattta tcagcaataa accagccagc cggaagggcc    1440
gagcgcagaa gtggtcctgc aactttatcc gcctccatcc agtctattaa ttgttgccgg    1500
gaagctagag taagtagttc gccagttaat agtttgcgca acgttgttgc cattgctaca    1560
ggcatcgtgg tgtcacgctc gtcgtttggt atggcttcat tcagctccgg ttcccaacga    1620
tcaaggcgag ttacatgatc ccccatgttg tgcaaaaaag cggttagctc cttcggtcct    1680
ccgatcgttg tcagaagtaa gttggccgca gtgttatcac tcatggttat ggcagcactg    1740
cataattctc ttactgtcat gccatccgta agatgctttt ctgtgactgg tgagtactca    1800
accaagtcat tctgagaata gtgtatgcgg cgaccgagtt gctcttgccc ggcgtcaata    1860
cgggataata ccgcgccaca tagcagaact ttaaaagtgc tcatcattgg aaaacgttct    1920
tcggggcgaa aactctcaag gatcttaccg ctgttgagat ccagttcgat gtaacccact    1980
cgtgcaccca actgatcttc agcatctttt actttcacca gcgtttctgg gtgagcaaaa    2040
acaggaaggc aaaatgccgc aaaaaaggga ataaggcga cacggaaatg ttgaatactc    2100
atactcttcc ttttttcaata ttattgaagc atttatcagg gttattgtct catgagcgga    2160
tacatatttg aatgtattta gaaaaataaa caaatagggg ttccgcgcac atttccccga    2220
aaagtgccac ctgacgtcta agaaaccatt attatcatga cattaaccta taaaaatagg    2280
cgtatcacga ggccctttcg tctcgcgcgt ttcggtgatg acggtgaaaa cctctgacac    2340
```

```
atgcagctcc cggagacggt cacagcttgt ctgtaagcgg atgccgggag cagacaagcc   2400
cgtcagggcg cgtcagcggg tgttggcggg tgtcggggct ggcttaacta tgcggcatca   2460
gagcagattg tactgagagt gcaccatatg cggtgtgaaa taccgcacag atgcgtaagg   2520
agaaaatacc gcatcaggcg ccattcgcca ttcaggctgc gcaactgttg ggaagggcga   2580
tcggtgcggg cctcttcgct attacgccag ctggcgaaag ggggatgtgc tgcaaggcga   2640
ttaagttggg taacgccagg gttttcccag tcacgacgtt gtaaaacgac ggccagtgaa   2700
ttcgagctcg gtacctaccg ttcgtataat gtatgctata cgaagttatg cggccgccac   2760
tattatttag tgaaatgaga tattatgata ttttctgaat tgtgattaaa aaggcaactt   2820
tatgcccatg caacagaaac tataaaaaat acagagaatg aaaagaaaca gatagatttt   2880
ttagttcttt aggcccgtag tctgcaaatc cttttatgat tttctatcaa acaaaagagg   2940
aaaatagacc agttgcaatc caaacgagag tctaatagaa tgaggtcgaa agtaaatcg    3000 cgcgggtttg ttactgataa agcaggcaag acctaaaatg tgtaaagggc aaagtgtata   3060
ctttggcgtc accccttaca tattttaggt cttttttat tgtgcgtaac taacttgcca    3120
tcttcaaaca ggagggctgg aagaagcaga ccgctaacac agtacataaa aaggagaca    3180 tgaacgatga acatcaaaaa gtttgcaaaa caagcaacag tattaaccct tactaccgca   3240
ctgctggcag gaggcgcaac tcaagcgttt gcgaaagaaa cgaaccaaaa gccatataag   3300
gaaacatacg gcatttccca tattacgcgc catgatatgc tgcaaatccc tgaacagcaa   3360
aaaaatgaaa aatatcaagt tcctgaattc gattcgtcca caattaaaaa tatctcttct   3420
gcaaaaggcc tggacgtttg ggacagctgg ccattacaaa acgctgacgg cactgtcgca   3480
aactatcgcg gctaccacat cgtctttgca ttagccggag atcctaaaaa tgcggatgac   3540
acatcgattt acatgttcta tcaaaaagtc ggcgaaactt ctattgacag ctggaaaaac   3600
gctggccgcg tctttaaaga cagcgacaaa ttcgatgcaa atgattctat cctaaaagac   3660
caaacacaag aatggtcagg ttcagccaca tttacatctg acggaaaaat ccgtttattc   3720
tacactgatt tctccggtaa acattacggc aaacaaacac tgacaactgc acaagttaac   3780
gtatcagcat cagacagctc tttgaacatc aacggtgtag aggattataa atcaatcttt   3840
gacggtgacg gaaaaacgta tcaaaatgta cagcagttca tcgatgaagg caactacagc   3900
tcaggcgaca ccatacgct gagagatcct cactacgtag aagataaagg ccacaaatac   3960
ttagtatttg aagcaaacac tggaactgaa gatggctacc aaggcgaaga atctttattt   4020
aacaaagcat actatggcaa aagcacatca ttcttccgtc aagaaagtca aaaacttctg   4080
caaagcgata aaaacgcac ggctgagtta gcaaacggcg ctctcggtat gattgagcta   4140
aacgatgatt acacactgaa aaagtgatg aaaccgctga ttgcatctaa cacagtaaca   4200
gatgaaattg aacgcgcgaa cgtctttaaa atgaacggca atggtacct gttcactgac   4260 tcccgcggat caaaaatgac gattgacggc atttcgtcta cgatattta catgcttggt   4320 tatgtttcta attctttaac tggcccatac aagccgctga caaaactgg ccttgtgtta   4380 aaaatggatc ttgatcctaa cgatgtaacc tttacttact cacacttcgc tgtacctcaa   4440 gcgaaggaa acaatgtcgt ggtgattaca agctatatga caaacagagg attctacgca   4500
gacaaacaat caacgtttgc gccaagcttc ctgctgaaca tcaaaggcaa gaaaacatct   4560
gttgtcaaag acagcatcct tgaacaagga caattaacag ttaacaaata aaaacgcaaa   4620
agaaaatgcc gatggccgcg gcgttgtgac aatttaccga acaactccgc ggccgggaag   4680
```

```
ccgatctcgg cttgaacgaa ttgttaggtg gcggtacttg ggtcgatatc aaagtgcatc    4740
acttctc                                                              4747

<210> SEQ ID NO 8
<211> LENGTH: 1772
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
atgaagcgcg caagaccgtc tgaagatacc ttcaacccg tgtatccata tgacacggaa      60
accggtcctc caactgtgcc ttttcttact cctcccttg tatcccccaa tgggtttcaa     120
gagagtcccc ctggggtact ctctttgcgc tatccgaac ctctagttac ctccaatggc     180
atgcttgcgc tcaaaatggg caacggcctc tctctggacg aggccggcaa ccttacctcc     240
caaaatgtaa ccactgtgag cccacctctc aaaaaaacca gtcaaacat aaacctggaa     300 atatctgcac ccctcacagt tacctcagaa gccctaactg tggctgccgc cgcacctcta     360
atggtcgcgg caacacact caccatgcaa tcacaggccc cgctaaccgt gcacgactcc     420
aaacttagca ttgccaccca aggacccctc acagtgtcag aaggaaagct agccctgcaa     480
acatcaggcc cctcaccac caccgatagc agtaccctta ctatcactgc ctcacccct      540 ctaactactg ccactggtag cttgggcatt gacttgaaag agcccatttta tacacaaaat     600 ggaaaactag gactaaagta cggggctcct ttgcatgtaa cagacgacct aaacactttg     660
accgtagcaa ctggtccagg tgtgactatt aataatactt ccttgcaaac taaagttact     720
ggagccttgg gttttgattc acaaggcaat atgcaactta atgtagcagg aggactaagg     780
attgattctc aaaacagacg ccttatactt gatgttagtt atccgtttga tgctcaaaac     840
caactaaatc taagactagg acagggccct ctttttataa actcagccca caacttggat     900
attaactaca caaaggcct ttacttgttt acagcttcaa acaattccaa aaagcttgag     960
gttaacctaa gcactgccaa ggggttgatg tttgacgcta cagccatagc cattaatgca    1020
ggagatgggc ttgaatttgg ttcacctaat gcaccaaaca caaatcccct caaaacaaaa    1080
attggccatg gcctagaatt tgattcaaac aaggctatgg ttcctaaact aggaactggc    1140
cttagttttg acagcacagg tgccattaca gtaggaaaca aaaataatga taagctaact    1200
ttgtggacca caccagctcc atctcctaac tgtagactaa atgcagagaa agatgctaaa    1260
ctcactttgg tcttaacaaa atgtggcagt caaatacttg ctacagtttc agttttggct    1320
gttaaaggca gtttggctcc aatatctgga acagttcaaa gtgctcatct tattataaga    1380
tttgacgaaa atggagtgct actaaacaat tccttcctgg acccagaata ttggaacttt    1440
agaaatggag atcttactga aggcaacgct gttggattta tgcctaacct atcagcttat    1500
ccaaaatctc acgtaaaac tgccaaaagt aacattgtca gtcaagttta cttaaacgga    1560
gacaaaacta aacctgtaac actaaccatt acactaaacg gtacacagga atccggcgaa    1620
ttatgcgact gcaggggcga ctgcttctgt gccggagaca caactccaag tgcatactct    1680
atgtcatttt catgggactg gtctggccac aactacatta tgaaatatt tgccacatcc    1740 tcttacactt tttcatacat tgcccaagaa ta                                   1772

<210> SEQ ID NO 9
<211> LENGTH: 88
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 9
tcgagaacta tcttcatgtt gttgcagatg aagcgcgcaa gaccgtctga agataccttc      60
aaccccgtgt atccatatga cacggaaa                                         88

<210> SEQ ID NO 10
<211> LENGTH: 88
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ccggtttccg tgtcatatgg atacacgggg ttgaaggtat cttcagacgg tcttgcgcgc      60
ttcatctgca acaacatgaa gatagttc                                         88

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Thr Gly Glu Lys Gly Gly
1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Gly Ala Ala Gly Ala
1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Gly Gly Asp Arg Gly
1               5

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14
```

Cys Asp Cys Arg Gly Asp Cys Phe Cys
1               5

<210> SEQ ID NO 15
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ataacttcgt atagcataca ttatacgaag ttat                              34

<210> SEQ ID NO 16
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ataacttcgt atagtataca ttatacgaag ttat                              34

<210> SEQ ID NO 17
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ataacttcgt atagcataca ttatacgaac ggta                              34

<210> SEQ ID NO 18
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
taccgttcgt atagcataca ttatacgaag ttat                              34

<210> SEQ ID NO 19
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
taccgttcgt atatggtttc ttatacgaag ttat                              34

<210> SEQ ID NO 20
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ataacttcgt atatggtttc ttatacgaac ggta                                34

<210> SEQ ID NO 21
<211> LENGTH: 34
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 21
taccgttcgt atagcataca ttatacgaac ggta                                34

<210> SEQ ID NO 22
<211> LENGTH: 34
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 22
ataacttcgt atatggtttc ttatacgaag ttat                                34

<210> SEQ ID NO 23
<211> LENGTH: 34
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 23
taccgttcgt atagcataca ttatacgaac ggta                                34

<210> SEQ ID NO 24
<211> LENGTH: 37
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 24
cgtaccgttc gtatagcata cattatacga agttata                             37

<210> SEQ ID NO 25
<211> LENGTH: 43
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 25
ccggtataac ttcgtataat gtatgctata cgaacggtac gat                      43

<210> SEQ ID NO 26
<211> LENGTH: 39
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 26
ccggtataac ttcgtatatg gtttcttata cgaacggta                           39

<210> SEQ ID NO 27
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gatctaccgt tcgtataaga aaccatatac gaagttata                    39

<210> SEQ ID NO 28
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
aaccggtata cattgcccaa gaataaag                                28

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
tcataagtgc ggcgacgata                                         20

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gttgtgtgga attgtgagcg g                                       21

<210> SEQ ID NO 31
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
catgtaccgg tgggtgcgga tggacaggaa c                            31

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ctaacaattc gttcaagccg                                         20

```
<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
tcagcggttt catcactttt                                              20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ctgaccattc ttgtgtttgg                                              20

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gtctcctttt ttatgtactg tg                                           22

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ttatacgaag ttataccggt                                              20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
aataaactgc tgccgccgcc                                              20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
atcaatgttg gcacaacaca                                              20
```

```
<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
ccgcagaata agccacaccc                                                  20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
taacaaaaat accgcgatcc                                                  20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
acagctcctc ggtcatgtcc                                                  20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
cgttttccca cgttacgtaa                                                  20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
cactataggg cgaattgggc                                                  20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gccctttttt acactgtgac                                                  20

<210> SEQ ID NO 45
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
tttatgcaga aacccgcaga                                                   20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
atattgagaa ggtggcgaga                                                   20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
tgtttgtcac gcccgcacct                                                   20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
agaggtttat atggtaccgg                                                   20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
acttaagtga gctgcccggg                                                   20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ttatgcccat gcaacagaaa                                                   20

<210> SEQ ID NO 51
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
tattacacgc catgatatgc                                                  20

<210> SEQ ID NO 52
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
cggtgtagag gattataaat caatc                                            25

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
catgcttggt tatgtttcta                                                  20

<210> SEQ ID NO 54
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ctagtaccgt tcgtatatgg tttcttatac gaagttatc                             39

<210> SEQ ID NO 55
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
tcgagataac ttcgtataag aaaccatata cgaacggta                             39

<210> SEQ ID NO 56
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
ggccgcataa cttcgtatag catacattat acgaacggta g                          41

<210> SEQ ID NO 57
<211> LENGTH: 41
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 57
gtacctaccg ttcgtataat gtatgctata cgaagttatg c                    41

<210> SEQ ID NO 58
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gttgtgtctc cggattcctg tgtaccgttt agtgtaatgg                       40

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ggacccagaa tattggaact                                             20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
ctcaccccct ctaactactg                                             20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
caggagatgg gcttgaattt                                             20

<210> SEQ ID NO 62
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
ccggcgaatt cgcaggtggt ggtggtggtt                                  30

<210> SEQ ID NO 63
<211> LENGTH: 30
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 63
ccggaaccac caccaccacc tgcgaattcg                                         30

<210> SEQ ID NO 64
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
aattgggaag aggtgacacc ccct                                               24

<210> SEQ ID NO 65
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
ccaaacacaa atcccctcaa a                                                  21

<210> SEQ ID NO 66
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
ataagaatgc ggccgcttta ttcttgggca atgtat                                  36

<210> SEQ ID NO 67
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
ccggaggggg tgtcacctct tccc                                               24

<210> SEQ ID NO 68
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
aattgcggcc gccactatta tttagtgaaa tgagatatta                              40
```

-continued

```
<210> SEQ ID NO 69
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
atctcgagag aagtgatgca ctttgatatc gacccaag                              38

<210> SEQ ID NO 70
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 70
acaaacucuu cgcggucuuu                                                  20

<210> SEQ ID NO 71
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 71
uaucuucaga cggucuugcg                                                  20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
atggctaccc cttcgatgat                                                  20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
gatgaaccgc agcgtcaaac                                                  20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
ttcattaatg tagttgtggc                                                  20

<210> SEQ ID NO 75
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
accattacac taaacggtac                                            20

<210> SEQ ID NO 76
<211> LENGTH: 57
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (19)..(36)
<223> OTHER INFORMATION: a, c, g, t, unknown or other

<400> SEQUENCE: 76
tggagttgtg tctccggann nnnnnnnnnn nnnnnntccg gattcctgtg taccgct    57

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
agcggtacac aggaatccgg a                                          21

<210> SEQ ID NO 78
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
agcggtacac aggaatcc                                              18

<210> SEQ ID NO 79
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
tggagttgtg tctccgga                                              18

<210> SEQ ID NO 80
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
tgttcctgtc catccgcacc cactatcttc atgttg                          36
```

```
<210> SEQ ID NO 81
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
aggactgtgt actctgtgtg ttgggaggga ggtggca                                37
```